(12) United States Patent
Smith et al.

(10) Patent No.: US 10,227,414 B2
(45) Date of Patent: Mar. 12, 2019

(54) ST2 ANTIGEN BINDING PROTEINS

(71) Applicant: Amgen Inc., Thousand Oaks, CA (US)

(72) Inventors: Dirk E. Smith, Bainbridge Island, WA (US); Ian Foltz, Burnaby (CA); Chadwick T. King, North Vancouver (CA); Ai Ching Lim, Mercer Island, WA (US); Rutilio Clark, Bainbridge Island, WA (US); Michael R. Comeau, Bainbridge, WA (US); Randal R. Ketchem, Snohomish, WA (US); Donghui Shi, Thousand Oaks, CA (US); Xiaoshan Min, Burlingame, CA (US); Zhulun Wang, Palo Alto, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 15/601,868

(22) Filed: May 22, 2017

(65) Prior Publication Data
US 2017/0267769 A1    Sep. 21, 2017

Related U.S. Application Data

(62) Division of application No. 15/178,652, filed on Jun. 10, 2016, now Pat. No. 9,982,054, which is a division of application No. 13/897,096, filed on May 17, 2013, now Pat. No. 9,382,318.

(60) Provisional application No. 61/792,619, filed on Mar. 15, 2013, provisional application No. 61/649,147, filed on May 18, 2012.

(51) Int. Cl.
*A61K 39/00* (2006.01)
*C07K 16/24* (2006.01)
*C07K 16/28* (2006.01)

(52) U.S. Cl.
CPC ........ *C07K 16/2866* (2013.01); *C07K 16/244* (2013.01); *A61K 2039/505* (2013.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,066,322 A | 5/2000 | Levinson |
| 6,323,334 B1 | 11/2001 | Kingsbury et al. |
| 6,326,472 B1 | 12/2001 | Timans et al. |
| 6,399,748 B1 | 6/2002 | Werenskiold |
| 6,455,685 B1 | 9/2002 | Levinson |
| 6,566,130 B1 | 5/2003 | Srivastava et al. |
| 6,812,339 B1 | 11/2004 | Venter et al. |
| 6,905,827 B2 | 6/2005 | Wohlgemuth et al. |
| 7,087,396 B2 | 8/2006 | Tominaga et al. |
| 7,452,980 B2 | 11/2008 | Kingsbury et al. |
| 7,560,530 B1 | 7/2009 | Chackerian et al. |
| 7,879,978 B2 | 2/2011 | Cotty et al. |
| 7,972,797 B2 | 7/2011 | Kingsbury et al. |
| 7,998,683 B2 | 8/2011 | Snider et al. |
| 8,187,596 B1 | 5/2012 | Chackerian et al. |
| 8,420,795 B2 | 4/2013 | Rodriguez et al. |
| 8,444,987 B2 | 5/2013 | Kingsbury et al. |
| 9,090,694 B2 | 7/2015 | Duffy et al. |
| 2003/0124624 A1 | 7/2003 | Tominaga et al. |
| 2003/0148295 A1 | 8/2003 | Wan et al. |
| 2003/0152926 A1 | 8/2003 | Murray et al. |
| 2003/0219767 A1 | 11/2003 | Ayers et al. |
| 2003/0224383 A1 | 12/2003 | West et al. |
| 2003/0224422 A1 | 12/2003 | Evans et al. |
| 2004/0001803 A1 | 1/2004 | Hancock et al. |
| 2004/0014064 A1 | 1/2004 | Brissette et al. |
| 2004/0048286 A1 | 3/2004 | Lee |
| 2004/0106113 A1 | 6/2004 | West et al. |
| 2004/0197325 A1 | 10/2004 | Law et al. |
| 2004/0219515 A1 | 11/2004 | Bentwich |
| 2004/0219579 A1 | 11/2004 | Aziz et al. |
| 2005/0058639 A1 | 3/2005 | Gudas et al. |

(Continued)

FOREIGN PATENT DOCUMENTS

| | | |
|---|---|---|
| EP | 2010912 | 8/2010 |
| EP | 1725261 | 1/2011 |

(Continued)

OTHER PUBLICATIONS

Blumberg et al., "Unraveling the autoimmune translational research process layer by layer," HHS Public Access Author manuscript available in PMC, 19 pages (2015) (published in final edited form as Nat. Med., 18(1): 35-41 (2012)).

(Continued)

*Primary Examiner* — Brian Gangle
*Assistant Examiner* — Andrea K McCollum
(74) *Attorney, Agent, or Firm* — McNeill Baur PLLC

(57) ABSTRACT

Described herein are compositions and methods related to antigen binding proteins that bind to human ST2, including antibodies. In particular embodiments, the disclosure provides fully human anti-ST2 antibodies and deriviatives and variants thereof. Further provided are nucleic acids encoding such antibodies and antibody fragments, variants, and derivatives. Also, provided are methods of making and using such antibodies including methods of treating and preventing autoimmune and inflammatory disorders.

45 Claims, 11 Drawing Sheets
Specification includes a Sequence Listing.

(56) References Cited

U.S. PATENT DOCUMENTS

| | | | |
|---|---|---|---|
| 2005/0170528 | A1 | 8/2005 | West et al. |
| 2005/0203046 | A1 | 9/2005 | Schmitz et al. |
| 2005/0208496 | A1 | 9/2005 | Ohtani et al. |
| 2006/0093599 | A1 | 5/2006 | Gazit-Bornstein et al. |
| 2007/0042978 | A1 | 2/2007 | Girard et al. |
| 2007/0166704 | A1 | 7/2007 | Huang et al. |
| 2009/0214559 | A1 | 8/2009 | Varnum et al. |
| 2009/0304699 | A1 | 12/2009 | Amatucci et al. |
| 2010/0221257 | A1 | 9/2010 | Campbell et al. |
| 2010/0247442 | A1 | 9/2010 | Cotty et al. |
| 2010/0247545 | A1 | 9/2010 | Bedian et al. |
| 2011/0256635 | A1 | 10/2011 | Snider |
| 2012/0207752 | A1 | 8/2012 | Chackerian et al. |
| 2012/0213774 | A1 | 8/2012 | Fertig et al. |
| 2012/0263709 | A1 | 10/2012 | Rankin et al. |
| 2013/0177931 | A1 | 7/2013 | Snider |
| 2014/0271658 | A1 | 9/2014 | Murphy et al. |

FOREIGN PATENT DOCUMENTS

| | | |
|---|---|---|
| EP | 1757621 | 9/2011 |
| JP | 2003235573 | 8/2003 |
| JP | 205204549 | 8/2005 |
| WO | WO 1999/34217 | 7/1999 |
| WO | WO 2000/073498 | 12/2000 |
| WO | WO 2001/021641 A1 | 3/2001 |
| WO | WO 2002/057414 | 7/2002 |
| WO | WO 2002/068579 | 9/2002 |
| WO | WO 2002/083876 | 10/2002 |
| WO | WO 2003/016475 | 2/2003 |
| WO | WO 2003/048383 | 6/2003 |
| WO | WO 2003/062395 | 7/2003 |
| WO | WO 2003/080640 | 10/2003 |
| WO | WO 2004/031413 | 4/2004 |
| WO | WO 2004/044123 | 5/2004 |
| WO | WO 2004/053157 | 6/2004 |
| WO | WO 2004/056868 | 7/2004 |
| WO | WO 2004/063355 | 7/2004 |
| WO | WO 2004/083818 | 9/2004 |
| WO | WO 2004/108899 | 12/2004 |
| WO | WO 2004/108964 | 12/2004 |
| WO | WO 2005/002414 | 1/2005 |
| WO | WO 2005/030124 A2 | 4/2005 |
| WO | WO 2005/100604 | 10/2005 |
| WO | WO 2005/108415 | 11/2005 |
| WO | WO 2008/024919 A9 | 2/2008 |
| WO | WO 2008/132709 | 11/2008 |
| WO | WO 2008/144610 | 11/2008 |
| WO | WO 2009/124090 | 10/2009 |
| WO | WO 2010/052505 A1 | 5/2010 |
| WO | WO 2011/031600 | 3/2011 |
| WO | WO 2011/127412 A2 | 10/2011 |
| WO | WO 2011/127412 A3 | 1/2012 |
| WO | WO 2012/083132 | 6/2012 |

OTHER PUBLICATIONS

Ma, "Animal Models of Disease," Modern Drug Discovery, 7(6): 30-36 (2004).
Martin et al., "Atheroschlerosis severity is not affected by a deficiency in IL-33/ST2 signaling," Immunity, Inflammation and Disease, 3(3): 239-246 (2015).
Monticelli et al., "Innate lymphoid cells promote lung tissue homeostasis following acute influenza virus infection," Nat. Immunol., 12(11): 1045-1054 (2011).
Steinman et al., "Optimization of current and future therapy for autoimmune diseases," Nat. Med., 18(1): 59-65 (2012).
Rößler et al., "Secreted and membrane-bound isoforms of T1, an orphan receptor related to IL-1 binding proteins, are differently expressed in vivo," Dev Biol 168:86-97, 1995.
Rößler et al., "T1, an immunoglobulin superfamily member, is expressed in H-ras-dependent epithelial tumours of mammary cells," Oncogene 8:609-617, 1993.
Sakashita et al., "Association of serum interleukin-33 level and the interleukin-33 genetic variant with Japanese color pollinosis," Clin Exp Allergy 38:1875-1881, 2008.
Schmitz et al., "IL-33, an interleukin-1-like cytokine that signals via the IL-1 receptor-related protein ST2 and induces T helper type 2-associated cytokines," Immunity 23:479-490, 2005.
Shah et al., "ST2: a novel remodeling biomarker in acute and chronic heart failure," Curr Heart Fail Rep 7:9-14, 2010.
Shimizu et al., "Functional SNPs in the distal promoter of the ST2 gene are associated with atopic dermatitis," Hum Mol Genet 14:2919-2927, 2005.
Silver et al., "IL-33 synergizes with IgE-dependent and IgE-independent agents to promote mast cell and basophil activation," Inflamm Res 59:207-218, 2010.
Sponheim et al., "Inflammatory bowel disease-associated interleukin-33 is preferentially expressed in ulceration-associated myofibroblasts," Am J Pathol 177:2804-2815, 2010.
Sweet et al., "A novel pathway regulating lipopolysaccharide-induced shock by ST2/T1 via inhibition of toll-like receptor 4 expression," J Immunol 166:6633-6639, 2001.
Tajima et al., "The increase in serum soluble ST2 protein upon acute exacerbation of idiopathic pulmonary fibrosis," Chest 124:1206-1214, 2003.
Takezako et al., "ST2 suppresses IL-6 production via the inhibition of IκB degradation induced by the LPS signal in THP-1 cells," J Biochem Biophys Res Commun 341:425-432, 2006.
Theoharides et al., "IL-33 augments substance P-induced VEGF secretion from human mast cells and is increased in psoriatic skin," PNAS 107:4448-4453, 2010.
Thomassen et al., "Role of cell type-specific promoters in the developmental regulation of T1, an interleukin 1 receptor homologue," Cell Growth Differ 6:179-184, 1995.
Tominaga, "A putative protein of a growth specific cDNA from BALB/c-3T3 cells is highly similar to the extracellular portion of mouse interleukin 1 receptor," FEBS Lett 258:301-304, 1989.
Tominaga et al., "Nucleotide sequence of a complementary DNA for human ST2," Biochim Biophys Acta 1171:215-218, 1992.
Tominaga, "Presence and expression of a novel variant form of ST2 gene product in human leukemic cell line UT-7/GM," Biochem Biophys Res Commun 264:14-18, 1999.
Verri Jr. et al., "IL-33 mediates antigen-induced cutaneous and articular hypernociception in mice," PNAS 105:2723-2728, 2008.
Werenskiold et al., "Induction of a mitogen-responsive gene after expression of the Ha-ras oncogene in NIH 3T3 fibroblasts," Mol Cell Biol 9:5207-5214, 1989.
Werenskiold, "Characterization of a secreted glycoprotein of the immunoglobulin superfamily inducible by mitogen and oncogene," Eur J Biochem 204:1041-1047, 1992.
Werenskiold et al., "Bone matrix deposition of T1, a homologue of interleukin 1 receptors," Cell Growth Differ 6:171-177, 1995.
Wu et al., "Evaluation of candidate genes in a genome-wide association study of childhood asthma in Mexicans," J Allergy Clin Immunol 125:321-327, 2010.
Xu et al., "Selective expression of a stable cell surface molecule on type 2 but not type 1 helper T cells," J Exp Med 187:787-794, 1998.
Xu et al., "IL-33 exacerbates antigen-induced arthritis by activating mast cells," PNAS 105:10913-10918, 2008.
Yanaba et al., "Serum IL-33 levels are raised in patients with systemic sclerosis: association with extent of skin sclerosis and severity of pulmonary fibrosis," Clin Rheumatol 30:825-830, 2011.
Yanagisawa et al., "Presence of a novel primary response gene ST2L, encoding a product highly similar to the interleukin 1 receptor type 1," FEBS Lett 318:83-87, 1993.
Yoshida et al., "Studies on natural ST2 gene products in the human leukemic cell line UT-7 using monoclonal antihuman ST2 antibodies," Hybridoma 14:419-427, 1995.
Ali et al., "Investigations into the role of ST2 in acute asthma in children," Tissue Antigens 73: 206-212, 2009.
Beltran et al., "Characterization of the novel ST2/IL-33 system in patients with inflammatory bowel disease," Inflamm Bowel Dis 16:1097-1107, 2010.

(56) References Cited

OTHER PUBLICATIONS

Bergers et al., "Alternative promoter usage of the Fos-responsive gene Fit-1 generates mRNA isoforms coding for either secreted or membrane-bound proteins related to the IL-1 receptor," EMBO J. 13:1176-1188, 1994.

Brunner et al., "Increased levels of soluble ST2 protein and IgG1 production in patients with sepsis and trauma," Intensive Care Med 30:1468-1473, 2004.

Buysschaert et al., "Genetic evidence for a role of IL33 in nasal polyposis," Allergy 65:616-622, 2010.

Carriere et al., "IL-33, the IL-1-like cytokine ligand for ST2 receptor, is a chromatin-associated nuclear factor in vivo," PNAS 104:282-287, 2007.

Castano et al., "Evidence of association of interleukin 1 receptor like 1 gene polymorphisms with surgery unresponsive chronic rhinosinusitis," Am J Rhinol 23:377-384, 2009.

Coyle et al., U.S. Appl. No. 60/155,862, filed Sep. 24, 1999.

Dinarello, "An IL-1 family member requires caspase-1 processing and signals through the ST2 receptor," Immunity 23:461-464, 2005.

Gudbjartsson et al., "Sequence variants affecting eosinophil numbers associate with asthma and myocardial infarction," Nat Genet 41:342-347, 2009.

Hacker et al., "Increased soluble serum markers caspase-cleaved cytokeratin-18, histones, and ST2 indicate apoptotic turnover and chronic immune response in COPD," J Clin Lab Anal 23:372-379, 2009.

Klemenz et al., "Serum- and oncoprotein-mediated induction of a gene with sequence similarity to the gene encoding carcinoembryonic antigen," PNAS 86:5708-5712, 1989.

Kuroiwa et al., "Construction of ELISA system to quantify human ST2 protein in sera of patients," Hybridoma 19:151-159, 2000.

Kuroiwa et al., Identification of human ST2 protein in the sera of patients with autoimmune diseases, Biochem Biophys Res Commun 284:1104-1108, 2001.

Li et al., "The cloning and nucleotide sequence of human ST2L cDNA," Genomics 67:284-290, 2000.

Manetti et al., "The IL-1-like cytokine IL-33 and its receptor ST2 are abnormally expressed in the affected skin and visceral organs of patients with systemic sclerosis," Ann Rheum Dis 69:598-605, 2010.

Marvie et al., "Interleukin-33 overexpression is associated with liver fibrosis in mice and humans," J Cell Mol Med 14:1726-1739, 2010.

Matsuyama et al., "Increased levels of interleukin 33 in sera and synovial fluid from patients with active rheumatoid arthritis," J Rheumatol 37:18-25, 2010.

Miyagaki et al., "High levels of soluble ST2 and low levels of IL-33 in sera of patients with HIV infection," J Invest Dermatol 131:794-796, 2011.

Moffatt et al., "A large-scale, consortium-based genomewide association study of asthma," N Engl J Med 363:1211-1221, 2010.

Mok et al., "Serum levels of IL-33 and soluble ST2 and their association with disease activity in systemic lupus erythematosus," Rheumatology (Oxford) 49:520-527, 2010.

Neill et al., "Nuocytes represent a new innate effector leukocyte that mediates type-2 immunity," Nature 464:1367-1371, 2010.

Oshikawa et al., "Elevated soluble ST2 protein levels in sera of patients with asthma with an acute exacerbation," Am J Respir Crit Care Med 164:277-281, 2001.

Oshikawa etal., "Acute eosinophilic pneumonia with increased soluble ST2 in serum and broncoalveolar lavage fluid," Respir Med 95:532-533, 2001.

Palmer et al., "Inhibition of interleukin-33 signaling attenuates the severity of experimental arthritis," Arthritis Rheum 60:738-749, 2009.

Pastorelli et al., "Epithelial-derived IL-33 and its receptor ST2 are dysregulated in ulcerative colitis and in experimental Th1/Th2 driven enteritis," PNAS 1:8017-8022, 2010.

Plager et al., "Gene transcription changes in asthmatic chronic rhinosinusitis with nasal polyps and comparison to those in atopic dermatitis," PLoS ONE 5:e11450(1-9), 2010.

Prefontaine et al., "Increased expression of IL-33 in severe asthma: evidence of expression by airway smooth muscle cells," J Immunol 183:5094-5103, 2009.

Prefontaine et al., "Increased IL-33 expression by epithelial cells in bronchial asthma," J Allergy Clin Immunol 125:752-754, 2010.

Pushparaj et al., "The cytokine interleukin-33 mediates anaphylactic shock," PNAS 106:9773-9778, 2009.

Retraction, Pushparaj et al., "The cytokine interleukin-33 mediates anaphylactic shock," PNAS 109:13877, 2012.

Ramaprakash et al., "Targeting ST2L potentiates CpG-mediated therapeutic effects in a chronic fungal asthma model," Am J Pathol 179:104-115, 2011.

Reijmerink et al., "Association of IL1RL1, IL18R1, and IL18RAP gene cluster polymorphisms with asthma and atopy," J Allergy Clin Immunol 122:651-654, e651-e658, 2008.

Suzukawa et al., "Interleukin-33 enhances adhesion, CD11b expression and survival in human eosinophils", Laboratory Investigation, Sep. 1, 2008, vol. 88, No. 11.

Johnson et al., "Matching amino acid and nucleotide sequences of mouse rheumatoid factor CDRH3-FRH4 segments to other mouse antibodies with known specificities," Bioinformatics, Oct. 2000, vol. 16, No. 10, pp. 941-943.

Martin et al., "Atherosclerosis severity is not affected by a deficiency in IL-33/ST2 signaling", *The Authors, Immunity, Inflammation and Disease*; Published by John Wiley & Sons Ltd. 2015.

Martin et al., "Atherosclerosis severity is not affected by a deficiency in IL-33/ST2 signaling", *The Authors, Immunity, Inflammation and Disease*; Published by John Wiley & Sons Ltd. 2015— "Supporting Information Table 1: Body weight (g) before and after cholesterol-rich." and "Supporting Information Table 2: Serum total cholesterol concentrations (mM) before and after cholesterol-rich diet."

Oboki et al., "IL-33 and IL-33 Receptors in Host Defense and Diseases," Allergology International, 59: 143-160 (2010).

Communication pursuant to Rule 164(1) EPC and Supplementary Partial European Search Report, dated Apr. 14, 2016 (11 pages).

Bork, "Powers and Pitfalls in Sequence Analysis: The 70% Hurdle," Genome Res., 10: 398-400 (2000).

Bowie et al., "Deciphering the Message in Protein Sequences: Tolerance to Amino Acid Substitutions," Science, 247(4948): 1306-1310 (1990).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Bio., 111: 2129-2138 (1990).

Lazar et al., "Transforming Growth Factor α: Mutation of Aspartic Acid 47 and Leucine 48 Results in Different Biological Activities," Mol. Cell. Bio., 8(3): 1247-1252 (1988).

Communication of the extended European search report, dated Aug. 2, 2016, for European Patent Application No. 13790269.8 (16 pages).

Barksby et al., "The expanding family of interleukin-1 cytokines and their role in destructive inflammatory disorders," Clin. Exp. Immunol., 149: 217-225 (2007).

Barnes, "The cytokine network in asthma and chronic obstructive pulmonary disease," J. Clin. Invest., 118: 3546-3556 (2008).

Bourgeois, "The pro-Th2 cytokine IL-33 directly interacts with invariant NKT and NK cells to induce IFN-γ production," Eur. J. Immunol., 39: 1046-1055 (2009).

Griesenauer et al., "The ST2/IL-33 Axis in Immune Cells during Inflammatory Disease," Front. Immunol., 8: Article 475 (17 pages) (2017).

Haenuki et al., "A critical role of IL-33 in experimental allergic rhinitis," J. Allergy Clin. Immunol.; 130(1): 184-194 (2012).

Hamzaoui et al., "Interleukin-33 and Behçet disease: Another cytokine among others," Human Immunol., 76: 301-306 (2015).

Leung et al., "A Novel Therapy of Murine Collagen-Induced Arthritis with Soluble T1/ST2," J. Immunol., 173: 145-150 (2004).

(56) References Cited

OTHER PUBLICATIONS

Li et al., "IL-33 blockade suppresses the development of experimental autoimmune encephalomyelitis in C57BL/6 mice," J. Neuroimmunol., 247(1-2): 25-31 (2012).

Manetti et al., "The IL-1-like cytokine IL-33 and its receptor ST2 are abnormally expressed in the affected skin and visceral organs of patients with systemic sclerosis," Annals Rheumatic Diseases, doi: 10.1136/ard.2009.119321, 22 pages, (2009).

Matsuba-Kitamura et al., "Contribution of IL-33 to induction and augmentation of experimental allergic conjunctivitis," Int'l Immunol., 22(6): 479-489 (2010).

Miller et al., "The IL-33/ST2 pathway—A new therapeutic target in cardiovascular disease," Pharmacol. Therap., 131: 179-186 (2011).

Nabe, "Interleukin (IL)-33: New Therapeutic Target for Atopic Diseases," J. Pharmacol. Sci., 126: 85-91 (2014).

Oboki et al., "IL-33 and IL-33 Receptors in Host Defense and Diseases," Allergology Int'l., 59: 143-160 (2010).

Saenz et al., "Welcome to the neighborhood: epithelial cell-derived cytokines license innate and adaptive immune responses at mucosal sites," Immun. Res., 226: 172-190 (2008).

Saluja et al., "The role of IL-33 and mast cells in allergy and inflammation," Clin. Transl. Allergy, 5: Article 33 (8 pages) (2015).

Smith, "IL-33: a tissue derived cytokine pathway involved in allergic inflammation and asthma," Clin. Exp. Allergy, 40: 200-208 (2009).

Theoharides et al., IL-33 augments substance P—induced VEGF secretion from human mast cells and is increased in psoriatic skin, PNAS, 107(9): 4448-4453 (2010).

Wang et al., "IL-33: A Potential Therapeutic Target in Autoimmune Diseases," J. Invest. Med., 60(8): 1151-1156 (2012).

Xu et al., "IL-33 exacerbates antigen-induced arthritis by activating mast cells," PNAS, 105(31): 10913-10918 (2008).

Xu et al., "Role of the IL-33-ST2 axis in sepsis," Military Med. Res. 4: Article 3 (9 pages) (2017).

Ab2 HC Variable region (SEQ ID NO:30)

EVQLVQSGAE VKKPGESLKI SCKGSGYSFT NYWIG WVRQM PGKGLEWMG I IYPGNSDTRF SPSFQG QVTI SADKSITTAY
LQWSSLKASD TAMYYCAR HG TSSDYY GLDV WGQGTTVTVS S

Ab2 LC Variable region (SEQ ID NO:96)

DIQMTQSPSS LSASVGDRVT ITC QASQDIS NYLN WYQQKP GKAPKLLIY D ASNLET GVPS RFSGSGSGTD FTFTISSLQP
EDIATYYC QQ DDNFPLT FGG GTKVEIKR

FIG. 10

SEQUENCE LISTING

```
<160> NUMBER OF SEQ ID NOS: 175

<210> SEQ ID NO 1
<211> LENGTH: 556
<212> TYPE: PRT
<213> ORGANISM: Homo sapiens
<220> FEATURE:
<221> NAME/KEY: misc_feature
<222> LOCATION: (78)..(78)
<223> OTHER INFORMATION: Xaa at position 78 is Glu or Ala

<400> SEQUENCE: 1

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Xaa Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205
```

```
Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Gly Gln
        260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                325                 330                 335

Ser Val Phe Leu Met Leu Ile Asn Val Leu Val Ile Ile Leu Lys Met
                340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
                435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
                515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 2
<211> LENGTH: 570
<212> TYPE: PRT
<213> ORGANISM: Homo sapiens

<400> SEQUENCE: 2

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
```

```
            20                  25                  30
Arg Gln Ile Gln Val Phe Glu Asp Glu Pro Ala Arg Ile Lys Cys Pro
                35                  40                  45
Leu Phe Glu His Phe Leu Lys Phe Asn Tyr Ser Thr Ala His Ser Ala
     50                  55                  60
Gly Leu Thr Leu Ile Trp Tyr Trp Thr Arg Gln Asp Arg Asp Leu Glu
 65                  70                  75                  80
Glu Pro Ile Asn Phe Arg Leu Pro Glu Asn Arg Ile Ser Lys Glu Lys
                 85                  90                  95
Asp Val Leu Trp Phe Arg Pro Thr Leu Leu Asn Asp Thr Gly Asn Tyr
                100                 105                 110
Thr Cys Met Leu Arg Asn Thr Thr Tyr Cys Ser Lys Val Ala Phe Pro
                115                 120                 125
Leu Glu Val Val Gln Lys Asp Ser Cys Phe Asn Ser Pro Met Lys Leu
        130                 135                 140
Pro Val His Lys Leu Tyr Ile Glu Tyr Gly Ile Gln Arg Ile Thr Cys
145                 150                 155                 160
Pro Asn Val Asp Gly Tyr Phe Pro Ser Ser Val Lys Pro Thr Ile Thr
                165                 170                 175
Trp Tyr Met Gly Cys Tyr Lys Ile Gln Asn Phe Asn Asn Val Ile Pro
                180                 185                 190
Glu Gly Met Asn Leu Ser Phe Leu Ile Ala Leu Ile Ser Asn Asn Gly
                195                 200                 205
Asn Tyr Thr Cys Val Val Thr Tyr Pro Glu Asn Gly Arg Thr Phe His
        210                 215                 220
Leu Thr Arg Thr Leu Thr Val Lys Val Val Gly Ser Pro Lys Asn Ala
225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
                260                 265                 270
Leu Met Asp Ser Arg Asn Glu Val Trp Trp Thr Ile Asp Gly Lys Lys
        275                 280                 285
Pro Asp Asp Ile Thr Ile Asp Val Thr Ile Asn Glu Ser Ile Ser His
        290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
                340                 345                 350
Ala Pro Arg Tyr Thr Val Glu Leu Ala Cys Gly Phe Gly Ala Thr Val
        355                 360                 365
Leu Leu Val Val Ile Leu Ile Val Val Tyr His Val Tyr Trp Leu Glu
        370                 375                 380
Met Val Leu Phe Tyr Arg Ala His Phe Gly Thr Asp Glu Thr Ile Leu
385                 390                 395                 400
Asp Gly Lys Glu Tyr Asp Ile Tyr Val Ser Tyr Ala Arg Asn Ala Glu
                405                 410                 415
Glu Glu Glu Phe Val Leu Leu Thr Leu Arg Gly Val Leu Glu Asn Glu
                420                 425                 430
Phe Gly Tyr Lys Leu Cys Ile Phe Asp Arg Asp Ser Leu Pro Gly Gly
        435                 440                 445
```

```
Ile Val Thr Asp Glu Thr Leu Ser Phe Ile Gln Lys Ser Arg Arg Leu
    450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
                500                 505                 510

Glu Leu Lys Arg Ala Lys Thr Val Leu Thr Val Ile Lys Trp Lys Gly
            515                 520                 525

Glu Lys Ser Lys Tyr Pro Gln Gly Arg Phe Trp Lys Gln Leu Gln Val
            530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565                 570

<210> SEQ ID NO 3
<211> LENGTH: 270
<212> TYPE: PRT
<213> ORGANISM: Homo sapiens

<400> SEQUENCE: 3

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45

Ser Gly Leu Met Ile Lys Lys Glu Ala Cys Tyr Phe Arg Arg Glu Thr
        50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
```

245                 250                 255
Asn Leu Cys Thr Glu Asn Ile Leu Phe Lys Leu Ser Glu Thr
            260                 265                 270

<210> SEQ ID NO 4
<211> LENGTH: 556
<212> TYPE: PRT
<213> ORGANISM: Macaca fascicularis

<400> SEQUENCE: 4

Met Gly Leu Trp Ile Leu Ala Ile Leu Thr Ile Leu Val Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Ser Ser Tyr Ile Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Glu Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Pro Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Lys
145                 150                 155                 160

Ala His Lys Ser Phe Leu Val Ile Asp Asn Val Met Thr Asp Asp Ala
                165                 170                 175

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
        195                 200                 205

Ser Arg Phe Pro Val Ile Arg Ala Pro Ala His Asn Glu Thr Lys Glu
    210                 215                 220

Val Glu Ile Gly Glu Asn Thr Asn Leu Thr Cys Ser Ala Cys Phe Gly
225                 230                 235                 240

Lys Gly Ala Gln Phe Leu Ala Thr Val Gln Trp Gln Leu Asn Gly Asn
                245                 250                 255

Lys Ile Thr Asp Phe Ser Glu Pro Arg Ile Gln Gln Glu Glu Gly Gln
            260                 265                 270

Asn Gln Ser Phe Ser Asn Gly Leu Ala Cys Val Asn Thr Val Leu Arg
        275                 280                 285

Ile Ala Asp Val Lys Glu Glu Asp Leu Leu Leu Arg Tyr Asp Cys Leu
    290                 295                 300

Ala Leu Asn Leu His Gly Leu Arg Arg His Thr Ile Arg Leu Ser Arg
305                 310                 315                 320

Lys Asn Pro Ile Asp His Gln Ser Thr Tyr Cys Ile Ile Ala Val Cys
                325                 330                 335

Ser Val Leu Leu Met Leu Ile Asn Ile Leu Val Ile Ile Leu Lys Thr
            340                 345                 350

-continued

```
Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Ile Tyr Pro
        370                 375                 380

Arg Asn Tyr Thr Ser Ser Ala Asp Gly Ala Ser Arg Val Glu Tyr Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Ser Glu Glu Phe Ala Tyr Glu Gln Glu Val
    450                 455                 460

Ala Leu His Ser Ala Leu Ile Gln Asn Asp Ser Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Arg His Leu Met Glu Val Gln Gly Thr Ile Lys Trp
            500                 505                 510

Arg Glu Asp His Val Ala Asn Lys Arg Ser Leu Asn Ser Lys Phe Trp
        515                 520                 525

Lys His Val Arg Tyr Gln Met Pro Val Pro Ser Lys Met Pro Arg Lys
    530                 535                 540

Ala Ser Ser Leu Thr Ser Leu Ala Ala Gln Lys Gln
545                 550                 555

<210> SEQ ID NO 5
<211> LENGTH: 570
<212> TYPE: PRT
<213> ORGANISM: Macaca fascicularis

<400> SEQUENCE: 5

Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175
```

Trp Tyr Met Gly Cys Tyr Lys Ile Gln Asn Phe Asn Val Ile Pro
            180                 185                 190

Glu Gly Met Asn Leu Ser Phe Leu Ile Ala Phe Ile Ser Asn Asn Gly
            195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Pro Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Thr Val Lys Gln Lys Val Pro
            340                 345                 350

Ala Pro Arg Tyr Thr Val Glu Leu Ala Cys Gly Phe Gly Ala Thr Val
            355                 360                 365

Leu Leu Val Val Ile Leu Ile Val Val Tyr His Val Tyr Trp Leu Glu
            370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
            435                 440                 445

Ile Val Thr Asp Glu Thr Leu Ser Phe Ile Gln Lys Ser Arg Arg Leu
450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Gln Gly Asn Ile
                485                 490                 495

Asn Val Ile Leu Val Gln Tyr Lys Ala Val Lys Glu Thr Lys Val Lys
            500                 505                 510

Glu Leu Lys Arg Ala Lys Thr Val Leu Thr Val Ile Lys Trp Lys Gly
            515                 520                 525

Glu Lys Ser Lys Tyr Pro Gln Gly Arg Phe Trp Lys Gln Leu Gln Val
            530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565                 570

<210> SEQ ID NO 6
<211> LENGTH: 270

<212> TYPE: PRT
<213> ORGANISM: Macaca fascicularis

<400> SEQUENCE: 6

Met Lys Pro Lys Met Lys Tyr Ser Thr Asn Lys Ile Ser Thr Ala Lys
1               5                   10                  15

Arg Lys Asn Thr Ala Ser Lys Ala Leu Cys Phe Lys Leu Gly Lys Ser
            20                  25                  30

Gln Gln Lys Ala Lys Glu Val Cys His Val Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Gly Lys His Lys Gly His Leu
65                  70                  75                  80

Val Leu Ala Ala Cys Gln Gln Gln Ser Thr Val Glu Cys Phe Ala Phe
                85                  90                  95

Gly Ile Ser Gly Val Pro Lys Tyr Thr Arg Ala Leu His Asp Ser Ser
            100                 105                 110

Ile Thr Gly Ile Ser Pro Ile Thr Glu Ser Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Lys Lys Asp Lys Val Leu
145                 150                 155                 160

Leu Ser Tyr Tyr Glu Ser Gln His Pro Ser Glu Ser Gly Asp Gly
                165                 170                 175

Val Asp Gly Lys Met Leu Met Val Thr Leu Ser Pro Thr Lys Asp Phe
            180                 185                 190

Trp Leu Gln Ala Asn Asn Lys Glu His Ser Val Glu Leu His Lys Cys
        195                 200                 205

Glu Lys Pro Leu Pro Asp Gln Ala Phe Phe Val Leu His Asn Arg Ser
    210                 215                 220

Phe Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp His Ser Glu
                245                 250                 255

Asn Leu Gly Ser Glu Asn Ile Leu Phe Lys Leu Ser Glu Ile
            260                 265                 270

<210> SEQ ID NO 7
<211> LENGTH: 1332
<212> TYPE: DNA
<213> ORGANISM: Homo sapiens

<400> SEQUENCE: 7
caggtccaac tggtacagtc tggggctgag gtgaagaagc ctggggcctc agtgaaggtc      60
tcctgcaagg tttccggata caccctcact gaattatcca tacactgggt gcgacaggct     120
cctggaaaag ggcttgagtg gatgggaggt tttggtcctg aagatggtga acaatctac     180 gcacagaagt tccagggcag agtcaccatg accgaggaca catctacaga cacagcctac     240
atggagctga gcagcctgag atctgaggac acggccgtgt attactgtac aacagaggat     300
agcagtggcc tctttgacta ctggggccag gaaccctgg tcaccgtctc ctcagctagc      360
accaagggcc catcggtctt ccccctggcg ccctgctcca ggagcacctc cgagagcaca     420
gcggccctgg gctgcctggt caaggactac ttccccgaac cggtgacggt gtcgtggaac     480

| | |
|---|---|
| tcaggcgctc tgaccagcgg cgtgcacacc ttcccagctg tcctacagtc ctcaggactc | 540 |
| tactccctca gcagcgtggt gaccgtgccc tccagcaact tcggcaccca gacctacacc | 600 |
| tgcaacgtag atcacaagcc cagcaacacc aaggtggaca agacagttga gcgcaaatgt | 660 |
| tgtgtcgagt gcccaccgtg cccagcacca cctgtggcag gaccgtcagt cttcctcttc | 720 |
| cccccaaaac ccaaggacac cctcatgatc tcccggaccc ctgaggtcac gtgcgtggtg | 780 |
| gtggacgtga gccacgaaga ccccgaggtc cagttcaact ggtacgtgga cggcgtggag | 840 |
| gtgcataatg ccaagacaaa gccacgggag gagcagttca acagcacgtt ccgtgtggtc | 900 |
| agcgtcctca ccgttgtgca ccaggactgg ctgaacggca aggagtacaa gtgcaaggtc | 960 |
| tccaacaaag gcctcccagc ccccatcgag aaaaccatct ccaaaaccaa agggcagccc | 1020 |
| cgagaaccac aggtgtacac cctgccccca tcccgggagg agatgaccaa gaaccaggtc | 1080 |
| agcctgacct gcctggtcaa aggcttctac cccagcgaca tcgccgtgga gtgggagagc | 1140 |
| aatgggcagc cggagaacaa ctacaagacc acacctccca tgctggactc cgacggctcc | 1200 |
| ttcttcctct acagcaagct caccgtggac aagagcaggt ggcagcaggg gaacgtcttc | 1260 |
| tcatgctccg tgatgcatga ggctctgcac aaccactaca cgcagaagag cctctccctg | 1320 |
| tctccgggta aa | 1332 |

<210> SEQ ID NO 8
<211> LENGTH: 1341
<212> TYPE: DNA
<213> ORGANISM: Homo sapiens

<400> SEQUENCE: 8

| | |
|---|---|
| gaggtgcagc tggtgcagtc tggagcagag gtgaaaaagc ccggggagtc tctgaagatc | 60 |
| tcctgtaagg gttctggata cagctttacc aactactgga tcggctgggt gcgccagatg | 120 |
| cccgggaaag gcctggagtg gatggggatc atctatcctg gtaactctga taccagattc | 180 |
| agcccgtcct tccaaggcca ggtcaccatc tcagccgaca gtccatcac caccgcctac | 240 |
| ctgcagtgga gcagcctgaa ggcctcggac accgccatgt attactgtgc gagacatggt | 300 |
| acctcgtccg actactacgg tctggacgtc tggggccaag gcaccacggt caccgtctcc | 360 |
| tcagctagca ccaagggccc atcggtcttc cccctggcgc cctgctccag gagcacctcc | 420 |
| gagagcacag cggccctggg ctgcctggtc aaggactact ccccgaaccc ggtgacggtg | 480 |
| tcgtggaact caggcgctct gaccagcggc gtgcacacct tcccagctgt cctacagtcc | 540 |
| tcaggactct actccctcag cagcgtggtg accgtgccct ccagcaactt cggcacccag | 600 |
| acctacacct gcaacgtaga tcacaagccc agcaacacca aggtggacaa gacagttgag | 660 |
| cgcaaatgtt gtgtcgagtg cccaccgtgc ccagcaccac ctgtggcagg accgtcagtc | 720 |
| ttcctcttcc ccccaaaacc caaggacacc ctcatgatct cccggacccc tgaggtcacg | 780 |
| tgcgtggtgg tggacgtgag ccacgaagac cccgaggtcc agttcaactg gtacgtggac | 840 |
| ggcgtggagg tgcataatgc caagacaaag ccacgggagg agcagttcaa cagcacgttc | 900 |
| cgtgtggtca gcgtcctcac cgttgtgcac caggactggc tgaacggcaa ggagtacaag | 960 |
| tgcaaggtct ccaacaaagg cctcccagcc cccatcgaga aaaccatctc caaaaccaaa | 1020 |
| gggcagcccc gagaaccaca ggtgtacacc ctgcccccat cccgggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cacctcccat gctggactcc | 1200 |

```
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341
```

<210> SEQ ID NO 9
<211> LENGTH: 1344
<212> TYPE: DNA
<213> ORGANISM: Homo sapiens

<400> SEQUENCE: 9

```
gaggtgcagc tggtggagtc tgggggaggc ttggtacagc ctggggggtc cctgagactc    60
tcctgtgcag cctctggatt caccttcagt acctacgaca tgcactggat ccgccaagct   120
ccaggaaaaa atctggagtg ggtctcagct attgatcttg ctggtgacac atactatcca   180
ggctccgtga agggccgatt caccatctcc agagaagatg ccaagaactc cttgtatctt   240
caaatgaaca gcctgagagc cggggacacg gctgtgtatt actgtgcaag aggggagat    300 ggctacaatt acgactacta cggtatagac gtctggggcc aagggaccac ggtcaccgtc   360
tcctcagcta gcaccaaggg cccatcggtc ttccccctgg cgccctgctc caggagcacc   420
tccgagagca cagcggccct gggctgcctg gtcaaggact acttccccga accggtgacg   480
gtgtcgtgga actcaggcgc tctgaccagc ggcgtgcaca ccttcccagc tgtcctacag   540
tcctcaggac tctactccct cagcagcgtg gtgaccgtgc cctccagcaa cttcggcacc   600
cagacctaca cctgcaacgt agatcacaag cccagcaaca ccaaggtgga caagacagtt   660
gagcgcaaat gttgtgtcga gtgcccaccg tgcccagcac cacctgtggc aggaccgtca   720
gtcttcctct tccccccaaa acccaaggac accctcatga tctcccggac ccctgaggtc   780
acgtgcgtgg tggtggacgt gagccacgaa gaccccgagg tccagttcaa ctggtacgtg   840
gacggcgtgg aggtgcataa tgccaagaca aagccacggg aggagcagtt caacagcacg   900
ttccgtgtgg tcagcgtcct caccgttgtg caccaggact ggctgaacgg caaggagtac   960
aagtgcaagg tctccaacaa aggcctccca gcccccatcg agaaaaccat ctccaaaacc  1020
aaagggcagc cccgagaacc acaggtgtac accctgcccc catcccggga ggagatgacc  1080
aagaaccagg tcagcctgac ctgcctggtc aaaggcttct accccagcga catcgccgtg  1140
gagtgggaga gcaatgggca gccggagaac aactacaaga ccacacctcc catgctggac  1200
tccgacggct ccttcttcct ctacagcaag ctcaccgtgg acaagagcag gtggcagcag  1260
gggaacgtct tctcatgctc cgtgatgcat gaggctctgc acaaccacta cacgcagaag  1320
agcctctccc tgtctccggg taaa                                         1344
```

<210> SEQ ID NO 10
<211> LENGTH: 1329
<212> TYPE: DNA
<213> ORGANISM: Homo sapiens

<400> SEQUENCE: 10

```
caggtccagc tggtacagtc tggggctgag gtgaagaagc ctggggcctc agtgaaggtc    60
tcctgcgagg tttccggatt catcctcact gaattatccg tgaactgggt gcgacaggct   120
cctggaaaag ggcttgagtg gatgggaggt tttgatcctg aagatggtaa acaatctac    180 gcacagaagt tccagggcag agtcaccttg accgaggaca catctacaga cacagcctac   240
atggagctga gcagcctgag atctgaggac acggccgtgt attactgtgc aacatggtgg   300
gactttcact ttgacttctg gggccaggga accctggtca ccgtctcctc agctagcacc   360
```

```
aagggcccat cggtcttccc cctggcgccc tgctccagga gcacctccga gagcacagcg     420
gccctgggct gcctggtcaa ggactacttc cccgaaccgg tgacggtgtc gtggaactca     480
ggcgctctga ccagcggcgt gcacaccttc ccagctgtcc tacagtcctc aggactctac     540
tccctcagca gcgtggtgac cgtgccctcc agcaacttcg gcacccagac ctacacctgc     600
aacgtagatc acaagcccag caacaccaag gtggacaaga cagttgagcg caaatgttgt     660
gtcgagtgcc caccgtgccc agcaccacct gtggcaggac cgtcagtctt cctcttcccc     720
ccaaaaccca aggacaccct catgatctcc cggacccctg aggtcacgtg cgtggtggtg     780
gacgtgagcc acgaagaccc cgaggtccag ttcaactggt acgtgacggg cgtggaggtg     840
cataatgcca agacaaagcc acgggaggag cagttcaaca gcacgttccg tgtggtcagc     900
gtcctcaccg ttgtgcacca ggactggctg aacggcaagg agtacaagtg caaggtctcc     960
aacaaaggcc tcccagcccc catcgagaaa accatctcca aaaccaaagg gcagcccga    1020 gaaccacagg tgtacaccct gcccccatcc cgggaggaga tgaccaagaa ccaggtcagc    1080
ctgacctgcc tggtcaaagg cttctacccc agcgacatcg ccgtggagtg ggagagcaat    1140
gggcagccgg agaacaacta caagaccaca cctcccatgc tggactccga cggctccttc    1200
ttcctctaca gcaagctcac cgtggacaag agcaggtggc agcaggggaa cgtcttctca    1260
tgctccgtga tgcatgaggc tctgcacaac cactacacgc agaagagcct ctccctgtct    1320
ccgggtaaa                                                             1329
```

<210> SEQ ID NO 11
<211> LENGTH: 1341
<212> TYPE: DNA
<213> ORGANISM: Homo sapiens

<400> SEQUENCE: 11

```
gaggtgcagt tggtggagtc tgggggaggc tgggtacagc ctggggggtc cctgagactc      60
tcctgtgcag cctctggatt caccttcagt agttatgaca tgtactgggt ccgccaagct     120
acagggaaag gtctggagtg ggtctcaggt attgatactg ttggggacac atattatcca     180
gactccgtga agggccgatt caccatctcc agagaaaatg ccaagaactc cgtgtatctt     240
caaatgaaca ccctgagagc cggggacacg gctgtgtatt actgtgtaag aggcatctac     300
ggtgactttt attattacgg tttggacgtc tggggccacg ggaccacggt caccgtctcc     360
tcagctagca ccaagggccc atcggtcttc cccctggcgc cctgctccag gagcacctcc     420
gagagcacag cggccctggg ctgcctggtc aaggactact cccccgaacc ggtgacggtg     480
tcgtggaact caggcgctct gaccagcggc gtgcacacct tcccagctgt cctacagtcc     540
tcaggactct actccctcag cagcgtggtg accgtgccct ccagcaactt cggcacccag     600
acctacacct gcaacgtaga tcacaagccc agcaacacca aggtggacaa gacagttgag     660
cgcaaatgtt gtgtcgagtg cccaccgtgc ccagcaccac ctgtggcagg accgtcagtc     720
ttcctcttcc ccccaaaacc caaggacacc ctcatgatct cccggacccc tgaggtcacg     780
tgcgtggtgg tggacgtgag ccacgaagac cccgaggtcc agttcaactg gtacgtggac     840
ggcgtggagg tgcataatgc caagacaaag ccacgggagg agcagttcaa cagcacgttc     900
cgtgtggtca gcgtcctcac cgttgtgcac caggactggc tgaacggcaa ggagtacaag     960
tgcaaggtct ccaacaaagg cctcccagcc ccatcgaga aaaccatctc caaaaccaaa    1020
gggcagcccc gagaaccaca ggtgtacacc ctgcccccat cccgggagga gatgaccaag    1080
```

-continued

| | |
|---|---|
| aaccaggtca gcctgacctg cctggtcaaa ggcttctacc ccagcgacat cgccgtggag | 1140 |
| tgggagagca atgggcagcc ggagaacaac tacaagacca cacctcccat gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctccctgt ctccgggtaa a | 1341 |

<210> SEQ ID NO 12
<211> LENGTH: 1344
<212> TYPE: DNA
<213> ORGANISM: Homo sapiens

<400> SEQUENCE: 12

| | |
|---|---|
| gaggtgcagc tggtggagtc tgggggaggc ttggtacagc ctggggggtc cctgagactc | 60 |
| tcctgtgcag cctctggatt caccttcagt acctacgaca tgcactgggt ccgccaaact | 120 |
| acaggaaaag gtctgagtg gtctcagct attgatcttg ctggtgacac atactatcca | 180 |
| ggctccgtga agggccgatt caccatctcc agagaagatg ccaagaactc cttgtatctt | 240 |
| caaatgaaca gcctgagagc cggggacacg gctgtgtatt actgtgcaag agggggagat | 300 |
| ggctacaatt acgactacta cggtatagac gtctggggcc aagggaccac ggtcaccgtc | 360 |
| tcctcagcta gcaccaaggg cccatcggtc ttccccctgg cgccctgctc caggagcacc | 420 |
| tccgagagca cagcggccct gggctgcctg gtcaaggact acttccccga accggtgacg | 480 |
| gtgtcgtgga actcaggcgc tctgaccagc ggcgtgcaca ccttcccagc tgtcctacag | 540 |
| tcctcaggac tctactccct cagcagcgtg gtgaccgtgc cctccagcaa cttcggcacc | 600 |
| cagacctaca cctgcaacgt agatcacaag cccagcaaca ccaaggtgga caagacagtt | 660 |
| gagcgcaaat gttgtgtcga gtgcccaccg tgcccagcac cacctgtggc aggaccgtca | 720 |
| gtcttcctct tccccccaaa acccaaggac accctcatga tctcccggac ccctgaggtc | 780 |
| acgtgcgtgg tggtggacgt gagccacgaa gaccccgagg tccagttcaa ctggtacgtg | 840 |
| gacggcgtgg aggtgcataa tgccaagaca aagccacggg aggagcagtt caacagcacg | 900 |
| ttccgtgtgg tcagcgtcct caccgttgtg caccaggact ggctgaacgg caaggagtac | 960 |
| aagtgcaagg tctccaacaa aggcctccca gcccccatcg agaaaaccat ctccaaaacc | 1020 |
| aaagggcagc cccgagaacc acaggtgtac accctgcccc catcccggga ggagatgacc | 1080 |
| aagaaccagg tcagcctgac ctgcctggtc aaaggcttct accccagcga catcgccgtg | 1140 |
| gagtgggaga gcaatgggca gccggagaac aactacaaga ccacacctcc catgctggac | 1200 |
| tccgacggct ccttcttcct ctacagcaag ctcaccgtgg acaagagcag gtggcagcag | 1260 |
| gggaacgtct tctcatgctc cgtgatgcat gaggctctgc acaaccacta cacgcagaag | 1320 |
| agcctctccc tgtctccggg taaa | 1344 |

<210> SEQ ID NO 13
<211> LENGTH: 1344
<212> TYPE: DNA
<213> ORGANISM: Homo sapiens

<400> SEQUENCE: 13

| | |
|---|---|
| gaggtgcagc tggtggagtc tgggggaggc ttggtacagc ctggggggtc cctgagactc | 60 |
| tcctgtgcag cctctggatt caccttcagt acctacgaca tgcactgggt ccgccaaact | 120 |
| acaggaaaag gtctgagtg gtctcagct attgatcttg ctggtgacac atactatcca | 180 |
| ggctccgtga agggccgatt caccatctcc agagaagatg ccaagaactc cttgtatctt | 240 |

```
caaatgaaca gcctgagagc cggggacacg gctgtgtatt actgtgcaag agggggagat    300
ggctacaatt acgactacta cggtatagac gtctggggcc aagggaccac ggtcaccgtc    360
tcctcagcta gcaccaaggg cccatcggtc ttccccctgg cgccctgctc caggagcacc    420
tccgagagca cagcggccct gggctgcctg gtcaaggact acttccccga accggtgacg    480
gtgtcgtgga actcaggcgc tctgaccagc ggcgtgcaca ccttcccagc tgtcctacag    540
tcctcaggac tctactccct cagcagcgtg gtgaccgtgc cctccagcaa cttcggcacc    600
cagacctaca cctgcaacgt agatcacaag cccagcaaca ccaaggtgga caagacagtt    660
gagcgcaaat gttgtgtcga gtgcccaccg tgcccagcac cacctgtggc aggaccgtca    720
gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgttgtg caccaggact ggctgaacgg caaggagtac    960
aagtgcaagg tctccaacaa aggcctccca gcccccatcg agaaaaccat ctccaaaacc   1020
aaagggcagc cccgagaacc acaggtgtac accctgcccc catcccggga ggagatgacc   1080
aagaaccagg tcagcctgac ctgcctggtc aaaggcttct accccagcga catcgccgtg   1140
gagtgggaga gcaatgggca gccggagaac aactacaaga ccacacctcc catgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344

<210> SEQ ID NO 14
<211> LENGTH: 1341
<212> TYPE: DNA
<213> ORGANISM: Homo sapiens

<400> SEQUENCE: 14
gaggtgcagc tggtggagtc tgggggaggc ttggtacagc ctggggggtc cctgagactc     60
tcctgtgcag cctctggatt caccttcagt agctacgaca tgtactgggt ccgccaagct    120
acaggaaaag gtctggagtg ggtctcagct attgatactg ttggtgacac atactatcca    180
ggctccgtga agggccgatt caccatctcc agagaaaatg ccaagaactc cttgtatctt    240
caaatgaaca gcctgagagt cggggacacg gctgtgtatt actgtgcaag aggcggtgac    300
tacgactact cttattacgg tatggacgtc tggggccaag ggaccacggt caccgtctcc    360
tcagctagca ccaagggccc atcggtcttc cccctggcgc cctgctccag gagcacctcc    420
gagagcacag cggccctggg ctgcctggtc aaggactact ccccgaaccc ggtgacggtg    480
tcgtggaact caggcgctct gaccagcggc gtgcacacct tcccagctgt cctacagtcc    540
tcaggactct actccctcag cagcgtggtg accgtgcccc cagcaacttc ggcacccag    600 acctacacct gcaacgtaga tcacaagccc agcaacacca aggtggacaa gacagttgag    660
cgcaaatgtt gtgtcgagtg cccaccgtgc ccagcaccac ctgtggcagg accgtcagtc    720
ttcctcttcc ccccaaaacc caaggacacc ctcatgatct cccggacccc tgaggtcacg    780
tgcgtggtgg tggacgtgag ccacgaagac cccgaggtcc agttcaactg gtacgtggac    840
ggcgtggagg tgcataatgc caagacaaag ccacggagg agcagttcaa cagcacgttc    900
cgtgtggtca gcgtcctcac cgttgtgcac caggactggc tgaacggcaa ggagtacaag    960
```

```
tgcaaggtct ccaacaaagg cctcccagcc cccatcgaga aaaccatctc caaaaccaaa    1020
gggcagcccc gagaaccaca ggtgtacacc ctgcccccat cccgggagga gatgaccaag    1080
aaccaggtca gcctgacctg cctggtcaaa ggcttctacc ccagcgacat cgccgtggag    1140
tgggagagca atgggcagcc ggagaacaac tacaagacca cacctcccat gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341

<210> SEQ ID NO 15
<211> LENGTH: 1326
<212> TYPE: DNA
<213> ORGANISM: Homo sapiens

<400> SEQUENCE: 15
caggtgcagc tggtggagtc tgggggaggc gtggtccagc ctgggaggtc cctgagactc      60
tcctgtgcag cgtctggatt caccttcagt agctatggca tgcactgggt ccgccaggct     120
ccaggcaagg ggctggagtg ggtggcagtt atatggtatg gtggaagtca taaatactat     180
gcagactccg tgaagggccg attcaccatc tccagagaca attccaagaa cacgctgtat     240
ctgcaattga acagcctgag agccgaagac acggctgtct attactgtgc gagagacaag     300
ggcgagtttg actactgggg ccagggaacc ctggtcaccg tctcctcagc tagcaccaag     360
ggcccatcgg tcttccccct ggcgccctgc tccaggagca cctccgagag cacagcggcc     420
ctgggctgcc tggtcaagga ctacttcccc gaaccggtga cggtgtcgtg gaactcaggc     480
gctctgacca gcggcgtgca caccttccca gctgtcctac agtcctcagg actctactcc     540
ctcagcagcg tggtgaccgt gccctccagc aacttcggca cccagaccta cacctgcaac     600
gtagatcaca agcccagcaa caccaaggtg gacaagacag ttgagcgcaa atgttgtgtc     660
gagtgcccac cgtgcccagc accacctgtg gcaggaccgt cagtcttcct cttcccccca     720
aaacccaagg acaccctcat gatctcccgg acccctgagg tcacgtgcgt ggtggtggac     780
gtgagccacg aagaccccga ggtccagttc aactggtacg tggacggcgt ggaggtgcat     840
aatgccaaga caaagccacg ggaggagcag ttcaacagca cgttccgtgt ggtcagcgtc     900
ctcaccgttg tgcaccagga ctggctgaac ggcaaggagt acaagtgcaa ggtctccaac     960
aaaggcctcc cagcccccat cgagaaaacc atctccaaaa ccaaagggca gccccgagaa    1020
ccacaggtgt acaccctgcc cccatcccgg gaggagatga ccaagaacca ggtcagcctg    1080
acctgcctgg tcaaaggctt ctaccccagc gacatcgccg tggagtggga gagcaatggg    1140
cagccggaga acaactacaa gaccacacct cccatgctgg actccgacgg ctccttcttc    1200
ctctacagca agctcaccgt ggacaagagc aggtggcagc aggggaacgt cttctcatgc    1260
tccgtgatgc atgaggctct gcacaaccac tacacgcaga gagcctctc cctgtctccg    1320 ggtaaa                                                              1326

<210> SEQ ID NO 16
<211> LENGTH: 1326
<212> TYPE: DNA
<213> ORGANISM: Homo sapiens

<400> SEQUENCE: 16
caggtgcagc tggtggagtc tgggggaggc gtggtccagc ctgggaggtc cctgagactc      60
tcctgtgcag cgtctggatt caccttcagt agctatggca tgcactgggt ccgccaggct     120
```

| | |
|---|---:|
| ccaggcaagg ggctggagtg ggtggcagtt atatggtata ctggaagtaa taaatactat | 180 |
| gcagactccg tgaagggccg attcaccatc tccagagaca attccaagaa cacgttgcat | 240 |
| ctgcaaatga acagcctgag agccgaggac acggctgtgt attactgtgc gagagataaa | 300 |
| gggtactttg actactgggg ccagggaacc ctggtcaccg tctcctcagc tagcaccaag | 360 |
| ggcccatcgg tcttccccct ggcgccctgc tccaggagca cctccgagag cacagcggcc | 420 |
| ctgggctgcc tggtcaagga ctacttcccc gaaccggtga cggtgtcgtg gaactcaggc | 480 |
| gctctgacca gcggcgtgca caccttccca gctgtcctac agtcctcagg actctactcc | 540 |
| ctcagcagcg tggtgaccgt gccctccagc aacttcggca cccagaccta cacctgcaac | 600 |
| gtagatcaca agcccagcaa caccaaggtg gacaagacag ttgagcgcaa atgttgtgtc | 660 |
| gagtgcccac cgtgcccagc accacctgtg gcaggaccgt cagtcttcct cttccccca | 720 |
| aaacccaagg acaccctcat gatctcccgg acccctgagg tcacgtgcgt ggtggtggac | 780 |
| gtgagccacg aagaccccga ggtccagttc aactggtacg tggacggcgt ggaggtgcat | 840 |
| aatgccaaga caaagccacg ggaggagcag ttcaacagca cgttccgtgt ggtcagcgtc | 900 |
| ctcaccgttg tgcaccagga ctggctgaac ggcaaggagt acaagtgcaa ggtctccaac | 960 |
| aaaggcctcc cagcccccat cgagaaaacc atctccaaaa ccaaagggca gccccgagaa | 1020 |
| ccacaggtgt acaccctgcc cccatcccgg gaggagatga ccaagaacca ggtcagcctg | 1080 |
| acctgcctgg tcaaaggctt ctaccccagc gacatcgccg tggagtggga gagcaatggg | 1140 |
| cagccggaga acaactacaa gaccacacct cccatgctgg actccgacgg ctccttcttc | 1200 |
| ctctacagca agctcaccgt ggacaagagc aggtggcagc aggggaacgt cttctcatgc | 1260 |
| tccgtgatgc atgaggctct gcacaaccac tacacgcaga agagcctctc cctgtctccg | 1320 |
| ggtaaa | 1326 |

<210> SEQ ID NO 17
<211> LENGTH: 1326
<212> TYPE: DNA
<213> ORGANISM: Homo sapiens

<400> SEQUENCE: 17

| | |
|---|---:|
| caggtgcagc tggtggagtc tgggggaggc gtggtccagc ctgggaggtc cctgagactc | 60 |
| tcctgtgcag cgtctggatt caccttcagt agctatggca tgcactgggt ccgccaggct | 120 |
| ccaggcaagg ggctggagtg ggtggcagtt atatggtatg gtggaagtca taaatactat | 180 |
| gcagactccg tgaagggccg attcaccatc tccagagaca attccaagaa cacgctgtat | 240 |
| ctgcaattga acagcctgag agccgaagac acggctgtct attactgtgc gagagacaag | 300 |
| ggcgagtttg actactgggg ccagggaacc ctggtcaccg tctcctcagc tagcaccaag | 360 |
| ggcccatcgg tcttccccct ggcgccctgc tccaggagca cctccgagag cacagcggcc | 420 |
| ctgggctgcc tggtcaagga ctacttcccc gaaccggtga cggtgtcgtg gaactcaggc | 480 |
| gctctgacca gcggcgtgca caccttccca gctgtcctac agtcctcagg actctactcc | 540 |
| ctcagcagcg tggtgaccgt gccctccagc aacttcggca cccagaccta cacctgcaac | 600 |
| gtagatcaca agcccagcaa caccaaggtg gacaagacag ttgagcgcaa atgttgtgtc | 660 |
| gagtgcccac cgtgcccagc accacctgtg gcaggaccgt cagtcttcct cttccccca | 720 |
| aaacccaagg acaccctcat gatctcccgg acccctgagg tcacgtgcgt ggtggtggac | 780 |
| gtgagccacg aagaccccga ggtccagttc aactggtacg tggacggcgt ggaggtgcat | 840 |

```
aatgccaaga caaagccacg ggaggagcag ttcaacagca cgttccgtgt ggtcagcgtc    900
ctcaccgttg tgcaccagga ctggctgaac ggcaaggagt acaagtgcaa ggtctccaac    960
aaaggcctcc cagcccccat cgagaaaacc atctccaaaa ccaaagggca gccccgagaa   1020
ccacaggtgt acaccctgcc cccatcccgg gaggagatga ccaagaacca ggtcagcctg   1080
acctgcctgg tcaaaggctt ctaccccagc gacatcgccg tggagtggga gagcaatggg   1140
cagccggaga caactacaa gaccacacct cccatgctgg actccgacgg ctccttcttc   1200
ctctacagca agctcaccgt ggacaagagc aggtggcagc aggggaacgt cttctcatgc   1260
tccgtgatgc atgaggctct gcacaaccac tacacgcaga gagcctctc cctgtctccg   1320 ggtaaa                                                              1326
```

<210> SEQ ID NO 18
<211> LENGTH: 444
<212> TYPE: PRT
<213> ORGANISM: Homo sapiens

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Gly Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Glu Asp Ser Ser Gly Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285
```

```
Arg Glu Glu Gln Phe Asn Ser Thr Phe Arg Val Val Ser Val Leu Thr
            290                 295                 300
Val Val His Gln Asp Trp Leu Asn Gly Lys Glu Tyr Lys Cys Lys Val
305                 310                 315                 320
Ser Asn Lys Gly Leu Pro Ala Pro Ile Glu Lys Thr Ile Ser Lys Thr
                325                 330                 335
Lys Gly Gln Pro Arg Glu Pro Gln Val Tyr Thr Leu Pro Pro Ser Arg
            340                 345                 350
Glu Glu Met Thr Lys Asn Gln Val Ser Leu Thr Cys Leu Val Lys Gly
            355                 360                 365
Phe Tyr Pro Ser Asp Ile Ala Val Glu Trp Ser Asn Gly Gln Pro
370                 375                 380
Glu Asn Asn Tyr Lys Thr Thr Pro Pro Met Leu Asp Ser Asp Gly Ser
385                 390                 395                 400
Phe Phe Leu Tyr Ser Lys Leu Thr Val Asp Lys Ser Arg Trp Gln Gln
                405                 410                 415
Gly Asn Val Phe Ser Cys Ser Val Met His Glu Ala Leu His Asn His
                420                 425                 430
Tyr Thr Gln Lys Ser Leu Ser Leu Ser Pro Gly Lys
            435                 440

<210> SEQ ID NO 19
<211> LENGTH: 447
<212> TYPE: PRT
<213> ORGANISM: Homo sapiens

<400> SEQUENCE: 19

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Asn Tyr
                20                  25                  30
Trp Ile Gly Trp Val Arg Gln Met Pro Gly Lys Gly Leu Glu Trp Met
            35                  40                  45
Gly Ile Ile Tyr Pro Gly Asn Ser Asp Thr Arg Phe Ser Pro Ser Phe
50                  55                  60
Gln Gly Gln Val Thr Ile Ser Ala Asp Lys Ser Ile Thr Thr Ala Tyr
65                  70                  75                  80
Leu Gln Trp Ser Ser Leu Lys Ala Ser Asp Thr Ala Met Tyr Tyr Cys
                85                  90                  95
Ala Arg His Gly Thr Ser Ser Asp Tyr Tyr Gly Leu Asp Val Trp Gly
            100                 105                 110
Gln Gly Thr Thr Val Thr Val Ser Ser Ala Ser Thr Lys Gly Pro Ser
            115                 120                 125
Val Phe Pro Leu Ala Pro Cys Ser Arg Ser Thr Ser Glu Ser Thr Ala
130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Asn Phe Gly Thr Gln Thr Tyr Thr Cys Asn Val Asp His
            195                 200                 205
Lys Pro Ser Asn Thr Lys Val Asp Lys Thr Val Glu Arg Lys Cys Cys
```

```
                210                 215                 220
Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 20
<211> LENGTH: 448
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Ile Arg Gln Ala Pro Gly Lys Asn Leu Glu Trp Val
        35                  40                  45

Ser Ala Ile Asp Leu Ala Gly Asp Thr Tyr Tyr Pro Gly Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asp Gly Tyr Asn Tyr Asp Tyr Tyr Gly Ile Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140
```

```
Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
        290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 21
<211> LENGTH: 443
<212> TYPE: PRT
<213> ORGANISM: Homo sapiens

<400> SEQUENCE: 21

Gln Val Gln Leu Val Gln Ser Gly Ala Glu Val Lys Lys Pro Gly Ala
1               5                   10                  15

Ser Val Lys Val Ser Cys Glu Val Ser Gly Phe Ile Leu Thr Glu Leu
                20                  25                  30

Ser Val Asn Trp Val Arg Gln Ala Pro Gly Lys Gly Leu Glu Trp Met
            35                  40                  45

Gly Gly Phe Asp Pro Glu Asp Gly Lys Thr Ile Tyr Ala Gln Lys Phe
        50                  55                  60

Gln Gly Arg Val Thr Leu Thr Glu Asp Thr Ser Thr Asp Thr Ala Tyr
65                  70                  75                  80
```

Met Glu Leu Ser Ser Leu Arg Ser Glu Asp Thr Ala Val Tyr Tyr Cys
            85                  90                  95

Ala Thr Trp Trp Asp Phe His Phe Asp Phe Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
            195                 200                 205

Thr Lys Val Asp Lys Thr Val Glu Arg Lys Cys Cys Val Glu Cys Pro
            210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
            290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
            325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 22
<211> LENGTH: 447
<212> TYPE: PRT
<213> ORGANISM: Homo sapiens

<400> SEQUENCE: 22

Glu Val Gln Leu Val Glu Ser Gly Gly Gly Trp Val Gln Pro Gly Gly

-continued

```
1               5                   10                  15
Ser Leu Arg Leu Ser Cys Ala Ala Ser Gly Phe Thr Phe Ser Ser Tyr
            20                  25                  30

Asp Met Tyr Trp Val Arg Gln Ala Thr Gly Lys Gly Leu Glu Trp Val
            35                  40                  45

Ser Gly Ile Asp Thr Val Gly Asp Thr Tyr Tyr Pro Asp Ser Val Lys
            50                  55                  60

Gly Arg Phe Thr Ile Ser Arg Glu Asn Ala Lys Asn Ser Val Tyr Leu
65                  70                  75                  80

Gln Met Asn Thr Leu Arg Ala Gly Asp Thr Ala Val Tyr Tyr Cys Val
            85                  90                  95

Arg Gly Ile Tyr Gly Asp Phe Tyr Tyr Tyr Gly Leu Asp Val Trp Gly
            100                 105                 110

His Gly Thr Thr Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
            210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
            290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly Lys
            435                 440                 445

<210> SEQ ID NO 23
<211> LENGTH: 448
<212> TYPE: PRT
<213> ORGANISM: Homo sapiens

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Val Arg Gln Thr Thr Gly Lys Gly Leu Glu Trp Val
        35                  40                  45

Ser Ala Ile Asp Leu Ala Gly Asp Thr Tyr Tyr Pro Gly Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asp Gly Tyr Asn Tyr Asp Tyr Tyr Gly Ile Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys

```
                355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Met Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
        420                 425                 430
Leu His Asn His Tyr Thr Gln Lys Ser Leu Ser Leu Ser Pro Gly Lys
                435                 440                 445

<210> SEQ ID NO 24
<211> LENGTH: 448
<212> TYPE: PRT
<213> ORGANISM: Homo sapiens

<400> SEQUENCE: 24

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Asp Met His Trp Val Arg Gln Thr Thr Gly Lys Gly Leu Glu Trp Val
        35                  40                  45
Ser Ala Ile Asp Leu Ala Gly Asp Thr Tyr Tyr Pro Gly Ser Val Lys
    50                  55                  60
Gly Arg Phe Thr Ile Ser Arg Glu Asp Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg Gly Gly Asp Gly Tyr Asn Tyr Asp Tyr Tyr Gly Ile Asp Val Trp
            100                 105                 110
Gly Gln Gly Thr Thr Val Thr Val Ser Ser Ala Ser Thr Lys Gly Pro
        115                 120                 125
Ser Val Phe Pro Leu Ala Pro Cys Ser Arg Ser Thr Ser Glu Ser Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Asn Phe Gly Thr Gln Thr Tyr Thr Cys Asn Val Asp
        195                 200                 205
His Lys Pro Ser Asn Thr Lys Val Asp Lys Thr Val Glu Arg Lys Cys
    210                 215                 220
Cys Val Glu Cys Pro Pro Cys Pro Ala Pro Pro Val Ala Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Gln Phe Asn Trp Tyr Val Asp Gly Val Glu Val His Asn Ala
        275                 280                 285
```

```
Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 25
<211> LENGTH: 447
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Tyr Trp Val Arg Gln Ala Thr Gly Lys Gly Leu Glu Trp Val
        35                  40                  45

Ser Ala Ile Asp Thr Val Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Asp Tyr Asp Tyr Ser Tyr Tyr Gly Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220
```

```
Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 26
<211> LENGTH: 442
<212> TYPE: PRT
<213> ORGANISM: Homo sapiens

<400> SEQUENCE: 26

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Gly Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
            85                  90                  95

Ala Arg Asp Lys Gly Glu Phe Asp Tyr Trp Gly Gln Gly Thr Leu Val
        100                 105                 110

Thr Val Ser Ser Ala Ser Thr Lys Gly Pro Ser Val Phe Pro Leu Ala
    115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
```

145                 150                 155                 160
Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Asn Phe
                180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Val Glu Cys Pro Pro
        210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
                260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
        290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
                340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
        370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
                420                 425                 430

Gln Lys Ser Leu Ser Leu Ser Pro Gly Lys
            435                 440

<210> SEQ ID NO 27
<211> LENGTH: 442
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Thr Gly Ser Asn Lys Tyr Tyr Ala Asp Ser Val
        50                  55                  60

Lys Gly Arg Phe Thr Ile Ser Arg Asp Asn Ser Lys Asn Thr Leu His
65                  70                  75                  80

```
Leu Gln Met Asn Ser Leu Arg Ala Glu Asp Thr Ala Val Tyr Tyr Cys
                 85                  90                  95

Ala Arg Asp Lys Gly Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 28
<211> LENGTH: 442
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Trp Tyr Gly Gly Ser His Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Leu Asn Ser Leu Arg Ala Glu Asp Thr Ala Val Tyr Tyr Cys
                85                  90                  95

Ala Arg Asp Lys Gly Glu Phe Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
            195                 200                 205

Lys Val Asp Lys Thr Val Glu Arg Lys Cys Cys Val Glu Cys Pro Pro
210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
            275                 280                 285

Glu Gln Phe Asn Ser Thr Phe Arg Val Val Ser Val Leu Thr Val Val
290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
            370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

```
Gln Lys Ser Leu Ser Leu Ser Pro Gly Lys
        435                 440
```

```
<210> SEQ ID NO 29
<211> LENGTH: 118
<212> TYPE: PRT
<213> ORGANISM: Homo sapiens

<400> SEQUENCE: 29
```

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Gly Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Thr Thr Glu Asp Ser Ser Gly Leu Phe Asp Tyr Trp Gly Gln Gly Thr
            100                 105                 110

Leu Val Thr Val Ser Ser
        115
```

```
<210> SEQ ID NO 30
<211> LENGTH: 121
<212> TYPE: PRT
<213> ORGANISM: Homo sapiens

<400> SEQUENCE: 30
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asn Ser Asp Thr Arg Phe Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Thr Ser Ser Asp Tyr Tyr Gly Leu Asp Val Trp Gly
            100                 105                 110

Gln Gly Thr Thr Val Thr Val Ser Ser
        115                 120
```

```
<210> SEQ ID NO 31
<211> LENGTH: 122
<212> TYPE: PRT
<213> ORGANISM: Homo sapiens

<400> SEQUENCE: 31
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
```

20                  25                  30
Asp Met His Trp Ile Arg Gln Ala Pro Gly Lys Asn Leu Glu Trp Val
                35                  40                  45

Ser Ala Ile Asp Leu Ala Gly Asp Thr Tyr Tyr Pro Gly Ser Val Lys
        50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asp Gly Tyr Asn Tyr Asp Tyr Tyr Gly Ile Asp Val Trp
            100                 105                 110

Gly Gln Gly Thr Thr Val Thr Val Ser Ser
            115                 120

<210> SEQ ID NO 32
<211> LENGTH: 117
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Lys Val Ser Cys Glu Val Ser Gly Phe Ile Leu Thr Glu Leu
            20                  25                  30

Ser Val Asn Trp Val Arg Gln Ala Pro Gly Lys Gly Leu Glu Trp Met
        35                  40                  45

Gly Gly Phe Asp Pro Glu Asp Gly Lys Thr Ile Tyr Ala Gln Lys Phe
    50                  55                  60

Gln Gly Arg Val Thr Leu Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Trp Trp Asp Phe His Phe Asp Phe Trp Gly Gln Gly Thr Leu
            100                 105                 110

Val Thr Val Ser Ser
        115

<210> SEQ ID NO 33
<211> LENGTH: 120
<212> TYPE: PRT
<213> ORGANISM: Homo sapiens

<400> SEQUENCE: 33

Glu Val Gln Leu Val Glu Ser Gly Gly Gly Trp Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Tyr Trp Val Arg Gln Ala Thr Gly Lys Gly Leu Glu Trp Val
        35                  40                  45

Ser Gly Ile Asp Thr Val Gly Asp Thr Tyr Tyr Pro Asp Ser Val Lys
    50                  55                  60

Gly Arg Phe Thr Ile Ser Arg Glu Asn Ala Lys Asn Ser Val Tyr Leu
65                  70                  75                  80

Gln Met Asn Thr Leu Arg Ala Gly Asp Thr Ala Val Tyr Tyr Cys Val
                85                  90                  95

Arg Gly Ile Tyr Gly Asp Phe Tyr Tyr Tyr Gly Leu Asp Val Trp Gly

His Gly Thr Thr Val Thr Val Ser
        115                 120

<210> SEQ ID NO 34
<211> LENGTH: 122
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Val Arg Gln Thr Thr Gly Lys Gly Leu Glu Trp Val
        35                  40                  45

Ser Ala Ile Asp Leu Ala Gly Asp Thr Tyr Tyr Pro Gly Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asp Gly Tyr Asn Tyr Asp Tyr Tyr Gly Ile Asp Val Trp
            100                 105                 110

Gly Gln Gly Thr Thr Val Thr Val Ser Ser
        115                 120

<210> SEQ ID NO 35
<211> LENGTH: 122
<212> TYPE: PRT
<213> ORGANISM: Homo sapiens

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Val Arg Gln Thr Thr Gly Lys Gly Leu Glu Trp Val
        35                  40                  45

Ser Ala Ile Asp Leu Ala Gly Asp Thr Tyr Tyr Pro Gly Ser Val Lys
    50                  55                  60

Gly Arg Phe Thr Ile Ser Arg Glu Asp Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Gly Asp Gly Tyr Asn Tyr Asp Tyr Tyr Gly Ile Asp Val Trp
            100                 105                 110

Gly Gln Gly Thr Thr Val Thr Val Ser Ser
        115                 120

<210> SEQ ID NO 36
<211> LENGTH: 121
<212> TYPE: PRT
<213> ORGANISM: Homo sapiens

<400> SEQUENCE: 36

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Asp Met Tyr Trp Val Arg Gln Ala Thr Gly Lys Gly Leu Glu Trp Val
        35                  40                  45

Ser Ala Ile Asp Thr Val Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Asp Tyr Asp Tyr Ser Tyr Tyr Gly Met Asp Val Trp Gly
                100                 105                 110

Gln Gly Thr Thr Val Thr Val Ser Ser
            115                 120
```

<210> SEQ ID NO 37
<211> LENGTH: 116
<212> TYPE: PRT
<213> ORGANISM: Homo sapiens

<400> SEQUENCE: 37

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Gly Gly Ser His Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Asp Lys Gly Glu Phe Asp Tyr Trp Gly Gln Gly Thr Leu Val
                100                 105                 110

Thr Val Ser Ser
        115
```

<210> SEQ ID NO 38
<211> LENGTH: 116
<212> TYPE: PRT
<213> ORGANISM: Homo sapiens

<400> SEQUENCE: 38

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Thr Gly Ser Asn Lys Tyr Tyr Ala Asp Ser Val
 50                  55                  60

Lys Gly Arg Phe Thr Ile Ser Arg Asp Asn Ser Lys Asn Thr Leu His
65                  70                  75                  80

Leu Gln Met Asn Ser Leu Arg Ala Glu Asp Thr Ala Val Tyr Tyr Cys
                85                  90                  95
```

Ala Arg Asp Lys Gly Tyr Phe Asp Tyr Trp Gly Gln Gly Thr Leu Val
            100                 105                 110

Thr Val Ser Ser
        115

<210> SEQ ID NO 39
<211> LENGTH: 116
<212> TYPE: PRT
<213> ORGANISM: Homo sapiens

<400> SEQUENCE: 39

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Gly Gly Ser His Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Leu Asn Ser Leu Arg Ala Glu Asp Thr Ala Val Tyr Tyr Cys
                85                  90                  95

Ala Arg Asp Lys Gly Glu Phe Asp Tyr Trp Gly Gln Gly Thr Leu Val
            100                 105                 110

Thr Val Ser Ser
        115

<210> SEQ ID NO 40
<211> LENGTH: 5
<212> TYPE: PRT
<213> ORGANISM: Homo sapiens

<400> SEQUENCE: 40

Glu Leu Ser Ile His
1               5

<210> SEQ ID NO 41
<211> LENGTH: 5
<212> TYPE: PRT
<213> ORGANISM: Homo sapiens

<400> SEQUENCE: 41

Asn Tyr Trp Ile Gly
1               5

<210> SEQ ID NO 42
<211> LENGTH: 5
<212> TYPE: PRT
<213> ORGANISM: Homo sapiens

<400> SEQUENCE: 42

Thr Tyr Asp Met His
1               5

<210> SEQ ID NO 43
<211> LENGTH: 5
<212> TYPE: PRT
<213> ORGANISM: Homo sapiens

<400> SEQUENCE: 43

Glu Leu Ser Val Asn
1               5

<210> SEQ ID NO 44
<211> LENGTH: 5
<212> TYPE: PRT
<213> ORGANISM: Homo sapiens

<400> SEQUENCE: 44

Ser Tyr Asp Met Tyr
1               5

<210> SEQ ID NO 45
<211> LENGTH: 5
<212> TYPE: PRT
<213> ORGANISM: Homo sapiens

<400> SEQUENCE: 45

Thr Tyr Asp Met His
1               5

<210> SEQ ID NO 46
<211> LENGTH: 5
<212> TYPE: PRT
<213> ORGANISM: Homo sapiens

<400> SEQUENCE: 46

Thr Tyr Asp Met His
1               5

<210> SEQ ID NO 47
<211> LENGTH: 5
<212> TYPE: PRT
<213> ORGANISM: Homo sapiens

<400> SEQUENCE: 47

Ser Tyr Asp Met Tyr
1               5

<210> SEQ ID NO 48
<211> LENGTH: 5
<212> TYPE: PRT
<213> ORGANISM: Homo sapiens

<400> SEQUENCE: 48

Ser Tyr Gly Met His
1               5

<210> SEQ ID NO 49
<211> LENGTH: 5
<212> TYPE: PRT
<213> ORGANISM: Homo sapiens

<400> SEQUENCE: 49

Ser Tyr Gly Met His
1               5

<210> SEQ ID NO 50
<211> LENGTH: 5
<212> TYPE: PRT
<213> ORGANISM: Homo sapiens

<400> SEQUENCE: 50

Ser Tyr Gly Met His

-continued

<210> SEQ ID NO 51
<211> LENGTH: 17
<212> TYPE: PRT
<213> ORGANISM: Homo sapiens

<400> SEQUENCE: 51

Gly Phe Gly Pro Glu Asp Gly Glu Thr Ile Tyr Ala Gln Lys Phe Gln
1               5                   10                  15

Gly

<210> SEQ ID NO 52
<211> LENGTH: 17
<212> TYPE: PRT
<213> ORGANISM: Homo sapiens

<400> SEQUENCE: 52

Ile Ile Tyr Pro Gly Asn Ser Asp Thr Arg Phe Ser Pro Ser Phe Gln
1               5                   10                  15

Gly

<210> SEQ ID NO 53
<211> LENGTH: 16
<212> TYPE: PRT
<213> ORGANISM: Homo sapiens

<400> SEQUENCE: 53

Ala Ile Asp Leu Ala Gly Asp Thr Tyr Tyr Pro Gly Ser Val Lys Gly
1               5                   10                  15

<210> SEQ ID NO 54
<211> LENGTH: 17
<212> TYPE: PRT
<213> ORGANISM: Homo sapiens

<400> SEQUENCE: 54

Gly Phe Asp Pro Glu Asp Gly Lys Thr Ile Tyr Ala Gln Lys Phe Gln
1               5                   10                  15

Gly

<210> SEQ ID NO 55
<211> LENGTH: 16
<212> TYPE: PRT
<213> ORGANISM: Homo sapiens

<400> SEQUENCE: 55

Gly Ile Asp Thr Val Gly Asp Thr Tyr Tyr Pro Asp Ser Val Lys Gly
1               5                   10                  15

<210> SEQ ID NO 56
<211> LENGTH: 16
<212> TYPE: PRT
<213> ORGANISM: Homo sapiens

<400> SEQUENCE: 56

Ala Ile Asp Leu Ala Gly Asp Thr Tyr Tyr Pro Gly Ser Val Lys Gly
1               5                   10                  15

<210> SEQ ID NO 57
<211> LENGTH: 16
<212> TYPE: PRT
<213> ORGANISM: Homo sapiens

```
<400> SEQUENCE: 57

Ala Ile Asp Leu Ala Gly Asp Thr Tyr Tyr Pro Gly Ser Val Lys Gly
1               5                   10                  15

<210> SEQ ID NO 58
<211> LENGTH: 16
<212> TYPE: PRT
<213> ORGANISM: Homo sapiens

<400> SEQUENCE: 58

Ala Ile Asp Thr Val Gly Asp Thr Tyr Tyr Pro Gly Ser Val Lys Gly
1               5                   10                  15

<210> SEQ ID NO 59
<211> LENGTH: 17
<212> TYPE: PRT
<213> ORGANISM: Homo sapiens

<400> SEQUENCE: 59

Val Ile Trp Tyr Gly Gly Ser His Lys Tyr Tyr Ala Asp Ser Val Lys
1               5                   10                  15

Gly

<210> SEQ ID NO 60
<211> LENGTH: 17
<212> TYPE: PRT
<213> ORGANISM: Homo sapiens

<400> SEQUENCE: 60

Val Ile Trp Tyr Thr Gly Ser Asn Lys Tyr Tyr Ala Asp Ser Val Lys
1               5                   10                  15

Gly

<210> SEQ ID NO 61
<211> LENGTH: 17
<212> TYPE: PRT
<213> ORGANISM: Homo sapiens

<400> SEQUENCE: 61

Val Ile Trp Tyr Gly Gly Ser His Lys Tyr Tyr Ala Asp Ser Val Lys
1               5                   10                  15

Gly

<210> SEQ ID NO 62
<211> LENGTH: 9
<212> TYPE: PRT
<213> ORGANISM: Homo sapiens

<400> SEQUENCE: 62

Glu Asp Ser Ser Gly Leu Phe Asp Tyr
1               5

<210> SEQ ID NO 63
<211> LENGTH: 12
<212> TYPE: PRT
<213> ORGANISM: Homo sapiens

<400> SEQUENCE: 63

His Gly Thr Ser Ser Asp Tyr Tyr Gly Leu Asp Val
1               5                   10
```

```
<210> SEQ ID NO 64
<211> LENGTH: 14
<212> TYPE: PRT
<213> ORGANISM: Homo sapiens

<400> SEQUENCE: 64

Gly Gly Asp Gly Tyr Asn Tyr Asp Tyr Tyr Gly Ile Asp Val
1               5                   10

<210> SEQ ID NO 65
<211> LENGTH: 8
<212> TYPE: PRT
<213> ORGANISM: Homo sapiens

<400> SEQUENCE: 65

Trp Trp Asp Phe His Phe Asp Phe
1               5

<210> SEQ ID NO 66
<211> LENGTH: 13
<212> TYPE: PRT
<213> ORGANISM: Homo sapiens

<400> SEQUENCE: 66

Gly Ile Tyr Gly Asp Phe Tyr Tyr Tyr Gly Leu Asp Val
1               5                   10

<210> SEQ ID NO 67
<211> LENGTH: 14
<212> TYPE: PRT
<213> ORGANISM: Homo sapiens

<400> SEQUENCE: 67

Gly Gly Asp Gly Tyr Asn Tyr Asp Tyr Tyr Gly Ile Asp Val
1               5                   10

<210> SEQ ID NO 68
<211> LENGTH: 14
<212> TYPE: PRT
<213> ORGANISM: Homo sapiens

<400> SEQUENCE: 68

Gly Gly Asp Gly Tyr Asn Tyr Asp Tyr Tyr Gly Ile Asp Val
1               5                   10

<210> SEQ ID NO 69
<211> LENGTH: 13
<212> TYPE: PRT
<213> ORGANISM: Homo sapiens

<400> SEQUENCE: 69

Gly Gly Asp Tyr Asp Tyr Ser Tyr Tyr Gly Met Asp Val
1               5                   10

<210> SEQ ID NO 70
<211> LENGTH: 7
<212> TYPE: PRT
<213> ORGANISM: Homo sapiens

<400> SEQUENCE: 70

Asp Lys Gly Glu Phe Asp Tyr
1               5

<210> SEQ ID NO 71
<211> LENGTH: 7
```

```
<212> TYPE: PRT
<213> ORGANISM: Homo sapiens

<400> SEQUENCE: 71

Asp Lys Gly Tyr Phe Asp Tyr
1               5

<210> SEQ ID NO 72
<211> LENGTH: 7
<212> TYPE: PRT
<213> ORGANISM: Homo sapiens

<400> SEQUENCE: 72

Asp Lys Gly Glu Phe Asp Tyr
1               5

<210> SEQ ID NO 73
<211> LENGTH: 660
<212> TYPE: DNA
<213> ORGANISM: Homo sapiens

<400> SEQUENCE: 73
gacctcgtga tgacccagtc tccagactcc ctggctgtgt ctccgggcga gagggccact    60
atcaactgca agtccagcca gagtctttta tacagctcca acaataagga ctacttagct   120
tggtaccagc agaagccggg acagcctcct aaactgctca tttactgggc atctacccgg   180
gaatccgggg tccctgaccg attcagtggc agcgggtctg ggacagattt cactctcacc   240
atcagcagcc tgcaggctga agatgtggca gtttattact gtcaccaata ttataatact   300
ccgtggacgt tcggccaagg gaccaaggtg gaaatcaaac gtacggtggc tgcaccatct   360
gtcttcatct cccgccatc tgatgagcag ttgaaatctg gaactgcctc tgttgtgtgc   420
ctgctgaata acttctatcc cagagaggcc aaagtacagt ggaaggtgga taacgccctc   480
caatcgggta actcccagga gagtgtcaca gagcaggaca gcaaggacag cacctacagc   540
ctcagcagca ccctgacgct gagcaaagca gactacgaga aacacaaagt ctacgcctgc   600
gaagtcaccc atcagggcct gagctcgccc gtcacaaaga gcttcaacag gggagagtgt   660

<210> SEQ ID NO 74
<211> LENGTH: 642
<212> TYPE: DNA
<213> ORGANISM: Homo sapiens

<400> SEQUENCE: 74
gacatccaga tgacccagtc tccatcctcc ctgtctgcat ctgtaggaga cagagtcacc    60
atcacttgcc aggcgagtca ggacattagt aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag gatgataatt cccctctcac tttcggcgga   300
gggaccaagg tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaacacaaa gtctacgcct gcgaagtcac ccatcagggc   600
ctgagctcgc ccgtcacaaa gagcttcaac aggggagagt gt                     642
```

<210> SEQ ID NO 75
<211> LENGTH: 654
<212> TYPE: DNA
<213> ORGANISM: Homo sapiens

<400> SEQUENCE: 75

```
gatattgtaa tgactcagtc tccactctcc ctgcccgtca cccctggaga gccggcctcc      60
atctcctgca ggtctagtca gagcctcctg catagtgatg gataccacta tttggattgg     120
tacctgcaga agccagggca gtctccacag ctcctgatct atttgggttc taatcgggcc     180
tccggggtcc ctgacaggtt cactggcagt ggatcaggca cagattttac actgaaaatc     240
agcagagtgg aggctgagga tgttggggtt tattactgca tgcaagctct acaaattctc     300
actttcggcg agggaccaa ggtggagatc aaacgtacgg tggctgcacc atctgtcttc      360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc      600
acccatcagg gcctgagctc gcccgtcaca aagagcttca caggggaga gtgt             654
```

<210> SEQ ID NO 76
<211> LENGTH: 657
<212> TYPE: DNA
<213> ORGANISM: Homo sapiens

<400> SEQUENCE: 76

```
gattttgtga tgacccagac tccactctct ctgtccgtca cccctggaca gccggcctcc      60
atctcctgta agtctagtca gagcctcctg catagtaatg gaaagaccta tttgtattgg     120
ttcctgcaga agccaggcca gcctccacaa ctcctgatct atgaagtttc aaccggttc      180
tctggagtgc cagataggtt cagtggcagc gggtcaggga cagatttcac actgaaaatc     240
agccgggtgg aggctgagga tgttggggtt tattactgca tgcaaagtat acagcttcct     300
ctcactttcg gcggagggac caaggtggag atcaaacgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgt         657
```

<210> SEQ ID NO 77
<211> LENGTH: 654
<212> TYPE: DNA
<213> ORGANISM: Homo sapiens

<400> SEQUENCE: 77

```
gatattgtga tgactcagtc tccactctcc ctgcccgtca cccctggaga gccggcctcc      60
atctcctgca ggtctagtca gagcctcctg tatagtgatg gaaacaacta tttggattgg     120
tacctgcaga agccagggca gtctccacac ctcctgatct atttgggttc taatcgggcc     180
tccggggtcc ctgacaggtt cagtggcagt ggatcaggca cagattttac actgaaaatc     240
agcagagtgg aggctgacga tgttggggtt tattactgca tgcaagctct acaaactctc     300
actttcggcg agggaccaa ggtggagatc aaacgtacgg tggctgcacc atctgtcttc      360
```

```
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca aagtctacgc ctgcgaagtc    600
acccatcagg gcctgagctc gcccgtcaca aagagcttca caggggaga gtgt           654

<210> SEQ ID NO 78
<211> LENGTH: 654
<212> TYPE: DNA
<213> ORGANISM: Homo sapiens

<400> SEQUENCE: 78
gatattgtaa tgactcagtc tccactctcc ctgcccgtca cccctggaga gccggcctcc    60
atctcctgca ggtctagtca gagcctcctg catagtgatg gatatcacta tttggattgg   120
tacctgcaga agccagggca gtctccacag ctcctgatct atttgggttc taatcgggcc   180
tccggggtcc ctgacaggtt cagtggcagt ggatcaggca cagattttac actgaacatc   240
agcagagtgg aggctgagga tgttggggtt tattactgca tgcaagctct acaaactctc   300
actttcggcg agggaccaa ggtggagatc aaacgtacgg tggctgcacc atctgtcttc    360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca aagtctacgc ctgcgaagtc   600
acccatcagg gcctgagctc gcccgtcaca aagagcttca caggggaga gtgt          654

<210> SEQ ID NO 79
<211> LENGTH: 654
<212> TYPE: DNA
<213> ORGANISM: Homo sapiens

<400> SEQUENCE: 79
gatattgtaa tgactcagtc tccactctcc ctgcccgtca cccctggaga gccggcctcc    60
atctcctgca ggtctagtca gagcctcctg catagtgatg gatatcacta tttggattgg   120
tacctgcaga agccagggca gtctccacag ctcctgatct atttgggttc taatcgggcc   180
tccggggtcc ctgacaggtt cagtggcagt ggatcaggca cagattttac actgaacatc   240
agcagagtgg aggctgagga tgttggggtt tattactgca tgcaagctct acaaactctc   300
actttcggcg agggaccaa ggtggagatc aaacgtacgg tggctgcacc atctgtcttc    360
atcttcccgc catctgatga gcagttgaaa tctggaactg cctctgttgt gtgcctgctg   420
aataacttct atcccagaga ggccaaagta cagtggaagg tggataacgc cctccaatcg   480
ggtaactccc aggagagtgt cacagagcag gacagcaagg acagcaccta cagcctcagc   540
agcaccctga cgctgagcaa agcagactac gagaaacaca aagtctacgc ctgcgaagtc   600
acccatcagg gcctgagctc gcccgtcaca aagagcttca caggggaga gtgt          654

<210> SEQ ID NO 80
<211> LENGTH: 654
<212> TYPE: DNA
<213> ORGANISM: Homo sapiens

<400> SEQUENCE: 80
```

```
gatattgtga tgactcagtc tccactctcc ctgcccgtca cccctggaga gccggcctcc      60
atctcctgta ggtctggtca gagcctcctg catagtgatg gatacaacta tttggattgg     120
tacctgcaga agccagggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactatc     300
accttcggcc aagggacacg actggagatt aaacgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc ctccaatcg      480 ggtaactccc aggagagtgt cacagagcag gacagcaagg acagcaccta cagcctcagc     540
agcaccctga cgctgagcaa agcagactac gagaaacaca agtctacgc ctgcgaagtc      600 acccatcagg gcctgagctc gcccgtcaca aagagcttca caggggaga gtgt            654

<210> SEQ ID NO 81
<211> LENGTH: 645
<212> TYPE: DNA
<213> ORGANISM: Homo sapiens

<400> SEQUENCE: 81
gaaattgtga tgacgcagtc tccaggcacc ctgtctttgt ctccagggga aagagccacc      60
ctctcctgca gggccagtca gagtgttagc agcagccact aggctggta tcagcagaaa     120 cctggccagg ctcccaggct cctcatctat ggtgcatcca acagggccac tggcatccca     180
gacaggttca gtggcagtgg gtctgggaca gacttcactc tcaccatcag caaactggag     240
cctgaagatt ttgcagtgta ttactgtcag cagtatggta gctcaccgtg acgttcggc     300 caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg cctccaatc gggtaactcc      480 caggagagtg tcacagagca ggacagcaag gacagcacct acagcctcag cagcaccctg     540
acgctgagca aagcagacta cgagaaacac aaagtctacg cctgcgaagt cacccatcag     600
ggcctgagct cgcccgtcac aaagagcttc aacagggag agtgt                      645

<210> SEQ ID NO 82
<211> LENGTH: 645
<212> TYPE: DNA
<213> ORGANISM: Homo sapiens

<400> SEQUENCE: 82
gaaattgtgt tgacgcagtc tccaggcacc ctgtctttgt ctccagggga aagagccacc      60
ctctcctgca gggccagtca gagtgttagt agcagccact agcctggta tcagcagaaa     120 cctggccaga ctcccaggtt cctcatctat gctgcatcca gcagggccac cggcatccca     180
gacaggttca gtggcagtgg gtctgggaca gacttcactc tcaccatcag cagactggag     240
cctgaggatt ttgcagtgtt ttactgtcag cagtatggta gctcaccgtg acgttcggc     300 caagggacca aggtggaaat caaacgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg cctccaatc gggtaactcc      480 caggagagtg tcacagagca ggacagcaag gacagcacct acagcctcag cagcaccctg     540
acgctgagca aagcagacta cgagaaacac aaagtctacg cctgcgaagt cacccatcag     600
```

```
ggcctgagct cgcccgtcac aaagagcttc aacaggggag agtgt            645
```

<210> SEQ ID NO 83
<211> LENGTH: 645
<212> TYPE: DNA
<213> ORGANISM: Homo sapiens

<400> SEQUENCE: 83

```
gaaattgtga tgacgcagtc tccaggcacc ctgtctttgt ctccagggga aagagccacc     60
ctctcctgca gggccagtca gagtgttagc agcagccact taggctggta tcagcagaaa    120
cctggccagg ctcccaggct cctcatctat ggtgcatcca gcagggccac tggcatccca    180
gacaggttca gtggcagtgg gtctgggaca gacttcactc tcaccatcag caaactggag    240
cctgaagatt ttgcagtgta ttactgtcag cagtatggta gctcaccgtg gacgttcggc    300
caagggacca aggtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt               645
```

<210> SEQ ID NO 84
<211> LENGTH: 220
<212> TYPE: PRT
<213> ORGANISM: Homo sapiens

<400> SEQUENCE: 84

```
Asp Leu Val Met Thr Gln Ser Pro Asp Ser Leu Ala Val Ser Pro Gly
1               5                   10                  15

Glu Arg Ala Thr Ile Asn Cys Lys Ser Ser Gln Ser Leu Leu Tyr Ser
            20                  25                  30

Ser Asn Asn Lys Asp Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Asn Thr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

Ser Pro Val Thr Lys Ser Phe Asn Arg Gly Glu Cys
    210                 215                 220

<210> SEQ ID NO 85
<211> LENGTH: 214
<212> TYPE: PRT
<213> ORGANISM: Homo sapiens

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asp Asn Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 218
<212> TYPE: PRT
<213> ORGANISM: Homo sapiens

<400> SEQUENCE: 86

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr His Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

```
Leu Gln Ile Leu Thr Phe Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
            210                 215

<210> SEQ ID NO 87
<211> LENGTH: 219
<212> TYPE: PRT
<213> ORGANISM: Homo sapiens

<400> SEQUENCE: 87

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asn Gly Lys Thr Tyr Leu Tyr Trp Phe Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 88
<211> LENGTH: 218
<212> TYPE: PRT
```

<213> ORGANISM: Homo sapiens

<400> SEQUENCE: 88

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Tyr Ser
            20                  25                  30
Asp Gly Asn Asn Tyr Leu Asp Trp Tyr Leu Gln Lys Pro Gly Gln Ser
        35                  40                  45
Pro His Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Asp Asp Val Gly Val Tyr Tyr Cys Met Gln Ala
                85                  90                  95
Leu Gln Thr Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
Tyr Ser Leu Ser Ser Thr Leu Thr Leu Ser Lys Ala Asp Tyr Glu Lys
            180                 185                 190
His Lys Val Tyr Ala Cys Glu Val Thr His Gln Gly Leu Ser Ser Pro
        195                 200                 205
Val Thr Lys Ser Phe Asn Arg Gly Glu Cys
    210                 215
```

<210> SEQ ID NO 89
<211> LENGTH: 218
<212> TYPE: PRT
<213> ORGANISM: Homo sapiens

<400> SEQUENCE: 89

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu His Ser
            20                  25                  30
Asp Gly Tyr His Tyr Leu Asp Trp Tyr Leu Gln Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Asn Ile
65                  70                  75                  80
Ser Arg Val Glu Ala Glu Asp Val Gly Val Tyr Tyr Cys Met Gln Ala
                85                  90                  95
Leu Gln Thr Leu Thr Phe Gly Gly Gly Thr Lys Val Glu Ile Lys Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
```

```
                      130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 90
<211> LENGTH: 218
<212> TYPE: PRT
<213> ORGANISM: Homo sapiens

<400> SEQUENCE: 90

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Tyr His Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                    165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 91
<211> LENGTH: 218
<212> TYPE: PRT
<213> ORGANISM: Homo sapiens

<400> SEQUENCE: 91

```
Asp Ile Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Ser
                20                  25                  30
```

```
            20                  25                  30
Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 92
<211> LENGTH: 215
<212> TYPE: PRT
<213> ORGANISM: Homo sapiens

<400> SEQUENCE: 92

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Gly Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Lys Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 93
<211> LENGTH: 215
<212> TYPE: PRT
<213> ORGANISM: Homo sapiens

<400> SEQUENCE: 93

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Ala Trp Tyr Gln Gln Lys Pro Gly Gln Thr Pro Arg Phe Leu
        35                  40                  45

Ile Tyr Ala Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 94
<211> LENGTH: 215
<212> TYPE: PRT
<213> ORGANISM: Homo sapiens

<400> SEQUENCE: 94

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60
```

```
Gly Ser Gly Ser Gly Thr Asp Phe Thr Leu Thr Ile Ser Lys Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 95
<211> LENGTH: 114
<212> TYPE: PRT
<213> ORGANISM: Homo sapiens

<400> SEQUENCE: 95

Asp Leu Val Met Thr Gln Ser Pro Asp Ser Leu Ala Val Ser Pro Gly
  1               5                  10                  15

Glu Arg Ala Thr Ile Asn Cys Lys Ser Ser Gln Ser Leu Leu Tyr Ser
                 20                  25                  30

Ser Asn Asn Lys Asp Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys His Gln
                 85                  90                  95

Tyr Tyr Asn Thr Pro Trp Thr Phe Gly Gln Gly Thr Lys Val Glu Ile
            100                 105                 110

Lys Arg

<210> SEQ ID NO 96
<211> LENGTH: 108
<212> TYPE: PRT
<213> ORGANISM: Homo sapiens

<400> SEQUENCE: 96

Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
```

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Asp Asn Phe Pro Leu
                85                  90                  95

Thr Phe Gly Gly Gly Thr Lys Val Glu Ile Lys Arg
                100                 105

<210> SEQ ID NO 97
<211> LENGTH: 112
<212> TYPE: PRT
<213> ORGANISM: Homo sapiens

<400> SEQUENCE: 97

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asp Gly Tyr His Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Ile Leu Thr Phe Gly Gly Gly Thr Lys Val Glu Ile Lys Arg
                100                 105                 110

<210> SEQ ID NO 98
<211> LENGTH: 113
<212> TYPE: PRT
<213> ORGANISM: Homo sapiens

<400> SEQUENCE: 98

Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
                20                  25                  30

Asn Gly Lys Thr Tyr Leu Tyr Trp Phe Leu Gln Lys Pro Gly Gln Pro
            35                  40                  45

Pro Gln Leu Leu Ile Tyr Glu Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
                100                 105                 110

Arg

<210> SEQ ID NO 99
<211> LENGTH: 112
<212> TYPE: PRT
<213> ORGANISM: Homo sapiens

<400> SEQUENCE: 99

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asp Gly Asn Asn Tyr Leu Asp Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Ala
                85                  90                  95

Leu Gln Thr Leu Thr Phe Gly Gly Gly Thr Lys Val Glu Ile Lys Arg
            100                 105                 110

<210> SEQ ID NO 100
<211> LENGTH: 112
<212> TYPE: PRT
<213> ORGANISM: Homo sapiens

<400> SEQUENCE: 100

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr His Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gly Gly Thr Lys Val Glu Ile Lys Arg
            100                 105                 110

<210> SEQ ID NO 101
<211> LENGTH: 112
<212> TYPE: PRT
<213> ORGANISM: Homo sapiens

<400> SEQUENCE: 101

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr His Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Asn Ile
65                  70                  75                  80

Ser Arg Val Glu Ala Glu Asp Val Gly Val Tyr Tyr Cys Met Gln Ala
                85                  90                  95

Leu Gln Thr Leu Thr Phe Gly Gly Gly Thr Lys Val Glu Ile Lys Arg
            100                 105                 110

<210> SEQ ID NO 102
<211> LENGTH: 112
<212> TYPE: PRT
<213> ORGANISM: Homo sapiens

<400> SEQUENCE: 102

Asp Ile Val Met Thr Gln Ser Pro Leu Ser Leu Pro Val Thr Pro Gly
1               5                   10                  15

Glu Pro Ala Ser Ile Ser Cys Arg Ser Gly Gln Ser Leu Leu His Ser
            20                  25                  30

Asp Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Ile Thr Phe Gly Gln Gly Thr Arg Leu Glu Ile Lys Arg
            100                 105                 110

<210> SEQ ID NO 103
<211> LENGTH: 109
<212> TYPE: PRT
<213> ORGANISM: Homo sapiens

<400> SEQUENCE: 103

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Gly Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Lys Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105

<210> SEQ ID NO 104
<211> LENGTH: 109
<212> TYPE: PRT
<213> ORGANISM: Homo sapiens

<400> SEQUENCE: 104

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Ala Trp Tyr Gln Gln Lys Pro Gly Gln Thr Pro Arg Phe Leu
        35                  40                  45

Ile Tyr Ala Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Phe Tyr Cys Gln Gln Tyr Gly Ser Ser Pro
                    85                  90                  95

Trp Thr Phe Gly Gln Gly Thr Lys Val Glu Ile Lys Arg
                100                 105
```

<210> SEQ ID NO 105
<211> LENGTH: 109
<212> TYPE: PRT
<213> ORGANISM: Homo sapiens

<400> SEQUENCE: 105

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

His Leu Gly Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Lys Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
                100                 105
```

<210> SEQ ID NO 106
<211> LENGTH: 17
<212> TYPE: PRT
<213> ORGANISM: Homo sapiens

<400> SEQUENCE: 106

```
Lys Ser Ser Gln Ser Leu Leu Tyr Ser Ser Asn Asn Lys Asp Tyr Leu
1               5                   10                  15

Ala
```

<210> SEQ ID NO 107
<211> LENGTH: 11
<212> TYPE: PRT
<213> ORGANISM: Homo sapiens

<400> SEQUENCE: 107

```
Gln Ala Ser Gln Asp Ile Ser Asn Tyr Leu Asn
1               5                   10
```

<210> SEQ ID NO 108
<211> LENGTH: 16
<212> TYPE: PRT
<213> ORGANISM: Homo sapiens

<400> SEQUENCE: 108

```
Arg Ser Ser Gln Ser Leu Leu His Ser Asp Gly Tyr His Tyr Leu Asp
1               5                   10                  15
```

<210> SEQ ID NO 109
<211> LENGTH: 16
<212> TYPE: PRT
<213> ORGANISM: Homo sapiens

<400> SEQUENCE: 109

```
Lys Ser Ser Gln Ser Leu Leu His Ser Asn Gly Lys Thr Tyr Leu Tyr
1               5                   10                  15
```

<210> SEQ ID NO 110
<211> LENGTH: 16
<212> TYPE: PRT
<213> ORGANISM: Homo sapiens

<400> SEQUENCE: 110

```
Arg Ser Ser Gln Ser Leu Leu Tyr Ser Asp Gly Asn Asn Tyr Leu Asp
1               5                   10                  15
```

<210> SEQ ID NO 111
<211> LENGTH: 16
<212> TYPE: PRT
<213> ORGANISM: Homo sapiens

<400> SEQUENCE: 111

```
Arg Ser Ser Gln Ser Leu Leu His Ser Asp Gly Tyr His Tyr Leu Asp
1               5                   10                  15
```

<210> SEQ ID NO 112
<211> LENGTH: 16
<212> TYPE: PRT
<213> ORGANISM: Homo sapiens

<400> SEQUENCE: 112

```
Arg Ser Ser Gln Ser Leu Leu His Ser Asp Gly Tyr His Tyr Leu Asp
1               5                   10                  15
```

<210> SEQ ID NO 113
<211> LENGTH: 16
<212> TYPE: PRT
<213> ORGANISM: Homo sapiens

<400> SEQUENCE: 113

```
Arg Ser Gly Gln Ser Leu Leu His Ser Asp Gly Tyr Asn Tyr Leu Asp
1               5                   10                  15
```

<210> SEQ ID NO 114
<211> LENGTH: 12
<212> TYPE: PRT
<213> ORGANISM: Homo sapiens

<400> SEQUENCE: 114

```
Arg Ala Ser Gln Ser Val Ser Ser Ser His Leu Gly
1               5                   10
```

<210> SEQ ID NO 115
<211> LENGTH: 12
<212> TYPE: PRT
<213> ORGANISM: Homo sapiens

<400> SEQUENCE: 115

```
Arg Ala Ser Gln Ser Val Ser Ser Ser His Leu Ala
1               5                   10
```

<210> SEQ ID NO 116
<211> LENGTH: 12
<212> TYPE: PRT
<213> ORGANISM: Homo sapiens

<400> SEQUENCE: 116

```
Arg Ala Ser Gln Ser Val Ser Ser Ser His Leu Gly
1               5                   10
```

<210> SEQ ID NO 117
<211> LENGTH: 7
<212> TYPE: PRT
<213> ORGANISM: Homo sapiens

<400> SEQUENCE: 117

Trp Ala Ser Thr Arg Glu Ser
1               5

<210> SEQ ID NO 118
<211> LENGTH: 7
<212> TYPE: PRT
<213> ORGANISM: Homo sapiens

<400> SEQUENCE: 118

Asp Ala Ser Asn Leu Glu Thr
1               5

<210> SEQ ID NO 119
<211> LENGTH: 7
<212> TYPE: PRT
<213> ORGANISM: Homo sapiens

<400> SEQUENCE: 119

Leu Gly Ser Asn Arg Ala Ser
1               5

<210> SEQ ID NO 120
<211> LENGTH: 7
<212> TYPE: PRT
<213> ORGANISM: Homo sapiens

<400> SEQUENCE: 120

Glu Val Ser Asn Arg Phe Ser
1               5

<210> SEQ ID NO 121
<211> LENGTH: 7
<212> TYPE: PRT
<213> ORGANISM: Homo sapiens

<400> SEQUENCE: 121

Leu Gly Ser Asn Arg Ala Ser
1               5

<210> SEQ ID NO 122
<211> LENGTH: 7
<212> TYPE: PRT
<213> ORGANISM: Homo sapiens

<400> SEQUENCE: 122

Leu Gly Ser Asn Arg Ala Ser
1               5

<210> SEQ ID NO 123
<211> LENGTH: 7
<212> TYPE: PRT
<213> ORGANISM: Homo sapiens

<400> SEQUENCE: 123

Leu Gly Ser Asn Arg Ala Ser
1               5

<210> SEQ ID NO 124
<211> LENGTH: 7
<212> TYPE: PRT
<213> ORGANISM: Homo sapiens

<400> SEQUENCE: 124

Leu Gly Ser Asn Arg Ala Ser
1               5

<210> SEQ ID NO 125
<211> LENGTH: 7
<212> TYPE: PRT
<213> ORGANISM: Homo sapiens

<400> SEQUENCE: 125

Gly Ala Ser Asn Arg Ala Thr
1               5

<210> SEQ ID NO 126
<211> LENGTH: 7
<212> TYPE: PRT
<213> ORGANISM: Homo sapiens

<400> SEQUENCE: 126

Ala Ala Ser Ser Arg Ala Thr
1               5

<210> SEQ ID NO 127
<211> LENGTH: 7
<212> TYPE: PRT
<213> ORGANISM: Homo sapiens

<400> SEQUENCE: 127

Gly Ala Ser Ser Arg Ala Thr
1               5

<210> SEQ ID NO 128
<211> LENGTH: 9
<212> TYPE: PRT
<213> ORGANISM: Homo sapiens

<400> SEQUENCE: 128

His Gln Tyr Tyr Asn Thr Pro Trp Thr
1               5

<210> SEQ ID NO 129
<211> LENGTH: 9
<212> TYPE: PRT
<213> ORGANISM: Homo sapiens

<400> SEQUENCE: 129

Gln Gln Asp Asp Asn Phe Pro Leu Thr
1               5

<210> SEQ ID NO 130
<211> LENGTH: 8
<212> TYPE: PRT
<213> ORGANISM: Homo sapiens

<400> SEQUENCE: 130

Met Gln Ala Leu Gln Ile Leu Thr
1               5

<210> SEQ ID NO 131

```
<211> LENGTH: 9
<212> TYPE: PRT
<213> ORGANISM: Homo sapiens

<400> SEQUENCE: 131

Met Gln Ser Ile Gln Leu Pro Leu Thr
1               5

<210> SEQ ID NO 132
<211> LENGTH: 8
<212> TYPE: PRT
<213> ORGANISM: Homo sapiens

<400> SEQUENCE: 132

Met Gln Ala Leu Gln Thr Leu Thr
1               5

<210> SEQ ID NO 133
<211> LENGTH: 8
<212> TYPE: PRT
<213> ORGANISM: Homo sapiens

<400> SEQUENCE: 133

Met Gln Ala Leu Gln Thr Leu Thr
1               5

<210> SEQ ID NO 134
<211> LENGTH: 8
<212> TYPE: PRT
<213> ORGANISM: Homo sapiens

<400> SEQUENCE: 134

Met Gln Ala Leu Gln Thr Leu Thr
1               5

<210> SEQ ID NO 135
<211> LENGTH: 8
<212> TYPE: PRT
<213> ORGANISM: Homo sapiens

<400> SEQUENCE: 135

Met Gln Ala Leu Gln Thr Ile Thr
1               5

<210> SEQ ID NO 136
<211> LENGTH: 9
<212> TYPE: PRT
<213> ORGANISM: Homo sapiens

<400> SEQUENCE: 136

Gln Gln Tyr Gly Ser Ser Pro Trp Thr
1               5

<210> SEQ ID NO 137
<211> LENGTH: 9
<212> TYPE: PRT
<213> ORGANISM: Homo sapiens

<400> SEQUENCE: 137

Gln Gln Tyr Gly Ser Ser Pro Trp Thr
1               5

<210> SEQ ID NO 138
<211> LENGTH: 9
<212> TYPE: PRT
```

<213> ORGANISM: Homo sapiens

<400> SEQUENCE: 138

Gln Gln Tyr Gly Ser Ser Pro Trp Thr
1               5

<210> SEQ ID NO 139
<211> LENGTH: 1335
<212> TYPE: DNA
<213> ORGANISM: Homo sapiens

<400> SEQUENCE: 139

| | | | | | |
|---|---|---|---|---|---|
| caggtgcagc | tggtggagtc | tgggggaggc | gtggtccagc | ctgggaggtc | cctgagactc | 60 |
| tcctgtacag | cgtctggatt | caccttcagt | agccatggca | tgcactgggt | ccgccaggct | 120 |
| ccaggcaagg | ggctggagtg | ggtgacaatt | atatggtttg | atggaaataa | taaatactat | 180 |
| gcagactccg | tggagggccg | cttcaccatc | tccagagaca | attccaagaa | cacgctgttt | 240 |
| ctgcaaatga | acagcctgag | agccgaggac | acggctgtct | attactgtgc | gagagaggggg | 300 |
| gcggaacagg | ggttcatcga | tctctggggc | cgtggcaccc | tggtcactgt | ctcctcagct | 360 |
| agcaccaagg | gcccatcggt | cttccccctg | gcgccctgct | ccaggagcac | ctccgagagc | 420 |
| acagcggccc | tgggctgcct | ggtcaaggac | tacttccccg | aaccggtgac | ggtgtcgtgg | 480 |
| aactcaggcg | ctctgaccag | cggcgtgcac | accttcccag | ctgtcctaca | gtcctcagga | 540 |
| ctctactccc | tcagcagcgt | ggtgaccgtg | ccctccagca | acttcggcac | ccagacctac | 600 |
| acctgcaacg | tagatcacaa | gcccagcaac | accaaggtgg | acaagacagt | tgagcgcaaa | 660 |
| tgttgtgtcg | agtgcccacc | gtgcccagca | ccacctgtgg | caggaccgtc | agtcttcctc | 720 |
| ttccccccaa | aacccaagga | caccctcatg | atctcccgga | cccctgaggt | cacgtgcgtg | 780 |
| gtggtggacg | tgagccacga | agaccccgag | gtccagttca | actggtacgt | ggacggcgtg | 840 |
| gaggtgcata | atgccaagac | aaagccacgg | gaggagcagt | tcaacagcac | gttccgtgtg | 900 |
| gtcagcgtcc | tcaccgttgt | gcaccaggac | tggctgaacg | gcaaggagta | caagtgcaag | 960 |
| gtctccaaca | aaggcctccc | agcccccatc | gagaaaacca | tctccaaaac | caaagggcag | 1020 |
| ccccgagaac | acaggtgtta | caccctgccc | ccatcccggg | aggagatgac | caagaaccag | 1080 |
| gtcagcctga | cctgcctggt | caaaggcttc | taccccagcg | acatcgccgt | ggagtgggag | 1140 |
| agcaatgggc | agccggagaa | caactacaag | accacacctc | ccatgctgga | ctccgacggc | 1200 |
| tccttcttcc | tctacagcaa | gctcaccgtg | gacaagagca | ggtggcagca | ggggaacgtc | 1260 |
| ttctcatgct | ccgtgatgca | tgaggctctg | cacaaccact | acacgcagaa | gagcctctcc | 1320 |
| ctgtctccgg | gtaaa | | | | | 1335 |

<210> SEQ ID NO 140
<211> LENGTH: 1347
<212> TYPE: DNA
<213> ORGANISM: Homo sapiens

<400> SEQUENCE: 140

| | | | | | |
|---|---|---|---|---|---|
| gaggtgcagc | tggtggagtc | tgggggaggc | ttggtacaac | ctgggggtc | cctgagactc | 60 |
| tcctgtgcag | cctctggatt | caccttcagt | accttcgaca | tgcactgggt | ccgccaagct | 120 |
| acaggaaaag | gtctggagtg | ggtctcaagt | attgatactg | aaggagacac | atactattca | 180 |
| ggctccgtga | agggccgatt | caccatctcc | agagaaaatg | ccaggaactc | cttgtatctt | 240 |
| caaatgaaca | gcctgagagc | cggggacacg | gctgtgtatt | actgtacaag | aggcgaggac | 300 |

| | |
|---|---|
| tggagcgacg acgactacta ctacggtttg dacgtctggg gccaagggac cacggtcacc | 360 |
| gtctcctcag ctagcaccaa gggcccatcg gtcttccccc tggcgccctg ctccaggagc | 420 |
| acctccgaga gcacagcggc cctgggctgc ctggtcaagg actacttccc cgaaccggtg | 480 |
| acggtgtcgt ggaactcagg cgctctgacc agcggcgtgc acaccttccc agctgtccta | 540 |
| cagtcctcag gactctactc cctcagcagc gtggtgaccg tgccctccag caacttcggc | 600 |
| acccagacct acacctgcaa cgtagatcac aagcccagca acaccaaggt ggacaagaca | 660 |
| gttgagcgca aatgttgtgt cgagtgccca ccgtgcccag caccacctgt ggcaggaccg | 720 |
| tcagtcttcc tcttcccccc aaaacccaag gacaccctca tgatctcccg gacccctgag | 780 |
| gtcacgtgcg tggtggtgga cgtgagccac gaagacccccg aggtccagtt caactggtac | 840 |
| gtggacggcg tggaggtgca taatgccaag acaaagccac gggaggagca gttcaacagc | 900 |
| acgttccgtg tggtcagcgt cctcaccgtt gtgcaccagg actggctgaa cggcaaggag | 960 |
| tacaagtgca aggtctccaa caaaggcctc ccagccccca tcgagaaaac catctccaaa | 1020 |
| accaaagggc agccccgaga accacaggtg tacaccctgc ccccatcccg ggaggagatg | 1080 |
| accaagaacc aggtcagcct gacctgcctg gtcaaaggct tctaccccag cgacatcgcc | 1140 |
| gtggagtggg agagcaatgg gcagccggag aacaactaca agaccacacc tcccatgctg | 1200 |
| gactccgacg gctccttctt cctctacagc aagctcaccg tggacaagag caggtggcag | 1260 |
| caggggaacg tcttctcatg ctccgtgatg catgaggctc tgcacaacca ctacacgcag | 1320 |
| aagagcctct ccctgtctcc gggtaaa | 1347 |

<210> SEQ ID NO 141
<211> LENGTH: 1347
<212> TYPE: DNA
<213> ORGANISM: Homo sapiens

<400> SEQUENCE: 141

| | |
|---|---|
| gaggtgcaac tggtggagtc tgggggaggc ttggtacagc ctgggggggtc cctgagactc | 60 |
| tcctgtgcag cctctggatt caccttcagt accttcgaca tgcactgggt ccgccaagtt | 120 |
| ccaggaaaag gtctggagtg gatctcaagt attgatactg aaggagacac atactatcca | 180 |
| ggctccgtga agggccgatt caccatctcc agagaaaatg ccaggaactc cttgtatctt | 240 |
| caaatgaaca gcctgagagc cggggacacg gctgtgtatt actgtacaag aggcgaggac | 300 |
| tggagcgacg acgactacta ctacggtttg dacgtctggg gccaagggac cacggtcacc | 360 |
| gtctcctcag ctagcaccaa gggcccatcg gtcttccccc tggcgccctg ctccaggagc | 420 |
| acctccgaga gcacagcggc cctgggctgc ctggtcaagg actacttccc cgaaccggtg | 480 |
| acggtgtcgt ggaactcagg cgctctgacc agcggcgtgc acaccttccc agctgtccta | 540 |
| cagtcctcag gactctactc cctcagcagc gtggtgaccg tgccctccag caacttcggc | 600 |
| acccagacct acacctgcaa cgtagatcac aagcccagca acaccaaggt ggacaagaca | 660 |
| gttgagcgca aatgttgtgt cgagtgccca ccgtgcccag caccacctgt ggcaggaccg | 720 |
| tcagtcttcc tcttcccccc aaaacccaag gacaccctca tgatctcccg gacccctgag | 780 |
| gtcacgtgcg tggtggtgga cgtgagccac gaagacccccg aggtccagtt caactggtac | 840 |
| gtggacggcg tggaggtgca taatgccaag acaaagccac gggaggagca gttcaacagc | 900 |
| acgttccgtg tggtcagcgt cctcaccgtt gtgcaccagg actggctgaa cggcaaggag | 960 |
| tacaagtgca aggtctccaa caaaggcctc ccagccccca tcgagaaaac catctccaaa | 1020 |
| accaaagggc agccccgaga accacaggtg tacaccctgc ccccatcccg ggaggagatg | 1080 |

```
accaagaacc aggtcagcct gacctgcctg gtcaaaggct tctacccag cgacatcgcc   1140 gtggagtggg agagcaatgg gcagccggag aacaactaca agaccacacc tcccatgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaa                                        1347
```

<210> SEQ ID NO 142
<211> LENGTH: 445
<212> TYPE: PRT
<213> ORGANISM: Homo sapiens

<400> SEQUENCE: 142

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser His
            20                  25                  30

Gly Met His Trp Val Arg Gln Ala Pro Gly Lys Gly Leu Glu Trp Val
        35                  40                  45

Thr Ile Ile Trp Phe Asp Gly Asn Asn Lys Tyr Tyr Ala Asp Ser Val
    50                  55                  60

Glu Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Glu Gly Ala Glu Gln Gly Phe Ile Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320
```

```
Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 143
<211> LENGTH: 449
<212> TYPE: PRT
<213> ORGANISM: Homo sapiens

<400> SEQUENCE: 143

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Asp Met His Trp Val Arg Gln Ala Thr Gly Lys Gly Leu Glu Trp Val
        35                  40                  45

Ser Ser Ile Asp Thr Glu Gly Asp Thr Tyr Tyr Ser Gly Ser Val Lys
    50                  55                  60

Gly Arg Phe Thr Ile Ser Arg Glu Asn Ala Arg Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Gly Glu Asp Trp Ser Asp Asp Tyr Tyr Gly Leu Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Val Asp Val Ser His Glu Asp
            260                 265                 270
Pro Glu Val Gln Phe Asn Trp Tyr Val Asp Gly Val Glu Val His Asn
            275                 280                 285
Ala Lys Thr Lys Pro Arg Glu Glu Gln Phe Asn Ser Thr Phe Arg Val
290                 295                 300
Val Ser Val Leu Thr Val Val His Gln Asp Trp Leu Asn Gly Lys Glu
305                 310                 315                 320
Tyr Lys Cys Lys Val Ser Asn Lys Gly Leu Pro Ala Pro Ile Glu Lys
            325                 330                 335
Thr Ile Ser Lys Thr Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Met Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 144
<211> LENGTH: 449
<212> TYPE: PRT
<213> ORGANISM: Homo sapiens

<400> SEQUENCE: 144

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Phe
            20                  25                  30
Asp Met His Trp Val Arg Gln Val Pro Gly Lys Gly Leu Glu Trp Ile
            35                  40                  45
Ser Ser Ile Asp Thr Glu Gly Asp Thr Tyr Tyr Pro Gly Ser Val Lys
    50                  55                  60
Gly Arg Phe Thr Ile Ser Arg Glu Asn Ala Arg Asn Ser Leu Tyr Leu
65              70                  75                  80
Gln Met Asn Ser Leu Arg Ala Gly Asp Thr Ala Val Tyr Tyr Cys Thr
            85                  90                  95
Arg Gly Glu Asp Trp Ser Asp Asp Tyr Tyr Tyr Gly Leu Asp Val
            100                 105                 110
Trp Gly Gln Gly Thr Thr Val Thr Val Ser Ser Ala Ser Thr Lys Gly
            115                 120                 125
Pro Ser Val Phe Pro Leu Ala Pro Cys Ser Arg Ser Thr Ser Glu Ser
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
            195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Phe Arg Val
290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                    325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 145
<211> LENGTH: 119
<212> TYPE: PRT
<213> ORGANISM: Homo sapiens

<400> SEQUENCE: 145

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Ser His
            20                  25                  30

Gly Met His Trp Val Arg Gln Ala Pro Gly Lys Gly Leu Glu Trp Val
        35                  40                  45

Thr Ile Ile Trp Phe Asp Gly Asn Asn Lys Tyr Ala Asp Ser Val
    50                  55                  60

Glu Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95
```

Ala Arg Glu Gly Ala Glu Gln Gly Phe Ile Asp Leu Trp Gly Arg Gly
            100                 105                 110

Thr Leu Val Thr Val Ser Ser
        115

<210> SEQ ID NO 146
<211> LENGTH: 123
<212> TYPE: PRT
<213> ORGANISM: Homo sapiens

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Asp Met His Trp Val Arg Gln Ala Thr Gly Lys Gly Leu Glu Trp Val
        35                  40                  45

Ser Ser Ile Asp Thr Glu Gly Asp Thr Tyr Tyr Ser Gly Ser Val Lys
    50                  55                  60

Gly Arg Phe Thr Ile Ser Arg Glu Asn Ala Arg Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Gly Glu Asp Trp Ser Asp Asp Tyr Tyr Tyr Gly Leu Asp Val
            100                 105                 110

Trp Gly Gln Gly Thr Thr Val Thr Val Ser Ser
        115                 120

<210> SEQ ID NO 147
<211> LENGTH: 123
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Asp Met His Trp Val Arg Gln Val Pro Gly Lys Gly Leu Glu Trp Ile
        35                  40                  45

Ser Ser Ile Asp Thr Glu Gly Asp Thr Tyr Tyr Pro Gly Ser Val Lys
    50                  55                  60

Gly Arg Phe Thr Ile Ser Arg Glu Asn Ala Arg Asn Ser Leu Tyr Leu
65                  70                  75                  80

Gln Met Asn Ser Leu Arg Ala Gly Asp Thr Ala Val Tyr Tyr Cys Thr
                85                  90                  95

Arg Gly Glu Asp Trp Ser Asp Asp Tyr Tyr Tyr Gly Leu Asp Val
            100                 105                 110

Trp Gly Gln Gly Thr Thr Val Thr Val Ser Ser
        115                 120

<210> SEQ ID NO 148
<211> LENGTH: 5
<212> TYPE: PRT
<213> ORGANISM: Homo sapiens

<400> SEQUENCE: 148

Ser His Gly Met His
1               5

<210> SEQ ID NO 149
<211> LENGTH: 5
<212> TYPE: PRT
<213> ORGANISM: Homo sapiens

<400> SEQUENCE: 149

Thr Phe Asp Met His
1               5

<210> SEQ ID NO 150
<211> LENGTH: 5
<212> TYPE: PRT
<213> ORGANISM: Homo sapiens

<400> SEQUENCE: 150

Thr Phe Asp Met His
1               5

<210> SEQ ID NO 151
<211> LENGTH: 17
<212> TYPE: PRT
<213> ORGANISM: Homo sapiens

<400> SEQUENCE: 151

Ile Ile Trp Phe Asp Gly Asn Asn Lys Tyr Tyr Ala Asp Ser Val Glu
1               5                   10                  15

Gly

<210> SEQ ID NO 152
<211> LENGTH: 16
<212> TYPE: PRT
<213> ORGANISM: Homo sapiens

<400> SEQUENCE: 152

Ser Ile Asp Thr Glu Gly Asp Thr Tyr Tyr Ser Gly Ser Val Lys Gly
1               5                   10                  15

<210> SEQ ID NO 153
<211> LENGTH: 16
<212> TYPE: PRT
<213> ORGANISM: Homo sapiens

<400> SEQUENCE: 153

Ser Ile Asp Thr Glu Gly Asp Thr Tyr Tyr Pro Gly Ser Val Lys Gly
1               5                   10                  15

<210> SEQ ID NO 154
<211> LENGTH: 10
<212> TYPE: PRT
<213> ORGANISM: Homo sapiens

<400> SEQUENCE: 154

Glu Gly Ala Glu Gln Gly Phe Ile Asp Leu
1               5                   10

<210> SEQ ID NO 155
<211> LENGTH: 15
<212> TYPE: PRT
<213> ORGANISM: Homo sapiens

<400> SEQUENCE: 155

```
Gly Glu Asp Trp Ser Asp Asp Asp Tyr Tyr Tyr Gly Leu Asp Val
 1               5                  10                  15
```

<210> SEQ ID NO 156
<211> LENGTH: 15
<212> TYPE: PRT
<213> ORGANISM: Homo sapiens

<400> SEQUENCE: 156

```
Gly Glu Asp Trp Ser Asp Asp Asp Tyr Tyr Tyr Gly Leu Asp Val
 1               5                  10                  15
```

<210> SEQ ID NO 157
<211> LENGTH: 642
<212> TYPE: DNA
<213> ORGANISM: Homo sapiens

<400> SEQUENCE: 157

| | | | | | |
|---|---|---|---|---|---|
| gacatccaga | tgacccagtc | tccatcctcc | ctgtctgcat | ctgtaggaga | cagagtcacc | 60 |
| atcacttgcc | aggcgagtca | ggacattagc | aactatttaa | attggtatca | ccagaaacca | 120 |
| gggaaagccc | ctaagctcct | gatctacgat | gcatccaatt | tggaaacagg | ggtcccatca | 180 |
| aggttcagtg | gaagtggatc | tgggacagat | tttactttca | ccatcagcgg | cctgcagcct | 240 |
| gaagatattg | caacatatta | ctgtcaacag | catgataatc | tcccgctcac | tttcggcgga | 300 |
| gggaccaagg | tggagatcaa | gcgaacggtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |
| gagagtgtca | cagagcagga | cagcaaggac | agcacctaca | gcctcagcag | caccctgacg | 540 |
| ctgagcaaag | cagactacga | gaacacaaa | gtctacgcct | gcgaagtcac | ccatcagggc | 600 |
| ctgagctcgc | ccgtcacaaa | gagcttcaac | aggggagagt | gt | | 642 |

<210> SEQ ID NO 158
<211> LENGTH: 654
<212> TYPE: DNA
<213> ORGANISM: Homo sapiens

<400> SEQUENCE: 158

| | | | | | |
|---|---|---|---|---|---|
| aatattgtga | tgacccagac | tccactctct | ctgtccgtca | cccctggaca | gccggcctcc | 60 |
| atctcctgca | agtctagtca | gagcctcctg | catagtgatg | gaaagaccta | tttattttgg | 120 |
| tacctgcaga | agccaggcca | gcctccacag | ctcctgatct | atggagtttc | caaccggttc | 180 |
| tctggagtgc | cagataggtt | cagtggcagc | gggtcaggga | cagatttcac | actgaaaatc | 240 |
| agccgggtgg | aggctgaaga | tgttggggtt | tattactgca | tgcaaagttt | acagctattc | 300 |
| actttcggcc | ctgggaccaa | agtggagatc | aagcgaacgg | tggctgcacc | atctgtcttc | 360 |
| atcttcccgc | catctgatga | gcagttgaaa | tctggaactg | cctctgttgt | gtgcctgctg | 420 |
| aataacttct | atcccagaga | ggccaaagta | cagtggaagg | tggataacgc | cctccaatcg | 480 |
| ggtaactccc | aggagagtgt | cacagagcag | gacagcaagg | acagcaccta | cagcctcagc | 540 |
| agcaccctga | cgctgagcaa | agcagactac | gagaacacac | aagtctacgc | ctgcgaagtc | 600 |
| acccatcagg | gcctgagctc | gcccgtcaca | aagagcttca | cagggggaga | gtgt | 654 |

<210> SEQ ID NO 159
<211> LENGTH: 657
<212> TYPE: DNA
<213> ORGANISM: Homo sapiens

<400> SEQUENCE: 159

```
aatattgtga tgacccagac tccactctct ctgtccgtca cccctggaca gccggcctcc    60
atctcctgca agtctagtca gagcctcctg catagtgatg gaaagaccta tttattttgg   120
tacctgcaga agccaggcca gcctccacag ctcctgatct atggagtttc caaccggttc   180
tctggagtgc cagataggtt cagtggcagc gggtcaggga cagatttcac actgaaaatc   240
agccgggtgg aggctgaaga tgttgggggtt tattcctgca tgcaaagttt acagctattc   300
actttcggcc ctgggaccaa agtggatatc aaacgacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgt     657
```

<210> SEQ ID NO 160
<211> LENGTH: 214
<212> TYPE: PRT
<213> ORGANISM: Homo sapiens

<400> SEQUENCE: 160

```
Asp Ile Gln Met Thr Gln Ser Pro Ser Ser Leu Ser Ala Ser Val Gly
  1               5                  10                  15
Asp Arg Val Thr Ile Thr Cys Gln Ala Ser Gln Asp Ile Ser Asn Tyr
             20                  25                  30
Leu Asn Trp Tyr His Gln Lys Pro Gly Lys Ala Pro Lys Leu Leu Ile
         35                  40                  45
Tyr Asp Ala Ser Asn Leu Glu Thr Gly Val Pro Ser Arg Phe Ser Gly
     50                  55                  60
Ser Gly Ser Gly Thr Asp Phe Thr Phe Thr Ile Ser Gly Leu Gln Pro
 65                  70                  75                  80
Glu Asp Ile Ala Thr Tyr Tyr Cys Gln Gln His Asp Asn Leu Pro Leu
                 85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 161
<211> LENGTH: 218
<212> TYPE: PRT

<213> ORGANISM: Homo sapiens

<400> SEQUENCE: 161

Asn Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Phe Trp Tyr Leu Gln Lys Pro Gly Gln Pro
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Gln Leu Phe Thr Phe Gly Pro Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 162
<211> LENGTH: 219
<212> TYPE: PRT
<213> ORGANISM: Homo sapiens

<400> SEQUENCE: 162

Asn Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Phe Trp Tyr Leu Gln Lys Pro Gly Gln Pro
        35                  40                  45

Pro Gln Leu Leu Ile Tyr Gly Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Ser Cys Met Gln Ser
                85                  90                  95

Leu Gln Leu Phe Thr Phe Gly Pro Gly Thr Lys Val Asp Ile Lys Arg
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe

```
                 130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 163
<211> LENGTH: 108
<212> TYPE: PRT
<213> ORGANISM: Homo sapiens

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr His Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro
65                  70                  75                  80

Glu Asp Ile Ala Thr Tyr Tyr Cys Gln Gln His Asp Asn Leu Pro Leu
                85                  90                  95

Thr Phe Gly Gly Gly Thr Lys Val Glu Ile Lys Arg
            100                 105

<210> SEQ ID NO 164
<211> LENGTH: 108
<212> TYPE: PRT
<213> ORGANISM: Homo sapiens

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr His Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro
65                  70                  75                  80

Glu Asp Ile Ala Thr Tyr Tyr Cys Gln Gln His Asp Asn Leu Pro Leu
                85                  90                  95

Thr Phe Gly Gly Gly Thr Lys Val Glu Ile Lys Arg
            100                 105

<210> SEQ ID NO 165
<211> LENGTH: 113
<212> TYPE: PRT
```

<213> ORGANISM: Homo sapiens

<400> SEQUENCE: 165

Asn Ile Val Met Thr Gln Thr Pro Leu Ser Leu Ser Val Thr Pro Gly
1               5                   10                  15
Gln Pro Ala Ser Ile Ser Cys Lys Ser Ser Gln Ser Leu Leu His Ser
            20                  25                  30
Asp Gly Lys Thr Tyr Leu Phe Trp Tyr Leu Gln Lys Pro Gly Gln Pro
        35                  40                  45
Pro Gln Leu Leu Ile Tyr Gly Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Ser Cys Met Gln Ser
                85                  90                  95
Leu Gln Leu Phe Thr Phe Gly Pro Gly Thr Lys Val Asp Ile Lys Arg
            100                 105                 110
Arg

<210> SEQ ID NO 166
<211> LENGTH: 11
<212> TYPE: PRT
<213> ORGANISM: Homo sapiens

<400> SEQUENCE: 166

Gln Ala Ser Gln Asp Ile Ser Asn Tyr Leu Asn
1               5                   10

<210> SEQ ID NO 167
<211> LENGTH: 16
<212> TYPE: PRT
<213> ORGANISM: Homo sapiens

<400> SEQUENCE: 167

Lys Ser Ser Gln Ser Leu Leu His Ser Asp Gly Lys Thr Tyr Leu Phe
1               5                   10                  15

<210> SEQ ID NO 168
<211> LENGTH: 16
<212> TYPE: PRT
<213> ORGANISM: Homo sapiens

<400> SEQUENCE: 168

Lys Ser Ser Gln Ser Leu Leu His Ser Asp Gly Lys Thr Tyr Leu Phe
1               5                   10                  15

<210> SEQ ID NO 169
<211> LENGTH: 7
<212> TYPE: PRT
<213> ORGANISM: Homo sapiens

<400> SEQUENCE: 169

Asp Ala Ser Asn Leu Glu Thr
1               5

<210> SEQ ID NO 170
<211> LENGTH: 7
<212> TYPE: PRT
<213> ORGANISM: Homo sapiens

<400> SEQUENCE: 170

Gly Val Ser Asn Arg Phe Ser
1               5

<210> SEQ ID NO 171
<211> LENGTH: 7
<212> TYPE: PRT
<213> ORGANISM: Homo sapiens

<400> SEQUENCE: 171

Gly Val Ser Asn Arg Phe Ser
1               5

<210> SEQ ID NO 172
<211> LENGTH: 9
<212> TYPE: PRT
<213> ORGANISM: Homo sapiens

<400> SEQUENCE: 172

Gln Gln His Asp Asn Leu Pro Leu Thr
1               5

<210> SEQ ID NO 173
<211> LENGTH: 8
<212> TYPE: PRT
<213> ORGANISM: Homo sapiens

<400> SEQUENCE: 173

Met Gln Ser Leu Gln Leu Phe Thr
1               5

<210> SEQ ID NO 174
<211> LENGTH: 8
<212> TYPE: PRT
<213> ORGANISM: Homo sapiens

<400> SEQUENCE: 174

Met Gln Ser Leu Gln Leu Phe Thr
1               5

<210> SEQ ID NO 175
<211> LENGTH: 187
<212> TYPE: PRT
<213> ORGANISM: Homo sapiens

<400> SEQUENCE: 175

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Glu Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

-continued

```
Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu
                180                 185
```

ST2 ANTIGEN BINDING PROTEINS

CROSS-REFERENCE TO RELATED APPLICATIONS

This application is a divisional of U.S. application Ser. No. 15/178,652, filed Jun. 10, 2016, which is a divisional of U.S. application Ser. No. 13/897,096, filed May 17, 2013, now U.S. Pat. No. 9,382,318, which claims priority to U.S. Provisional Patent Application No. 61/792,619, filed Mar. 15, 2013, and U.S. Provisional Patent Application No. 61/649,147, filed May 18, 2012, which are incorporated herein by reference in their entirety.

REFERENCE TO THE SEQUENCE LISTING

The present application is being filed along with a Sequence Listing in electronic format via EFS-Web. The Sequence Listing is provided as a text file entitled A1712USNP_ST25.txt, created May 17, 2013, which is 189,576 bytes in size. The information in the electronic format of the Sequence Listing is incorporated herein by reference in its entirety.

BACKGROUND OF THE INVENTION

ST2 is a binding receptor for interleukin-33 (IL-33), a cytokine related to IL-1 and IL-18 and also known as NF-HEV or IL-1F11. ST2 is expressed as both a soluble non-signaling variant (soluble ST2 or sST2) and a full-length membrane-spanning form (FL ST2, ST2 or ST2L) that mediates cellular responses to IL-33. The latter form is expressed on a wide range of cell types implicated in pathologic inflammation in a number of disease settings. These include lymphocytes, particularly IL-5 and IL-13-expressing T helper cells, natural killer (NK) and natural killer-T (NKT) cells, as well as many so-called innate immune cells, such as mast cells, basophils, eosinophils, macrophages and innate helper cells (also known as nuocytes (Neill, Wong et al. 2010)). IL-33 binding to ST2 on these cells leads to the recruitment of a broadly-expressed co-receptor known as the IL-1R Accessory Protein (AcP) and the activation of pro-inflammatory signaling, similar to IL-1 and IL-18. IL-33 is thus able to directly activate ST2-expressing cells or enhance their activation when in the presence of other activating stimuli. Examples of IL-33-induced cellular responses include the production of inflammatory cytokines, such as IL-5, IL-6, IL-13, TNF, IFN-γ and GM-CSF as well as the production of chemokines, such as CXCL8, CCL17 and CCL24. IL-33 has also been shown to enhance acute allergic responses by augmenting mast cell and basophil activation triggered by IgE receptor signaling or other mast cell and basophil activators. IL-33 will also enhance the recruitment, survival and adhesive properties of ST2 expressing immune cells and thus is important in provoking and sustaining cellular inflammation in local tissues.

The pro-inflammatory actions of IL-33 on innate and adaptive immune cells culminate to promote a number of pathologic processes. In the lungs, these include increased airway inflammation, mucus production, airway hyper responsiveness and fibrotic remodeling. IL-33 can also contribute to localized inflammation in the joints as well as cutaneous and articular hypernociception, by promoting the production of proinflammatory cytokines (Verri, Guerrero et al. 2008; Xu, Jiang et al. 2008). Excessive IL-33 has been linked to pathologic collagen deposition and fibrosis and also contributes to epithelial damage in the setting of inflammatory bowel disease. Through its potent effects on basophils and IgE-sensitized mast cells, IL-33 can also trigger anaphylactic shock (Pushparaj, Tay et al. 2009) and may play a contributing role in allergic disease. Many of these diseases are chronic and progressive in nature and difficult to treat and there is a need for more effective treatments.

Consistent with its documented biologic effects, there are several lines of evidence that the IL-33/ST2 pathway contributes to human disease. For example, abnormally high expression of IL-33 is found in diseases involving inflammation in mucosal tissues and articular inflammation. These include asthma (Prefontaine, Lajoie-Kadoch et al. 2009; Prefontaine, Nadigel et al. 2010), inflammatory bowel disease (Beltran, Nunez et al. 2010; Pastorelli, Garg et al. 2010; Sponheim, Pollheimer et al. 2010) and rheumatoid arthritis (Palmer, Talabot-Ayer et al. 2009; Matsuyama, Okazaki et al. 2010). IL-33 expression is elevated in psoriatic skin (Theoharides Zhang et al. 2010) and the skin of atopic dermatitis patients (Pushparaj, Tay et al. 2009) and is also increased in pathologic settings of fibrosis, such as systemic sclerosis (Yanaba. Yoshizaki et al. 2011) (Manetti, Ibba-Manneschi et al. 2009) and liver fibrosis (Marvie, Lisbonne et al. 2009). The concentration of circulating soluble ST2 is also elevated in numerous disease situations, further indicating a link between this cytokine pathway and these diseases. Examples include asthma (Kuroiwa, Arai et al. 2001; Oshikawa, Kuroiwa et al. 2001; Ali, Zhang et al. 2009), chronic obstructive pulmonary disease (Hacker, Lambers et al. 2009), pulmonary fibrosis (Tajima, Oshikawa et al. 2003), sepsis and trauma (Brunner, Krenn et al. 2004), HIV infection (Miyagaki, Sugaya et al. 2011), systemic lupus erythematosus (Mok, Huang et al. 2010), inflammatory bowel disease (Beltran, Nunez et al. 2010) as well as rheumatoid arthritis, sclerosis, Wegener's granulomatosis and Behcet disease (Kuroiwa, Arai et al. 2001) and cardiovascular disease (Shah and Januzzi 2010). IL-33 potentiates eosinophilic inflammation and there is evidence this pathway is involved in eosinophil-associated disease, such as rhinosinusitis and nasal polyposis (Plager, Kahl et al. 2010) and eosinophilic bronchitis (Oshikawa, Kuroiwa et al. 2001).

Additional evidence linking the IL-33/ST2 pathway to human disease is provided by genetic studies, which have identified IL-33 and/or ST2 gene polymorphisms in the general population that are significantly associated with increased risk of disease or parameters of disease severity. Several large genome-wide association studies have linked genetic variation in ST2 (IL1RL1) or IL-33 with increased risk of asthma (Gudbjartsson, Bjornsdottir et al. 2009; Moffatt, Gut et al. 2010; Wu, Romieu et al. 2010) and other studies have genetically linked this pathway to increased asthma severity (Ali, Zhang et al. 2009) and bronchial hyper responsiveness (Reijmerink, Postma et al. 2008). Similar findings have genetically implicated this pathway in allergic disorders such as atopic dermatitis (Shimizu, Matsuda et al 2005), rhinosinusitis (Sakashita, Yoshimoto et al. 2008; Castano R 2009) as well as nasal polyposis (Buysschaert, Grulois et al. 2010).

Collectively, these links to several human diseases and the ability of this cytokine axis to promote many forms of harmful inflammation imply this is a useful target for therapeutic intervention.

SUMMARY OF THE INVENTION

The invention provides anti-ST2 antigen binding proteins, e.g., antibodies and functional fragments thereof, having properties amenable to commercial production and therapeutic use in humans. The anti-ST2 antigen binding proteins are particularly useful in methods of treating diseases and disorders associated with the IL-33/ST2 axis. Provided herein are ST2-binding antibodies that bind ST2 with high affinity and effectively block IL-33-binding, thereby reducing IL-33-mediated signaling in the cell.

In a first aspect, the ST2 antigen binding protein comprises a) a light chain variable domain having at least 90% identity, at least 95% identity, or is identical to the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165; b) a heavy chain variable domain having at least 90% identity, at least 95% identity, or is identical to the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147; or c) the light chain variable domain of a) and the heavy chain variable domain of b).

Preferred antigen binding proteins of the first aspect include those comprising a light chain variable domain having at least 90%, at least 95%, or is identical to the amino acid sequence set forth in SEQ ID NO:95 and a heavy chain variable domain having at least 90%, at least 95%, or is identical to the amino acid sequence set forth in SEQ ID NO:29; those comprising a light chain variable domain having at least 90%, at least 95%, or is identical to the amino acid sequence set forth in SEQ ID NO:96 and a heavy chain variable domain having at least 90%, at least 95%, or is identical to the amino acid sequence set forth in SEQ ID NO:30; those comprising a light chain variable domain having at least 90%, at least 95%, or is identical to the amino acid sequence set forth in SEQ ID NO:97 and a heavy chain variable domain having at least 90%, at least 95%, or is identical to the amino acid sequence set forth in SEQ ID NO:31; those comprising a light chain variable domain having at least 90%, at least 95%, or is identical to the amino acid sequence set forth in SEQ ID NO:98 and a heavy chain variable domain having at least 90%, at least 95%, or is identical to the amino acid sequence set forth in SEQ ID NO:32; those comprising a light chain variable domain having at least 90%, at least 95%, or is identical to the amino acid sequence set forth in SEQ ID NO:99 and a heavy chain variable domain having at least 90%, at least 95%, or is identical to the amino acid sequence set forth in SEQ ID NO:33; those comprising a light chain variable domain having at least 90%, at least 95%, or is identical to the amino acid sequence set forth in SEQ ID NO:100 and a heavy chain variable domain having at least 90%, at least 95%, or is identical to the amino acid sequence set forth in SEQ ID NO:34; those comprising a light chain variable domain having at least 90%, at least 95%, or is identical to the amino acid sequence set forth in SEQ ID NO:101 and a heavy chain variable domain having at least 90%, at least 95%, or is identical to the amino acid sequence set forth in SEQ ID NO:35; those comprising a light chain variable domain having at least 90%, at least 95%, or is identical to the amino acid sequence set forth in SEQ ID NO:102 and a heavy chain variable domain having at least 90%, at least 95%, or is identical to the amino acid sequence set forth in SEQ ID NO:36; those comprising a light chain variable domain having at least 90%, at least 95%, or is identical to the amino acid sequence set forth in SEQ ID NO:103 and a heavy chain variable domain having at least 90%, at least 95%, or is identical to the amino acid sequence set forth in SEQ ID NO:37; those comprising a light chain variable domain having at least 90%, at least 95%, or is identical to the amino acid sequence set forth in SEQ ID NO:104 and a heavy chain variable domain having at least 90%, at least 95%, or is identical to the amino acid sequence set forth in SEQ ID NO:38; those comprising a light chain variable domain having at least 90%, at least 95%, or is identical to the amino acid sequence set forth in SEQ ID NO:105 and a heavy chain variable domain having at least 90%, at least 95%, or is identical to the amino acid sequence set forth in SEQ ID NO:39; those comprising a light chain variable domain having at least 90%, at least 95%, or is identical to the amino acid sequence set forth in SEQ ID NO:163 and a heavy chain variable domain having at least 90%, at least 95%, or is identical to the amino acid sequence set forth in SEQ ID NO:145; those comprising a light chain variable domain having at least 90%, at least 95%, or is identical to the amino acid sequence set forth in SEQ ID NO:164 and a heavy chain variable domain having at least 90%, at least 95%, or is identical to the amino acid sequence set forth in SEQ ID NO:146; and those comprising a light chain variable domain having at least 90%, at least 95%, or is identical to the amino acid sequence set forth in SEQ ID NO:165 and a heavy chain variable domain having at least 90%, at least 95%, or is identical to the amino acid sequence set forth in SEQ ID NO:147.

In a second aspect, the ST2 antigen binding protein comprises a) a light chain variable domain having no more than ten or no more than five amino acid additions, deletions or substitutions from the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165; b) a heavy chain variable domain having no more than ten or no more than five amino acid additions, deletions or substitutions from the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147; or c) the light chain variable domain of a) and the heavy chain variable domain of b).

Preferred antigen binding proteins of the second aspect include those comprising a light chain variable domain having no more than ten or no more than five amino acid additions, deletions or substitutions from the amino acid sequence set forth in SEQ ID NO:95 and a heavy chain variable domain having no more than ten or no more than five amino acid additions, deletions or substitutions from the amino acid sequence set forth in SEQ ID NO:29; those comprising a light chain variable domain having no more than ten or no more than five amino acid additions, deletions or substitutions from the amino acid sequence set forth in SEQ ID NO:96 and a heavy chain variable domain having no more than ten or no more than five amino acid additions, deletions or substitutions from the amino acid sequence set forth in SEQ ID NO:30; those comprising a light chain variable domain having no more than ten or no more than five amino acid additions, deletions or substitutions from the amino acid sequence set forth in SEQ ID NO:97 and a heavy chain variable domain having no more than ten or no more than five amino acid additions, deletions or substitutions from the amino acid sequence set forth in SEQ ID NO:31; those comprising a light chain variable domain having no more than ten or no more than five amino acid additions, deletions or substitutions from the amino acid sequence set forth in SEQ ID NO:98 and a heavy chain variable domain having no more than ten or no more than five amino acid additions, deletions or substitutions from the amino acid sequence set forth in SEQ ID NO:32; those comprising a light chain variable domain having no more than ten or no more than five amino acid additions, deletions or substitutions from the amino acid sequence set forth in SEQ ID NO:99 and a heavy chain variable domain having no more than ten or no more than five amino acid additions, deletions or substitutions from the amino acid sequence set forth in SEQ ID NO:33; those comprising a light chain variable domain having no more than ten or no more than five amino acid additions, deletions or substitutions from the amino acid sequence set forth in SEQ ID NO:100 and a heavy chain variable domain having no more than ten or no more than five amino acid additions, deletions or substitutions from the amino acid sequence set forth in SEQ ID NO:34; those comprising a light chain variable domain having no more than ten or no more than five amino acid additions, deletions or substitutions from the amino acid sequence set forth in SEQ ID NO:101 and a heavy chain variable domain having no more than ten or no more than five amino acid additions, deletions or substitutions from the amino acid sequence set forth in SEQ ID NO:35; those comprising a light chain variable domain having no more than ten or no more than five amino acid additions, deletions or substitutions from the amino acid sequence set forth in SEQ ID NO:102 and a heavy chain variable domain having no more than ten or no more than five amino acid additions, deletions or substitutions from the amino acid sequence set forth in SEQ ID NO:36; those comprising a light chain variable domain having no more than ten or no more than five amino acid additions, deletions or substitutions from the amino acid sequence set forth in SEQ ID NO:103 and a heavy chain variable domain having no more than ten or no more than five amino acid additions, deletions or substitutions from the amino acid sequence set forth in SEQ ID NO:37; those comprising a light chain variable domain having no more than ten or no more than five amino acid additions, deletions or substitutions from the amino acid sequence set forth in SEQ ID NO:104 and a heavy chain variable domain having no more than ten or no more than five amino acid additions, deletions or substitutions from the amino acid sequence set forth in SEQ ID NO:38; those comprising a light chain variable domain having no more than ten or no more than five amino acid additions, deletions or substitutions from the amino acid sequence set forth in SEQ ID NO:105 and a heavy chain variable domain having no more than ten or no more than five amino acid additions, deletions or substitutions from the amino acid sequence set forth in SEQ ID NO:39; those comprising a light chain variable domain having no more than ten or no more than five amino acid additions, deletions or substitutions from the amino acid sequence set forth in SEQ ID NO:163 and a heavy chain variable domain having no more than ten or no more than five amino acid additions, deletions or substitutions from the amino acid sequence set forth in SEQ ID NO:145; those comprising a light chain variable domain having no more than ten or no more than five amino acid additions, deletions or substitutions from the amino acid sequence set forth in SEQ ID NO:164 and a heavy chain variable domain having no more than ten or no more than five amino acid additions, deletions or substitutions from the amino acid sequence set forth in SEQ ID NO:146; and those comprising a light chain variable domain having no more than ten or no more than five amino acid additions, deletions or substitutions from the amino acid sequence set forth in SEQ ID NO:165 and a heavy chain variable domain having no more than ten or no more than five amino acid additions, deletions or substitutions from the amino acid sequence set forth in SEQ ID NO:147.

In a third aspect, the ST2 antigen binding protein contains a light chain variable domain comprising a) an LCDR1 having no more than three amino acid additions, deletions, or substitutions from the LCDR1 sequence set forth in SEQ ID NO:106; an LCDR2 having no more than three amino acid additions, deletions, or substitutions from the LCDR2 sequence set forth in SEQ ID NO:117; and an LCDR3 having no more than three amino acid additions, deletions, or substitutions from the LCDR3 sequence set forth in SEQ ID NO:128; b) an LCDR1 having no more than three amino acid additions, deletions, or substitutions from the LCDR1 sequence set forth in SEQ ID NO:107; an LCDR2 having no more than three amino acid additions, deletions, or substitutions from the LCDR2 sequence set forth in SEQ ID NO:118; and an LCDR3 having no more than three amino acid additions, deletions, or substitutions from the LCDR3 sequence set forth in SEQ ID NO:129; c) an LCDR1 having no more than three amino acid additions, deletions, or substitutions from the LCDR1 sequence set forth in SEQ ID NO:108; an LCDR2 having no more than three amino acid additions, deletions, or substitutions from the LCDR2 sequence set forth in SEQ ID NO:119; and an LCDR3 having no more than three amino acid additions, deletions, or substitutions from the LCDR3 sequence set forth in SEQ ID NO:130; d) an LCDR1 having no more than three amino acid additions, deletions, or substitutions from the LCDR1 sequence set forth in SEQ ID NO:109; an LCDR2 having no more than three amino acid additions, deletions, or substitutions from the LCDR2 sequence set forth in SEQ ID NO:120; and an LCDR3 having no more than three amino acid additions, deletions, or substitutions from the LCDR3 sequence set forth in SEQ ID NO:131; e) an LCDR1 having no more than three amino acid additions, deletions, or substitutions from the LCDR1 sequence set forth in SEQ ID NO:110; an LCDR2 having no more than three amino acid additions, deletions, or substitutions from the LCDR2 sequence set forth in SEQ ID NO:121; and an LCDR3 having no more than three amino acid additions, deletions, or substitutions from the LCDR3 sequence set forth in SEQ ID NO:132; f) an LCDR1 having no more than three amino acid additions, deletions, or substitutions from the LCDR1 sequence set forth in SEQ ID NO:111; an LCDR2 having no more than three amino acid additions, deletions, or substitutions from the LCDR2 sequence set forth in SEQ ID NO:122; and an LCDR3 having no more than three amino acid additions, deletions, or substitutions from the LCDR3 sequence set forth in SEQ ID NO:133; g) an LCDR1 having no more than three amino acid additions, deletions, or substitutions from the LCDR1 sequence set forth in SEQ ID NO:112; an LCDR2 having no more than three amino acid additions, deletions, or substitutions from the LCDR2 sequence set forth in SEQ ID NO:123; and an LCDR3 having no more than three amino acid additions, deletions, or substitutions from the LCDR3 sequence set forth in SEQ ID NO:134; h) an LCDR1 having no more than three amino acid additions, deletions, or substitutions from the LCDR1 sequence set forth in SEQ ID NO:113; an LCDR2 having no more than three amino acid additions, deletions, or substitutions from the LCDR2 sequence set forth in SEQ ID NO:124; and an LCDR3 having no more than three amino acid additions, deletions, or substitutions from the LCDR3 sequence set forth in SEQ ID NO:135; i) an LCDR1 having no more than three amino acid additions, deletions, or substitutions from the LCDR1 sequence set forth in SEQ ID NO:114; an LCDR2 having no more than three amino acid additions, deletions, or substitutions from the LCDR2 sequence set forth in SEQ ID NO:125; and an LCDR3 having no more than three amino acid additions, deletions, or substitutions from the LCDR3 sequence set forth in SEQ ID NO:136; j) an LCDR1 having no more than three amino acid additions, deletions, or substitutions from the LCDR1 sequence set forth in SEQ ID NO:115; an LCDR2 having no more than three amino acid additions, deletions, or substitutions from the LCDR2 sequence set forth in SEQ ID NO:126; and an LCDR3 having no more than three amino acid additions, deletions, or substitutions from the LCDR3 sequence set forth in SEQ ID NO:137; k) an LCDR1 having no more than three amino acid additions, deletions, or substitutions from the LCDR1 sequence set forth in SEQ ID NO:116; an LCDR2 having no more than three amino acid additions, deletions, or substitutions from the LCDR2 sequence set forth in SEQ ID NO:127; and an LCDR3 having no more than three amino acid additions, deletions, or substitutions from the LCDR3 sequence set forth in SEQ ID NO:138; l) an LCDR1 having no more than three amino acid additions, deletions, or substitutions from the LCDR1 sequence set forth in SEQ ID NO:166; an LCDR2 having no more than three amino acid additions, deletions, or substitutions from the LCDR2 sequence set forth in SEQ ID NO:169; and an LCDR3 having no more than three amino acid additions, deletions, or substitutions from the LCDR3 sequence set forth in SEQ ID NO:172; m) an LCDR1 having no more than three amino acid additions, deletions, or substitutions from the LCDR1 sequence set forth in SEQ ID NO:167; an LCDR2 having no more than three amino acid additions, deletions, or substitutions from the LCDR2 sequence set forth in SEQ ID NO:170; and an LCDR3 having no more than three amino acid additions, deletions, or substitutions from the LCDR3 sequence set forth in SEQ ID NO:173; or n) an LCDR1 having no more than three amino acid additions, deletions, or substitutions from the LCDR1 sequence set forth in SEQ ID NO:168; an LCDR2 having no more than three amino acid additions, deletions, or substitutions from the LCDR2 sequence set forth in SEQ ID NO:171; and an LCDR3 having no more than three amino acid additions, deletions, or substitutions from the LCDR3 sequence set forth in SEQ ID NO:174; and a heavy chain variable domain comprising o) an HCDR1 having no more than three amino acid additions, deletions, or substitutions from the HCDR1 sequence set forth in SEQ ID NO:40; an HCDR2 having no more than three amino acid additions, deletions, or substitutions from the HCDR2 sequence set forth in SEQ ID NO:51; and an HCDR3 having no more than three amino acid additions, deletions, or substitutions from the HCDR3 sequence set forth in SEQ ID NO:62; p) an HCDR1 having no more than three amino acid additions, deletions, or substitutions from the HCDR1 sequence set forth in SEQ ID NO:41; an HCDR2 having no more than three amino acid additions, deletions, or substitutions from the HCDR2 sequence set forth in SEQ ID NO:52; and an HCDR3 having no more than three amino acid additions, deletions, or substitutions from the HCDR3 sequence set forth in SEQ ID NO:63; q) an HCDR1 having no more than three amino acid additions, deletions, or substitutions from the HCDR1 sequence set forth in SEQ ID NO:42; an HCDR2 having no more than three amino acid additions, deletions, or substitutions from the HCDR2 sequence set forth in SEQ ID NO:53; and an HCDR3 having no more than three amino acid additions, deletions, or substitutions from the HCDR3 sequence set forth in SEQ ID NO:64; r) an HCDR1 having no more than three amino acid additions, deletions, or substitutions from the HCDR1 sequence set forth in SEQ ID NO:43; an HCDR2 having no more than three amino acid additions, deletions, or substitutions from the HCDR2 sequence set forth in SEQ ID NO:54; and an HCDR3 having no more than three amino acid additions, deletions, or substitutions from the HCDR3 sequence set forth in SEQ ID NO:65; s) an HCDR1 having no more than three amino acid additions, deletions, or substitutions from the HCDR1 sequence set forth in SEQ ID NO:44; an HCDR2 having no more than three amino acid additions, deletions, or substitutions from the HCDR2 sequence set forth in SEQ ID NO:55; and an HCDR3 having no more than three amino acid additions, deletions, or substitutions from the HCDR3 sequence set forth in SEQ ID NO:66; t) an HCDR1 having no more than three amino acid additions, deletions, or substitutions from the HCDR1 sequence set forth in SEQ ID NO:45; an HCDR2 having no more than three amino acid additions, deletions, or substitutions from the HCDR2 sequence set forth in SEQ ID NO:56; and an HCDR3 having no more than three amino acid additions, deletions, or substitutions from the HCDR3 sequence set forth in SEQ ID NO:67; u) an HCDR1 having no more than three amino acid additions, deletions, or substitutions from the HCDR1 sequence set forth in SEQ ID NO:46; an HCDR2 having no more than three amino acid additions, deletions, or substitutions from the HCDR2 sequence set forth in SEQ ID NO:57; and an HCDR3 having no more than three amino acid additions, deletions, or substitutions from the HCDR3 sequence set forth in SEQ ID NO:68; v) an HCDR1 having no more than three amino acid additions, deletions, or substitutions from the HCDR1 sequence set forth in SEQ ID NO:47; an HCDR2 having no more than three amino acid additions, deletions, or substitutions from the HCDR2 sequence set forth in SEQ ID NO:58; and an HCDR3 having no more than three amino acid additions, deletions, or substitutions from the HCDR3 sequence set forth in SEQ ID NO:69; w) an HCDR1 having no more than three amino acid additions, deletions, or substitutions from the HCDR1 sequence set forth in SEQ ID NO:48; an HCDR2 having no more than three amino acid additions, deletions, or substitutions from the HCDR2 sequence set forth in SEQ ID NO:59; and an HCDR3 having no more than three amino acid additions, deletions, or substitutions from the HCDR3 sequence set forth in SEQ ID NO:70; x) an HCDR1 having no more than three amino acid additions, deletions, or substitutions from the HCDR1 sequence set forth in SEQ ID NO:49; an HCDR2 having no more than three amino acid additions, deletions, or substitutions from the HCDR2 sequence set forth in SEQ ID NO:60; and an HCDR3 having no more than three amino acid additions, deletions, or substitutions from the HCDR3 sequence set forth in SEQ ID NO:71; y) an HCDR1 having no more than three amino acid additions, deletions, or substitutions from the HCDR1 sequence set forth in SEQ ID NO:50; an HCDR2 having no more than three amino acid additions, deletions, or substitutions from the HCDR2 sequence set forth in SEQ ID NO:61; and an HCDR3 having no more than three amino acid additions, deletions, or substitutions from the HCDR3 sequence set forth in SEQ ID NO:72; z) an HCDR1 having no more than three amino acid additions, deletions, or substitutions from the HCDR1 sequence set forth in SEQ ID NO:148; an HCDR2 having no more than three amino acid additions, deletions, or substitutions from the HCDR2 sequence set forth in SEQ ID NO:151; and an HCDR3 having no more than three amino acid additions, deletions, or substitutions from the HCDR3 sequence set forth in SEQ ID NO:154; aa) an HCDR1 having no more than three amino acid additions, deletions, or substitutions from the HCDR1 sequence set forth in SEQ ID NO:149; an HCDR2 having no more than three amino acid additions, deletions, or substitutions from the HCDR2 sequence set forth in SEQ ID NO:152; and an HCDR3 having no more than three amino acid additions, deletions, or substitutions from the HCDR3 sequence set forth in SEQ ID NO:155; or bb) an HCDR1 having no more than three amino acid additions, deletions, or substitutions from the HCDR1 sequence set forth in SEQ ID NO:150; an HCDR2 having no more than three amino acid additions, deletions, or substitutions from the HCDR2 sequence set forth in SEQ ID NO:153; and an HCDR3 having no more than three amino acid additions, deletions, or substitutions from the HCDR3 sequence set forth in SEQ ID NO:156.

Preferred ST2 antigen binding proteins of third aspect include those comprising the light chain variable domain of a) and the heavy chain variable domain of o); those comprising the light chain variable domain of b) and the heavy chain variable domain of p); those comprising the light chain variable domain of c) and the heavy chain variable domain of q); those comprising the light chain variable domain of d) and the heavy chain variable domain of r); those comprising the light chain variable domain of e) and the heavy chain variable domain of s); those comprising the light chain variable domain of f) and the heavy chain variable domain of t); those comprising the light chain variable domain of g) and the heavy chain variable domain of u); those comprising the light chain variable domain of h) and the heavy chain variable domain of v); those comprising the light chain variable domain of i) and the heavy chain variable domain of w); those comprising the light chain variable domain of j) and the heavy chain variable domain of x); those comprising the light chain variable domain of k) and the heavy chain variable domain of y); those comprising the light chain variable domain of l) and the heavy chain variable domain of z); those comprising the light chain variable domain of m) and the heavy chain variable domain of aa); and those comprising the light chain variable domain of n) and the heavy chain variable domain of bb).

In a fourth aspect of the invention, the ST2 antigen binding protein of the first, second, or third aspect binds to human ST2 with an affinity of less than or equal to $1\times10^{-10}$ M.

In a fifth aspect of the invention, the ST2 antigen binding protein of the first, second, third, or fourth aspect inhibits binding of human ST2 to human IL-33.

In a sixth aspect of the invention, the ST2 antigen binding protein of the first, second, third, fourth, or fifth aspect reduces human IL-33-mediated ST2 signaling in human ST2-expressing cells.

In a seventh aspect of the invention, the ST2 antigen binding protein of the sixth aspect, reduces IL-33-mediated cynomolgus monkey ST2 signaling in cynomolgous monkey ST2-expressing cells.

In an eighth aspect of the invention, the ST2 antigen binding protein of the first, second, third, fourth, fifth, sixth or seventh aspect is an antibody, such as a human antibody. Preferred antibodies include those antibodies that comprise a light chain having the amino acid sequence set forth in SEQ ID:84 and a heavy chain having the amino acid sequence set forth in SEQ ID NO:18; those that comprise a light chain having the amino acid sequence set forth in SEQ ID:85 and a heavy chain having the amino acid sequence set forth in SEQ ID NO:19; those that comprise a light chain having the amino acid sequence set forth in SEQ ID:86 and a heavy chain having the amino acid sequence set forth in SEQ ID NO:20; those that comprise a light chain having the amino acid sequence set forth in SEQ ID:87 and a heavy chain having the amino acid sequence set forth in SEQ ID NO:21; those that comprise a light chain having the amino acid sequence set forth in SEQ ID:88 and a heavy chain having the amino acid sequence set forth in SEQ ID NO:22; those that comprise a light chain having the amino acid sequence set forth in SEQ ID:89 and a heavy chain having the amino acid sequence set forth in SEQ ID NO:23; those that comprise a light chain having the amino acid sequence set forth in SEQ ID:90 and a heavy chain having the amino acid sequence set forth in SEQ ID NO:24; those that comprise a light chain having the amino acid sequence set forth in SEQ ID:91 and a heavy chain having the amino acid sequence set forth in SEQ ID NO:25; those that comprise a light chain having the amino acid sequence set forth in SEQ ID:92 and a heavy chain having the amino acid sequence set forth in SEQ ID NO:26; those that comprise a light chain having the amino acid sequence set forth in SEQ ID:93 and a heavy chain having the amino acid sequence set forth in SEQ ID NO:27; those that comprise a light chain having the amino acid sequence set forth in SEQ ID:94 and a heavy chain having the amino acid sequence set forth in SEQ ID NO:28; those that comprise a light chain having the amino acid sequence set forth in SEQ ID:160 and a heavy chain having the amino acid sequence set forth in SEQ ID NO:142; those that comprise a light chain having the amino acid sequence set forth in SEQ ID:161 and a heavy chain having the amino acid sequence set forth in SEQ ID NO:143; and those that comprise a light chain having the amino acid sequence set forth in SEQ ID:162 and a heavy chain having the amino acid sequence set forth in SEQ ID NO:144.

In a ninth aspect, the invention provides isolated nucleic acids encoding one or more polypeptide components of a ST2 antigen binding protein, e.g., an antibody light chain or antibody heavy chain. In preferred embodiments the nucleic acid encodes a polypeptide comprising:

a) a light chain variable domain having at least 95% identity to the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165;

b) a heavy chain variable domain having at least 95% identity to the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147;

c) a light chain variable domain having no more than five amino acid additions, deletions or substitutions from the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165;

d) a heavy chain variable domain having no more than five amino acid additions, deletions or substitutions from the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147;

e) a light chain variable domain comprising:
   i) an LCDR1 having no more than three amino acid additions, deletions, or substitutions from the LCDR1 sequence set forth in SEQ ID NO:106; an LCDR2 having no more than three amino acid additions, deletions, or substitutions from the LCDR2 sequence set forth in SEQ ID NO:117; and an LCDR3 having no more than three amino acid additions, deletions, or substitutions from the LCDR3 sequence set forth in SEQ ID NO:128;
   ii) an LCDR1 having no more than three amino acid additions, deletions, or substitutions from the LCDR1 sequence set forth in SEQ ID NO:107; an LCDR2 having no more than three amino acid additions, deletions, or substitutions from the LCDR2 sequence set forth in SEQ ID NO:118; and an LCDR3 having no more than three amino acid additions, deletions, or substitutions from the LCDR3 sequence set forth in SEQ ID NO:129;
   iii) an LCDR1 having no more than three amino acid additions, deletions, or substitutions from the LCDR1 sequence set forth in SEQ ID NO:108; an LCDR2 having no more than three amino acid additions, deletions, or substitutions from the LCDR2 sequence set forth in SEQ ID NO:119; and an LCDR3 having no more than three amino acid additions, deletions, or substitutions from the LCDR3 sequence set forth in SEQ ID NO:130;
   iv) an LCDR1 having no more than three amino acid additions, deletions, or substitutions from the LCDR1 sequence set forth in SEQ ID NO:109; an LCDR2 having no more than three amino acid additions, deletions, or substitutions from the LCDR2 sequence set forth in SEQ ID NO:120; and an LCDR3 having no more than three amino acid additions, deletions, or substitutions from the LCDR3 sequence set forth in SEQ ID NO:131;
   v) an LCDR1 having no more than three amino acid additions, deletions, or substitutions from the LCDR1 sequence set forth in SEQ ID NO:110; an LCDR2 having no more than three amino acid additions, deletions, or substitutions from the LCDR2 sequence set forth in SEQ ID NO:121; and an LCDR3 having no more than three amino acid additions, deletions, or substitutions from the LCDR3 sequence set forth in SEQ ID NO:132;
   vi) an LCDR1 having no more than three amino acid additions, deletions, or substitutions from the LCDR1 sequence set forth in SEQ ID NO:111; an LCDR2 having no more than three amino acid additions, deletions, or substitutions from the LCDR2 sequence set forth in SEQ ID NO:122; and an LCDR3 having no more than three amino acid additions, deletions, or substitutions from the LCDR3 sequence set forth in SEQ ID NO:133;
   vii) an LCDR1 having no more than three amino acid additions, deletions, or substitutions from the LCDR1 sequence set forth in SEQ ID NO:112; an LCDR2 having no more than three amino acid additions, deletions, or substitutions from the LCDR2 sequence set forth in SEQ ID NO:123; and an LCDR3 having no more than three amino acid additions, deletions, or substitutions from the LCDR3 sequence set forth in SEQ ID NO:134;
   viii) an LCDR1 having no more than three amino acid additions, deletions, or substitutions from the LCDR1 sequence set forth in SEQ ID NO:113; an LCDR2 having no more than three amino acid additions, deletions, or substitutions from the LCDR2 sequence set forth in SEQ ID NO:124; and an LCDR3 having no more than three amino acid additions, deletions, or substitutions from the LCDR3 sequence set forth in SEQ ID NO:135;
   ix) an LCDR1 having no more than three amino acid additions, deletions, or substitutions from the LCDR1 sequence set forth in SEQ ID NO:114; an LCDR2 having no more than three amino acid additions, deletions, or substitutions from the LCDR2 sequence set forth in SEQ ID NO:125; and an LCDR3 having no more than three amino acid additions, deletions, or substitutions from the LCDR3 sequence set forth in SEQ ID NO:136;
   x) an LCDR1 having no more than three amino acid additions, deletions, or substitutions from the LCDR1 sequence set forth in SEQ ID NO:115; an LCDR2 having no more than three amino acid additions, deletions, or substitutions from the LCDR2 sequence set forth in SEQ ID NO:126; and an LCDR3 having no more than three amino acid additions, deletions, or substitutions from the LCDR3 sequence set forth in SEQ ID NO:137;
   xi) an LCDR1 having no more than three amino acid additions, deletions, or substitutions from the LCDR1 sequence set forth in SEQ ID NO:116; an LCDR2 having no more than three amino acid additions, deletions, or substitutions from the LCDR2 sequence set forth in SEQ ID NO:127; and an LCDR3 having no more than three amino acid additions, deletions, or substitutions from the LCDR3 sequence set forth in SEQ ID NO:138;
   xii) an LCDR1 having no more than three amino acid additions, deletions, or substitutions from the LCDR1 sequence set forth in SEQ ID NO:166; an LCDR2 having no more than three amino acid additions, deletions, or substitutions from the LCDR2 sequence set forth in SEQ ID NO:169; and an LCDR3 having no more than three amino acid additions, deletions, or substitutions from the LCDR3 sequence set forth in SEQ ID NO:172;
   xiii) an LCDR1 having no more than three amino acid additions, deletions, or substitutions from the LCDR1 sequence set forth in SEQ ID NO:167; an LCDR2 having no more than three amino acid additions, deletions, or substitutions from the LCDR2 sequence set forth in SEQ ID NO:170; and an LCDR3 having no more than three amino acid additions, deletions, or substitutions from the LCDR3 sequence set forth in SEQ ID NO:173; or
   xiv) an LCDR1 having no more than three amino acid additions, deletions, or substitutions from the LCDR1 sequence set forth in SEQ ID NO:168; an LCDR2 having no more than three amino acid additions, deletions, or substitutions from the LCDR2 sequence set forth in SEQ ID NO:171; and an LCDR3 having no more than three amino acid additions, deletions, or substitutions from the LCDR3 sequence set forth in SEQ ID NO:174; or f) a heavy chain variable domain comprising:
   i) an HCDR1 having no more than three amino acid additions, deletions, or substitutions from the HCDR1 sequence set forth in SEQ ID NO:40; an HCDR2 having no more than three amino acid additions, deletions, or substitutions from the HCDR2 sequence set forth in SEQ ID NO:51; and an HCDR3 having no more than three amino acid additions, deletions, or substitutions from the HCDR3 sequence set forth in SEQ ID NO:62;

ii) an HCDR1 having no more than three amino acid additions, deletions, or substitutions from the HCDR1 sequence set forth in SEQ ID NO:41; an HCDR2 having no more than three amino acid additions, deletions, or substitutions from the HCDR2 sequence set forth in SEQ ID NO:52; and an HCDR3 having no more than three amino acid additions, deletions, or substitutions from the HCDR3 sequence set forth in SEQ ID NO:63;

iii) an HCDR1 having no more than three amino acid additions, deletions, or substitutions from the HCDR1 sequence set forth in SEQ ID NO:42; an HCDR2 having no more than three amino acid additions, deletions, or substitutions from the HCDR2 sequence set forth in SEQ ID NO:53; and an HCDR3 having no more than three amino acid additions, deletions, or substitutions from the HCDR3 sequence set forth in SEQ ID NO:64;

iv) an HCDR1 having no more than three amino acid additions, deletions, or substitutions from the HCDR1 sequence set forth in SEQ ID NO:43; an HCDR2 having no more than three amino acid additions, deletions, or substitutions from the HCDR2 sequence set forth in SEQ ID NO:54; and an HCDR3 having no more than three amino acid additions, deletions, or substitutions from the HCDR3 sequence set forth in SEQ ID NO:65;

v) an HCDR1 having no more than three amino acid additions, deletions, or substitutions from the HCDR1 sequence set forth in SEQ ID NO:44; an HCDR2 having no more than three amino acid additions, deletions, or substitutions from the HCDR2 sequence set forth in SEQ ID NO:55; and an HCDR3 having no more than three amino acid additions, deletions, or substitutions from the HCDR3 sequence set forth in SEQ ID NO:66;

vi) an HCDR1 having no more than three amino acid additions, deletions, or substitutions from the HCDR1 sequence set forth in SEQ ID NO:45; an HCDR2 having no more than three amino acid additions, deletions, or substitutions from the HCDR2 sequence set forth in SEQ ID NO:56; and an HCDR3 having no more than three amino acid additions, deletions, or substitutions from the HCDR3 sequence set forth in SEQ ID NO:67;

vii) an HCDR1 having no more than three amino acid additions, deletions, or substitutions from the HCDR1 sequence set forth in SEQ ID NO:46; an HCDR2 having no more than three amino acid additions, deletions, or substitutions from the HCDR2 sequence set forth in SEQ ID NO:57; and an HCDR3 having no more than three amino acid additions, deletions, or substitutions from the HCDR3 sequence set forth in SEQ ID NO:68;

viii) an HCDR1 having no more than three amino acid additions, deletions, or substitutions from the HCDR1 sequence set forth in SEQ ID NO:47; an HCDR2 having no more than three amino acid additions, deletions, or substitutions from the HCDR2 sequence set forth in SEQ ID NO:58; and an HCDR3 having no more than three amino acid additions, deletions, or substitutions from the HCDR3 sequence set forth in SEQ ID NO:69;

ix) an HCDR1 having no more than three amino acid additions, deletions, or substitutions from the HCDR1 sequence set forth in SEQ ID NO:48; an HCDR2 having no more than three amino acid additions, deletions, or substitutions from the HCDR2 sequence set forth in SEQ ID NO:59; and an HCDR3 having no more than three amino acid additions, deletions, or substitutions from the HCDR3 sequence set forth in SEQ ID NO:70;

x) an HCDR1 having no more than three amino acid additions, deletions, or substitutions from the HCDR1 sequence set forth in SEQ ID NO:49; an HCDR2 having no more than three amino acid additions, deletions, or substitutions from the HCDR2 sequence set forth in SEQ ID NO:60; and an HCDR3 having no more than three amino acid additions, deletions, or substitutions from the HCDR3 sequence set forth in SEQ ID NO:71;

xi) an HCDR1 having no more than three amino acid additions, deletions, or substitutions from the HCDR1 sequence set forth in SEQ ID NO:50; an HCDR2 having no more than three amino acid additions, deletions, or substitutions from the HCDR2 sequence set forth in SEQ ID NO:61; and an HCDR3 having no more than three amino acid additions, deletions, or substitutions from the HCDR3 sequence set forth in SEQ ID NO:72;

xii) an HCDR1 having no more than three amino acid additions, deletions, or substitutions from the HCDR1 sequence set forth in SEQ ID NO:148; an HCDR2 having no more than three amino acid additions, deletions, or substitutions from the HCDR2 sequence set forth in SEQ ID NO:151; and an HCDR3 having no more than three amino acid additions, deletions, or substitutions from the HCDR3 sequence set forth in SEQ ID NO:154;

xiii) an HCDR1 having no more than three amino acid additions, deletions, or substitutions from the HCDR1 sequence set forth in SEQ ID NO:149; an HCDR2 having no more than three amino acid additions, deletions, or substitutions from the HCDR2 sequence set forth in SEQ ID NO:152; and an HCDR3 having no more than three amino acid additions, deletions, or substitutions from the HCDR3 sequence set forth in SEQ ID NO:155; or xiv) an HCDR1 having no more than three amino acid additions, deletions, or substitutions from the HCDR1 sequence set forth in SEQ ID NO:150; an HCDR2 having no more than three amino acid additions, deletions, or substitutions from the HCDR2 sequence set forth in SEQ ID NO:153; and an HCDR3 having no more than three amino acid additions, deletions, or substitutions from the HCDR3 sequence set forth in SEQ ID NO:156.

In certain embodiments of the ninth aspect, the polypeptide encodes an antibody light chain and is at least 80%, at least 90%, at least 95%, or is 100% identical to the nucleotide sequence set forth in SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:157, SEQ ID NO:158, or SEQ ID NO:159. In other embodiments of the ninth aspect, the polypeptide encodes an antibody heavy chain and is at least 80%, at least 90%, at least 95%, or is 100% identical to the nucleotide sequence set forth in SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:139, SEQ ID NO:140, or SEQ ID NO:141.

In a tenth aspect, the invention provides an expression vector comprising one or more isolated nucleic acids of the eighth aspect. In certain embodiments, the expression vector encodes an antibody light chain, an antibody heavy chain, or both an antibody light chain and a heavy chain.

In an eleventh aspect, the invention provides a recombinant host cell comprising one or more isolated nucleic acids of the ninth aspect operably linked to a promoter, including recombinant host cells comprising one or more expression vectors of the tenth aspect of the invention. In preferred embodiments, the recombinant host cell secretes an antibody that binds ST2. Preferred host cells are mammalian host cells, including CHO cell lines.

In a twelfth aspect, the invention provides methods of treating an autoimmune or inflammatory disorder said method comprising administering a therapeutically effective amount of a ST2 antigen binding protein of any one of the first, second, third, fourth, fifth, sixth, sixth, seventh, or eighth aspects to a patient in need thereof. In preferred embodiments, the ST2 antigen binding protein is an antibody comprising a light chain variable domain amino acid sequence as set forth in SEQ ID NO:95 and a heavy chain variable domain amino acid sequence as set forth in SEQ ID NO:29 (e.g., Ab1), an antibody comprising a light chain variable domain amino acid sequence as set forth in SEQ ID NO:96 and a heavy chain variable domain amino acid sequence as set forth in SEQ ID NO:30 (e.g., Ab2), an antibody comprising a light chain variable domain amino acid sequence as set forth in SEQ ID NO:97 and a heavy chain variable domain amino acid sequence as set forth in SEQ ID NO:31 (e.g., Ab3), an antibody comprising a light chain variable domain amino acid sequence as set forth in SEQ ID NO:98 and a heavy chain variable domain amino acid sequence as set forth in SEQ ID NO:32 (e.g., Ab4), an antibody comprising a light chain variable domain amino acid sequence as set forth in SEQ ID NO:99 and a heavy chain variable domain amino acid sequence as set forth in SEQ ID NO:33 (e.g., Ab5), an antibody comprising a light chain variable domain amino acid sequence as set forth in SEQ ID NO:100 and a heavy chain variable domain amino acid sequence as set forth in SEQ ID NO:34 (e.g., Ab6), an antibody comprising a light chain variable domain amino acid sequence as set forth in SEQ ID NO:101 and a heavy chain variable domain amino acid sequence as set forth in SEQ ID NO:35 (e.g., Ab7), an antibody comprising a light chain variable domain amino acid sequence as set forth in SEQ ID NO:102 and a heavy chain variable domain amino acid sequence as set forth in SEQ ID NO:36 (e.g., Ab8), an antibody comprising a light chain variable domain amino acid sequence as set forth in SEQ ID NO:103 and a heavy chain variable domain amino acid sequence as set forth in SEQ ID NO:37 (e.g., Ab9), an antibody comprising a light chain variable domain amino acid sequence as set forth in SEQ ID NO:104 and a heavy chain variable domain amino acid sequence as set forth in SEQ ID NO:38 (e.g., Ab10), an antibody comprising a light chain variable domain amino acid sequence as set forth in SEQ ID NO:105 and a heavy chain variable domain amino acid sequence as set forth in SEQ ID NO:39 (e.g., Ab11); an antibody comprising a light chain variable domain amino acid sequence as set forth in SEQ ID NO:163 and a heavy chain variable domain amino acid sequence as set forth in SEQ ID NO:145 (e.g., Ab30); an antibody comprising a light chain variable domain amino acid sequence as set forth in SEQ ID NO:164 and a heavy chain variable domain amino acid sequence as set forth in SEQ ID NO:146 (e.g., Ab32); or an antibody comprising a light chain variable domain amino acid sequence as set forth in SEQ ID NO:165 and a heavy chain variable domain amino acid sequence as set forth in SEQ ID NO:147 (e.g., Ab33). In preferred embodiments, the ST2 antigen binding protein inhibits binding of IL-33 to ST2. In particularly preferred embodiments, the autoimmune or inflammatory disorder is asthma, inflammatory bowel disease, rheumatoid arthritis, psoriasis, atopic dermatitis, fibrosis, chronic obstructive pulmonary disease, systemic lupus erythematosus, sclerosis, Wegener's granulomatosis, Behchet disease, rhinosinusitis, nasal polyposis, eosinophilic bronchitis, and cardiovascular disease.

In a thirteenth aspect, the invention provides a method of making an ST2 antigen binding protein of any one of the first, second, third, fourth, fifth, sixth, sixth, seventh, or eighth aspects by culturing a recombinant host cell of the eleventh aspect and isolating the ST2 antigen binding protein from said culture.

In a fourteenth aspect, the invention provides ST2 antigen binding proteins of any one of the first, second, third, fourth, fifth, sixth, sixth, seventh, or eighth aspects that cross-compete with an antibody selected from the group consisting of:

a) an antibody comprising a light chain comprising the amino acid sequence set forth in SEQ ID:84 and a heavy chain comprising the amino acid sequence set forth in SEQ ID NO:18;

b) an antibody comprising a light chain comprising the amino acid sequence set forth in SEQ ID:85 and a heavy chain comprising the amino acid sequence set forth in SEQ ID NO:19;

c) an antibody comprising a light chain comprising the amino acid sequence set forth in SEQ ID:86 and a heavy chain comprising the amino acid sequence set forth in SEQ ID NO:20;

d) an antibody comprising a light chain comprising the amino acid sequence set forth in SEQ ID:87 and a heavy chain comprising the amino acid sequence set forth in SEQ ID NO:21;

e) an antibody comprising a light chain comprising the amino acid sequence set forth in SEQ ID:88 and a heavy chain comprising the amino acid sequence set forth in SEQ ID NO:22;

f) an antibody comprising a light chain comprising the amino acid sequence set forth in SEQ ID:89 and a heavy chain comprising the amino acid sequence set forth in SEQ ID NO:23;

g) an antibody comprising a light chain comprising the amino acid sequence set forth in SEQ ID:90 and a heavy chain comprising the amino acid sequence set forth in SEQ ID NO:24;

h) an antibody comprising a light chain comprising the amino acid sequence set forth in SEQ ID:91 and a heavy chain comprising the amino acid sequence set forth in SEQ ID NO:25;

i) an antibody comprising a light chain comprising the amino acid sequence set forth in SEQ ID:92 and a heavy chain comprising the amino acid sequence set forth in SEQ ID NO:26;

j) an antibody comprising a light chain comprising the amino acid sequence set forth in SEQ ID:93 and a heavy chain comprising the amino acid sequence set forth in SEQ ID NO:27;

k) an antibody comprising a light chain comprising the amino acid sequence set forth in SEQ ID:94 and a heavy chain comprising the amino acid sequence set forth in SEQ ID NO:28;

l) an antibody comprising a light chain comprising the amino acid sequence set forth in SEQ ID:160 and a heavy chain comprising the amino acid sequence set forth in SEQ ID NO:142;

m) an antibody comprising a light chain comprising the amino acid sequence set forth in SEQ ID:161 and a heavy chain comprising the amino acid sequence set forth in SEQ ID NO:143; and n) an antibody comprising a light chain comprising the amino acid sequence set forth in SEQ ID:162 and a heavy chain comprising the amino acid sequence set forth in SEQ ID NO:144.

In a fifteenth aspect, the invention provides an isolated ST2 antigen binding protein, preferably an antibody or antigen binding fragment thereof, that binds a polypeptide comprising human ST2 domain 1 and domain 2 (SEQ ID NO:175), wherein binding is significantly inhibited when a single mutation is introduced into human ST2 domain 1 or domain 2 of the polypeptide, wherein the single mutation is selected from the group consisting of L14R, I15R, S33R, E43R, V47R, A62R, G65R, T79R, D92R, D97R, V104R, G138R, N152R, and V176R. By "significantly inhibited" it is meant that the measured difference in binding is statistically significant. In preferred embodiments, binding is significantly inhibited for two or more members of the group including all members of the group. In certain embodiments of the fifteenth aspect, binding also is significantly activated when a single mutation is introduced into human ST2 domain 1 or domain 2 of the polypeptide, wherein the single mutation is selected from the group consisting of L53R, R72A, and S73R. By "significantly activated" it is meant that the measured difference in binding is statistically significant. In preferred embodiments, binding is significantly activated for all members of the group. In certain embodiments of the fifteenth aspect, the ST2 binding protein cross-competes for binding to human ST2 with an antibody comprising a light chain comprising the amino acid sequence set forth in SEQ ID:85 and a heavy chain comprising the amino acid sequence set forth in SEQ ID NO:19. In particularly preferred embodiments, the antigen binding protein is an antigen binding protein of the first, second, third, fourth, fifth, sixth, seventh, or eighth aspect.

In a sixteenth aspect, the invention provides an antigen binding protein of the first, second, third, fourth, fifth, sixth, seventh, eighth, fourteenth, or fifteenth aspect wherein said ST2 binding protein preferably an antibody or antigen binding fragment thereof, binds a portion of ST2 comprising amino acids 33-44 and/or 88-94 of SEQ ID NO:1 as determined by hydrogen/deuterium exchange analysis.

In a seventeenth aspect, the invention provides an antigen binding protein preferably an antibody or antigen binding fragment thereof, of the first, second, third, fourth, fifth, sixth, seventh, eighth, fourteenth, fifteenth, or sixteenth aspect which binds to ST2 creating an interface, wherein the interface created by said binding comprises an ST2 residue selected from the group consisting of K1, F2, P19, R20, Q21, G22, K23, Y26, I70, V71, R72, S73, P74, T75, F76, N77, R78, T79, and Y81. In preferred embodiments of the seventeenth aspect, the interface created by said binding comprises ST2 residue P19, R20, Q21, G22, K23, and/or Y26, ST2 residue I70, V71, R72, S73, P74, T75, F76, N77, R78, T79, and/or Y81, or ST2 residues P19, R20, Q21, G22, K23, Y26, I70, V71, R72, S73, P74, T75, F76, N77, R78, T79, and Y81. The interface may be determined by solvent exposure difference between bound and unbound ST2 and interface residues are defined as those amino acids having a difference greater than 10% and those that form water-mediated hydrogen bonds with said antibody or determined by as those amino acids having at least one atom within 5 Å of the antibody.

In an eighteenth aspect, the invention provides an isolated ST2 antigen binding protein, preferably an antibody or antigen binding fragment thereof, comprising a) a light chain variable domain having at least 90% or at least 95% identity to the amino acid sequence set forth in SEQ ID NO:96, b) a heavy chain variable domain having at least 90% or at least 95% identity to the amino acid sequence set forth in SEQ ID NO:30; c) a light chain variable domain of a) and a heavy chain variable domain of b), d) a light chain variable domain having no more than ten or no more than five amino acid additions, deletions or substitutions from the amino acid sequence set forth SEQ ID NO:96; e) a heavy chain variable domain having no more than ten or no more than five amino acid additions, deletions or substitutions from the amino acid sequence set forth in SEQ ID NO:30; f) a light chain variable domain of d) and the heavy chain variable domain of e), g) a light chain variable domain comprising an LCDR1 having no more than three amino acid additions, deletions, or substitutions from the LCDR1 sequence set forth in SEQ ID NO:107; an LCDR2 having no more than three amino acid additions, deletions, or substitutions from the LCDR2 sequence set forth in SEQ ID NO:118; and an LCDR3 having no more than three amino acid additions, deletions, or substitutions from the LCDR3 sequence set forth in SEQ ID NO:129, h) a heavy chain variable domain comprising an HCDR1 having no more than three amino acid additions, deletions, or substitutions from the HCDR1 sequence set forth in SEQ ID NO:41; an HCDR2 having no more than three amino acid additions, deletions, or substitutions from the HCDR2 sequence set forth in SEQ ID NO:52; and an HCDR3 having no more than three amino acid additions, deletions, or substitutions from the HCDR3 sequence set forth in SEQ ID NO:63, or i) a light chain variable domain of g) and the heavy chain variable domain of h).

In preferred embodiments of the eighteenth aspect, the light chain variable region comprises D28 or a conservative substitution thereof, I29 or a conservative substitution thereof, S30 or a conservative substitution thereof, N31 or a conservative substitution thereof, Y32 or a conservative substitution thereof, Y49 or a conservative substitution thereof, D50 or a conservative substitution thereof, N53 or a conservative substitution thereof, E55 or a conservative substitution thereof, T56 or a conservative substitution thereof, D91 or a conservative substitution thereof, D92 or a conservative substitution thereof, N93 or a conservative substitution thereof, F94 or a conservative substitution thereof, or L96 or a conservative substitution thereof. In other preferred embodiments, the light chain variable region comprises D28 or a conservative substitution thereof, N31 or a conservative substitution thereof, D50 or a conservative substitution thereof, N53 or a conservative substitution thereof, E55 or a conservative substitution thereof, D91 or a conservative substitution thereof, and D92 or a conservative substitution thereof. In still other preferred embodiments, the light chain variable region comprises D28, N31, D50, N53, E55, D91, and D92.

The eighteenth aspect also includes ST2 binding proteins, preferably antibodies or antigen binding fragment thereof, wherein the heavy chain variable region comprises W33 or a conservative substitution thereof, 150 or a conservative substitution thereof, D57 or a conservative substitution thereof, R59 or a conservative substitution thereof, H99 or a conservative substitution thereof, G100 or a conservative substitution thereof, T101 or a conservative substitution thereof, S102 or a conservative substitution thereof, S103 or a conservative substitution thereof, D104 or a conservative substitution thereof, Y105 or a conservative substitution thereof, or Y106 or a conservative substitution thereof; wherein the heavy chain variable region comprises S102 or a conservative substitution thereof, S103 or a conservative substitution thereof, D104 or a conservative substitution thereof, and Y105 or a conservative substitution thereof; and wherein the heavy chain variable region comprises S102, S103, D104, and Y105.

In certain embodiments of the eighteenth aspect, the ST2 antigen binding protein specifically binds human ST2 with an affinity of less than or equal to $1 \times 10^{-10}$ M, inhibits binding of human ST2 to human IL-33, reduces human IL-33-mediated ST2 signaling in human ST2-expressing cells, inhibits binding of cynomolgus monkey ST2 to cynomolgus monkey IL-33, reduces IL-33-mediated cynomolgus monkey ST2 signaling in cynomolgus monkey ST2-expressing cells, and/or is an antibody such as a human antibody.

BRIEF DESCRIPTION OF THE DRAWINGS

FIG. 9A) Charge and surface complementarity of ST2 and Ab2 sc-dsFv. The binding interface is highlighted in circle. FIG. 9B) Left: Ab2 (grey/wheat cartoon) binds to the positive-charged patch on ST2 (surface); Right: ST2 (yellow cartoon) binds to the acidic patch of Ab2 sc-dsFv (surface). For the electrostatic potential map, red surface represents negative charge and blue surface represents positive charge.

FIG. 10 Residues within the Ab2 variable domains that form an interface with ST2 when bound to the antigen. The CDR regions are boxed. Residues within the interface are shown in bold. Residues that form hydrogen bonds or salt bridges with amino acids within ST2 are italicized.

DETAILED DESCRIPTION

Figure 1:
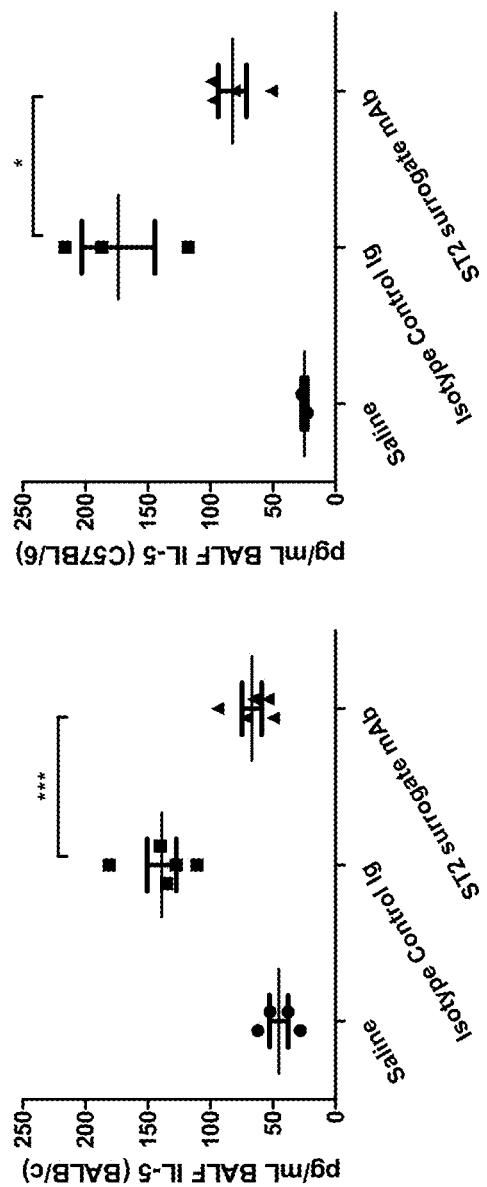
FIG. 1 ST2 mAb treatment significantly inhibited IL-33-induced IL-5 in the bronchoalveolar lavage fluid (BALF) Balb/c and C57Bl/6 mice.

The section headings used herein are for organizational purposes only and are not to be construed as limiting the subject matter described. All references cited within the body of this specification are expressly incorporated by reference in their entirety.

Standard techniques may be used for recombinant DNA, oligonucleotide synthesis, tissue culture and transformation, protein purification, etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001, *Molecular Cloning: A Laboratory Manuel*, 3$^{rd}$ ed., Cold Spring Harbor Laboratory Press, cold Spring Harbor, N.Y., which is incorporated herein by reference for any purpose. Unless specific definitions are provided, the nomenclature used in connection with, and the laboratory procedures and techniques of, analytic chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

ST2

The antigen binding proteins described herein bind to ST2. ST2 is expressed as both a soluble non-signaling variant (soluble ST2 or sST2) and a full-length membrane-spanning form (FL ST2, ST2 or ST2L). An exemplary human ST2L amino acid sequence is provided herein in Table 1. The protein is made up of several domains: Amino acids 1-18 of correspond to the leader sequence which may be cleaved during processing of the protein in mammalian cells; amino acids 19-331 correspond to the extracellular domain; amino acids 332-350 correspond to the transmembrane domain; and amino acids 351-556 correspond to the intracellular domain. In preferred embodiments, the antigen binding protein binds to the extracellular domain of ST2L and prevents the interaction of ST2 with IL-33. An exemplary human IL-33 amino acid sequence is provided in Table 1.

IL-33 signals through a heterodimeric receptor comprising ST2L and AcP. An exemplary human AcP amino acid sequence is provided in Table 1. This protein also is made up of several domains: Amino acids 1-20 correspond to the leader sequence which may be cleaved during processing of the protein in mammalian cells; amino acids 21-367 correspond to the extracellular domain; amino acids 368-388 correspond to the transmembrane domain; and amino acids 389-570 correspond to the intracellular domain. In exemplary embodiments, an ST2 antigen binding protein binds ST2L and prevents IL-33-mediated signaling in cells expressing ST2L and AcP.

TABLE 1

```
Human ST2 amino acid sequence (SEQ ID NO: 1)
MGFWILAILTILMYSTAAKFSKQSWGLENEALIVRCPRQGKPSYTVDWYY
SQTNKSIPTQERNRVFASGQLLKFLPAXVADSGIYTCIVRSPTFNRTGYA
NVTIYKKQSDCNVPDYLMYSTVSGSEKNSKIYCPTIDLYNWTAPLEWFKN
CQALQGSRYRAHKSFLVIDNVMTEDAGDYTCKFIHNENGANYSVTATRSF
TVKDEQGFSLFPVIGAPAQNEIKEVEIGKNANLTCSACFGKGTQFLAAVL
WQLNGTKITDFGEPRIQQEEGQNQSFSNGLACLDMVLRIADVKEEDLLLQ
YDCLALNLHGLRRHTVRLSRKNPIDHHISIYCIIAVCSVFLMLINVLVII
LKMFWIEATLLWRDIAKPYKTRNDGKLYDAYVVYPRNYKSSTDGASRVEH
FVHQILPDVLENKCGYTLCIYGRDMLPGEDVVTAVETNIRKSRRHIFILT
PQITHNKEFAYEQEVALHCALIQNDAKVILIEMEALSELDMLQAEALQDS
LQHLMKVQGTIKWREDHIANKRSLNSKFWKHVRYQMPVPSKIPRKASSLT
PLAAQKQ
X = E or A Human AcP amino acid sequence (SEQ ID NO: 2)
MTLLWCVVSLYFYGILQSDASERCDDWGLDTMRQIQVFEDEPARIKCPLF
EHFLKFNYSTAHSAGLTLIWYWTRQDRDLEEPINFRLPENRISKEKDVLW
FRPTLLNDTGNYTCMLRNTTYCSKVAFPLEVVQKDSCFNSPMKLPVHKLY
IEYGIQRITCPNVDGYFPSSVKPTITWYMGCYKIQNFNNVIPEGMNLSFL
IALISNNGNYTCVVTYPENGRTFHLTRTLTVKVVGSPKNAVPPVIHSPND
HVVYEKEPGEELLIPCTVYFSFLMDSRNEVWWTIDGKKPDDITIDVTINE
SISHSRTEDETRTQILSIKKVTSEDLKRSYVCHARSAKGEVAKAAKVKQK
VPAPRYTVELACGFGATVLLVVILIVVYHVYWLEMVLFYRAHFGTDETIL
DGKEYDIYVSYARNAEEEEFVLLTLRGVLENEFGYKLCIFDRDSLPGGIV
TDETLSFIQKSRRLLVVLSPNYVLQGTQALLELKAGLENMASRGNINVIL
VQYKAVKETKVKELKRAKTVLTVIKWKGEKSKYPQGRFWKQLQVAMPVKK
SPRRSSSDEQGLSYSSLKNV Human IL-33 amino acid sequence (SEQ ID NO: 3)
MKPKMKYSTNKISTAKWKNTASKALCFKLGKSQQKAKEVCPMYFMKLRSG
LMIKKEACYFRRETTKRPSLKTGRKHKRHLVLAACQQQSTVECFAFGISG
VQKYTRALHDSSITGISPITEYLASLSTYNDQSITFALEDESYEIYVEDL
KKDEKKDKVLLSYYESQHPSNESGDGVDGKMLMVTLSPTKDFWLHANNKE
HSVELHKCEKPLPDQAFFVLHNMHSNCVSFECKTDPGVFIGVKDNHLALI
KVDSSENLCTENILFKLSET
```

Exemplary embodiments of the present invention bind both human and cynomolgus monkey ST2 with high affinity, including those that bind with high affinity and block interaction of cynomolgus monkey IL-33 to cynomolgus monkey ST2. These characteristics allow informative toxicology studies in non-human primates.

An exemplary amino acid sequence of cynomolgus monkey ST2L is provided in Table 2. The protein is made up of several domains: amino acids 1-18 of correspond to the leader sequence which may be cleaved during processing of the protein in mammalian cells; amino acids 19-331 correspond to the extracellular domain; amino acids 332-350 correspond to the transmembrane domain; and amino acids 351-556 correspond to the intracellular domain.

An exemplary amino acid sequences of cynomolgus monkey AcP is provided in Table 2. The protein is made up of several domains: amino acids 1-20 of correspond to the leader sequence which may be cleaved during processing of the protein in mammalian cells; amino acids 21-367 correspond to the extracellular domain; amino acids 368-388 correspond to the transmembrane domain; and amino acids 389-570 correspond to the intracellular domain.

An exemplary amino acid sequence of cynomolgus monkey IL-33 is provided in Table 2.

TABLE 2

```
Cynomolgus monkey ST2 amino acid sequence (SEQ ID NO: 4)
MGLWILAILTILVYSTAAKFSKQSWGLENEALIVRCPRQGKSSYIVDWYY
SQTNKSIPTQERNRVFASGQLLKFLPAEVADSGIYTCIVRSPTFNRTGYA
NVTIYKKQPDCNVPDYLMYSTVSGSEKNSKIYCPTIDLYNWTAPLEWFKN
CQALQGSRYKAHKSFLVIDNVMTDDAGDYTCKFIHNENGANYSVTATRSF
TVKDEQGFSRFPVIRAPAHNETKEVEIGENTNLTCSACFGKGAQFLATVQ
WQLNGNKITDFSEPRIQQEEGQNQSFSNGLACVNTVLRIADVKEEDLLLR
YDCLALNLHGLRRHTIRLSRKNPIDHQSTYCIIAVCSVLLMLINILVIIL
KTFWIEATLLWRDIAKPYKTRNDGKLYDAYVIYPRNYTSSADGASRVEYF
VHQILPDVLENKCGYTLCIYGRDMLPGEDVVTAVETNIRKSRRHIFILTP
QITHSEEFAYEQEVALHSALIQNDSKVILIEMEALSELDMLQAEALQDSL
RHLMEVQGTIKWREDHVANKRSLNSKFWKHVRYQMPVPSKMPRKASSLTS
LAAQKQ Cynomolgus monkey AcP amino acid sequence (SEQ ID NO: 5)
MTLLWCVVSLYFYGILQSDASERCDDWGLDTMRQIQVFEDEPARIKCPLF
EHFLKFNYSTAHSAGLTLIWYWTRQDRDLEEPINFRLPENRISKEKDVLW
FRPTLLNDTGNYTCMLRNTTYCSKVAFPLEVVQKDSCFNSPMKLPVHKLY
IEYGIQRITCPNVDGYFPSSVKPTITWYMGCYKIQNFNNVIPEGMNLSFL
IAFISNNGNYTCVVTYPENGRTFHLTRTLTVKVVGSPKNAVPPVIHSPND
HVVYEKEPGEELLIPCTVYFSFLMDSRNEVWWTIDGKKPDDIPIDVTINE
SISHSRTEDETRTQILSIKKVTSEDLKRSYVCHARSAKGEVAKAATVKQK
VPAPRYTVELACGFGATVLLVVILIVVYHVYWLEMVLFYRAHFGTDETIL
DGKEYDIYVSYARNAEEEEFVLLTLRGVLENEFGYKLCIFDRDSLPGGIV
TDETLSFIQKSRRLLVVLSPNYVLQGTQALLELKAGLENMASQGNINVIL
VQYKAVKETKVKELKRAKTVLTVIKWKGEKSKYPQGRFWKQLQVANIPVK
KSPRRSSSDEQGLSYSSLKNV Cynomolgus monkey IL-33 amino acid sequence (SEQ ID NO: 6)
MKPKMKYSTNKISTAKRKNTASKALCFKLGKSQQKAKEVCHVYFMKLRSG
LMIKKEACYFRRETTKRPSLKTGGKHKGHLVLAACQQQSTVECFAFGISG
VPKYTRALHDSSITGISPITESLASLSTYNDQSITFALEDESYEIYVEDL
KKDKKKDKVLLSYYESQHPSSESGDGVDGKMLMVTLSPTKDFWLQANNKE
HSVELHKCEKPLPDQAFFVLHNRSFNCVSFECKTDPGVFIGVKDNHLALI
KVDHSENLGSENILFKLSEI
```

ST2 Antigen Binding Proteins

The present invention provides antigen binding proteins that specifically bind ST2. Embodiments of antigen binding proteins comprise peptides and/or polypeptides that specifically bind ST2. Such peptides or polypeptides may optionally include one or more port-translational modifications. Embodiments of antigen binding proteins include antibodies and fragments thereof, as variously defined herein, that specifically bind ST2. These include antibodies that specifically bind human ST2, including those that inhibit IL-33 from binding and/or activating ST2.

The antigen binding proteins of the invention specifically bind to ST2. "Specifically binds" as used herein means that the antigen binding protein preferentially binds ST2 over other proteins. In some embodiments "specifically binds" means the ST2 antigen binding protein has a higher affinity for ST2 than for other proteins. ST2 antigen binding proteins that specifically bind ST2 may have a binding affinity for human ST2 of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6 \times 10^{-7}$ M, less than or equal to $7 \times 10^{-7}$ M, less than or equal to $8 \times 10^{-7}$ M, less than or equal to $9 \times 10^{-7}$ M, less than or equal to $1 \times 10^{-8}$ M, less than or equal to $2 \times 10^{-8}$ M, less than or equal to $3 \times 10^{-8}$ M, less than or equal to $4 \times 10^{-8}$ M, less than or equal to $5 \times 10^{-8}$ M, less than or equal to $6 \times 10^{-8}$ M, less than or equal to $7 \times 10^{-8}$ M, less than or equal to $8 \times 10^{-8}$ M, less than or equal to $9 \times 10^{-8}$ M, less than or equal to $1 \times 10^{-9}$ M, less than or equal to $2 \times 10^{-9}$ M, less than or equal to $3 \times 10^{-9}$ M, less than or equal to $4 \times 10^{-9}$ M, less than or equal to $5 \times 10^{-9}$ M, less than or equal to $6 \times 10^{-9}$ M, less than or equal to $7 \times 10^{-9}$ M, less than or equal to $8 \times 10^{-9}$ M, less than or equal to $9 \times 10^{-9}$ M, less than or equal to $1 \times 10^{-10}$ M, less than or equal to $2 \times 10^{-10}$ M, less than or equal to $3\times10^{-10}$ M, less than or equal to $4\times10^{-10}$ M, less than or equal to $5\times10^{-10}$ M, less than or equal to $6\times10^{-10}$ M, less than or equal to $7\times10^{-10}$ M, less than or equal to $8\times10^{-10}$ M, less than or equal to $9\times10^{-10}$ M, less than or equal to $1\times10^{-11}$ M, less than or equal to $2\times10^{-11}$ M, less than or equal to $3\times10^{-11}$M, less than or equal to $4\times10^{-11}$ M, less than or equal to $5\times10^{-11}$ M, less than or equal to $6\times10^{-11}$M, less than or equal to $7\times10^{-11}$ M, less than or equal to $8\times10^{-11}$ M, less than or equal to $9\times10^{-11}$M, less than or equal to $1\times10^{-12}$ M, less than or equal to $2\times10^{-12}$ M, less than or equal to $3\times10^{-12}$M, less than or equal to $4\times10^{-12}$ M, less than or equal to $5\times10^{-12}$ M, less than or equal to $6\times10^{-12}$M, less than or equal to $7\times10^{-12}$ M, less than or equal to $8\times10^{-12}$M, or less than or equal to $9\times10^{-12}$M.

Methods of measuring the binding affinity of an antigen binding protein are well known in the art. Methods in common use for affinity determination include Surface Plasmon Resonance (SPR) (Morton and Myszka "Kinetic analysis of macromolecular interactions using surface plasmon resonance biosensors" *Methods in Enzymology* (1998) 295, 268-294), Bio-Layer interferometry, (Abdiche et al "Determining Kinetics and Affinities of Protein Interactions Using a Parallel Real-time Label-free Biosensor, the Octet" *Analytical Biochemistry* (2008) 377, 209-217), Kinetic Exclusion Assay (KinExA) (Darling and Brault "Kinetic exclusion assay technology: characterization of molecular interactions" *Assay and Drug Dev Tech* (2004) 2, 647-657), isothermal calorimetry (Pierce et al "Isothermal Titration Calorimetry of Protein-Protein Interactions" *Methods* (1999) 19, 213-221) and analytical ultracentrifugation (Lebowitz et al "Modern analytical ultracentrifugation in protein science: A tutorial review" *Protein Science* (2002), 11:2067-2079). Example 3 provides exemplary methods.

It is understood that when reference is made to the various embodiments of the ST2-binding antibodies herein, that it also encompasses ST2-binding fragments thereof. An ST2-binding fragment comprises any of the antibody fragments or domains described herein that retains the ability to specifically bind to ST2. The ST2-binding fragment may be in any of the scaffolds described herein.

In certain therapeutic embodiments, an ST2 antigen binding protein inhibits binding of ST2 to IL-33 and/or inhibits one or more biological activities associated with the binding of ST2 to IL-33, e.g., IL-33-mediated signaling. Such antigen binding proteins are said to be "neutralizing." In certain embodiments, the neutralizing ST2 antigen binding protein specifically binds ST2 and inhibits binding of ST2 to IL-33 from anywhere between 10% to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more. For example, ST2 antigen binding proteins may be tested for neutralizing ability by determining the ability of the antigen binding protein to block binding of IL-33 to ST2 or IL-33 to co-receptors ST2 and AcP, see, e.g., the IL-33 blocking assays of Example 6. Alternatively, ST2 antigen binding proteins may be tested for neutralizing ability in an assay that measures the effect of the presence of the ST2 antigen binding protein in an assay measuring an IL-33 mediated biological function. For example, the ability of IL-33 to induce a biological response, such as intracellular signaling or increased mRNA expression of mediators or secretion of mediators such as cytokines and chemokines from cells such as eosinophils, T cells, mast cells, NK cells, NKT cells, neutrophils, or innate helper cells. Alternatively, the ability of IL-33 to promote the differentiation, proliferation, survival, chemotaxis, shape change or adhesive properties of cells such as eosinophils, basophils, T cells, mast cells, NK cells, NKT cells, neutrophils, or innate helper cells. Alternatively, the ability of IL-33 to induce cell surface expression of certain markers of cell activation, such as CD11b, on cells such as eosinophils, basophils, T cells, mast cells, NK cells, NKT cells, neutrophils, or innate helper cells. Exemplary methods are provided in Examples 7-10.

Embodiments of antigen binding proteins comprise a scaffold structure, as variously defined herein, with one or more complementarity determining regions (CDRs). Embodiments further include antigen binding proteins comprising a scaffold structure with one or more antibody variable domains, either heavy or light. Embodiments include antibodies that comprise a light chain variable domain selected from the group consisting of Ab1 Light Chain Variable Domain (LCv), Ab2 LCv, Ab3 LCv, Ab4 LCv, Ab5 LCv, Ab6 LCv, Ab7 LCv, Ab8 LCv, Ab9 LCv, Ab10LCv, Ab11 LCv, Ab30 LCv, Ab32 LCv, and Ab33 LCv (SEQ ID NO:95-105, 163-165, respectively) and/or a heavy chain variable domain selected from the group consisting of Ab1 Heavy Chain Variable Domain (HCv), Ab2 HCv, Ab3 HCv, Ab4 HCv, Ab5 HCv, Ab6 HCv, Ab7 HCv, Ab8 HCv, Ab9 HCv, Ab10 HCv, Ab11HCv, Ab30HCv, Ab32HCv, and Ab33HCv (SEQ ID NO:29-39, 145-147, respectively), and fragments, derivatives, muteins, and variants thereof.

An exemplary light chain comprising Ab1 LCv is a light chain comprising the amino acid sequence set forth in SEQ ID NO:84.

An exemplary light chain comprising Ab2 LCv is a light chain comprising the amino acid sequence set forth in SEQ ID NO:85.

An exemplary light chain comprising Ab3 LCv is a light chain comprising the amino acid sequence set forth in SEQ ID NO:86.

An exemplary light chain comprising Ab4 LCv is a light chain comprising the amino acid sequence set forth in SEQ ID NO:87.

An exemplary light chain comprising Ab5 LCv is a light chain comprising the amino acid sequence set forth in SEQ ID NO:88.

An exemplary light chain comprising Ab6 LCv is a light chain comprising the amino acid sequence set forth in SEQ ID NO:89.

An exemplary light chain comprising Ab7 LCv is a light chain comprising the amino acid sequence set forth in SEQ ID NO:90.

An exemplary light chain comprising Ab8 LCv is a light chain comprising the amino acid sequence set forth in SEQ ID NO:91.

An exemplary light chain comprising Ab9 LCv is a light chain comprising the amino acid sequence set forth in SEQ ID NO:92.

An exemplary light chain comprising Ab10 LCv is a light chain comprising the amino acid sequence set forth in SEQ ID NO:93.

An exemplary light chain comprising Ab11 LCv is a light chain comprising the amino acid sequence set forth in SEQ ID NO:94.

An exemplary light chain comprising Ab30 LCv is a light chain comprising the amino acid sequence set forth in SEQ ID NO:160.

An exemplary light chain comprising Ab32 LCv is a light chain comprising the amino acid sequence set forth in SEQ ID NO:161.

An exemplary light chain comprising Ab33 LCv is a light chain comprising the amino acid sequence set forth in SEQ ID NO:162.

An exemplary heavy chain comprising Ab1 HCv is a heavy chain comprising the amino acid sequence set forth in SEQ ID NO:18.

An exemplary heavy chain comprising Ab2 HCv is a heavy chain comprising the amino acid sequence set forth in SEQ ID NO:19.

An exemplary heavy chain comprising Ab3 HCv is a heavy chain comprising the amino acid sequence set forth in SEQ ID NO:20.

An exemplary heavy chain comprising Ab4 HCv is a heavy chain comprising the amino acid sequence set forth in SEQ ID NO:21.

An exemplary heavy chain comprising Ab5 HCv is a heavy chain comprising the amino acid sequence set forth in SEQ ID NO:22.

An exemplary heavy chain comprising Ab6 HCv is a heavy chain comprising the amino acid sequence set forth in SEQ ID NO:23.

An exemplary heavy chain comprising Ab7 HCv is a heavy chain comprising the amino acid sequence set forth in SEQ ID NO:24.

An exemplary heavy chain comprising Ab8 HCv is a heavy chain comprising the amino acid sequence set forth in SEQ ID NO:25.

An exemplary heavy chain comprising Ab9 HCv is a heavy chain comprising the amino acid sequence set forth in SEQ ID NO:26.

An exemplary heavy chain comprising Ab10 HCv is a heavy chain comprising the amino acid sequence set forth in SEQ ID NO:27.

An exemplary heavy chain comprising Ab11 HCv is a heavy chain comprising the amino acid sequence set forth in SEQ ID NO:28.

An exemplary heavy chain comprising Ab30 HCv is a heavy chain comprising the amino acid sequence set forth in SEQ ID NO:142.

An exemplary heavy chain comprising Ab32 HCv is a heavy chain comprising the amino acid sequence set forth in SEQ ID NO:143.

An exemplary heavy chain comprising Ab33 HCv is a heavy chain comprising the amino acid sequence set forth in SEQ ID NO:144.

Additional examples of scaffolds that are envisioned include: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDZ domains, TEM-1 beta-lactamase, thioredoxin, staphylococcal nuclease, PHD-finger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and or C-type lectin-like domains. Non-antibody scaffolds and their use as therapeutics are reviewed in Gebauer and Skerra, *Curr. Opin. Chem. Biol.*, 13:245-255 (2009) and Binz et al., Nat. Biotech., 23(10): 1257-1268 (2005), which are incorporated herein by reference in its entirety.

Aspects of the invention include antibodies comprising the following variable domains: Ab1 LCv/Ab1 HCv (SEQ ID NO:95/SEQ ID NO:29), Ab2 LCv/Ab2 HCv (SEQ ID NO:96/SEQ ID NO:30), Ab3 LCv/Ab3 HCv (SEQ ID NO:97/SEQ ID NO:31), Ab4 LCv/Ab4 HCv (SEQ ID NO:98/SEQ ID NO:32), Ab5 LCv/Ab5 HCv (SEQ ID NO:99/SEQ ID NO:33), Ab6 LCv/Ab6 HCv (SEQ ID NO:100/SEQ ID NO:34), Ab7 LCv/Ab7 HCv (SEQ ID NO:101/SEQ ID NO:35), Ab8 LCv/Ab8 HCv (SEQ ID NO:102/SEQ ID NO:36), Ab9 LCv/Ab9 HCv (SEQ ID NO:103/SEQ ID NO:37), Ab10 LCv/Ab10 HCv (SEQ ID NO:104/SEQ ID NO:38), Ab11 LCv/Ab11 HCv (SEQ ID NO:105/SEQ ID NO:39), Ab30 LCv/Ab30 HCv (SEQ ID NO:163/SEQ ID NO:145), Ab32 LCv/Ab32 HCv (SEQ ID NO:164/SEQ ID NO:146), Ab33 LCv/Ab33 HCv (SEQ ID NO:165/SEQ ID NO:147), and combinations thereof, as well as fragments, derivatives, muteins and variants thereof.

Exemplary antibodies of the invention include Ab1 (SEQ ID NO:84/SEQ ID NO:18), Ab2 (SEQ ID NO:85/SEQ ID NO:19), Ab3 (SEQ ID NO:86/SEQ ID NO:20), Ab4 (SEQ ID NO:87/SEQ ID NO:21), Ab5 (SEQ ID NO:88/SEQ ID NO:22), Ab6 (SEQ ID NO:89/SEQ ID NO:23), Ab7 (SEQ ID NO:90/SEQ ID NO:24), Ab8 (SEQ ID NO:91/SEQ ID NO:25), Ab9 (SEQ ID NO:92/SEQ ID NO:26), Ab10 (SEQ ID NO:93/SEQ ID NO:27), Ab11 (SEQ ID NO:94/SEQ ID NO:28), Ab30 (SEQ ID NO:160/SEQ ID NO:142), Ab32 (SEQ ID NO:161/SEQ ID NO:143), and Ab33 (SEQ ID NO:162/SEQ ID NO:144).

Typically, each variable domain of an antibody light or heavy chain comprises three CDRs. The heavy chain variable domain comprises a heavy chain CDR1 (HCDR1), a heavy chain CDR2 (HCDR2), and a heavy chain CDR3 (HCDR3). The light chain variable domain comprises a light chain CDR1 (LCDR1), a light chain CDR2 (LCDR2), and a light chain CDR3 (LCDR3). In certain embodiments, an antigen binding protein comprises one or more CDRs contained within the preferred variable domains described herein.

Examples of such CDRs include, but are not limited to:
the CDRs of Ab1 LCv: LCDR1 (SEQ ID NO:106), LCDR2 (SEQ ID NO:117), and LCDR3 (SEQ ID NO:128);
the CDRs of Ab2 LCv: LCDR1 (SEQ ID NO:107), LCDR2 (SEQ ID NO:118), and LCDR3 (SEQ ID NO:129);
the CDRs of Ab3 LCv: LCDR1 (SEQ ID NO:108), LCDR2 (SEQ ID NO:119), and LCDR3 (SEQ ID NO:130);
the CDRs of Ab4 LCv: LCDR1 (SEQ ID NO:109), LCDR2 (SEQ ID NO:120), and LCDR3 (SEQ ID NO:131);
the CDRs of Ab5 LCv: LCDR1 (SEQ ID NO:110), LCDR2 (SEQ ID NO:121), and LCDR3 (SEQ ID NO:132);
the CDRs of Ab6 LCv: LCDR1 (SEQ ID NO:111), LCDR2 (SEQ ID NO:122), and LCDR3 (SEQ ID NO:133);
the CDRs of Ab7 LCv: LCDR1 (SEQ ID NO:112), LCDR2 (SEQ ID NO:123), and LCDR3 (SEQ ID NO:134);
the CDRs of Ab8 LCv: LCDR1 (SEQ ID NO:113), LCDR2 (SEQ ID NO:124), and LCDR3 (SEQ ID NO:135);
the CDRs of Ab9 LCv: LCDR1 (SEQ ID NO:114), LCDR2 (SEQ ID NO:125), and LCDR3 (SEQ ID NO:136);
the CDRs of Ab10 LCv: LCDR1 (SEQ ID NO:115), LCDR2 (SEQ ID NO:126), and LCDR3 (SEQ ID NO:137);
the CDRs of Ab11 LCv: LCDR1 (SEQ ID NO:116), LCDR2 (SEQ ID NO:127), and LCDR3 (SEQ ID NO:138);
the CDRs of Ab30 LCv: LCDR1 (SEQ ID NO:166), LCDR2 (SEQ ID NO:169), and LCDR3 (SEQ ID NO:172);
the CDRs of Ab32 LCv: LCDR1 (SEQ ID NO:167), LCDR2 (SEQ ID NO:170), and LCDR3 (SEQ ID NO:173);
the CDRs of Ab33 LCv: LCDR1 (SEQ ID NO:168), LCDR2 (SEQ ID NO:171), and LCDR3 (SEQ ID NO:174);
the CDRs of Ab1 HCv: HCDR1 (SEQ ID NO:40), HCDR2 (SEQ ID NO:51), and HCDR3 (SEQ ID NO:62);
the CDRs of Ab2 HCv: HCDR1 (SEQ ID NO:41), HCDR2 (SEQ ID NO:52), and HCDR3 (SEQ ID NO:63);
the CDRs of Ab3 HCv: HCDR1 (SEQ ID NO:42), HCDR2 (SEQ ID NO:53), and HCDR3 (SEQ ID NO:64);

the CDRs of Ab4 HCv: HCDR1 (SEQ ID NO:43), HCDR2 (SEQ ID NO:54), and HCDR3 (SEQ ID NO:65);

the CDRs of Ab5 HCv: HCDR1 (SEQ ID NO:44), HCDR2 (SEQ ID NO:55), and HCDR3 (SEQ ID NO:66);

the CDRs of Ab6 HCv: HCDR1 (SEQ ID NO:45), HCDR2 (SEQ ID NO:56), and HCDR3 (SEQ ID NO:67);

the CDRs of Ab7 HCv: HCDR1 (SEQ ID NO:46), HCDR2 (SEQ ID NO:57), and HCDR3 (SEQ ID NO:68);

the CDRs of Ab8 HCv: HCDR1 (SEQ ID NO:47), HCDR2 (SEQ ID NO:58), and HCDR3 (SEQ ID NO:69);

the CDRs of Ab9 HCv: HCDR1 (SEQ ID NO:48), HCDR2 (SEQ ID NO:59), and HCDR3 (SEQ ID NO:70);

the CDRs of Ab10 HCv: HCDR1 (SEQ ID NO:49), HCDR2 (SEQ ID NO:60), and HCDR3 (SEQ ID NO:71);

the CDRs of Ab11 HCv: HCDR1 (SEQ ID NO:50), HCDR2 (SEQ ID NO:61), and HCDR3 (SEQ ID NO:72);

the CDRs of Ab30 HCv: HCDR1 (SEQ ID NO:148), HCDR2 (SEQ ID NO:151), and HCDR3 (SEQ ID NO:154);

the CDRs of Ab32 HCv: HCDR1 (SEQ ID NO:149), HCDR2 (SEQ ID NO:152), and HCDR3 (SEQ ID NO:155); and the CDRs of Ab33 HCv: HCDR1 (SEQ ID NO:150), HCDR2 (SEQ ID NO:153), and HCDR3 (SEQ ID NO:156).

In some embodiments, the antigen binding protein comprises: A) a polypeptide, e.g., a light chain, that comprises an LCDR1 having an amino acid sequence selected from the group consisting of SEQ ID NOS:106, 107, 108, 109, 110, 111, 112, 113, 114, 115, 116, 166, 167, and 168; an LCDR2 having an amino acid sequence selected from the group consisting of SEQ ID NOS:117, 118, 119, 120, 121, 122, 123, 124, 125, 126, 127, 169, 170, and 171; and/or an LCDR3 having an amino acid sequence selected from the group consisting of SEQ ID NOS:128, 129, 130, 131, 132, 133, 134, 135, 136, 137, 138, 172, 173, and 174; and/or B) a polypeptide, e.g., a heavy chain, that comprises an HCDR1 having an amino acid sequence selected from the group consisting of SEQ ID NOS:40, 41, 42, 43, 44, 45, 46, 47, 48, 49, 50, 148, 149, and 150; an HCDR2 having an amino acid sequence selected from the group consisting of SEQ ID NOS:51, 52, 53, 54, 55, 56, 57, 58, 59, 60, 61, 151, 152, and 153; and/or an HCDR3 having an amino acid sequence selected from the group consisting of SEQ ID NOS:62, 63, 64, 65, 66, 67, 68, 69, 70, 71, 72, 154, 155, and 156.

In further embodiments, the antigen binding protein comprise A) a light chain amino acid sequence that comprises a LCDR1, LCDR2, and LCDR3 of any of Ab1 LCv, Ab2 LCv, Ab3 LCv, Ab4 LCv, Ab5 LCv, Ab6 LCv, Ab7 LCv, Ab8 LCv, Ab9 LCv, Ab10 LCv, Ab11 LCv, Ab30 LCv, Ab32 LCv, and Ab33 LCv and B) a heavy chain amino acid sequence that comprises a HCDR1, HCDR2, and HCDR3 of any of Ab1 HCv, Ab2 HCv, Ab3 HCv, Ab4 HCv, Ab5 HCv, Ab6 HCv, Ab7 HCv, Ab8 HCv, Ab9 HCv, Ab10 HCv, Ab11 HCv, Ab30 HCv, Ab32 HCv, and Ab33 HCv.

In certain embodiments, the CDRs include no more than one, no more than two, no more than three, no more than four, no more than five, or no more than six amino acid additions, deletions, or substitutions from an exemplary CDR set forth herein.

Aspects of the invention include antibodies comprising a light chain variable domain selected from the group consisting of SEQ ID NOS:95, 96, 97, 98, 99, 100, 101, 102, 103, 104, 105, 163, 164, and 165. Aspects of the invention include antibodies comprising a heavy chain variable domain selected from the group consisting of SEQ ID NOS:29, 30, 31, 32, 33, 34, 35, 36, 37, 38, 39, 145, 146, and 147. Further aspects of the invention include antibodies comprising A) a light chain variable domain selected from the group consisting of SEQ ID NOS: 95, 96, 97, 98, 99, 100, 101, 102, 103, 104, 105, 163, 164, and 165, and B) a heavy chain variable domain selected from the group consisting of SEQ ID NOS: 29, 30, 31, 32, 33, 34, 35, 36, 37, 38, 39, 145, 146, and 147.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant region, e.g., a human alpha-, delta-, epsilon-, gamma-, or mu-type heavy chain constant region. In one embodiment the light or heavy chain constant region is a fragment, derivative, variant, or mutein of a naturally occurring constant region.

Aspects of the invention include antibodies comprising a light chain variable region selected from the group consisting of SEQ ID NOS: 95, 96, 97, 98, 99, 100, 101, 102, 103, 104, 105, 163, 164, and 165 having no more than one, no more than two, no more than three, no more than four, no more than five, no more than six, no more than seven, no more than eight, no more than nine, or no more than ten amino acid additions, deletions, or substitutions. Aspects of the invention include antibodies comprising a heavy chain variable region selected from the group consisting of SEQ ID NOS: 29, 30, 31, 32, 33, 34, 35, 36, 37, 38, 39, 145, 146, and 147 having no more than one, no more than two, no more than three, no more than four, no more than five, no more than six, no more than seven, no more than eight, no more than nine, or no more than ten amino acid additions, deletions, or substitutions. Further aspects of the invention include antibodies comprising A) comprising a light chain variable region selected from the group consisting of SEQ ID NOS: 95, 96, 97, 98, 99, 100, 101, 102, 103, 104, 105, 163, 164, and 165 having no more than one, no more than two, no more than three, no more than four, no more than five, no more than six, no more than seven, no more than eight, no more than nine, or no more than ten amino acid additions, deletions, or substitutions, and B) a heavy chain variable region selected from the group consisting of SEQ ID NOS: 29, 30, 31, 32, 33, 34, 35, 36, 37, 38, 39, 145, 146, and 147 having no more than one, no more than two, no more than three, no more than four, no more than five, no more than six, no more than seven, no more than eight, no more than nine, or no more than ten amino acid additions, deletions, or substitutions.

In one variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain variable region amino acid sequence selected from the group consisting of SEQ ID NOS: 95, 96, 97, 98, 99, 100, 101, 102, 103, 104, 105, 163, 164, and 165. In another variation, the antigen binding protein comprises an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain variable region amino acid sequence selected from the group consisting of SEQ ID NOS: 29, 30, 31, 32, 33, 34, 35, 36, 37, 38, 39, 145, 146, and 147. In yet a further embodiment, the antigen binding protein comprises A) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a light chain variable region amino acid sequence selected from the group consisting of SEQ ID NOS: 95, 96, 97, 98, 99, 100, 101, 102, 103, 104, 105, 163, 164, and 165, and B) an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a heavy chain variable region amino acid sequence selected from the group consisting of SEQ ID NOS: 29, 30, 31, 32, 33, 34, 35, 36, 37, 38, 39, 145, 146, and 147.

In certain embodiments, the antigen binding protein comprises a light chain and/or heavy chain CDR3. In some embodiments, the antigen binding protein comprises an amino acid sequence selected from the group of sequences set forth in SEQ ID NOS:128, 129, 130, 131, 132, 133, 134, 135, 136, 137, 138, 172, 173, 174, 62, 63, 64, 65, 66, 67, 68, 69, 70, 71, 72, 154, 155, and 156. In certain embodiments, the amino acid sequence includes no more than one, no more than two, no more than three, no more than four, no more than five, or no more than six amino acid additions, deletions, or substitutions from the exemplary sequence set forth in SEQ ID NOS: 128, 129, 130, 131, 132, 133, 134, 135, 136, 137, 138, 172, 173, 174, 62, 63, 64, 65, 66, 67, 68, 69, 70, 71, 72, 154, 155, and 156. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS: 128, 129, 130, 131, 132, 133, 134, 135, 136, 137, 138, 172, 173, 174, 62, 63, 64, 65, 66, 67, 68, 69, 70, 71, 72, 154, 155, and 156.

In certain embodiments, the antigen binding protein comprises a light chain and/or heavy chain CDR2. In some embodiments, the antigen binding protein comprises an amino acid sequence selected from the group of sequences set forth in SEQ ID NOS:117, 118, 119, 120, 121, 122, 123, 124, 125, 126, 127, 169, 170, 171, 51, 52, 53, 54, 55, 56, 57, 58, 59, 60, 61, 151, 152, and 153. In certain embodiments, the amino acid sequence includes no more than one, no more than two, no more than three, no more than four, no more than five, or no more than six amino acid additions, deletions, or substitutions from the exemplary sequence set forth in SEQ ID NOS: 117, 118, 119, 120, 121, 122, 123, 124, 125, 126, 127, 169, 170, 171, 51, 52, 53, 54, 55, 56, 57, 58, 59, 60, 61, 151, 152, and 153. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS: 117, 118, 119, 120, 121, 122, 123, 124, 125, 126, 127, 169, 170, 171, 51, 52, 53, 54, 55, 56, 57, 58, 59, 60, 61, 151, 152, and 153.

In certain embodiments, the antigen binding protein comprises a light chain and/or heavy chain CDR1. In some embodiments, the antigen binding protein comprises an amino acid sequence selected from the group of sequences set forth in SEQ ID NOS:106, 107, 108, 109, 110, 111, 112, 113, 114, 115, 116, 166, 167, 168, 40, 41, 42, 43, 44, 45, 46, 47, 48, 49, 50, 148, 149, and 150. In certain embodiments, the amino acid sequence includes no more than one, no more than two, no more than three, no more than four, no more than five, or no more than six amino acid additions, deletions, or substitutions from the exemplary sequence set forth in SEQ ID NOS: 106, 107, 108, 109, 110, 111, 112, 113, 114, 115, 116, 166, 167, 168, 40, 41, 42, 43, 44, 45, 46, 47, 48, 49, 50, 148, 149, and 150. Thus, embodiments of the invention include antigen binding protein comprising an amino acid sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group of sequences set forth in SEQ ID NOS: 106, 107, 108, 109, 110, 111, 112, 113, 114, 115, 116, 166, 167, 168, 40, 41, 42, 43, 44, 45, 46, 47, 48, 49, 50, 148, 149, and 150.

The antigen binding proteins of the invention comprise the scaffolds of traditional antibodies, including human and monoclonal antibodies, bispecific antibodies, diabodies, minibodies, domain antibodies, synthetic antibodies (sometimes referred to herein as "antibody mimetics"), chimeric antibodies, antibody fusions (sometimes referred to as "antibody conjugates"), and fragments of each, respectively. The above described CDRs, including various combinations of the CDRs, may be grafted into any of the following scaffolds.

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a) a human antibody; b) a humanized antibody; c) a chimeric antibody; d) a monoclonal antibody; e) a polyclonal antibody; f) a recombinant antibody; g) an antigen-binding fragment; h) a single chain antibody; i) a diabody; j) a triabody, k) a tetrabody, l) a Fab fragment; m) a F(ab')$_2$ fragment, n) an IgA antibody, o) an IgD antibody, p) an IgE antibody, q) an IgG1 antibody, r) an IgG2 antibody, s) an IgG3 antibody, t) an IgG4 antibody, and u) an IgM antibody.

A variable region or domain comprises at least three heavy or light chain CDRs embedded within a framework region (designated framework regions FR1, FR2, FR3, and FR4). Kabat et al., 1991, *Sequences of Proteins of Immunological Interest*, Public Health Service N.I.H., Bethesda, Md. Traditional antibody structural units typically comprise a tetramer. Each tetramer is typically composed of two identical pairs of polypeptide chains, each pair having one "light" and one "heavy" chain. The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to IgM1 and IgM2. Embodiments of the invention include all such classes and subclasses of antibodies that incorporate a variable domain or CDR of the antigen binding proteins, as described herein.

Some naturally occurring antibodies, such as those found in camels and llamas, are dimers consisting of two heavy chains and include no light chains. The invention encompasses dimeric antibodies of two heavy chains, or fragments thereof, that can bind to ST2.

The variable regions of the heavy and light chains typically exhibit the same general structure of relatively conserved framework regions (FR) joined by three hypervariable regions, i.e., the complementarity determining regions or CDRs. The CDRs are primarily responsible for antigen recognition and binding. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3, and FR4. The assignment of amino acids to each domain is in accordance with the definitions of Kabat.

CDRs constitute the major surface contact points for antigen binding. The CDR3 or the light chain and, particularly, CDR3 of the heavy chain may constitute the most important determinants in antigen binding within the light and heavy chain variable regions. In some antibodies, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen.

Naturally occurring antibodies typically include a signal sequence, which directs the antibody into the cellular pathway for protein secretion and which is typically not present in the mature antibody. A polynucleotide encoding an antibody of the invention may encode a naturally occurring a signal sequence or a heterologous signal sequence as described below.

In one embodiment, the antigen binding protein is an antibody comprising from one to six of the exemplary CDRs described herein. The antibodies of the invention may be of any type including IgM, IgG (including IgG1, IgG2, IgG3, IgG4), IgD, IgA, or IgE antibody. In a specific embodiment the antigen binding protein is an IgG type antibody, e.g., a IgG1 antibody.

In some embodiments, for example when the antigen binding protein is an antibody with complete heavy and light chains, the CDRs are all from the same species, e.g., human. Alternatively, for example in embodiments wherein the antigen binding protein contains less than six CDRs from the sequences outlined above, additional CDRs may be either from other species or may be different human CDRs than those depicted in the exemplary sequences. For example, HCDR3 and LCDR3 regions from the appropriate sequences identified herein may be used with HCDR1, HCDR2, LCDR1, and LCDR2 being optionally selected from alternate species or different human antibody sequences, or combinations thereof. For example, the CDRs of the invention can replace the CDR regions of commercially relevant chimeric or humanized antibodies.

Specific embodiments utilize scaffold components of the antigen binding proteins that are human components. In some embodiments, however, the scaffold components can be a mixture from different species. As such, if the antigen binding protein is an antibody, such antibody may be a chimeric antibody and/or humanized antibody. In general, both "chimeric antibodies" and humanized antibodies" refer to antibodies that combine regions from more than one species. For example, "chimeric antibodies" traditionally comprise variable region(s) from a mouse (or rat, in some cases) and the constant region(s) from a human.

"Humanized antibodies" generally refer to non-human antibodies that have had the variable domain framework regions swapped for sequences found in human antibodies. Generally, in a humanized antibody, the entire antibody, except one or more CDRs, is encoded by a polynucleotide of human origin or is identical to such an antibody except within one or more CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones 1986, *Nature* 321:522-525, Verhoeyen et al., 1988, *Science* 239:1534-1536. Humanized antibodies can also be generated using mice with a genetically engineered immune system. Roque et al., 2004, Biotechnol. Prog. 20:639-654. In the exemplary embodiments described herein, the identified CDRs are human, and thus both humanized and chimeric antibodies in this context include some non-human CDRs; for example, humanized antibodies may be generated that comprise the HCDR3 and LCDR3 regions, with one or more of the other CDR regions being of a different species origin.

In one embodiment, the ST2 antigen binding protein is a multispecific antibody, and notably a bispecific antibody, also sometimes referred to as "diabodies." These are antibodies that bind to two or more different antigens or different epitopes on a single antigen. In certain embodiments, a bispecific antibody binds ST2 and an antigen on a human effector cell (e.g., T cell). Such antibodies are useful in targeting an effector cell response against a ST2 expressing cells, such as an ST2-expressing tumor cell. In preferred embodiments, the human effector cell antigen is CD3. U.S. Pat. No. 7,235,641. Methods of making bispecific antibodies are known in the art. One such method involves engineering the Fc portion of the heavy chains such as to create "knobs" and "holes" which facilitate heterodimer formation of the heavy chains when co-expressed in a cell. U.S. Pat. No. 7,695,963. Another method also involves engineering the Fc portion of the heavy chain but uses electrostatic steering to encourage heterodimer formation while discouraging homodimer formation of the heavy chains when co-expressed in a cell. WO 09/089,004, which is incorporated herein by reference in its entirety.

In one embodiment, the ST2 antigen binding protein is a minibody. Minibodies are minimized antibody-like proteins comprising a scFv joined to a CH3 domain. Hu et al., 1996, *Cancer Res.* 56:3055-3061.

In one embodiment, the ST2 antigen binding protein is a domain antibody; see, for example U.S. Pat. No. 6,248,516. Domain antibodies (dAbs) are functional binding domains of antibodies, corresponding to the variable regions of either the heavy (VH) or light (VL) chains of human antibodies. dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the ST2 antigen binding protein is an antibody fragment, that is a fragment of any of the antibodies outlined herein that retain binding specificity to ST2. In various embodiments, the antibody binding proteins comprise, but are not limited to, a F(ab), F(ab'), F(ab')2, Fv, or a single chain Fv fragments. At a minimum, an antibody, as meant herein, comprises a polypeptide that can bind specifically to ST2 comprising all or part of a light or heavy chain variable region, such as one or more CDRs.

Further examples of ST2-binding antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments may be modified. For example, the molecules may be stabilized by the incorporation of disulphide bridges linking the VH and VL domains (Reiter et al., 1996, *Nature Biotech.* 14:1239-1245). Aspects of the invention include embodiments wherein the non-CDR components of these fragments are human sequences.

In one embodiment, the ST2 antigen binding protein is a fully human antibody. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein (including but not limited to scFvs comprising the variable domain combinations of Ab1 LCv/Ab1 HCv (SEQ ID NO:95/SEQ ID NO:29), Ab2 LCv/Ab2 HCv (SEQ ID NO:96/SEQ ID NO:30), Ab3 LCv/Ab3 HCv (SEQ ID NO:97/SEQ ID NO:31), Ab4 LCv/Ab4 HCv (SEQ ID NO:98/SEQ ID NO:32), Ab5 LCv/Ab5 HCv (SEQ ID NO:99/SEQ ID NO:33), Ab6 LCv/Ab6 HCv (SEQ ID NO:100/SEQ ID NO:34), Ab7 LCv/Ab7 HCv (SEQ ID NO:101/SEQ ID NO:35), Ab8 LCv/Ab8 HCv (SEQ ID NO:102/SEQ ID NO:36), Ab9 LCv/Ab9 HCv (SEQ ID NO:103/SEQ ID NO:37), Ab10 LCv/Ab10 HCv (SEQ ID NO:104/SEQ ID NO:38), and Ab11 LCv/Ab11 HCv (SEQ ID NO:105/SEQ ID NO:39), Ab30 LCv/Ab30 HCv (SEQ ID NO:163/SEQ ID NO:145), Ab32 LCv/Ab32 HCv (SEQ ID NO:164/SEQ ID NO:146), Ab33 LCv/Ab33 HCv (SEQ ID NO:165/SEQ ID NO:147), and combinations thereof are encompassed by the present invention.

In one embodiment, the ST2 antigen binding protein is an antibody fusion protein (sometimes referred to herein as an "antibody conjugate"). The conjugate partner can be proteinaceous or non-proteinaceous; the latter generally being generated using functional groups on the antigen binding protein and on the conjugate partner. In certain embodiments, the antibody is conjugated to a non-proteinaceous chemical (drug) to form an antibody drug conjugate.

In one embodiment, the ST2 antigen binding protein is an antibody analog, sometimes referred to as "synthetic antibodies." For example, a variety of work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics ("PAMs") can be used, as well as work based on antibody mimetics utilizing fibronection components as a scaffold.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, *Proc. Natl. Acad. Sci. U.S.A.* 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

In certain aspects, the invention provides recombinant antigen binding proteins that bind ST2 and, in some embodiments, a recombinant human ST2 or portion thereof. In this context, a "recombinant protein" is a protein made using recombinant techniques using any techniques and methods known in the art, i.e., through the expression of a recombinant nucleic acid as described herein. Methods and techniques for the production of recombinant proteins are well known in the art. Embodiments of the invention include recombinant antigen binding proteins that bind wild-type ST2 and variants thereof.

"Consisting essentially of" means that the amino acid sequence can vary by about 1, 2, 3, 4, 5, 6, 7, 8, 9, 10, 11, 12, 13, 14, or 15% relative to the recited SEQ ID NO: sequence and still retain biological activity, as described herein.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs are at least 80% to the sequences depicted herein, and more typically with preferably increasing homologies or identities of at least 85%, 90%, 91%, 92%, 93%, 94%, 95%, 96%, 97%, 98%, 99%, and almost 100%. In a similar manner, "percent (%) nucleic acid sequence identity" with respect to the nucleic acid sequence of the binding proteins identified herein is defined as the percentage of nucleotide residues in a candidate sequence that are identical with the nucleotide residues in the coding sequence of the antigen binding protein. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and the nucleotide sequences depicted herein are at least 80%, and more typically with preferably increasing homologies or identities of at least 80%, 81%, 82%, 83%, 84%, 85%, 86%, 87%, 88%, 89%, 90%, 91%, 92%, 93%, 94%, 95%, 96%, 97%, 98%, or 99%, and almost 100%.

Thus, a "variant CDR" is one with the specified homology, similarity, or identity to the parent CDR of the invention, and shares biological function, including, but not limited to, at least 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen binding protein CDR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of antigen binding protein activities, such as ST2 binding.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 3.

TABLE 3

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 3. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein.

Other derivatives of ST2 antibodies within the scope of this invention include covalent or aggregative conjugates of ST2 antibodies, or fragments thereof, with other proteins or polypeptides, such as by expression of recombinant fusion proteins comprising heterologous polypeptides fused to the N-terminus or C-terminus of a ST2 antibody polypeptide. For example, the conjugated peptide may be a heterologous signal (or leader) polypeptide, e.g., the yeast alpha-factor leader, or a peptide such as an epitope tag. ST2 antibody-containing fusion proteins can comprise peptides added to facilitate purification or identification of the ST2 antibody (e.g., poly-His). A ST2 antibody polypeptide also can be linked to the FLAG peptide as described in Hopp et al., *Bio/Technology* 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing a ST2 binding fragment of a ST2 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of a ST2 antibody may be substituted for the variable portion of an antibody heavy and/or light chain.

Another method for preparing oligomeric ST2 antibody derivatives involves use of a leucine zipper. Leucine zipper domains are peptides that promote oligomerization of the proteins in which they are found. Leucine zippers were originally identified in several DNA-binding proteins (Landschulz et al., 1988, *Science* 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, *FEBS Letters* 344:191, hereby incorporated by reference. The use of a modified leucine zipper that allows for stable trimerization of a heterologous protein fused thereto is described in Fanslow et al., 1994, *Semin. Immunol.* 6:267-78. In one approach, recombinant fusion proteins comprising ST2 antibody fragment or derivative fused to a leucine zipper peptide are expressed in suitable host cells, and the soluble oligomeric ST2 antibody fragments or derivatives that form are recovered from the culture supernatant.

Covalent modifications of antigen binding proteins are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antigen binding proteins to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antigen binding protein included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antigen binding protein amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antigen binding protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting antigen binding protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, 1 *Biol. Chem.* 257:3105. Tunicamycin blocks the formation of protein-N-glycoside linkages.

Another type of covalent modification of the antigen binding protein comprises linking the antigen binding protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antigen binding protein to facilitate the addition of polymers such as PEG.

In some embodiments, the covalent modification of the antigen binding proteins of the invention comprises the addition of one or more labels.

The term "labeling group" means any detectable label. Examples of suitable labeling groups include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labeling group is coupled to the antigen binding protein via spacer arms of various lengths to reduce potential steric hindrance. Various methods for labeling proteins are known in the art and may be used in performing the present invention.

In general, labels fall into a variety of classes, depending on the assay in which they are to be detected: a) isotopic labels, which may be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labeling group is coupled to the antigen binding protein via spacer arms of various lengths to reduce potential steric hindrance. Various methods for labeling proteins are known in the art and may be used in performing the present invention.

Specific labels include optical dyes, including, but not limited to, chromophores, phosphors and fluorophores, with the latter being specific in many instances. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, *Lucifer* Yellow, CASCADE® BlueJ, TEXAS RED®, IAEDANS, EDANS, BODIPY FL, LC Red 640, Cy 5, Cy 5.5, LC Red 705, OREGON GREEN®, the ALEXA FLUOR® dyes (ALEXA FLUOR® 350, ALEXA FLUOR® 430, ALEXA FLUOR® 488, ALEXA FLUOR® 546, ALEXA FLUOR® 568, ALEXA FLUOR® 594, ALEXA FLUOR® 633, ALEXA FLUOR® 660, ALEXA FLUOR® 680), CASCADE® Blue, CASCADE® Yellow and Rphycoerythrin (PE) (Molecular Probes, Eugene, Oreg.), FITC, Rhodamine, and TEXAS RED® (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus*, or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, 1 *Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558). All of the above-cited references are expressly incorporated herein by reference.

The exemplary antigen binding proteins described herein have properties based on the distinct epitope on ST2 bound by the antigen binding protein. The term "epitope" means the amino acids of a target molecule that are contacted by an antigen binding protein, e.g., an antibody, when the antigen binding protein is bound to the target molecule. An epitope can be contiguous or non-contiguous (e.g., (i) in a single-chain polypeptide, amino acid residues that are not contiguous to one another in the polypeptide sequence but that within the context of the target molecule are bound by the antigen binding protein, or (ii) in a multimeric receptor comprising two or more individual components, e.g., ST2 and AcP, amino acid residues are present on one or more of the individual components but are still bound by the antigen binding protein. Epitope determinants can include chemically active surface groupings of molecules such as amino acids, sugar side chains, phosphoryl or sulfonyl groups, and can have specific three dimensional structural characteristics, and/or specific charge characteristics. Generally, antigen binding proteins specific for a particular target molecule will preferentially recognize an epitope on the target molecule in a complex mixture of proteins and/or macromolecules.

Methods of characterizing the epitope bound by an antigen binding protein are well known in the art, including, but not limited to, binning (cross-competition) (Miller et al "Epitope binning of murine monoclonal antibodies by a multiplexed pairing assay" *J Immunol Methods* (2011) 365, 118-25), peptide mapping (e.g., PEPSPOT™) (Albert et al "*The B-cell Epitope of the Monoclonal Anti-Factor VIII Antibody ESH8 Characterized by Peptide Array Analysis*" 2008 *Thromb Haemost* 99, 634-7), mutagenesis methods such as chimeras (Song et al "Epitope Mapping of Ibalizumab, a Humanized Anti-CD4 Monoclonal Antibody with Anti-HIV-1 Activity in Infected Patients" *J. Virol*. (2010) 84, 6935-6942), alanine scanning (Cunningham and Wells "High-resolution epitope mapping of HGH-receptor interactions by alanine-scanning mutagenesis" *Science* (1989) 244, 1081-1085), arginine scanning (Lim et al "A diversity of antibody epitopes can induce signaling through the erythropoietin receptor" *Biochemistry* (2010) 49, 3797-3804), HD exchange methods (Coates et al "Epitope mapping by amide hydrogen/deuterium exchange coupled with immobilization of antibody, on-line proteolysis, liquid chromatography and mass spectrometry" *Rapid Commun. Mass Spectrom*. (2009) 23 639-647), NMR cross saturation methods (Morgan et al "Precise epitope mapping of malaria parasite inhibitory antibodies by TROSY NMR cross-saturation" *Biochemistry* (2005) 44, 518-23), and crystallography (Gerhardt et al "Structure of IL-17A in complex with a potent, fully human neutralizing antibody" *J Mol. Biol* (2009) 394, 905-21). The methods vary in the level of detail they provide as to the amino acids comprising the epitope.

Antigen binding proteins of the present invention include those that have an overlapping epitope with an exemplary antigen binding protein described herein, e.g., Ab1, Ab2, Ab3, Ab4, Ab5, Ab6, Ab7, Ab8, Ab9, Ab10, Ab11, Ab30, Ab32, or Ab33. In certain embodiments, the antigen binding protein has an identical epitope as to the exemplary antigen binding proteins. In other embodiments, the antigen binding protein binds only a subset of the same amino acids as the exemplary antigen binding protein.

In certain embodiments, the ST2 antigen binding protein has an identical or overlapping epitope as Ab1, Ab2, Ab3, Ab4, Ab5, Ab6, Ab7, Ab8, Ab9, Ab10, Ab11, Ab30, Ab32, or Ab33 and comprises a) a light chain variable domain having at least 90% identity, at least 95% identity, or is identical to the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165; b) a heavy chain variable domain having at least 90% identity, at least 95% identity, or is identical to the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147; or c) the light chain variable domain of a) and the heavy chain variable domain of b).

In certain embodiments, the ST2 antigen binding protein has an identical or overlapping epitope as Ab1, Ab2, Ab3, Ab4, Ab5, Ab6, Ab7, Ab8, Ab9, Ab10, Ab11, Ab30, Ab32, or Ab33, and comprises a light chain variable domain having at least 90%, at least 95%, or is identical to the amino acid sequence set forth in SEQ ID NO:95 and a heavy chain variable domain having at least 90%, at least 95%, or is identical to the amino acid sequence set forth in SEQ ID NO:29; those comprising a light chain variable domain having at least 90%, at least 95%, or is identical to the amino acid sequence set forth in SEQ ID NO:96 and a heavy chain variable domain having at least 90%, at least 95%, or is identical to the amino acid sequence set forth in SEQ ID NO:30; those comprising a light chain variable domain having at least 90%, at least 95%, or is identical to the amino acid sequence set forth in SEQ ID NO:97 and a heavy chain variable domain having at least 90%, at least 95%, or is identical to the amino acid sequence set forth in SEQ ID NO:31; those comprising a light chain variable domain having at least 90%, at least 95%, or is identical to the amino acid sequence set forth in SEQ ID NO:98 and a heavy chain variable domain having at least 90%, at least 95%, or is identical to the amino acid sequence set forth in SEQ ID NO:32; those comprising a light chain variable domain having at least 90%, at least 95%, or is identical to the amino acid sequence set forth in SEQ ID NO:99 and a heavy chain variable domain having at least 90%, at least 95%, or is identical to the amino acid sequence set forth in SEQ ID NO:33; those comprising a light chain variable domain having at least 90%, at least 95%, or is identical to the amino acid sequence set forth in SEQ ID NO:100 and a heavy chain variable domain having at least 90%, at least 95%, or is identical to the amino acid sequence set forth in SEQ ID NO:34; those comprising a light chain variable domain having at least 90%, at least 95%, or is identical to the amino acid sequence set forth in SEQ ID NO:101 and a heavy chain variable domain having at least 90%, at least 95%, or is identical to the amino acid sequence set forth in SEQ ID NO:35; those comprising a light chain variable domain having at least 90%, at least 95%, or is identical to the amino acid sequence set forth in SEQ ID NO:102 and a heavy chain variable domain having at least 90%, at least 95%, or is identical to the amino acid sequence set forth in SEQ ID NO:36; those comprising a light chain variable domain having at least 90%, at least 95%, or is identical to the amino acid sequence set forth in SEQ ID NO:103 and a heavy chain variable domain having at least 90%, at least 95%, or is identical to the amino acid sequence set forth in SEQ ID NO:37; those comprising a light chain variable domain having at least 90%, at least 95%, or is identical to the amino acid sequence set forth in SEQ ID NO:104 and a heavy chain variable domain having at least 90%, at least 95%, or is identical to the amino acid sequence set forth in SEQ ID NO:38; those comprising a light chain variable domain having at least 90%, at least 95%, or is identical to the amino acid sequence set forth in SEQ ID NO:105 and a heavy chain variable domain having at least 90%, at least 95%, or is identical to the amino acid sequence set forth in SEQ ID NO:39; those comprising a light chain variable domain having at least 90%, at least 95%, or is identical to the amino acid sequence set forth in SEQ ID NO:163 and a heavy chain variable domain having at least 90%, at least 95%, or is identical to the amino acid sequence set forth in SEQ ID NO:145; those comprising a light chain variable domain having at least 90%, at least 95%, or is identical to the amino acid sequence set forth in SEQ ID NO:164 and a heavy chain variable domain having at least 90%, at least 95%, or is identical to the amino acid sequence set forth in SEQ ID NO:146; and those comprising a light chain variable domain having at least 90%, at least 95%, or is identical to the amino acid sequence set forth in SEQ ID NO:165 and a heavy chain variable domain having at least 90%, at least 95%, or is identical to the amino acid sequence set forth in SEQ ID NO:147.

In certain embodiments, the ST2 antigen binding protein has an identical or overlapping epitope as Ab1, Ab2, Ab3, Ab4, Ab5, Ab6, Ab7, Ab8, Ab9, Ab10, Ab11, Ab30, Ab32, or Ab33 and comprises a) a light chain variable domain having no more than ten or no more than five amino acid additions, deletions or substitutions from the amino acid sequence set forth in SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:163, SEQ ID NO:164, or SEQ ID NO:165; b) a heavy chain variable domain having no more than ten or no more than five amino acid additions, deletions or substitutions from the amino acid sequence set forth in SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:145, SEQ ID NO:146, or SEQ ID NO:147; or c) the light chain variable domain of a) and the heavy chain variable domain of b).

In certain embodiments, the ST2 antigen binding protein has an identical or overlapping epitope as Ab1, Ab2, Ab3, Ab4, Ab5, Ab6, Ab7, Ab8, Ab9, Ab10, Ab11, Ab30, Ab32, or Ab33 and comprises a light chain variable domain having no more than ten or no more than five amino acid additions, deletions or substitutions from the amino acid sequence set forth in SEQ ID NO:95 and a heavy chain variable domain having no more than ten or no more than five amino acid additions, deletions or substitutions from the amino acid sequence set forth in SEQ ID NO:29; those comprising a light chain variable domain having no more than ten or no more than five amino acid additions, deletions or substitutions from the amino acid sequence set forth in SEQ ID NO:96 and a heavy chain variable domain having no more than ten or no more than five amino acid additions, deletions or substitutions from the amino acid sequence set forth in SEQ ID NO:30; those comprising a light chain variable domain having no more than ten or no more than five amino acid additions, deletions or substitutions from the amino acid sequence set forth in SEQ ID NO:97 and a heavy chain variable domain having no more than ten or no more than five amino acid additions, deletions or substitutions from the amino acid sequence set forth in SEQ ID NO:31; those comprising a light chain variable domain having no more than ten or no more than five amino acid additions, deletions or substitutions from the amino acid sequence set forth in SEQ ID NO:98 and a heavy chain variable domain having no more than ten or no more than five amino acid additions, deletions or substitutions from the amino acid sequence set forth in SEQ ID NO:32; those comprising a light chain variable domain having no more than ten or no more than five amino acid additions, deletions or substitutions from the amino acid sequence set forth in SEQ ID NO:99 and a heavy chain variable domain having no more than ten or no more than five amino acid additions, deletions or substitutions from the amino acid sequence set forth in SEQ ID NO:33; those comprising a light chain variable domain having no more than ten or no more than five amino acid additions, deletions or substitutions from the amino acid sequence set forth in SEQ ID NO:100 and a heavy chain variable domain having no more than ten or no more than five amino acid additions, deletions or substitutions from the amino acid sequence set forth in SEQ ID NO:34; those comprising a light chain variable domain having no more than ten or no more than five amino acid additions, deletions or substitutions from the amino acid sequence set forth in SEQ ID NO:101 and a heavy chain variable domain having no more than ten or no more than five amino acid additions, deletions or substitutions from the amino acid sequence set forth in SEQ ID NO:35; those comprising a light chain variable domain having no more than ten or no more than five amino acid additions, deletions or substitutions from the amino acid sequence set forth in SEQ ID NO:102 and a heavy chain variable domain having no more than ten or no more than five amino acid additions, deletions or substitutions from the amino acid sequence set forth in SEQ ID NO:36; those comprising a light chain variable domain having no more than ten or no more than five amino acid additions, deletions or substitutions from the amino acid sequence set forth in SEQ ID NO:103 and a heavy chain variable domain having no more than ten or no more than five amino acid additions, deletions or substitutions from the amino acid sequence set forth in SEQ ID NO:37; those comprising a light chain variable domain having no more than ten or no more than five amino acid additions, deletions or substitutions from the amino acid sequence set forth in SEQ ID NO:104 and a heavy chain variable domain having no more than ten or no more than five amino acid additions, deletions or substitutions from the amino acid sequence set forth in SEQ ID NO:38; those comprising a light chain variable domain having no more than ten or no more than five amino acid additions, deletions or substitutions from the amino acid sequence set forth in SEQ ID NO:105 and a heavy chain variable domain having no more than ten or no more than five amino acid additions, deletions or substitutions from the amino acid sequence set forth in SEQ ID NO:39; those comprising a light chain variable domain having no more than ten or no more than five amino acid additions, deletions or substitutions from the amino acid sequence set forth in SEQ ID NO:163 and a heavy chain variable domain having no more than ten or no more than five amino acid additions, deletions or substitutions from the amino acid sequence set forth in SEQ ID NO:145; those comprising a light chain variable domain having no more than ten or no more than five amino acid additions, deletions or substitutions from the amino acid sequence set forth in SEQ ID NO:164 and a heavy chain variable domain having no more than ten or no more than five amino acid additions, deletions or substitutions from the amino acid sequence set forth in SEQ ID NO:146; and those comprising a light chain variable domain having no more than ten or no more than five amino acid additions, deletions or substitutions from the amino acid sequence set forth in SEQ ID NO:165 and a heavy chain variable domain having no more than ten or no more than five amino acid additions, deletions or substitutions from the amino acid sequence set forth in SEQ ID NO:147.

In certain embodiments, the ST2 antigen binding protein has an identical or overlapping epitope as Ab1, Ab2, Ab3, Ab4, Ab5, Ab6, Ab7, Ab8, Ab9, Ab10, Ab11, Ab30, Ab32, or Ab33 and comprises a light chain variable domain comprising a) an LCDR1 having no more than three amino acid additions, deletions, or substitutions from the LCDR1 sequence set forth in SEQ ID NO:106; an LCDR2 having no more than three amino acid additions, deletions, or substitutions from the LCDR2 sequence set forth in SEQ ID NO:117; and an LCDR3 having no more than three amino acid additions, deletions, or substitutions from the LCDR3 sequence set forth in SEQ ID NO:128; b) an LCDR1 having no more than three amino acid additions, deletions, or substitutions from the LCDR1 sequence set forth in SEQ ID NO:107; an LCDR2 having no more than three amino acid additions, deletions, or substitutions from the LCDR2 sequence set forth in SEQ ID NO:118; and an LCDR3 having no more than three amino acid additions, deletions, or substitutions from the LCDR3 sequence set forth in SEQ ID NO:129; c) an LCDR1 having no more than three amino acid additions, deletions, or substitutions from the LCDR1 sequence set forth in SEQ ID NO:108; an LCDR2 having no more than three amino acid additions, deletions, or substitutions from the LCDR2 sequence set forth in SEQ ID NO:119; and an LCDR3 having no more than three amino acid additions, deletions, or substitutions from the LCDR3 sequence set forth in SEQ ID NO:130; d) an LCDR1 having no more than three amino acid additions, deletions, or substitutions from the LCDR1 sequence set forth in SEQ ID NO:109; an LCDR2 having no more than three amino acid additions, deletions, or substitutions from the LCDR2 sequence set forth in SEQ ID NO:120; and an LCDR3 having no more than three amino acid additions, deletions, or substitutions from the LCDR3 sequence set forth in SEQ ID NO:131; e) an LCDR1 having no more than three amino acid additions, deletions, or substitutions from the LCDR1 sequence set forth in SEQ ID NO:110; an LCDR2 having no more than three amino acid additions, deletions, or substitutions from the LCDR2 sequence set forth in SEQ ID NO:121; and an LCDR3 having no more than three amino acid additions, deletions, or substitutions from the LCDR3 sequence set forth in SEQ ID NO:132; f) an LCDR1 having no more than three amino acid additions, deletions, or substitutions from the LCDR1 sequence set forth in SEQ ID NO:111; an LCDR2 having no more than three amino acid additions, deletions, or substitutions from the LCDR2 sequence set forth in SEQ ID NO:122; and an LCDR3 having no more than three amino acid additions, deletions, or substitutions from the LCDR3 sequence set forth in SEQ ID NO:133; g) an LCDR1 having no more than three amino acid additions, deletions, or substitutions from the LCDR1 sequence set forth in SEQ ID NO:112; an LCDR2 having no more than three amino acid additions, deletions, or substitutions from the LCDR2 sequence set forth in SEQ ID NO:123; and an LCDR3 having no more than three amino acid additions, deletions, or substitutions from the LCDR3 sequence set forth in SEQ ID NO:134; h) an LCDR1 having no more than three amino acid additions, deletions, or substitutions from the LCDR1 sequence set forth in SEQ ID NO:113; an LCDR2 having no more than three amino acid additions, deletions, or substitutions from the LCDR2 sequence set forth in SEQ ID NO:124; and an LCDR3 having no more than three amino acid additions, deletions, or substitutions from the LCDR3 sequence set forth in SEQ ID NO:135; i) an LCDR1 having no more than three amino acid additions, deletions, or substitutions from the LCDR1 sequence set forth in SEQ ID NO:114; an LCDR2 having no more than three amino acid additions, deletions, or substitutions from the LCDR2 sequence set forth in SEQ ID NO:125; and an LCDR3 having no more than three amino acid additions, deletions, or substitutions from the LCDR3 sequence set forth in SEQ ID NO:136; j) an LCDR1 having no more than three amino acid additions, deletions, or substitutions from the LCDR1 sequence set forth in SEQ ID NO:115; an LCDR2 having no more than three amino acid additions, deletions, or substitutions from the LCDR2 sequence set forth in SEQ ID NO:126; and an LCDR3 having no more than three amino acid additions, deletions, or substitutions from the LCDR3 sequence set forth in SEQ ID NO:137; k) an LCDR1 having no more than three amino acid additions, deletions, or substitutions from the LCDR1 sequence set forth in SEQ ID NO:116; an LCDR2 having no more than three amino acid additions, deletions, or substitutions from the LCDR2 sequence set forth in SEQ ID NO:127; and an LCDR3 having no more than three amino acid additions, deletions, or substitutions from the LCDR3 sequence set forth in SEQ ID NO:138; l) an LCDR1 having no more than three amino acid additions, deletions, or substitutions from the LCDR1 sequence set forth in SEQ ID NO:166; an LCDR2 having no more than three amino acid additions, deletions, or substitutions from the LCDR2 sequence set forth in SEQ ID NO:169; and an LCDR3 having no more than three amino acid additions, deletions, or substitutions from the LCDR3 sequence set forth in SEQ ID NO:172; m) an LCDR1 having no more than three amino acid additions, deletions, or substitutions from the LCDR1 sequence set forth in SEQ ID NO:167; an LCDR2 having no more than three amino acid additions, deletions, or substitutions from the LCDR2 sequence set forth in SEQ ID NO:170; and an LCDR3 having no more than three amino acid additions, deletions, or substitutions from the LCDR3 sequence set forth in SEQ ID NO:173; or n) an LCDR1 having no more than three amino acid additions, deletions, or substitutions from the LCDR1 sequence set forth in SEQ ID NO:168; an LCDR2 having no more than three amino acid additions, deletions, or substitutions from the LCDR2 sequence set forth in SEQ ID NO:171; and an LCDR3 having no more than three amino acid additions, deletions, or substitutions from the LCDR3 sequence set forth in SEQ ID NO:174; and a heavy chain variable domain comprising o) an HCDR1 having no more than three amino acid additions, deletions, or substitutions from the HCDR1 sequence set forth in SEQ ID NO:40; an HCDR2 having no more than three amino acid additions, deletions, or substitutions from the HCDR2 sequence set forth in SEQ ID NO:51; and an HCDR3 having no more than three amino acid additions, deletions, or substitutions from the HCDR3 sequence set forth in SEQ ID NO:62; p) an HCDR1 having no more than three amino acid additions, deletions, or substitutions from the HCDR1 sequence set forth in SEQ ID NO:41; an HCDR2 having no more than three amino acid additions, deletions, or substitutions from the HCDR2 sequence set forth in SEQ ID NO:52; and an HCDR3 having no more than three amino acid additions, deletions, or substitutions from the HCDR3 sequence set forth in SEQ ID NO:63; q) an HCDR1 having no more than three amino acid additions, deletions, or substitutions from the HCDR1 sequence set forth in SEQ ID NO:42; an HCDR2 having no more than three amino acid additions, deletions, or substitutions from the HCDR2 sequence set forth in SEQ ID NO:53; and an HCDR3 having no more than three amino acid additions, deletions, or substitutions from the HCDR3 sequence set forth in SEQ ID NO:64; r) an HCDR1 having no more than three amino acid additions, deletions, or substitutions from the HCDR1 sequence set forth in SEQ ID NO:43; an HCDR2 having no more than three amino acid additions, deletions, or substitutions from the HCDR2 sequence set forth in SEQ ID NO:54; and an HCDR3 having no more than three amino acid additions, deletions, or substitutions from the HCDR3 sequence set forth in SEQ ID NO:65; s) an HCDR1 having no more than three amino acid additions, deletions, or substitutions from the HCDR1 sequence set forth in SEQ ID NO:44; an HCDR2 having no more than three amino acid additions, deletions, or substitutions from the HCDR2 sequence set forth in SEQ ID NO:55; and an HCDR3 having no more than three amino acid additions, deletions, or substitutions from the HCDR3 sequence set forth in SEQ ID NO:66; t) an HCDR1 having no more than three amino acid additions, deletions, or substitutions from the HCDR1 sequence set forth in SEQ ID NO:45; an HCDR2 having no more than three amino acid additions, deletions, or substitutions from the HCDR2 sequence set forth in SEQ ID NO:56; and an HCDR3 having no more than three amino acid additions, deletions, or substitutions from the HCDR3 sequence set forth in SEQ ID NO:67; u) an HCDR1 having no more than three amino acid additions, deletions, or substitutions from the HCDR1 sequence set forth in SEQ ID NO:46; an HCDR2 having no more than three amino acid additions, deletions, or substitutions from the HCDR2 sequence set forth in SEQ ID NO:57; and an HCDR3 having no more than three amino acid additions, deletions, or substitutions from the HCDR3 sequence set forth in SEQ ID NO:68; v) an HCDR1 having no more than three amino acid additions, deletions, or substitutions from the HCDR1 sequence set forth in SEQ ID NO:47; an HCDR2 having no more than three amino acid additions, deletions, or substitutions from the HCDR2 sequence set forth in SEQ ID NO:58; and an HCDR3 having no more than three amino acid additions, deletions, or substitutions from the HCDR3 sequence set forth in SEQ ID NO:69; w) an HCDR1 having no more than three amino acid additions, deletions, or substitutions from the HCDR1 sequence set forth in SEQ ID NO:48; an HCDR2 having no more than three amino acid additions, deletions, or substitutions from the HCDR2 sequence set forth in SEQ ID NO:59; and an HCDR3 having no more than three amino acid additions, deletions, or substitutions from the HCDR3 sequence set forth in SEQ ID NO:70; x) an HCDR1 having no more than three amino acid additions, deletions, or substitutions from the HCDR1 sequence set forth in SEQ ID NO:49; an HCDR2 having no more than three amino acid additions, deletions, or substitutions from the HCDR2 sequence set forth in SEQ ID NO:60; and an HCDR3 having no more than three amino acid additions, deletions, or substitutions from the HCDR3 sequence set forth in SEQ ID NO:71; y) an HCDR1 having no more than three amino acid additions, deletions, or substitutions from the HCDR1 sequence set forth in SEQ ID NO:50; an HCDR2 having no more than three amino acid additions, deletions, or substitutions from the HCDR2 sequence set forth in SEQ ID NO:61; and an HCDR3 having no more than three amino acid additions, deletions, or substitutions from the HCDR3 sequence set forth in SEQ ID NO:72; z) an HCDR1 having no more than three amino acid additions, deletions, or substitutions from the HCDR1 sequence set forth in SEQ ID NO:148; an HCDR2 having no more than three amino acid additions, deletions, or substitutions from the HCDR2 sequence set forth in SEQ ID NO:151; and an HCDR3 having no more than three amino acid additions, deletions, or substitutions from the HCDR3 sequence set forth in SEQ ID NO:154; aa) an HCDR1 having no more than three amino acid additions, deletions, or substitutions from the HCDR1 sequence set forth in SEQ ID NO:149; an HCDR2 having no more than three amino acid additions, deletions, or substitutions from the HCDR2 sequence set forth in SEQ ID NO:152; and an HCDR3 having no more than three amino acid additions, deletions, or substitutions from the HCDR3 sequence set forth in SEQ ID NO:155; or bb) an HCDR1 having no more than three amino acid additions, deletions, or substitutions from the HCDR1 sequence set forth in SEQ ID NO:150; an HCDR2 having no more than three amino acid additions, deletions, or substitutions from the HCDR2 sequence set forth in SEQ ID NO:153; and an HCDR3 having no more than three amino acid additions, deletions, or substitutions from the HCDR3 sequence set forth in SEQ ID NO:156.

Preferred ST2 antigen binding proteins described immediately above include those comprising the light chain variable domain of a) and the heavy chain variable domain of o); those comprising the light chain variable domain of b) and the heavy chain variable domain of p); those comprising the light chain variable domain of c) and the heavy chain variable domain of q); those comprising the light chain variable domain of d) and the heavy chain variable domain of r); those comprising the light chain variable domain of e) and the heavy chain variable domain of s); those comprising the light chain variable domain of f) and the heavy chain variable domain of t); those comprising the light chain variable domain of g) and the heavy chain variable domain of u); those comprising the light chain variable domain of h) and the heavy chain variable domain of v); those comprising the light chain variable domain of i) and the heavy chain variable domain of w); those comprising the light chain variable domain of j) and the heavy chain variable domain of x); those comprising the light chain variable domain of k) and the heavy chain variable domain of y); those comprising the light chain variable domain of l) and the heavy chain variable domain of z); those comprising the light chain variable domain of m) and the heavy chain variable domain of aa); and those comprising the light chain variable domain of n) and the heavy chain variable domain of bb).

Antigen binding proteins that have an identical epitope or overlapping epitope will often cross-compete for binding to the antigen. Thus, in certain embodiments, an antigen binding protein of the invention cross-competes with Ab1, Ab2, Ab3, Ab4, Ab5, Ab6, Ab7, Ab8, Ab9, Ab10, Ab11, Ab30, Ab32, or Ab33. To "cross-compete" or "cross-competition" means the antigen binding proteins compete for the same epitope or binding site on a target. Such competition can be determined by an assay in which the reference antigen binding protein (e.g., antibody or antigen-binding portion thereof) prevents or inhibits specific binding of a test antigen binding protein, and vice versa. Numerous types of competitive binding assays can be used to determine if a test molecule competes with a reference molecule for binding. Examples of assays that can be employed include solid phase direct or indirect radioimmunoassay (MA), solid phase direct or indirect enzyme immunoassay (EIA), sandwich competition assay (see, e.g., Stahli et al. (1983) *Methods in Enzymology* 9:242-253), solid phase direct biotin-avidin EIA (see, e.g., Kirkland et al., (1986) *J Immunol.* 137:3614-3619), solid phase direct labeled assay, solid phase direct labeled sandwich assay, LUMINEX® (Jia et al "A novel method of Multiplexed Competitive Antibody Binning for the characterization of monoclonal antibodies" *J. Immunological Methods* (2004) 288, 91-98) and surface plasmon resonance ((Song et al "Epitope Mapping of Ibalizumab, a Humanized Anti-CD4 Monoclonal Antibody with Anti-HIV-1 Activity in Infected Patients" *J Virol.* (2010) 84, 6935-6942). An exemplary method of determining cross-competition is described in Example 5. Usually, when a competing antigen binding protein is present in excess, it will inhibit binding of a reference antigen binding protein to a common antigen by at least 50%, 55%, 60%, 65%, 70%, or 75%. In some instances, binding is inhibited by at least 80%, 85%, 90%, 95%, 96%, 97%, 98%, 99%, or more.

Ab2 binds human and cyo ST2 with high affinity and blocks IL-33 binding to ST2, thus blocking IL-33 mediated ST2 signalling. Antibodies with identical to, similar, or overlapping epitopes with Ab2 may share these unique characteristics. In preferred embodiments, an ST2 antigen binding protein cross-competes with Ab2 for binding to ST2. Exemplary ST2 antigen binding proteins that cross-compete with Ab2 include Ab1, Ab3, Ab5, Ab7, Ab8, and Ab30 (see Example 5). If attempting to find antibodies that bind an overlapping, similar, or identical epitpoe as Ab2, one may screen one or more antibodies for cross-competition with Ab2. Moreover, when making variants to an antibody that cross-reacts with Ab2, one may screen such antibodies to determine if the cross-competition is maintained after variation, suggesting that the epitope of the variant is not significantly altered from the parent molecule. Thus, in certain embodiments, the invention provides antibody variants that cross-compete with Ab2 for binding to ST2.

Besides cross-competing with each other, antibodies with overlapping, similar, or identical epitopes may be affected by mutagenesis of ST2 similarly. Certain mutations may inhibit binding of an antibody; others may enhance or activate binding. In Example 11, scanning arginine/alanine mutagenesis was performed on a portion of the extracellular domain of ST2 and the effect on exemplary antibodies determined. Included with the scope of the invention are ST2 binding proteins having characteristics such that they are affected in a similar way as an exemplary antibody to mutagenesis.

In certain embodiments, binding of an ST2 antigen binding protein is inhibited by a single mutation in ST2, wherein the single mutation is selected from the group consisting of L14R, I15R, S33R, E43R, V47R, A62R, G65R, T79R, D92R, D97R, V104R, G138R, N152R, and V176R. In preferred embodiments, any of two or more, three or more, four or more, five or more, six or more, seven or more, eight or more nine or more, ten or more, or all of the single mutations of the group individually inhibit binding of the ST2 binding protein. In other embodiments, binding of an ST2 antigen binding protein is activated by a single mutation in ST2, wherein the single mutation is selected from the group consisting of L53R, R72A, and S73R. In preferred embodiments, all of the single mutations of the group individually activate binding of the ST2 binding protein. In preferred embodiments, the ST2 antigen binding protein shares the attributes of Ab2 and are inhibited by any of L14R, I15R, S33R, E43R, V47R, A62R, G65R, T79R, D92R, D97R, V104R, G138R, N152R, and V176R and are activated by any of L53R, R72A, S73R.

Another method of characterizing an antibody based on its epitope is amide hydrogen/deuterium exchange (HDX). HDX has been widely used to study protein conformation and dynamics, protein-ligand interactions and protein-protein interactions (Zhang and Smith Engen and Smith 2001). Mass spectrometric detection provides a powerful tool to determine the extent of the exchange, because the replacement of a single hydrogen with deuterium results in a mass increase of 1 Da for each exchange. The extent of HDX can be readily measured at the peptide level by analysis of the protein proteolytic digest by liquid chromatography in conjunction with tandem mass spectrometry under controlled conditions (Engen and Smith 2001 Baerga-Ortiz, Hughes et al. 2002, Codreanu, Ladner et al. 2002, Hamuro, Coales et al. 2006, Coales, Tuske et al. 2009, Zhang al. 2012).

Comparison of antigen HDX profiles between proteotlyic digests of ST2 with the absence and the presence of an antibody (free versus bound state) can reveal the interaction sites. Specifically, when the antibody binds to ST2, solvent accessible amide hydrogens in free ST2 can become protected, and as a result, slower exchange rates are observed. Therefore, regions that gained less deuterium in the presence of the antibody than in its absence are potential binding epitopes. Other factors, including exchange rate in the free-state, knowledge of the antigen protein structure, as well as results from other epitope mapping efforts, are considered when the epitopes are determined.

Ab2 binding to ST2 was analyzed by HDX as described in Example 12. The analysis demonstrated that Ab2 binds to/alters the exchange rate of the portion of the ST2 structure comprising amino acids 33-44 and 88-94 of amino acids 19-322 of SEQ ID NO:1 (amino acids 15-26 and 70-76 of mature ST2, respectively). Antibodies with overlapping epitopes, similar, or identical epitopes as Ab2 will also bind to/alter the exchange rate of amino acids within 33-44 and 88-94 of SEQ ID NO:1. In certain embodiments, an ST2 binding protein, e.g., antibody, protects any of the amino acids 33-44 of SEQ ID NO:1 when bound to ST2 and analyzed by HDX. In other embodiments, any of amino acids 88-94 are protected. Both indicate partial overlap of binding epitopes with Ab2. In preferred embodiments, both any of 33-44 and any of 88-94 are protected. In certain embodiments, an ST2 binding protein, e.g., antibody, protects all of the amino acids 33-44 of SEQ ID NO:1 when bound to ST2 and analyzed by HDX. In other embodiments, all of amino acids 88-94 are protected. Both indicate a similar binding epitope with Ab2. In preferred embodiments, both all of 33-44 and all of 88-94 are protected, indicating an identical or nearly identical epitope as Ab2.

Binding of Ab2 to ST2 was further analyzed using X-ray crystallography. The X-ray crystallography was consistent with the HDX analysis. The interface between the Ab and the antigen can be determined/defined a number of ways. In Example 13, the interface was determined using solvent exposure differential and by distance. ST2 residues that are within the interface with Ab2 as determined by solvent exposure differences or distance of less than 5 Å are (corresponding to position in mature ST2 (lacking leader sequence)) K1, F2, P19, R20, Q21, G22, K23, Y26, I70, V71, R72, S73, P74, T75, F76, N77, R78, T79, and Y81. In certain embodiments, the ST2 binding protein forms an interface with ST2 that overlaps with that of Ab2, including those wherein any of K1, F2, P19, R20, Q21, G22, K23, Y26, I70, V71, R72, S73, P74, T75, F76, N77, R78, T79, or Y81 are within the interface. In some embodiments, the ST2 binding protein forms an interface with ST2 wherein P19, R20, Q21, G22, K23, and/or Y26 are within the interface. In other embodiments, I70, V71, R72, S73, P74, T75, F76, N77, R78, T79, and/or Y81 are within the interface. In preferred embodiments, K1, F2, P19, R20, Q21, G22, K23, Y26, I70, V71, R72, S73, P74, T75, F76, N77, R78, T79, and Y81 are within the interface.

The crystal structure indicated that certain amino acid residues formed hydrogen bonds or salt bridges with amino acids with Ab2. Those residues include K1, R20, K23, Y26, T75, N77, R78, and T79. In certain embodiments, an ST2 antigen binding protein forms hydrogen bonds or a salt bridge with one or more of K1, R20, K23, Y26, T75, N77, R78, and T79.

The crystal structure further provides information as to which residues of Ab2 form the interface with ST2. FIG. 10 indicates the residues in the light chain variable region and heavy chain variable region that form an interface with ST2. Also indicated are the residues that form hydrogen bonds or salt bridges with amino acids in ST2. One may use this information to design variants of Ab2, including those that contain variable domains having 90% identity, 95% identity, and 10 or less insertions, deletions, and/or substitutions within the light chain or heavy chain variable domain of Ab2. One may wish to maintain the amino acids within the interface while altering non-interface residues. Thus, one may design and create variants of Ab2 having one or more amino acid additions, substitutions, and/or deletions within one or more CDRs of Ab2 that maintain binding to ST2.

In some embodiments, an ST2 binding protein comprises a variant of Ab2 light chain variable region (SEQ ID NO:96) wherein D28, I29, S30, N31, Y32, Y49, D50, N53, E55, T56, D91, D92, N93, F94, and/or L96 remain unchanged or comprise a conservative substitution thereof, and/or a variant of Ab2 heavy chain variable region (SEQ ID NO:30) wherein W33, I50, D57, R59, H99, G100, T101, S102, S103, D104, Y105, and/or Y106 remain unchanged or comprise a conservative mutation. In preferred embodiments, D28, N31, D50, N53, E55, D91 and D92 of the light chain variable region remain unchanged and S102, S103, D104, and Y105 of the heavy chain remain unchanged.

Polynucleotides Encoding ST2 Antigen Binding Proteins

Encompassed within the invention are nucleic acids encoding ST2 antigen binding proteins, including antibodies, as defined herein. Preferred nucleic acids include those that encode the exemplary light and heavy chains described herein.

An exemplary nucleic acid encoding Ab1 LC is a nucleic acid comprising the sequence set forth in SEQ ID NO:73.

An exemplary nucleic acid encoding Ab2 LC is a nucleic acid comprising the sequence set forth in SEQ ID NO:74.

An exemplary nucleic acid encoding Ab3 LC is a nucleic acid comprising the sequence set forth in SEQ ID NO:75.

An exemplary nucleic acid encoding Ab4 LC is a nucleic acid comprising the sequence set forth in SEQ ID NO:76.

An exemplary nucleic acid encoding Ab5 LC is a nucleic acid comprising the sequence set forth in SEQ ID NO:77.

An exemplary nucleic acid encoding Ab6 LC is a nucleic acid comprising the sequence set forth in SEQ ID NO:78.

An exemplary nucleic acid encoding Ab7 LC is a nucleic acid comprising the sequence set forth in SEQ ID NO:79.

An exemplary nucleic acid encoding Ab8 LC is a nucleic acid comprising the sequence set forth in SEQ ID NO:80.

An exemplary nucleic acid encoding Ab9 LC is a nucleic acid comprising the sequence set forth in SEQ ID NO:81.

An exemplary nucleic acid encoding Ab10 LC is a nucleic acid comprising the sequence set forth in SEQ ID NO:82.

An exemplary nucleic acid encoding Ab11 LC is a nucleic acid comprising the sequence set forth in SEQ ID NO:83.

An exemplary nucleic acid encoding Ab30 LC is a nucleic acid comprising the sequence set forth in SEQ ID NO:157.

An exemplary nucleic acid encoding Ab32 LC is a nucleic acid comprising the sequence set forth in SEQ ID NO:158.

An exemplary nucleic acid encoding Ab33 LC is a nucleic acid comprising the sequence set forth in SEQ ID NO:159.

An exemplary nucleic acid encoding Ab1 HC is a nucleic acid comprising the sequence set forth in SEQ ID NO:7.

An exemplary nucleic acid encoding Ab2 HC is a nucleic acid comprising the sequence set forth in SEQ ID NO:8.

An exemplary nucleic acid encoding Ab3 HC is a nucleic acid comprising the sequence set forth in SEQ ID NO:9.

An exemplary nucleic acid encoding Ab4 HC is a nucleic acid comprising the sequence set forth in SEQ ID NO:10.

An exemplary nucleic acid encoding Ab5 HC is a nucleic acid comprising the sequence set forth in SEQ ID NO:11.

An exemplary nucleic acid encoding Ab6 HC is a nucleic acid comprising the sequence set forth in SEQ ID NO:12.

An exemplary nucleic acid encoding Ab7 HC is a nucleic acid comprising the sequence set forth in SEQ ID NO:13.

An exemplary nucleic acid encoding Ab8 HC is a nucleic acid comprising the sequence set forth in SEQ ID NO:14.

An exemplary nucleic acid encoding Ab9 HC is a nucleic acid comprising the sequence set forth in SEQ ID NO:15.

An exemplary nucleic acid encoding Ab10 HC is a nucleic acid comprising the sequence set forth in SEQ ID NO:16.

An exemplary nucleic acid encoding Ab11 HC is a nucleic acid comprising the sequence set forth in SEQ ID NO:17.

An exemplary nucleic acid encoding Ab30 HC is a nucleic acid comprising the sequence set forth in SEQ ID NO:139.

An exemplary nucleic acid encoding Ab32 HC is a nucleic acid comprising the sequence set forth in SEQ ID NO:140.

An exemplary nucleic acid encoding Ab33 HC is a nucleic acid comprising the sequence set forth in SEQ ID NO:141.

Aspects of the invention include polynucleotide variants (e.g., due to degeneracy) that encode the amino acid sequences described herein.

Aspects of the invention include a variety of embodiments including, but not limited to, the following exemplary embodiments.

An isolated polynucleotide, wherein said polynucleotide encodes one or more polypeptides comprising an amino acid sequence selected from the group consisting of:

A. 1. a light chain variable domain sequence that is at least 90% identical to a light chain variable domain sequence set forth in SEQ ID NOs:95-105, 163-165;
   2. a heavy chain variable domain sequence that is at least 90% identical to a heavy chain variable domain sequence set forth in SEQ ID NOs:29-39, 145-147;
   3. a light chain variable domain of (1) and a heavy chain variable domain of (2); and B. a light chain variable domain comprising a CDR1, CDR2, CDR3 and/or a heavy chain variable domain comprising a CDR1, CDR2, CDR3 that are the same or differ by no more than a total of three amino acid additions, substitutions, and/or deletions in each CDR from the following sequences:

1. a light chain CDR1 (SEQ ID NO:106), CDR2 (SEQ ID NO:117), CDR3 (SEQ ID NO:128) or a heavy chain CDR1 (SEQ ID NO:40), CDR2 (SEQ ID NO:51), CDR3 (SEQ ID NO:62) of Ab1;
2. a light chain CDR1 (SEQ ID NO:107), CDR2 (SEQ ID NO:118), CDR3 (SEQ ID NO:129) or a heavy chain CDR1 (SEQ ID NO:41), CDR2 (SEQ ID NO:52), CDR3 (SEQ ID NO:63) of Ab2;
3. a light chain CDR1 (SEQ ID NO:108), CDR2 (SEQ ID NO:119), CDR3 (SEQ ID NO:130) or a heavy chain CDR1 (SEQ ID NO:42), CDR2 (SEQ ID NO:53), CDR3 (SEQ ID NO:64) of Ab3;
4. a light chain CDR1 (SEQ ID NO:109), CDR2 (SEQ ID NO:120), CDR3 (SEQ ID NO:131) or a heavy chain CDR1 (SEQ ID NO:43), CDR2 (SEQ ID NO:54), CDR3 (SEQ ID NO:65) of Ab4;
5. a light chain CDR1 (SEQ ID NO:110), CDR2 (SEQ ID NO:121), CDR3 (SEQ ID NO:132) or a heavy chain CDR1 (SEQ ID NO:44), CDR2 (SEQ ID NO:55), CDR3 (SEQ ID NO:66) of Ab5;
6. a light chain CDR1 (SEQ ID NO:111), CDR2 (SEQ ID NO:122), CDR3 (SEQ ID NO:133) or a heavy chain CDR1 (SEQ ID NO:45), CDR2 (SEQ ID NO:56), CDR3 (SEQ ID NO:67) of Ab6;
7. a light chain CDR1 (SEQ ID NO:112), CDR2 (SEQ ID NO:123), CDR3 (SEQ ID NO:134) or a heavy chain CDR1 (SEQ ID NO:46), CDR2 (SEQ ID NO:57), CDR3 (SEQ ID NO:68) of Ab7;
8. a light chain CDR1 (SEQ ID NO:113), CDR2 (SEQ ID NO:124), CDR3 (SEQ ID NO:135) or a heavy chain CDR1 (SEQ ID NO:47), CDR2 (SEQ ID NO:58), CDR3 (SEQ ID NO:69) of Ab8;

9. a light chain CDR1 (SEQ ID NO:114), CDR2 (SEQ ID NO:125), CDR3 (SEQ ID NO:136) or a heavy chain CDR1 (SEQ ID NO:48), CDR2 (SEQ ID NO:59), CDR3 (SEQ ID NO:70) of Ab9;

10. a light chain CDR1 (SEQ ID NO:115), CDR2 (SEQ ID NO:126), CDR3 (SEQ ID NO:137) or a heavy chain CDR1 (SEQ ID NO:49), CDR2 (SEQ ID NO:60), CDR3 (SEQ ID NO:71) of Ab10;

11. a light chain CDR1 (SEQ ID NO:116), CDR2 (SEQ ID NO:127), CDR3 (SEQ ID NO:138) or a heavy chain CDR1 (SEQ ID NO:50), CDR2 (SEQ ID NO:61), CDR3 (SEQ ID NO:72) of Ab11;

12. a light chain CDR1 (SEQ ID NO:166), CDR2 (SEQ ID NO:169), CDR3 (SEQ ID NO:172) or a heavy chain CDR1 (SEQ ID NO:148), CDR2 (SEQ ID NO:151), CDR3 (SEQ ID NO:154) of Ab30;

13. a light chain CDR1 (SEQ ID NO:167), CDR2 (SEQ ID NO:170), CDR3 (SEQ ID NO:173) or a heavy chain CDR1 (SEQ ID NO:149), CDR2 (SEQ ID NO:152), CDR3 (SEQ ID NO:155) of Ab32; and 14. a light chain CDR1 (SEQ ID NO:168), CDR2 (SEQ ID NO:171), CDR3 (SEQ ID NO:174) or a heavy chain CDR1 (SEQ ID NO:150), CDR2 (SEQ ID NO:153), CDR3 (SEQ ID NO:156) of Ab33.

In preferred embodiments, the polypeptide encoded by the isolated nucleic acid is a component of an antigen binding protein that binds ST2.

Nucleotide sequences corresponding to the amino acid sequences described herein, to be used as probes or primers for the isolation of nucleic acids or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a ST2 antigen binding proteins or a desired combination of ST2 antigen binding protein polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., *Science* 239:487 (1988); *Recombinant DNA Methodology*, Wu et al., eds., Academic Press, Inc., San Diego (1989), pp. 189-196; and *PCR Protocols: A Guide to Methods and Applications*, Innis et. al., eds., Academic Press, Inc. (1990).

Nucleic acid molecules of the invention include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The nucleic acid molecules of the invention include full-length genes or cDNA molecules as well as a combination of fragments thereof. The nucleic acids of the invention are preferentially derived from human sources, but the invention includes those derived from non-human species, as well.

An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized enzymatically from a template or chemically, such as PCR products, cDNA molecules, or oligonucleotides for example, it is understood that the nucleic acids resulting from such processes are isolated nucleic acids. An isolated nucleic acid molecule refers to a nucleic acid molecule in the form of a separate fragment or as a component of a larger nucleic acid construct. In one preferred embodiment, the nucleic acids are substantially free from contaminating endogenous material. The nucleic acid molecule has preferably been derived from DNA or RNA isolated at least once in substantially pure form and in a quantity or concentration enabling identification, manipulation, and recovery of its component nucleotide sequences by standard biochemical methods (such as those outlined in Sambrook et al., *Molecular Cloning: A Laboratory Manual,* 2nd ed., Cold Spring Harbor Laboratory, Cold Spring Harbor, N.Y. (1989)). Such sequences are preferably provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

The present invention also includes nucleic acids that hybridize under moderately stringent conditions, and more preferably highly stringent conditions, to nucleic acids encoding ST2 antigen binding proteins as described herein. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. One way of achieving moderately stringent conditions involves the use of a pre-washing solution containing 5×SSC, 0.5% SDS, 1.0 mM EDTA (pH 8.0), hybridization buffer of about 50% formamide, 6×SSC, and a hybridization temperature of about 55 degrees C. (or other similar hybridization solutions, such as one containing about 50% formamide, with a hybridization temperature of about 42 degrees C.), and washing conditions of about 60 degrees C., in 0.5×SSC, 0.1% SDS. Generally, highly stringent conditions are defined as hybridization conditions as above, but with washing at approximately 68 degrees C., 0.2×SSC, 0.1% SDS. SSPE (1×SSPE is 0.15M NaCl, 10 mM NaH.sub.2 PO.sub.4, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, e.g., Sambrook et al., 1989). When hybridizing a nucleic acid to a target nucleic acid of unknown sequence, the hybrid length is assumed to be that of the hybridizing nucleic acid. When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10.degrees C. less than the melting temperature (Tm) of the hybrid, where Tm is determined according to the following equations. For hybrids less than 18 base pairs in length, Tm (degrees C.)=2(# of A+T bases)+4(# of #G+C bases). For hybrids above 18 base pairs in length, Tm (degrees C.)=81.5+16.6($\log_{10}$ [Na$^+$])+0.41(% G+C)−(600/N), where N is the number of bases in the hybrid, and [Na$^+$] is the concentration of sodium ions in the hybridization buffer ([Na$^+$] for 1×SSC=0.165M). Preferably, each such hybridizing nucleic acid has a length that is at least 15 nucleotides (or more preferably at least 18 nucleotides, or at least 20 nucleotides, or at least 25 nucleotides, or at least 30 nucleotides, or at least 40 nucleotides, or most preferably at least 50 nucleotides), or at least 25% (more preferably at least 50%, or at least 60%, or at least 70%, and most preferably at least 80%) of the length of the nucleic acid of the present invention to which it hybridizes, and has at least 60% sequence identity (more preferably at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%, and most preferably at least 99.5%) with the nucleic acid of the present invention to which it hybridizes, where sequence identity is determined by comparing the sequences of the hybridizing nucleic acids when aligned so as to maximize overlap and identity while minimizing sequence gaps as described in more detail above.

The variants according to the invention are ordinarily prepared by site specific mutagenesis of nucleotides in the DNA encoding the antigen binding protein, using cassette or PCR mutagenesis or other techniques well known in the art, to produce DNA encoding the variant, and thereafter expressing the recombinant DNA in cell culture as outlined herein. However, antigen binding protein fragments comprising variant CDRs having up to about 100-150 residues may be prepared by in vitro synthesis using established techniques. The variants typically exhibit the same qualitative biological activity as the naturally occurring analogue, e.g., binding to ST2, although variants can also be selected which have modified characteristics as will be more fully outlined below.

As will be appreciated by those in the art, due to the degeneracy of the genetic code, an extremely large number of nucleic acids may be made, all of which encode the CDRs (and heavy and light chains or other components of the antigen binding protein) of the present invention. Thus, having identified a particular amino acid sequence, those skilled in the art could make any number of different nucleic acids, by simply modifying the sequence of one or more codons in a way which does not change the amino acid sequence of the encoded protein.

The present invention also provides expression systems and constructs in the form of plasmids, expression vectors, transcription or expression cassettes which comprise at least one polynucleotide as above. In addition, the invention provides host cells comprising such expression systems or constructs.

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the ST2 antigen binding protein coding sequence; the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the ST2 antigen binding protein from the host cell. Affinity purification can be accomplished, for example, by column chromatography using antibodies against the tag as an affinity matrix. Optionally, the tag can subsequently be removed from the purified ST2 antigen binding protein by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thyrnidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antigen binding protein antibody that binds to ST2 polypeptide. As a result, increased quantities of a polypeptide such as an ST2 antigen binding protein are synthesized from the amplified DNA.

A ribosome-binding site is usually necessary for translation initiation of rnRNA and is characterized by a Shine-Dalgarno sequence (prokaryotes) or a Kozak sequence (eukaryotes). The element is typically located 3' to the promoter and 5' to the coding sequence of the polypeptide to be expressed. In certain embodiments, one or more coding regions may be operably linked to an internal ribosome binding site (IRES), allowing translation of two open reading frames from a single RNA transcript.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the ST2 antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an ST2 antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, *Nature* 290:304-310); CMV promoter (Thomsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-fetoprotein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987,

*Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence may be inserted into the vector to increase transcription of DNA encoding light chain or heavy chain comprising a ST2 antigen binding protein of the invention by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

The vector may contain one or more elements that facilitate expression when the vector is integrated into the host cell genome. Examples include an EASE element (Aldrich et al. 2003 *Biotechnol Prog.* 19:1433-38) and a matrix attachment region (MAR). MARs mediate structural organization of the chromatin and may insulate the integrated vactor from "position" effect. Thus, MARs are particularly useful when the vector is used to create stable transfectants. A number of natural and synthetic MAR-containing nucleic acids are known in the art, e.g., U.S. Pat. Nos. 6,239,328; 7,326,567; 6,177,612; 6,388,066; 6,245,974; 7,259,010; 6,037,525; 7,422,874; 7,129,062.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an ST2 antigen binding sequence has been inserted into the proper site of the vector, the completed vector may be inserted into a suitable host cell for amplification and/or polypeptide expression. The transformation of an expression vector for an ST2 antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes an ST2 antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell may be eukaryotic or prokaryotic.

Mammalian cell lines available as hosts for expression are well known in the art and include, but are not limited to, immortalized cell lines available from the American Type Culture Collection (ATCC) and any cell lines used in an expression system known in the art can be used to make the recombinant polypeptides of the invention. In general, host cells are transformed with a recombinant expression vector that comprises DNA encoding a desired anti-ST2 antibody polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, or their derivatives such as Veggie CHO and related cell lines which grow in serum-free media (Rasmussen et al., 1998, *Cytotechnology* 28: 31), HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821, human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Optionally, mammalian cell lines such as HepG2/3B, KB, NIH 3T3 or S49, for example, can be used for expression of the polypeptide when it is desirable to use the polypeptide in various signal transduction or reporter assays. Alternatively, it is possible to produce the polypeptide in lower eukaryotes such as yeast or in prokaryotes such as bacteria. Suitable yeasts include *Saccharomyces cerevisiae, Schizosaccharomyces pombe, Kluyveromyces strains, Candida*, or any yeast strain capable of expressing heterologous polypeptides. Suitable bacterial strains include *Escherichia coli, Bacillus subtilis, Salmonella typhimurium*, or any bacterial strain capable of expressing heterologous polypeptides. If the polypeptide is made in yeast or bacteria, it may be desirable to modify the polypeptide produced therein, for example by phosphorylation or glycosylation of the appropriate sites, in order to obtain the functional polypeptide. Such covalent attachments can be accomplished using known chemical or enzymatic methods. The polypeptide can also be produced by operably linking the isolated nucleic acid of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, *Bio/Technology* 6:47 (1988). Cell-free translation systems could also be employed to produce polypeptides using RNAs derived from nucleic acid constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, New York, 1985). A host cell that comprises an isolated nucleic acid of the invention, preferably operably linked to at least one expression control sequence, is a "recombinant host cell".

In certain embodiments, cell lines may be selected through determining which cell lines have high expression levels and constitutively produce antigen binding proteins with ST2 binding properties. In another embodiment, a cell line from the B cell lineage that does not make its own antibody but has a capacity to make and secrete a heterologous antibody can be selected.

Cell-Depleting ST2 Antigen Binding Proteins

In preferred embodiments, the ST2 antigen binding protein binds ST2 and inhibits IL-33 binding, thereby reducing IL-33 mediated signaling in ST2-expressing cells. In certain embodiments, however, the ST2 antigen binding protein binds ST2 and targets an ST2-expressing cell for depletion. Of course, the ST2 antigen binding protein may inhibit IL-33 binding and target the ST2 cell for depletion.

Cell-depleting ST2 antigen binding proteins are particularly useful for treating diseases associated with over expression of ST2, e.g., an inflammatory disease or an ST2-expressing tumor. Methods of targeting cells with antigen binding proteins, e.g. antibodies, are well known in the art. Exemplary embodiments are discussed below.

Antibody Drug Conjugates

Embodiments of the invention include antibody drug conjugates (ADCs). Generally the ADC comprises an antibody conjugated to a chemotherapeutic agent, e.g., a cytotoxic agent, a cytostatic agent, a toxin, or a radioactive agent. A linker molecule can be used to conjugate the drug to the antibody. A wide variety of linkers and drugs useful in ADC technology are known in the art and may be used in embodiments of the present invention. (See US20090028856; US2009/0274713; US2007/0031402; WO2005/084390; WO2009/099728; U.S. Pat. No. 5,208,020; U.S. Pat. No. 5,416,064; U.S. Pat. Nos. 5,475,092; 5,585,499; 6,436,931; 6,372,738; and 6,340,701, all incorporated herein by reference).

Linkers

In certain embodiments, the ADC comprises a linker made up of one or more linker components. Exemplary linker components include 6-maleimidocaproyl, maleimidopropanoyl, valine-citrulline, alanine-phenylalanine, p-aminobenzyloxycarbonyl, and those resulting from conjugation with linker reagents, including, but not limited to, N-succinimidyl 4-(2-pyridylthio) pentanoate ("SPP"), N-succinimidyl 4-(N-maleimidomethyl) cyclohexane-1 carboxylate ("SMCC," also referred to herein also as "MCC"), and N-succinimidyl (4-iodo-acetyl) aminobenzoate ("STAB").

Linkers may be a "cleavable" linker or a "non-cleavable" linker (Ducry and Stump, Bioconjugate Chem. 2010, 21, 5-13; incorporated herein by reference in its entirety) Cleavable linkers are designed to release the drug when subjected to certain environment factors, e.g., when internalized into the target cell. Cleavable linkers include acid labile linkers, protease sensitive linkers, photolabile linkers, dimethyl linker or disulfide-containing linkers. Non-cleavable linkers tend to remain covalently associated with at least one amino acid of the antibody and the drug upon internalization by and degradation within the target cell. An exemplary non-cleavable linker is MCC.

Drugs

In certain embodiments, the antibody is conjugated to a chemotherapeutic agent. Examples of chemotherapeutic agents include alkylating agents, such as thiotepa and cyclophosphamide (CYTOXAN™); alkyl sulfonates such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics, such as the enediyne antibiotics (e.g. calicheamicin, especially calicheamicin .gamma1 and calicheamicin theta I, see, e.g., Angew Chem. Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, caminomycin, carzinophilin; chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs such as, ancitabine, azacitidine, 6-azauridine, carmofur, cytarabine, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenisher, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; siRNA and pharmaceutically acceptable salts, acids or derivatives of any of the above. Other chemotherapeutic agents that can be used with the present invention are disclosed in US Publication No. 20080171040 or US Publication No. 20080305044 and are incorporated in their entirety by reference.

It is contemplated that an antibody may be conjugated to two or more different chemotherapeutic agents or a pharmaceutical composition may comprise a mixture of antibodies wherein the antibody component is identical except for being conjugated to a different chemotherapeutic agent. Such embodiments may be useful for targeting multiple biological pathways with a target cell.

In preferred embodiments, the ADC comprises an antibody conjugated to one or more maytansinoid molecules, which are mitotic inhibitors that act by inhibiting tubulin polymerization. Maytansinoids, including various modifications, are described in U.S. Pat. Nos. 3,896,111; 4,151,042; 4,137,230; 4,248,870; 4,256,746; 4,260,608; 4,265,814; 4,294,757; 4,307,016; 4,308,268; 4,309,428; 4,313,946; 4,315,929; 4,317,821; 4,322,348; 4,331,598; 4,361,650; 4,364,866; 4,424,219; 4,450,254; 4,362,663; 4,371,533; and WO 2009/099728. Maytansinoid drug moieties may be isolated from natural sources, produced using recombinant technology, or prepared synthetically. Exemplary maytansinoids include C-19-dechloro (U.S. Pat. No. 4,256,746), C-20-hydroxy (or C-20-demethyl)+/-C-19-dechloro (U.S. Pat. Nos. 4,307,016 and 4,361,650), C-20-demethoxy (or C-20-acyloxy (—OCOR), +/-dechrolo (U.S. Pat. No. 4,294,757), C-9-SH (U.S. Pat. No. 4,424,219), C-14-alkoxymethyl (demethoxy/CH2OR) (U.S. Pat. No. 4,331,598), C-14-hydroxymethyl or acyloxymethyl (CH2OH or CH2OAc) (U.S. Pat. No. 4,450,254), C-15-hydroxy/acyloxy (U.S. Pat. No. 4,364,866), C-15-methoxy (U.S. Pat. Nos. 4,313,946 and 4,315,929), C-18-N-demethyl (U.S. Pat. Nos. 4,362,663 and 4,322,348), and 4,5-deoxy (U.S. Pat. No. 4,371,533).

Various positions on maytansinoid compounds may be used as the linkage position, depending upon the type of link desired. For example, for forming an ester linkage, the C-3 position having a hydroxyl group, the C-14 position modified with hydroxymethyl, the C-15 position modified with a hydroxyl group, and the C-20 position having a hydroxyl group are all suitable (U.S. Pat. Nos. 5,208,020, RE39151, and 6,913,748; US Patent Appl. Pub. Nos. 20060167245 and 20070037972, and WO 2009099728).

Preferred maytansinoids include those known in the art as DM1, DM3, and DM4 (US Pat. Appl. Pub. Nos. 2009030924 and 20050276812, incorporated herein by reference).

ADCs containing maytansinoids, methods of making such ADCs, and their therapeutic use are disclosed in U.S. Pat. Nos. 5,208,020 and 5,416,064, US Pat. Appl. Pub. No. 20050276812, and WO 2009099728 (all incorporated by reference herein). Linkers that are useful for making maytansinoid ADCs are know in the art (U.S. Pat. No. 5,208,020 and US Pat. Appl. Pub. Nos. 2005016993 and 20090274713; all incorporated herein by reference). Maytansinoid ADCs comprising an SMCC linker may be prepared as disclosed in US Pat. Publ. No. 2005/0276812.

Effector Function-Enhanced Antibodies

One of the functions of the Fc portion of an antibody is to communicate to the immune system when the antibody binds its target. This is considered "effector function." Communication leads to antibody-dependent cellular cytotoxicity (ADCC), antibody-dependent cellular phagocytosis (ADCP), and/or complement dependent cytotoxicity (CDC). ADCC and ADCP are mediated through the binding of the Fc to Fc receptors on the surface of cells of the immune system. CDC is mediated through the binding of the Fc with proteins of the complement system, e.g., C1q.

The IgG subclasses vary in their ability to mediate effector functions. For example, IgG1 is much superior to IgG2 and IgG4 at mediating ADCC and CDC. Thus, in embodiments wherein a cell expressing ST2 is targeted for destruction, an anti-ST2 IgG1 antibody would be preferred.

The effector function of an antibody can be increased, or decreased, by introducing one or more mutations into the Fc. Embodiments of the invention include antigen binding proteins, e.g., antibodies, having an Fc engineered to increase effector function (U.S. Pat. No. 7,317,091 and Strohl, Curr. Opin. Biotech., 20:685-691, 2009; both incorporated herein by reference in its entirety). Exemplary IgG1 Fc molecules having increased effector function include (based on the Kabat numbering scheme) those have the following substitutions: S239D/I332E
S239D/A330S/I332E
S239D/A330L/I332E
S298A/D333A/K334A
P247I/A339D
P247I/A339Q
D280H/K290S
D280H/K290S/S298D
D280H/K290S/S298V
F243L/R292P/Y300L
F243L/R292P/Y300L/P396L
F243L/R292P/Y300L/V305I/P396L
G236A/S239D/I332E
K326A/E333A
K326W/E333S
K290E/S298G/T299A
K290N/S298G/T299A
K290E/S298G/T299A/K326E
K290N/S298G/T299A/K326E Further embodiments of the invention include antigen binding proteins, e.g., antibodies, having an Fc engineered to decrease effector function. Exemplary Fc molecules having decreased effector function include (based on the Kabat numbering scheme) those have the following substitutions:

N297A (IgG1)
L234A/L235A (IgG1)
V234A/G237A (IgG2)
L235A/G237A/E318A (IgG4)
H268Q/V309L/A330S/A331S (IgG2)
C220S/C226S/C229S/P238S (IgG1)
C226S/C229S/E233P/L234V/L235A (IgG1)
L234F/L235E/P331S (IgG1)
S267E/L328F (IgG1)

Another method of increasing effector function of IgG Fc-containing proteins is by reducing the fucosylation of the Fc. Removal of the core fucose from the biantennary complex-type oligosachharides attached to the Fc greatly increased ADCC effector function without altering antigen binding or CDC effector function. Several ways are known for reducing or abolishing fucosylation of Fc-containing molecules, e.g., antibodies. These include recombinant expression in certain mammalian cell lines including a FUT8 knockout cell line, variant CHO line Lec13, rat hybridoma cell line YB2/0, a cell line comprising a small interfering RNA specifically against the FUT8 gene, and a cell line coexpressing β-1,4-N-acetylglucosaminyltransferase III and Golgi α-mannosidase II. Alternatively, the Fc-containing molecule may be expressed in a non-mammalian cell such as a plant cell, yeast, or prokaryotic cell, e.g., E. coli. Thus, in certain embodiments of the invention, a composition comprises an antibody, e.g., Ab1, Ab2, Ab3, Ab4, Ab5, Ab6, Ab7, Ab8, Ab9, Ab10, or Ab11 having reduced fucosylation or lacking fucosylation altogether.

Pharmaceutical Compositions

In some embodiments, the invention provides a pharmaceutical composition comprising a therapeutically effective amount of one or a plurality of the antigen binding proteins of the invention together with a pharmaceutically effective diluents, carrier, solubilizer, emulsifier, preservative, and/or adjuvant. In certain embodiments, the antigen binding protein is an antibody. Pharmaceutical compositions of the invention include, but are not limited to, liquid, frozen, and lyophilized compositions.

Preferably, formulation materials are nontoxic to recipients at the dosages and concentrations employed. In specific embodiments, pharmaceutical compositions comprising a therapeutically effective amount of a ST2 antigen binding protein, e.g, a ST2-binding antibody, are provided.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine, proline, or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antigen binding proteins of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, ST2 antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the ST2 antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art. The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired ST2 antigen binding protein in a pharmaceutically acceptable vehicle. A particularly suitable vehicle for parenteral injection is sterile distilled water in which the ST2 antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antigen binding protein.

Pharmaceutical compositions of the invention can be formulated for inhalation. In these embodiments, ST2 antigen binding proteins are advantageously formulated as a dry, inhalable powder. In specific embodiments, ST2 antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. ST2 antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. Additional agents can be included to facilitate absorption of the ST2 antigen binding protein. Diluents, flavorings, low melting point waxes, vegetable oils, lubricants, suspending agents, tablet disintegrating agents, and binders may also be employed.

Additional pharmaceutical compositions will be evident to those skilled in the art, including formulations involving ST2 antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Aspects of the invention includes self-buffering ST2 antigen binding protein formulations, which can be used as pharmaceutical compositions, as described in international patent application WO 06138181A2 (PCT/US2006/022599), which is incorporated by reference in its entirety herein.

As discussed above, certain embodiments provide ST2 antigen binding proteins protein compositions, particularly pharmaceutical ST2 antigen binding protein compositions, that comprise, in addition to the ST2 antigen binding protein, one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution," in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions," Pharm Biotechnol. 13: 159-75 (2002), each of which is herein incorporated by reference in its entirety, particularly in parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention.

As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in ST2 antigen binding protein formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations.

Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the ST2 antigen binding protein formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product.

Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188.

Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of ST2 antigen binding protein formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard.

Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins.

Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the ST2 antigen binding protein formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. NORDITROPIN® (liquid, Novo Nordisk), NUTROPIN AQ® (liquid, Genentech) & GENOTROPIN® (lyophilized—dual chamber cartridge, Pharmacia & Upjohn) contain phenol while SOMATROPE® (Eli Lilly) is formulated with m-cresol.

Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (.about.18 to 24 months). An important point to note is that preservative effectiveness should be demonstrated in the final formulation containing the active drug and all excipient components.

ST2 antigen binding protein formulations generally will be designed for specific routes and methods of administration, for specific administration dosages and frequencies of administration, for specific treatments of specific diseases, with ranges of bio-availability and persistence, among other things. Formulations thus may be designed in accordance with the invention for delivery by any suitable route, including but not limited to orally, aurally, opthalmically, rectally, and vaginally, and by parenteral routes, including intravenous and intraarterial injection, intramuscular injection, and subcutaneous injection.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

The therapeutically effective amount of an ST2 antigen binding protein-containing pharmaceutical composition to be employed will depend, for example, upon the therapeutic context and objectives. One skilled in the art will appreciate that the appropriate dosage levels for treatment will vary depending, in part, upon the molecule delivered, the indication for which the ST2 antigen binding protein is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of a ST2 antigen binding protein preferably results in a decrease in severity of disease symptoms, in an increase in frequency or duration of disease symptom-free periods, or in a prevention of impairment or disability due to the disease affliction.

Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163, all incorporated by reference herein.

Methods of Diagnosing or Treating a ST2-Associated Disease or Disorder

The ST2 antigen binding proteins of the invention are particularly useful for detecting ST2 in a biological sample. In certain embodiments, a biological sample obtained from a patient is contacted with a ST2 antigen binding protein. Binding of the ST2 antigen binding protein to ST2 is then detected to determine the presence or relative amount of ST2 in the sample. Such methods may be useful in diagnosing or determining patients that are amenable to treatment with a ST2 antigen binding protein.

In certain embodiments, a ST2 antigen binding protein of the invention is used to diagnose, detect, or treat an autoimmune or inflammatory disorder. In treating autoimmune or inflammatory disorders, the ST2 antigen binding protein may target ST2-expressing cells of the immune system for destruction and/or may block the interaction of ST2 with IL-33.

Disorders that are associated with IL-33-mediated signaling are particularly amenable to treatment with one or more ST2 antigen binding proteins disclosed herein. Such disorders include, but are not limited to, inflammation, autoimmune disease, paraneoplastic autroimmune diseases, cartilage inflammation, fibrotic disease and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, polyarteritis nodossa, Wegener's granulomatosis, arteritis, ploymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple schlerosis (MS), asthma, COPD, rhinosinusitis, rhinosinusitis with polyps, eosinophilic esophagitis, eosinophilic bronchitis, Guillain-Barre disease, Type I diabetes mellitus, thyroiditis (e.g., Graves' disease), Addison's disease, Raynaud's phenomenon, autoimmune hepatitis, GVHD, transplantation rejection, kidney damage, and the like.

In preferred embodiments, the autoimmune or inflammatory disorder is asthma, atopic dermatitis, chronic obstructive pulmonary disease, pulmonary fibrosis, sepsis and trauma, HIV infection, systemic lupus erythematosus, inflammatory bowel disease, rheumatoid arthritis, sclerosis, Wegener's granulomatosis, Behchet disease, cardiovascular disease, rhinosinusitis, nasal polyposis, and eosinophilic bronchitis.

In certain embodiments, a ST2 antigen binding protein of the invention is used to diagnose, detect, or treat a cancer or tumorigenic disorder. In treating a cancer or tumorigenic disorder, the ST2 antigen binding protein may target ST2-expressing cells for destruction and/or may block the interaction of ST2 with IL-33, thereby reducing IL-33 mediated signaling. For example, high soluble ST2 expression is associated with improved survival in breast cancer patients. (Prechtel et al. *Lab Invest* (2001) 81:159-165) Because soluble ST2 binds and blocks IL-33-mediated signaling, it is contemplate that the ST2 antigen binding proteins that block IL-33-mediated signaling would be useful in promoting improved survival in breast cancer patients. Cancer or tumorigenic disorders that may be diagnosed, detected or treated with an ST2 antigen binding protein include, but are not limited to, solid tumors generally, lung cancer, ovarian cancer, breast cancer, prostate cancer, endometrial cancer, renal cancer, esophageal cancer, pancreatic cancer, squamous cell carcinoma, uveal melanoma, cervical cancer, colorectal cancer, bladder, brain, pancreatic, head, neck, liver, leukemia, lymphoma and Hodgkin's disease, multiple myeloma, melanoma, gastric cancer, astrocytic cancer, stomach, and pulmonary adenocarcinoma.

The antigen binding proteins may be used to inhibit tumor growth, progression, and/or metastasis. Such inhibition can be monitored using various methods. For instance, inhibition can result in reduced tumor size and/or a decrease in metabolic activity within a tumor. Both of these parameters can be measured by MM or PET scans, for example. Inhibition can also be monitored by biopsy to ascertain the level of necrosis, tumor cell death, and the level of vascularity within the tumor. The extent of metastasis can be monitored using known methods.

EXAMPLES

The following examples, both actual and prophetic, are provided for the purpose of illustrating specific embodiments or features of the present invention and are not intended to limit its scope.

Example 1: ST2 Antibodies are Efficacious in an Animal Model of Asthma

This example demonstrates that administering antibodies that bind ST2 and inhibit IL-33-mediated signaling are efficacious in an animal model of an inflammatory disease, i.e., asthma. A neutralizing mouse ST2 mAb (ST2 surrogate mAb) inhibited the activity of exogenously administered IL-33 in vivo. Mice were administered 200 ng of recombinant mouse IL-33 intranasally two hours after intravenous injection of 100 ug of anti-ST2 mAb. The next day, bronchoalveolar lavage fluid (BALF) IL-5 concentrations were measured by ELISA. Baseline IL-5 concentrations were obtained from the BALF of mice treated with saline before saline challenge. Maximum BALF IL-5 concentrations were obtained from isotype control Ig-treated mice challenged with IL-33. Compared to isotype control Ig treatment, ST2 mAb treatment significantly inhibited IL-33-induced IL-5 in the BALF of both BALB/c and C57BL/6 mouse strains (FIG. 1).

Figure 2:
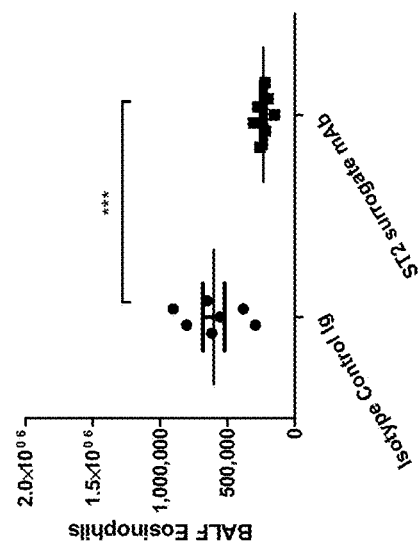
FIG. 2 ST2 mAb treatment is efficacious in a cockroach allergen (CRA)-induced model of asthma. ST2 antibody-treated mice had significantly fewer BALF eosinophils than isotype control Ig-treated mice.
Figure 2:
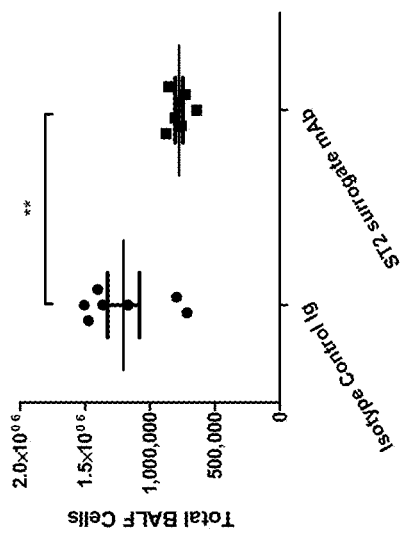

The ST2 surrogate mAb was efficacious in a cockroach allergen (CRA)-induced model of asthma, with ST2 antibody-treated mice having significantly fewer BALF eosinophils than isotype control Ig-treated mice. BALB/c mice were challenged with 100 μg CRA on days 1, 3, 6, 8, 10, and 13. Mice were injected with 250 μg of either anti-ST2 mAb or isotype control Ig on days 0, 7, and 13, with the day 13 antibody injection occurring before the final intranasal CRA challenge. On day 14, the mice were anesthetized and subjected to lung lavage. BALF cell populations were enumerated and treatment with anti-ST2 mAb resulted in the presence of significantly fewer total BALF cells, with eosinophils comprising the significantly impacted cell population (FIG. 2).

Example 2: Production of Anti-ST2 Antibodies Using the Xenomouse® Platform

The generation of fully human antibodies directed against human ST2 was carried out using XENOMOUSE® technology (U.S. Pat. Nos. 6,114,598; 6,162,963; 6,833,268; 7,049,426; 7,064,244, which are incorporated herein by reference in their entirety; Green et al., 1994, *Nature Genetics* 7:13-21; Mendez et al., 1997, *Nature Genetics* 15:146-156; Green and Jakobovitis, 1998, 1 Ex. Med. 188:483-495, Kellermann and Green, 2002, *Current Opinion in Biotechnology*, 13:593-597

Immunizations of XMG2K, XMG4K and XMG4KL XENOMOUSE® animals were carried out with either a polypeptide comprising the extracellular domain of human ST2 fused to a human antibody Fc domain or with the human ST2-Fc fusion protein complexed with human IL-33. A suitable amount of immunogen (i.e., ten μg/mouse of soluble ST2) was used for initial immunization of XENOMOUSE® animals according to the methods disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. Following the initial immunization, subsequent boost immunizations of immunogen (five μg/mouse of either soluble ST2 or ST2/IL33 complex) were administered on a schedule and for the duration necessary to induce a suitable titer of anti-ST2 antibody in the mice. Titers were determined a suitable method, for example, ELISA or by fluorescence activated cell sorting (FACs).

Animals exhibiting suitable titers were identified, and lymphocytes obtained from draining lymph nodes and, when necessary, pooled for each cohort. Lymphocytes were dissociated from lymphoid tissue by grinding in a suitable medium (for example, Dulbecco's Modified Eagle Medium; DMEM; obtainable from Invitrogen, Carlsbad, Calif.) to release the cells from the tissues, and suspended in DMEM. B cells were selected and/or expanded using a suitable method, and fused with a suitable fusion partner, for example, nonsecretory myeloma P3X63Ag8.653 cells (American Type Culture Collection CRL 1580; Kearney et al. *J. Immunol.* 123, 1979, 1548-1550), using techniques that are known in the art.

In one fusion method, lymphocytes were mixed with fusion partner cells at a ratio of 1:4. The cell mixture was gently pelleted by centrifugation at 400×g for 4 minutes, the supernatant decanted, and the cell mixture gently mixed (for example, by using a 1 mL pipette). Fusion was induced with PEG/DMSO (polyethylene glycol/dimethyl sulfoxide; obtainable from Sigma-Aldrich, St. Louis Mo.; 1 mL per million of lymphocytes). PEG/DMSO was slowly added with gentle agitation over one minute followed, by one minute of mixing. IDMEM (DMEM without glutamine; 2 mL per million of B cells), was then added over 2 minutes with gentle agitation, followed by additional IDMEM (8 mL per million B-cells) which was added over 3 minutes.

The fused cells were gently pelleted (400×g 6 minutes) and resuspended in 20 mL Selection media (DMEM containing Azaserine and Hypoxanthine [HA] and other supplemental materials as necessary) per million B-cells. Cells were incubated for 20-30 minutes at 37° C. and then re-suspended in 200 mL Selection media and cultured for three to four days in T175 flasks prior to 96 well plating.

Cells were distributed into 96-well plates using standard techniques to maximize clonality of the resulting colonies. After several days of culture, supernatants were collected and subjected to screening assays. The hybridoma supernatants generated from mice immunized with the ST2-Fc/IL33 complex were screened with an ELISA-based assay performed using 96-well polystyrene ELISA plates passively coated overnight at 4° C. with 0.5 ug/mL of ST2-Flag/his complexed to human IL-33. To determine ST-2 specific binding, a second ELISA screen was performed using 96-well polystyrene plates passively coated overnight at 4° C. with 10 ug/mL of neutravidin. Plates were then washed and loaded with 0.5 ug/mL biotinylated human IL33. This ELISA screen identified over 1200 anti-ST2 specific binders.

Hybridoma supernatants generated from mice immunized with soluble ST2-Fc were screened for ST2 antigen specific antibodies by Fluorometric Microvolume Assay Technology (FMAT) by screening against recombinant HEK293T cells transiently transfected with full-length human ST2 and counter-screening against mock-transfected HEK293T cells. Briefly, the cells were seeded into 384-well FMAT plates in a volume of 40 ul/well at a density of 6,000 ST2 positive cells/well and 14,000 mock transfected ST2 negative cells/well. Hybridoma supernatant was then added and allowed to bind for 1 hour at room temperature followed by a wash and secondary detection using anti-Human Fc-Cy5 secondary antibody. This FMAT screen identified over 2200 anti-ST2 specific binders from hybridomas generated from mice immunized with the extracellular domain of ST2.

This combined panel of 3400 anti-ST2 specific hybridoma supernatants were then further characterized for the ability to functional antagonize ST2 signalling using a Interferon-γ cytokine release assay. Briefly, either purified human peripheral blood mononuclear cells (PBMNCs) or purified human NK cells were seeded into 96 well tissue culture plates and stimulated with human IL-33 and IL-12, inducing the release of interferon-gamma into the supernatant. Interferon-gamma levels in the supernatant were quantified and were directly correlated to Il-33/ST2 dependant signalling. Using this bioassay, hybridoma samples were tested for the ability to block interferon-gamma release through blockade of the ST2 signalling pathway. This screen identified 578 hybridoma supernatants generated from the ST2-Fc immunization that inhibited interferon-gamma release by greater than 80%. In addition, 505 hybridoma supernatants generated from the ST2Fc/IL-33 complex immunization were identified that inhibited interferon-gamma release by greater than 70%.

This panel of 1083 hybridoma supernatants was then further characterized for cross-reactive binding to mouse and cynomolgus monkey ST2, for relative affinity ranking by limited antigen ELISA, for biochemical receptor/ligand blocking by ELISA and for endogenous binding by FACs using cell lines. The data generated in these secondary assays was used to diversify the large panel into 2 sets of 40 hybridoma lines which were advanced to sub-cloning, scale-up and purification.

Example 3: $K_D$ Determinations

In this example, the affinity of ST2-binding antibodies was determined. Surface plasmon resonance evaluations were carried out using a PROTEON™ XPR-36 optical biosensor equipped with a GLC sensor chip (Bio-Rad). Biosensor analysis was conducted at 25° C. in a HBS-EP+ (1×) buffer system (10 mM HEPES pH 7.4, 150 mM NaCl, 3.0 mM EDTA, 0.05% Surfactant P20, GE Heathcare). All reagents were kept at 8° C. prior to injection.

Goat anti-human IgG (Fc fragment specific, Jackson ImmunoResearch) was immobilized to the sensor surface in the vertical direction via standard amine coupling to lanes 1-6 (~4000 RU) and then blocked with ethanolamine. The antibodies were captured (~40-100 RU) in the vertical direction to lanes 1-5. Vertical lane 6 was left blank and used for reference purposes. The data were collected in groups of 15 antibodies (three sets of 5).

The ST2 reagents (human or cyno) were prepared in running buffer to a concentration of 25 nM and then diluted 3-fold to 309 pM. A single injection along the horizontal direction delivered a full concentration series of each ST2 molecule, using buffer to complete a row of six samples and provide an in-line blank for double-referencing the response data. The association (3 min) and dissociation (30 min) rates were monitored at a flow rate of 100 uL/min.

The surface was regenerated at a flow rate of 100 uL/min with 10 mM glycine (pH 1.5, 30 uL).

The data were baseline corrected, cropped, aligned, reference subtracted (interspot), and then fit to a 1:1 binding model using PROTEON™ Manager (version 2.1.2.05). The results are shown in Table 4.

TABLE 4

| Antibody | Analyte | ka | kd | KD (pM) | Antibody | Analyte | ka | kd | KD (pM) |
|---|---|---|---|---|---|---|---|---|---|
| Ab12 | cy ST2 | 2.50E+06 | 5.60E−05 | 22.5 | Ab12 | hu ST2 | 2.35E+06 | 3.41E−05 | 14.5 |
| Ab13 | cy ST2 | 1.40E+06 | 1.80E−04 | 128.0 | Ab13 | hu ST2 | 1.30E+06 | 9.12E−05 | 70.3 |
| Ab14 | cy ST2 | 3.57E+06 | 1.59E−03 | 445.0 | Ab14 | hu ST2 | 4.22E+06 | 2.57E−05 | 6.1 |
| Ab15 | cy ST2 | 2.67E+06 | 6.23E−05 | 23.4 | Ab15 | hu ST2 | 1.83E+06 | 5.38E−05 | 29.3 |
| Ab16 | cy ST2 | 2.61E+06 | 2.18E−04 | 83.7 | Ab16 | hu ST2 | 1.28E+06 | 1.47E−04 | 115.0 |
| Ab17 | cy ST2 | 3.38E+06 | 1.43E−04 | 42.2 | Ab17 | hu ST2 | 2.86E+06 | 1.04E−04 | 36.4 |
| Ab18 | cy ST2 | 3.16E+06 | 1.44E−04 | 45.7 | Ab18 | hu ST2 | 2.67E+06 | 1.19E−04 | 44.5 |
| Ab19 | cy ST2 | 3.07E+06 | 1.59E−04 | 51.8 | Ab19 | hu ST2 | 2.81E+06 | 1.25E−04 | 44.5 |
| Ab20 | cy ST2 | 2.61E+06 | 6.64E−05 | 25.5 | Ab20 | hu ST2 | 2.41E+06 | 5.68E−05 | 23.5 |
| Ab21 | cy ST2 | 3.21E+06 | 4.92E−05 | 15.3 | Ab21 | hu ST2 | 2.83E+06 | 3.07E−05 | 10.8 |
| Ab22 | cy ST2 | 2.87E+06 | 5.33E−05 | 18.6 | Ab22 | hu ST2 | 2.50E+06 | 4.05E−05 | 16.2 |
| Ab23 | cy ST2 | 3.29E+06 | 3.23E−04 | 98.2 | Ab23 | hu ST2 | 2.70E+06 | 2.24E−04 | 83.1 |
| Ab24 | cy ST2 | 2.03E+06 | 1.54E−04 | 75.9 | Ab24 | hu ST2 | 2.89E+06 | 1.50E−04 | 51.7 |
| Ab25 | cy ST2 | 6.42E+06 | 5.75E−04 | 89.6 | Ab25 | hu ST2 | 4.00E+06 | 5.44E−04 | 136.0 |
| Ab26 | cy ST2 | 5.65E+06 | 3.08E−04 | 54.5 | Ab26 | hu ST2 | 5.22E+06 | 2.97E−04 | 56.9 |

TABLE 4-continued

| Antibody | Analyte | ka | kd | KD (pM) | Antibody | Analyte | ka | kd | KD (pM) |
|---|---|---|---|---|---|---|---|---|---|
| Ab27 | cy ST2 | 1.63E+06 | 3.75E-04 | 230.0 | Ab27 | hu ST2 | 1.35E+06 | 3.12E-04 | 230.0 |
| Ab28 | cy ST2 | 2.97E+06 | 1.35E-05 | 4.5 | Ab28 | hu ST2 | 2.37E+06 | 1.98E-05 | 8.4 |
| Ab29 | cy ST2 | 3.97E+05 | 9.45E-05 | 238.0 | Ab29 | hu ST2 | 3.76E+05 | 8.96E-05 | 238.0 |
| Ab30 | cy ST2 | 3.09E+06 | 3.17E-05 | 10.2 | Ab30 | hu ST2 | 2.79E+06 | 2.71E-05 | 9.7 |
| Ab31 | cy ST2 | 1.07E+06 | 2.08E-04 | 194.0 | Ab31 | hu ST2 | 8.78E+05 | 2.43E-04 | 277.0 |
| Ab32 | cy ST2 | 4.81E+06 | 2.69E-04 | 55.8 | Ab32 | hu ST2 | 4.37E+06 | 2.63E-04 | 60.2 |
| Ab33 | cy ST2 | 4.26E+06 | 3.31E-04 | 77.6 | Ab33 | hu ST2 | 4.04E+06 | 3.41E-04 | 84.4 |
| Ab34 | cy ST2 | 2.78E+06 | 4.60E-05 | 16.5 | Ab34 | hu ST2 | 2.61E+06 | 3.19E-05 | 12.3 |
| Ab35 | cy ST2 | 9.76E+05 | 1.00E-04 | 103.0 | Ab35 | hu ST2 | 8.17E+05 | 1.15E-04 | 141.0 |
| Ab36 | cy ST2 | 4140000 | 0.000278 | 67.1 | Ab36 | hu ST2 | 4.12E+06 | 2.80E-04 | 68.1 |

The affinity of additional antibodies were determined using a slightly modified Plasmon resonance protocol. The surface plasmon resonance evaluations for the antibodies Ab1, Ab2, Ab3, and Ab4 were conducted at 25° C. using a BIACORE™ 3000 instrument (Biacore International AB, Uppsala, Sweden) equipped with a CM5 sensor chip. Anti-Fcγ specific capture antibodies were covalently immobilized to two flow cells on the CM4 chip using standard amine-coupling chemistry with HBS-EP ((10 mM HEPES pH 7.4, 150 mM NaCl, 3 mM EDTA, 0.005% Surfactant P20, GE Heathcare) as the running buffer. Briefly, each flow cell was activated with a 1:1 (v/v) mixture of 0.1 M NHS and 0.4 M EDC. AFFINIPURE™ Goat Anti-Human IgG, Fcγ Fragment Specific antibody (Jackson ImmunoResearch Inc. West Grove, Pa.) at 30 ug/ml in 10 mM sodium acetate, pH 5.0 was immobilized with a target level of 3,000 RUs on two flow cells. Residual reactive surfaces were deactivated with an injection of 1 M ethanolamine. The running buffer was then switched to HBS-EP+0.1 mg/ml BSA for all remaining steps.

All antibodies were prepared in running buffer in triplicate and diluted 3-fold, and injected so that a three minute injection at 10 µl/min over the test flow cell resulted in approximately 75-90 response units of antibody captured on the test flow cell surface. No antibody was captured on the control flow cell surface. Human or cyno ST2 at various concentrations (200 nM-0.0914 nM), along with buffer blanks were then flown over the two flow cells. A flow rate of 50 ul/min was used and a two minute association phase followed by a four min dissociation phase. After each cycle the surfaces were regenerated with a 50 uL injection of 10 mM glycine pH 1.5. Fresh antibody was then captured on the test flow cell to prepare for the next cycle. A separate long dissociation experiment (60 min) was performed in triplicate at a concentration of 200 nM.

Data was double referenced by subtracting the control surface responses to remove bulk refractive index changes, and then subtracting the averaged buffer blank response to remove systematic artifacts from the experimental flow cells. The ST2 data were processed and globally fit to a 1:1 interaction model with a local Rmax in BIA evaluation Software v 4.1. (Biacore International AB, Uppsala, Sweden). Association ($k_a$) and dissociation ($k_d$) rate constants were determined and used to calculate the dissociation equilibrium constant ($K_D$). The dissociation rate constants and dissociation equilibrium constants for Ab1, Ab2, Ab3, and Ab4 are summarized in Table 5.

TABLE 5

| Antibody | ST2 | $k_a$ (1/Ms) | $k_d$ (1/s) | $K_D$ (pM) |
|---|---|---|---|---|
| Ab1 | Human | 1.43E+06 | 1.11E-04 | 77.7 |
| Ab1 | Cyno | 1.69E+06 | 1.97E-04 | 117 |

TABLE 5-continued

| Antibody | ST2 | $k_a$ (1/Ms) | $k_d$ (1/s) | $K_D$ (pM) |
|---|---|---|---|---|
| Ab2 | Human | 3.33E+05 | 1.13E-05 | 33.9 |
| Ab2 | Cyno | 3.60E+05 | 1.16E-05 | 32.2 |
| Ab3 | Human | 4.00E+05 | 9.50E-05 | 238 |
| Ab3 | Cyno | 6.74E+05 | 8.55E-05 | 127 |
| Ab4 | Human | 2.35E+06 | 7.06E-04 | 301 |
| Ab4 | Cyno | 2.50E+06 | 1.29E-03 | 516 |

Example 4: pH-Sensitive Binding of Antibodies

Therapeutic antibodies that bind with decrease affinity at low pH to their targets may have enhanced PK properties that will allow them to be delivered less frequently or at lower doses. (*Nat Biotechnol.* 2010 28(11):1203-7 T. Igawa et al Antibody recycling by engineered pH-dependent antigen binding improves the duration of antigen neutralization) This is due to target release by the antibody at the low pH of the lyzosome, followed by subsequent target degradation and antibody recycling.

Biosensor analysis of the pH sensitive binding of the antibodies Ab1, Ab2, Ab3, and Ab4 was carried out on a BIACORE™ 4000. The setup was similar to Example 3, where the KD measurements of these antibodies were conducted, except that data was fit for a duplicate injection of a single concentration of 2.46 nM of (-ST2 antibody. The association (5 min) rates at pH 7.4 and dissociation (10 min) rates at pH 5.5 and 7.4 were monitored at a flow rate of 30 uL/min. The reference subtracted data was fit to a 1:1 model in Scrubber. Several of the antibodies displayed dramatically faster off rates at lower pH, as shown in Table 6.

TABLE 6

| Antibody | pH | Estimated $k_d$ (1/s)* | pH 7.4/ pH 5.5 kd fold change |
|---|---|---|---|
| Ab1 | 7.4 | 0.000134 | 88.1 |
| Ab1 | 5.5 | 0.0118 | |
| Ab2 | 7.4 | 0.0000298 | 8.0 |
| Ab2 | 5.5 | 0.000238 | |
| Ab3 | 7.4 | 0.0000273 | 2.9 |
| Ab3 | 5.5 | 0.0000791 | |
| Ab4 | 7.4 | 0.000632 | 16.9 |
| Ab4 | 5.5 | 0.0107 | |

Example 5: Antibody Cross-Competition

A common way to characterize epitopes is through competition experiments. Antibodies that compete with each other can be thought of as binding the same site on the target.

This example describes a method of determining competition for binding to ST2 and the results of the method when applied to a number of antibodies described herein.

Binning experiments can be conducted in a number of ways, and the method employed may have an effect on the assay results. Common to these methods is that ST2 is typically bound by one reference antibody and probed by another. If the reference antibody prevents the binding of the probe antibody then the antibodies are said to be in the same bin. The order in which the antibodies are employed is important. If antibody A is employed as the reference antibody and blocks the binding of antibody B the converse is not always true: antibody B used as the reference antibody will not necessarily block antibody A. There are a number of factors in play here: the binding of an antibody can cause conformational changes in the target which prevent the binding of the second antibody, or epitopes which overlap but do not completely occlude each other may allow for the second antibody to still have enough high-affinity interactions with the target to allow binding. In general, if competition is observed in either order the antibodies are said to bin together, and if both antibodies can block each other then it is likely that the epitopes overlap more completely.

For this Example, a modification of the Multiplexed Binning method described by Jia, et al (J. Immunological Methods, 288 (2004) 91-98) was used. Soluble ST2-FLAG His was used. Each Bead Code of streptavidin-coated LUMINEX® beads (LUMINEX®, #L100-L1XX-01, XX specifies the bead code) was incubated in 100 ul of 6 pg/bead biotinylated monovalent mouse-antihuman IgG capture antibody (BD Pharmingen, #555785) for 1 hour at room temperature in the dark, then washed 3× with PBSA, phosphate buffered saline (PBS) plus 1% bovine serum albumin (BSA). Each bead code was separately incubated with 100 ul of a 1:10 dilution anti-ST2 antibody (Coating Antibody) for 1 hour then washed. The beads were pooled then dispensed to a 96-well filter plate (Millipore, #MSBVN1250). 100 ul of 2 ug/ml ST2 was added to half the wells and buffer to the other half and incubated for 1 hour then washed. 100 ul of a 1:10 dilution anti-ST2 antibody (Detection Ab) was added to one well with ST2 and one well without ST2, incubated for 1 hour then washed. An irrelevant human-IgG (Jackson, #009-000-003) as well as a no antibody condition (blank) were run as negative controls. 20 ul PE-conjugated monovalent mouse-anti-human IgG (BD Pharmingen, #555787) was added to each well and incubated for 1 hour then washed. Beads were resuspended in 75 ul PBSA and at least 100 events/bead code were collected on the BIOPLEX® instrument (BioRad).

Median Fluorescent Intensity (MFI) of the antibody pair without ST2 was subtracted from signal of the corresponding reaction containing ST2. For the antibody pair to be considered bound simultaneously, and therefore in different bins, the value of the reaction had to meet two criteria: 1) the values had to be 2 times greater than the coating antibody paired with itself, the irrelevant or the blank, whichever was highest, and 2) the values had to be greater than the signal of the detection antibody present with the irrelevant or the blank coated bead. A minimum of three bins were found as shown in Table 7 below.

TABLE 7

| Bin | Antibody |
| --- | --- |
| Bin 1 | Ab23 |
| | Ab17 |
| | Ab24 |
| | Ab25 |
| | Ab12 |
| | Ab36 |
| | Ab14 |
| | Ab18 |
| | Ab19 |
| | Ab20 |
| | Ab33 |
| | Ab34 |
| | Ab1 |
| | Ab7 |
| | Ab3 |
| | Ab15 |
| | Ab16 |
| | Ab27 |
| | Ab5 |
| | Ab2 |
| | Ab8 |
| | Ab13 |
| | Ab30 |
| | Ab35 |
| | Ab28 |
| Bin 2 | Ab9 |
| | Ab10 |
| | Ab11 |
| Bin 3 | Ab29 |

Example 6: IL-33-Blocking Assays

The mechanism of action of the ST2 antibodies was explored using two AlphaScreens. In combination, the assays were used to determine if the antibodies could inhibit the association of IL-33 with ST2 or in contrast if the antibodies could specifically block the association of the co-receptors ST2 and AcP while still allowing IL-33 to associate with ST2. AlphaScreen is an acronym for Amplified Luminescent Proximity Homogenous Assay screen.

In the first screen, antibodies were evaluated for the ability to block an association between IL-33 and ST2. This assay measured the ability of the anti-ST2 antibodies to block the association of biotinylated human IL-33 (coupled with a Streptavidin donor bead) with 6×histidine tagged human ST2 (coupled with a Ni-chelate acceptor bead). The IL-33/ST2 AlphaScreen was conducted using 40 ul reactions in a 96 well half area plate (Perkin Elmer). The assay buffer that was used for both AlphaScreens contained 40 mM HEPES (pH=7.4), 1 mM CaCl2, 0.1% BSA, 0.05% Tween-20 and 100 mM NaCl. Each assay well contained 0.3 nM biotinylated human IL-33, 0.3 nM human ST2-FH (FH stands for FLAG and 6×Histidine tags), 10 ug/ml Streptavidin coated donor beads (Perkin Elmer, Waltham, Mass.), 10 ug/ml Ni-chelate coated acceptor beads (Perkin Elmer) and 12.5 ug/ml of an anti-ST2 Ab. After the addition of all assay components the plates were incubated overnight in the dark at room temperature. The next day the plates were read on a 2103 Envision multilabel reader (Perkin Elmer). Laser excitation of the donor beads at 680 nm was used to generate reactive oxygen that could initiate a luminescent/fluorescent cascade in the acceptor beads that were in close proximity due to the interaction of the bead coupled proteins resulting in the emission of light which was detected at 570 nm.

In the second assay, antibodies were evaluated for the ability to inhibit the IL-33 mediated association of ST2 with the co-receptor AcP. This assay measured the ability of the anti-ST2 antibodies to block the IL-33 mediated association of biotinylated human ST2-Fc (coupled with a Streptavidin donor bead) with 6×histidine tagged human AcP (coupled with a Ni-chelate acceptor bead). The ST2/AcP AlphaScreen was conducted in 8 ul reactions in a 384 well optiplate (Perkin Elmer). Each assay well contained 5 nM human IL-33, 5 nM biotinylated human ST2-Fc, 5 nM human AcP-FH, 10 ug/ml Streptavidin coated donor beads, 10 ug/ml Ni-chelate coated acceptor beads and 12.5 ug/ml of an anti-ST2 Ab. After the addition of all assay components the plates were incubated overnight in the dark at room temperature. The next day the plates were read on a 2103 Envision multilable reader (Perkin Elmer) using the same parameters as above for the first assay.

The results of the two AlphaScreens are presented in Table 8 below. The inhibition of each antibody is presented as the percentage of inhibition of signal in the AlphaScreen using a given antibody at a concentration of 12.5 ug/ml relative to the signal in the assay when no antibody was included in the assay well. Some antibodies inhibited the ST2 and IL-33 interaction more completely than they inhibited the ST2/IL-33/AcP interaction and some antibodies inhibited the ST2/IL-33/AcP interaction more completely than the ST2 and IL-33 interaction. All antibodies inhibited the IL-33 interaction with ST2 by at least 50%.

TABLE 8

| Name | % inhib ST2-IL33 AS 12.5 ug/ml | % inhib ST2-AcP AS 12.5 ug/ml |
|---|---|---|
| Ab6 | 98.5 | 71.2 |
| Ab4 | 98.4 | 77.8 |
| Ab9 | 75.9 | 93.1 |
| Ab10 | 51.8 | 73.2 |
| Ab1 | 98.1 | 86.9 |
| Ab7 | 98.9 | 75.7 |
| Ab3 | 98.8 | 68.7 |
| Ab11 | 75.8 | 93.6 |
| Ab5 | 96.3 | 33.8 |
| Ab2 | 99.2 | 96.4 |

Example 7: In Vitro Human IL-33 Bioassay

Exemplary ST2 human mAbs were tested in a human bioassay utilizing purified CD4+ T cells obtained from various donors stimulated with human IL-33 and human IL-2. The procedure for the assay is as follows. Cells are seeded at 250,000 cells per well in 60 ul volume in a 96 well round bottom plate. After preincubation, add 30 ul of 4× mixture of huIL-2+huIL-33 to each well. Total volume in 96-well round bottom plate is 120 ul. Start antibodies at 20 ug/ml and do 1:3 dilutions to generate 10 point curve. Make 4× in 30 ul. After preincubation of Abs with cells, add 30 ul of 4× mixture of huIL-2+huIL-33 to each well. 37° C., 5% CO2 for 48 hours. Harvest supernatants. Analyze inhibition of IL-5 by huIL-5 ELISA.

Figure 3:
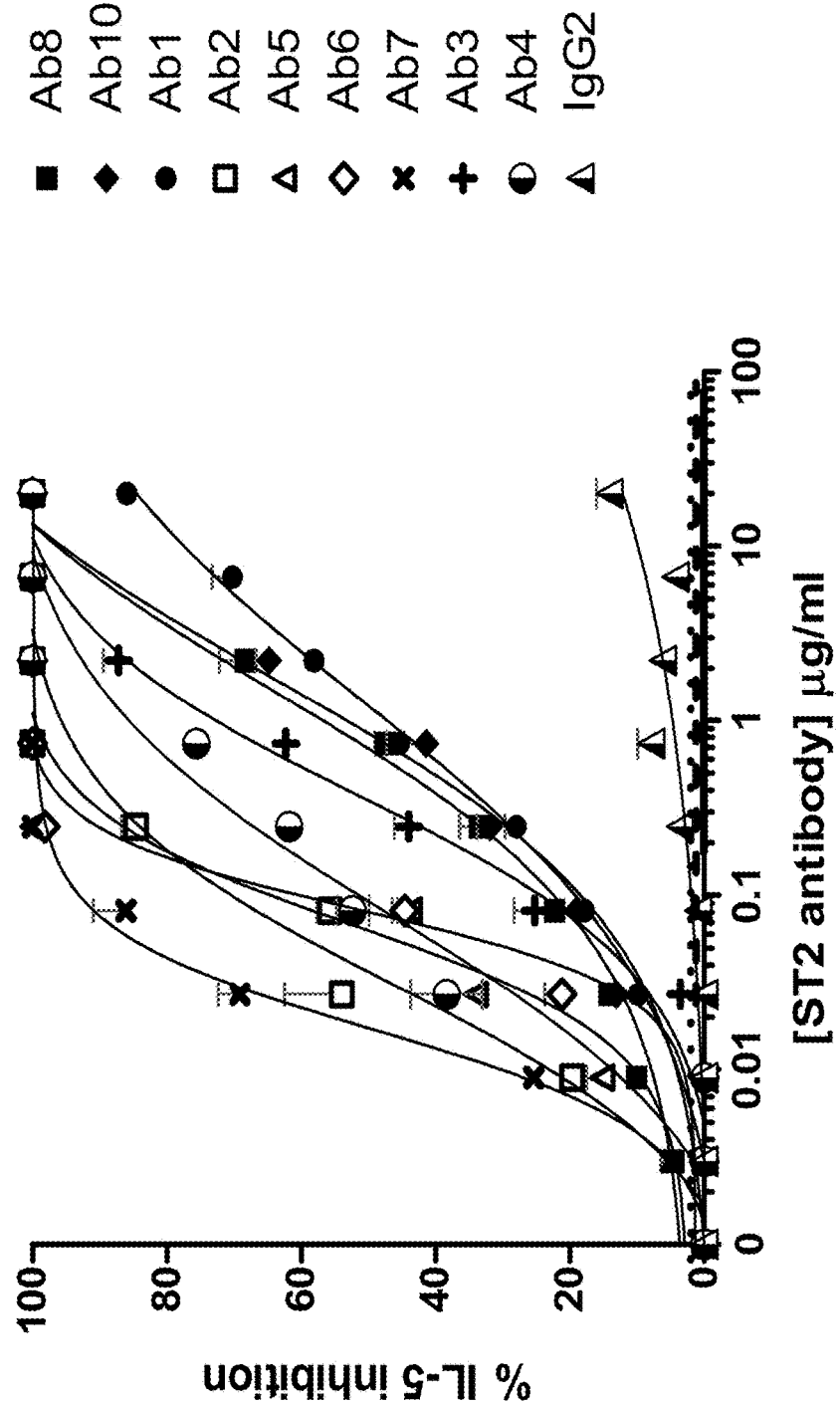
FIG. 3 ST2 mAbs in the inhibition of human IL-33-induced IL-5 production from CD4+ T cells from various donors. The (-) line depicts the positive control value of human IL-33 in combination with human IL-2 without inhibition. The (• • • •) depicts the positive control value of human IL-2. The (- -) line depicts the media control value.

FIG. 3 shows ST2 mAbs in the inhibition of human IL-33-induced IL-5 production from CD4+ T cells from various donors. The (-) line depicts the positive control value of human IL-33 in combination with human IL-2 without inhibition. The (• • •) depicts the positive control value of human IL-2. The (- -) line depicts the media control value. Human CD4+ T cells were preincubated for 30 minutes with anti-ST2 mAbs and then stimulated for 48 hours with human IL-33 (4 ng/ml) and human IL-2 (10 ng/ml). FIG. 3 shows that ST2 antibodies are able to inhibit human IL-33-induced ST2 activation, as determined by IL-5 production from CD4+ T cells. The ST2 antibodies were able to antagonize IL-33 induced IL-5 production from CD4+ T cells with IC50s of approximately <100 nM. Table 9 shows representative IC50 values.

TABLE 9

| Ab | IC50 (nM) |
|---|---|
| 2 | 5.25 |
| 8 | 6.90 |
| 10 | 6.90 |
| 1 | 10.68 |
| 9 | 62.01 |
| 5 | 64.54 |
| 11 | 479.86 |

Example 8: Cynomolgus Monkey CD4+ T-Cell IFNγ Release Assay

Cynomolgus monkey peripheral blood mononuclear cells (PBMC) were enriched from acid citrate dextrose (ACD) treated normal donor peripheral blood by ISOLYMPH (Gallard-Schlesinger Industries, Plainview, N.Y.) gradient centrifugation. Subsequent isolation of cynomolgus monkey CD4+ T cells was performed using Miltenyi Biotec's cynomolgus monkey CD4+ T cell Isolation Kit. Isolated cyno CD4+ T cells ($2 \times 10^5$ cells/well in 96 well plates) were incubated with purified monoclonal antibodies at various concentrations for 30 minutes at room temperature and then stimulated with IL-33 (10 ng/mL), IL-2 (10 ng/mL), and IL-12p70 (50 ng/mL) for eighty-four hours. The resulting cell-free cynomolgus monkey CD4+ T cell culture supernatants were then analyzed for the presence of cynomolgus monkey IFNγ by ELISA (example data is provided in Table 10). The potency of purified monoclonal antibodies was determined in the cynomolgus monkey CD4+ T cell IFNγ release assay from three separate donors.

TABLE 10

| IC-50 Values | pM |
|---|---|
| Ab1 | 15.82 |
| Ab2 | 79.5 |
| Ab3 | 15.15 |
| Ab4 | 4.03 |
| Ab5 | 12.9 |
| Ab6 | 47.1 |
| Ab7 | 40.01 |
| Ab8 | 158.07 |

Example 9: Human Eosinophil IL-8 Release Assay

Human erythrocytes and granulocytes were enriched from heparinized, normal donor peripheral blood by ISOLYMPH (Gallard-Schlesinger Industries, Plainview, N.Y.) gradient centrifugation. The erythrocytes were removed using ACK lysing buffer (Gibco, Carlsbad, Calif.). Subsequent isolation of eosinophils was performed using Miltenyi Biotec's Eosinophil Isolation Kit. Isolated eosinophils ($2 \times 10^5$ cells/well in 96 well plates) were incubated with non-clonal or clonal supernatants at several dilutions, or purified monoclonal antibodies at various concentrations for 30 minutes at room temperature and then stimulated with IL-33 (2 ng/mL) and IL-3 (100 ng/mL) for three days. The resulting cell-free eosinophil culture supernatants were then analyzed for the presence of IL-8 by ELISA. Example data is shown in Table 11. The potency of purified monoclonal antibodies was determined in the eosinophil IL-8 release assay from three separate donors.

TABLE 11

| IC-50's | pM |
|---|---|
| Ab1 | 51.45 |
| Ab2 | 52.75 |
| Ab3 | 50.38 |
| Ab4 | 14.12 |
| Ab5 | 73.27 |
| Ab6 | 63.02 |
| Ab7 | 40.68 |
| Ab8 | 3120 |

Figure 4:
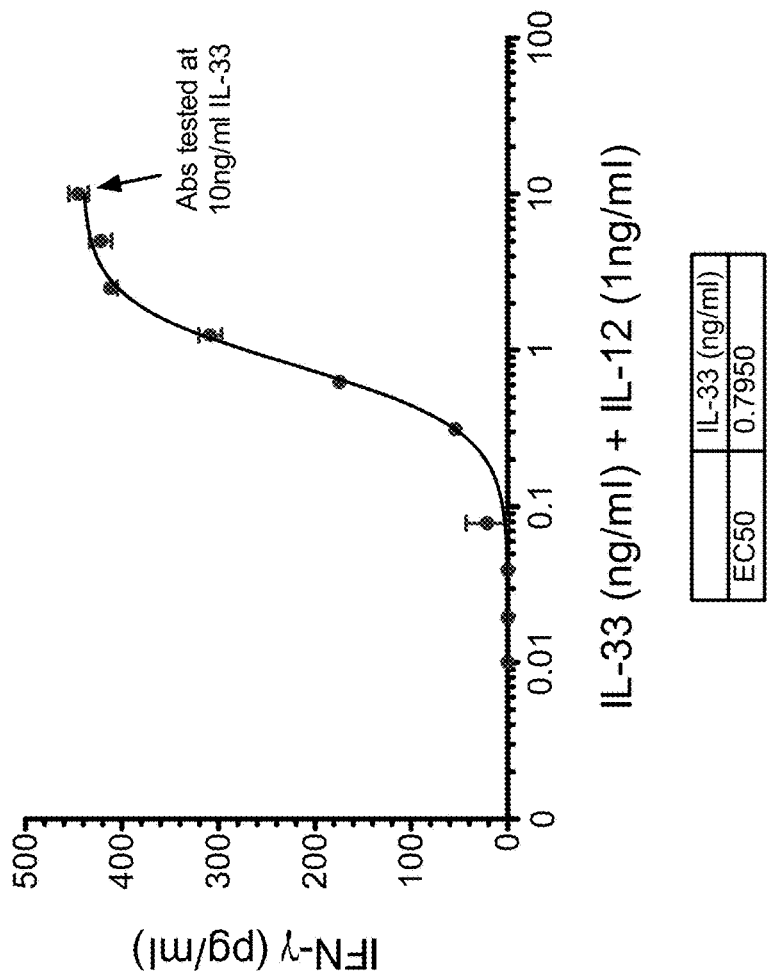
FIG. 4 Dose response of human IL-33 in human NK cell assay.

Example 10: Potency of Anti-ST2 Antibody Compared to Commercially Available Antibodies Dose Response of Human IL-33 in Human NK Cell Assay Primary CD56-positive human NK cells (5×10e4 cells) were treated with human IL-12 (1 ng/mL) plus increasing amounts of human IL-33, as shown in FIG. 4. Twenty-two hours later, cell-free supernatants were collected and measured for IFN-γ concentration using a commercial assay (R&D Systems). 10 ng/mL IL-33 was used as the stimulation dose for the ST2 antibody inhibition.

Antibody Inhibition of IL-33 Activity

Figure 5:
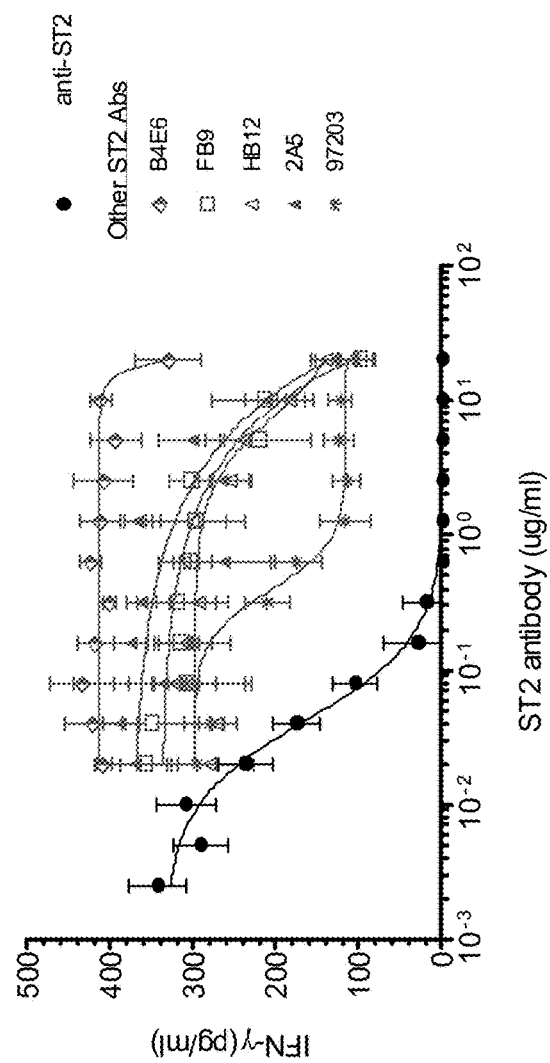
FIG. 5 Reduction of IL-33 activity in a human NK cell assay caused by Ab2 versus commercially-available ST2 antibodies. Clones HB12, FB9 and 2A5 were obtained from MBL International Corporation. Clone B4E6 was obtained from MD Biosciences. Clone 97203 was obtained from R&D Systems.

Human NK cells were stimulated as above. Thirty minutes prior to IL-33 and IL-12 addition, ST2 antibodies were added to cells at the concentrations as indicated in FIG. 5. Twenty-two hours following IL-33 treatment, cell-free supernatants were collected and measured for IFN-γ concentration using a commercial assay (R&D Systems). Clone names are indicated for the commercially available antibodies. Only Ab2 completely inhibited the IL-33-dependent IFN-γ response and it was significantly more potent than any of the commercially available huST2 antibodies. The IC50 value corresponding to each antibody is shown in Table 12.

TABLE 12

| Antibody | IC50 (ug/ml) |
|---|---|
| 2A5 | ~608 |
| HB12 | 7.700 |
| B4E6 | ~43.54 |
| FB9 | ~498.4 |
| 97203 | 0.3851 |
| Ab2 | 0.04123 |

Example 11: Alanine/Arginine Scanning Mutagenesis of ST2

This Example characterizes ST2 antibodies based on the effect of mutagenesis of ST2 on their ability to bind the target. Previous binding data indicated that ST2 domains 1 and 2 are primarily responsible for antibody binding for the panel of antibodies analyzed by ST2 scanning mutagenesis in this Example. As such, only domains 1 and 2 (D1D2) of ST2 were considered structurally in the context of the full length ST2 in the designs of mutation sites.

The ST2 and IL-33 complex model coordinates were obtained from Lingel et al., Structure (London, England: 1993). Elsevier Ltd 17, 1398-410. The per residue sidechain solvent accessibility of ST2 was calculated in the Molecular Operating Environment (*Molecular Operating Environment* (*MOE*), 2011.10; Chemical Computing Group Inc., 1010 Sherbooke St. West, Suite #910, Montreal, QC, Canada, H3A 2R7, 2011.). These solvent accessibility values were then used in the selection of D1D2 surface residues for mutagenesis by first selecting all D1D2 residues with sidechain exposures of at least 10 Å$^2$ or glycine residues with total exposures of at least 10 Å$^2$. Glycine residues with a positive Phi angle were removed, as were proline residues, since mutations at such positions have a higher probability of distorting the local protein structure. Cysteine residues were also removed from the selection to maintain disulfide linkages. Residue A82 was removed after visual inspection. This method produced a list of 140 residues for mutagenesis. All residues were mutated to arginine except for arginine and lysine residues, which were mutated to alanine.

All mutant constructs of parental His-Avi-tagged ST2 extracellular domain (ECD), in pTT5 vector, were expressed in transiently transfected 293-6E suspension cells (NRCC) in 24-well plates. In-vivo biotinylation was achieved by co-transfection of BiR A in pTT5 vector. The supernatants were dialyzed with PBS to remove excess biotin.

BIOPLEX® binding assay is used to measure binding of anti-ST2 antibodies to point mutations of ST2. The biotinylated mutants were bound onto 80 bead codes of streptavidin-coated beads (LUMINEX®, #L100-L1XX-01, XX specifies the bead code). The 80 bead codes allowed the multiplexing of two sets of 70 mutants for 140 total. Each set included 6 parental controls, 3 irrelevant protein controls and 1 blank. Antibody binding to mutant protein was compared to antibody binding to the parental.

100 ul of a 1:7 dilution of the ST2 mutants, parental and controls or no protein pre bound to the beads were washed 5× with PBS+1% BSA, pooled and aliquoted into a 96-well filter plate (Millipore) then washed again. 100 ul anti-ST2 antibodies in 3-fold dilutions were added to triplicate wells, incubated for 1 hour at RT and washed. 100 ul of 1:500 dilution of PE-conjugated anti-human IgG Fc (Jackson, #109-116-170) was added to each well, incubated for 0.5 hour and washed. Beads were resuspended in 75 uL, shaken for at least 3 mins, and read on the BIOPLEX®.

Before running the binding assay, a validation experiment was conducted to assess the "bead region" to "bead region" (B-B) variability. In the validation experiment, all beads were conjugated with the same wild-type control protein. Therefore, the difference between beads regions was due to purely B-B variance and was not confounded by difference between wild type and mutant proteins. The titration of antibody was run with twelve replications in different wells.

The objective of this statistical analysis was to estimate the B-B variability of the estimated EC50 of binding curves. The estimated B-B standard deviation (SD) was then used to build the EC50 confidence intervals of wild type and mutant proteins during curve comparison experiments.

A four-parameter logistic model was fitted to the binding data for each bead region. The resulting "sumout.xls" file, containing curve quality control (QC) results and parameter estimates for top (max), bottom (min), Hillslope (slope), and natural log of EC50 (xmid) of the curves, was used as the raw data for the analysis. B-B variability for each parameter was then estimated by fitting mixed effect model using SAS PROC MIXED procedure. Only curves with "good" QC status were included in the analysis. The final mixed effect model included only residual (i.e. individual bead regions) as random effect. Least squares means (LS-mean) for each parameter were estimated by the mixed effect model as well. B-B SD was calculated by taking square root of B-B variance. Fold change between LS-mean+2SD and LS-mean−2SD, which represent approximately upper and lower 97.5 percentile of the population, was also calculated.

To identify mutants that did not produce much response relative to WT control, for each antibody, mutants where max (MFI) are less than 30% of the max(MFI) for WT control are identified and flagged as Hitmax.

The EC50s of the mutant binding curves and wild type binding curves were compared. Statistically significant differences were identified as hits for further consideration. The curves with "nofit" or "badfit" flags were excluded from this analysis.

Two sources of variations are considered in the comparison of EC50 estimates, variation from the curve fit and the bead-bead variation. Wild types and mutants were linked to different beads, hence their difference are confounded with the bead-bead difference. The curve fit variation is estimated by the standard error of the log EC50 estimates. Bead-bead variation is experimentally determined using an experiment where wild type controls were linked to each one of the beads. The bead variation in EC50 estimates of wild type binding curve from this experiment is used to estimate the bead-bead variation in the actual mapping experiment.

The comparisons of two EC50s (in log scale) are conducted using Student's t-test. A t-statistics is calculated as the ratio between delta (the absolute differences between EC50 estimates) and the standard deviation of delta. The variance of delta is estimated by the sum of the three components, variance estimate of EC50 for mutant and wild type curves in the nonlinear regression and two times the bead-bead variance estimated from a separate experiment. The multiple of two for the bead-bead variance is due to the assumption that both mutant and wild type beads have the same variance.

The degree of freedom of the standard deviation of delta was calculated using the Satterthwaite's (1946) approximation.

Individual p-values and confidence intervals (95% and 99%) were derived based on Student's t distribution for each comparison.

In the case of multiple wild type controls, a conservative approach was taken by picking the wild type control that was most similar to the mutant, i.e., picking the ones with the largest p-values.

Multiplicity adjustments are important to control the false positive while conducting a large number of tests simultaneously. Two forms of multiplicity adjustment were implemented for this analysis: family wise error (FWE) control and false discovery rate (FDR) control. The FWE approach controls the probability that one or more hits are not real; FDR approach controls the expected proportion of false positive among the selected hits. The former approach is more conservative and less powerful than the latter one. There are many methods available for both approaches, for this analysis, we chose Hochberg's (1988) method for FWE analysis and Benjamini-Hochberg's (1995) FDR method for FDR analysis. Adjusted p-values for both approaches are calculated either for each antibody or the whole assay.

A mutant was selected as having an effect by the following criteria if: 1) a bad fit or no fit results was returned for that mutant, 2) the mutant was selected for the hitmax criteria, 3) the family wise error pValue was less than 0.01, or 4) the Bmax value was greater than 200% of parental. A hit was designated as an inhibitor if the effect reduced Bmax or increased the EC50 value, a hit was designated as an activator if it increased Bmax or decreased the EC50 value. 8 mutation were excluded from the hit list due to their effect on >90% of the antibodies tested, they are: K37A, R46A, D63R, V71R, G106R, K112A, N132R, Q137R, and Y141R.

The results of the analysis are provided in Tables 13 and 14.

TABLE 13

| Ab | Bin | Inhibiting mutants | Activating mutants |
|---|---|---|---|
| Ab2 | 1 | L14R, I15R, S33R, E43R, V47R, A62R, G65R, T79R, D92R, D97R, V104R, G138R, N152R, V176R | L53R, R72A, S73R |
| Ab3 | I | S3R, E10R, I15R, S33R, E43R, V47R, A62R, G65R, F76R, T79R, D92R, D97R, V104R, T124R, K131A, Q134R, G138R, F147R, V176R, V184R | D29R, L53R, V61R, R72A, T162R |
| Ab32 | 1 | S3R, I15R, Y32R, S33R, E43R, V47R, S50R, K55A, A62R, G65R, T79R, D92R, V95R, D97R, V104R, E128R, Q134R, G138R, S146R, F147R, V176R | D29R, R72A |
| Ab33 | I | S3R, I15R, Y32R, S33R, T35R, E43R, V47R, S50R, K55A, A62R, G65R, T79R, D92R, V95R, D97R, V104R, E128R, Q134R, G138R, S146R, F147R, N152R, V176R | D29R, R72A |
| Ab30 | I | S3R, L14R, Y26R, S33R, T35R, E43R, V47R, A62R, G65R, T79R, D92R, V104R,, G138R,, A143R, F147R, N152R, V176R, V184R | R72A |
| Ab11 | 2 | S50R, S175R | W7R, E10R, L14R, Q21R, E43R, T79R, N110R, T177R, V184R, K185A |
| Ab10 | 2 | A49R, S50R, I70R, S175R, S181R | K4A, Q5R, W7R, E10R, L14R, I15R, Q21R, Y26R, E43R, T79R, M100R, K109A, N110R, T124R, K145A, T177R, V184R, K185A |
| Ab29 | 3 | N11R, V47R, S50R, Y67R, N83R, V104R, L120R, G138R, S139R, S146R, F147R, A172R | |

TABLE 14

| Ab | No Effect mutants |
|---|---|
| Ab2 | K1A, F2R, S3R, K4A, Q5R, S6R, W7R, L9R, E10R, N11R, E12R, A13R, V16R, R17A, R20A, Q21R, K23A, S25R, Y26R, V28R, D29R, Y31R, Y32R, Q34R, T35R, N36R, S38R, T41R, Q42R, R44A, N45R, A49R, S50R, G51R, Q52R, K55A, L57R, E60R, V61R, S64R, I66R, Y67R, T68R, I70R, T75R, F76R, N77R, R78A, G80R, Y81R, N83R, T85R, Y87R, K88A, K89A, Q90R, S91R, N94R, V95R, Y98R, M100R, Y101R, S102R, T103R, S107R, E108R, K109A, N110R, Y114R, T117R, D119R, L120R, Y121R, N122R, W123R, T124R, E128R, F130R, K131A, Q134R, A135R, S139R, R140A, R142A, A143R, H144R, K145A, S146R, F147R, V149R, D151R, M154R, T155R, E156R, A158R, D160R, T162R, K164A, I166R, N168R, N170R, A172R, N173R, Y174R, S175R, T177R, R180A, S181R, T183R, V184R, K185A, D186R, E187R |
| Ab3 | K1A, F2R, K4A, Q5R, S6R, W7R, L9R, N11R, E12R, A13R, L14R, V16R, R17A, R20A, Q21R, K23A, S25R, Y26R, V28R, Y31R, Y32R, Q34R, T35R, N36R, S38R, T41R, Q42R, R44A, N45R, A49R, S50R, G51R, Q52R, K55A, L57R, E60R, S64R, I66R, Y67R, T68R, I70R, S73R, T75R, N77R, R78A, G80R, Y81R, N83R, T85R, Y87R, K88A, K89A, Q90R, S91R, N94R, V95R, Y98R, M100R, Y101R, S102R, T103R, S107R, E108R, K109A, N110R, Y114R, T117R, D119R, L120R, Y121R, N122R, W123R, E128R, F130R, A135R, S139R, R140A, R142A, A143R, H144R, K145A, S146R, V149R, D151R, N152R, M154R, T155R, E156R, A158R, D160R, K164A, I166R, H176R, N168R, N170R, A172R, N173R, Y174R, S175R, T177R, R180A, S181R, T183R, K185A, D186R, E187R |
| Ab32 | K1A, F2R, K4A, Q5R, S6R, W7R, L9R, E10R, N11R, E12R, A13R, L14R, V16R, R17A, R20A, Q21R, K23A, S25R, Y26R, V28R, Y31R, Q34R, T35R, N36R, S38R, T41R, Q42R, R44A, N45R, A49R, G51R, Q52R, L53R, L57R, E60R, V61R, S64R, I66R, Y67R, T68R, I70R, S73R, T75R, F76R, N77R, R78A, G80R, Y81R, N83R, T85R, Y87R, K88A, K89A, Q90R, S91R, N94R, Y98R, M100R, Y101R, S102R, T103R, S107R, E108R, K109A, N110R, Y114R, T117R, D119R, L120R, Y121R, N122R, W123R, T124R, F130R, K131A, A135R, S139R, R140A, R142A, A143R, H144R, K145A, V149R, D151R, N152R, M154R, T155R, E156R, A158R, D160R, T162R, K164A, I166R, H176R, N168R, N170R, A172R, N173R, Y174R, S175R, T177R, R180A, S181R, T183R, V184R, K185A, D186R, E187R |
| Ab33 | K1A, F2R, K4A, Q5R, S6R, W7R, L9R, E10R, N11R, E12R, A13R, L14R, V16R, R17A, R20A, Q21R, K23A, S25R, Y26R, V28R, Y31R, Q34R, N36R, S38R, T41R, Q42R, R44A, N45R, A49R, G51R, Q52R, L53R, L57R, E60R, V61R, S64R, I66R, Y67R, T68R, I70R, S73R, T75R, F76R, N77R, R78A, G80R, Y81R, N83R, T85R, Y87R, K88A, K89A, Q90R, S91R, N94R, Y98R, M100R, Y101R, S102R, T103R, S107R, E108R, K109A, N110R, Y114R, T117R, D119R, L120R, Y121R, N122R, W123R, T124R, F130R, K131A, A135R, S139R, R140A, R142A, A143R, H144R, K145A, V149R, D151R, M154R, T155R, E156R, A158R, D160R, T162R, K164A, I166R, H176R, N168R, N170R, A172R, N173R, Y174R, S175R, T177R, R180A, S181R, T183R, V184R, K185A, D186R, E187R |
| Ab30 | K1A, F2R, K4A, Q5R, S6R, W7R, L9R, E10R, N11R, E12R, A13R, I15R, V16R, R17A, R20A, Q21R, K23A, S25R, V28R, D29R, Y31R, Y32R, Q34R, N36R, S38R, T41R, Q42R, R44A, N45R, A49R, S50R, G51R, Q52R, L53R, K55A, L57R, E60R, V61R, S64R, I66R, Y67R, T68R, I70R, S73R, T75R, F76R, N77R, R78A, G80R, Y81R, N83R, T85R, Y87R, K88A, K89A, Q90R, S91R, N94R, V95R, D97R, Y98R, M100R, Y101R, S102R, T103R, S107R, E108R, K109A, N110R, Y114R, T117R, D119R, L120R, Y121R, N122R, W123R, T124R, E128R, F130R, K131A, Q134R, A135R, S139R, R140A, R142A, H144R, K145A, S146R, V149R, D151R, M154R, T155R, E156R, A158R, D160R, T162R, K164A, I166R, H176R, N168R, N170R, A172R, N173R, Y174R, S175R, T177R, R180A, S181R, T183R, K185A, D186R, E187R |
| Ab11 | K1A, F2R, S3R, K4A, Q5R, S6R, L9R, N11R, E12R, A13R, I15R, V16R, R17A, R20A, K23A, S25R, Y26R, V28R, D29R, Y31R, Y31R, Y32R, S33R, Q34R, T35R, N36R, S38R, T41R, Q42R, R44A, N45R, V47R, A49R, G51R, Q52R, L53R, K55A, L57R, E60R, V61R, A62R, S64R, G65R, I66R, Y67R, T68R, I70R, R72A, S73R, T75R, F76R, N77R, R78A, G80R, Y81R, N83R, T85R, Y87R, K88A, K89A, Q90R, S91R, D92R, N94R, V95R, D97R, Y98R, M100R, Y101R, S102R, T103R, V104R, S107R, E108R, K109A, Y114R, T117R, D119R, L120R, Y121R, N122R, W123R, T124R, E128R, F130R, K131A, Q134R, A135R, G138R, S139R, R140A, R142A, A143R, H144R, K145A, S146R, F147R, V149R, D151R, N152R, M154R, T155R, E156R, A158R, D160R, T162R, K164A, I166R, H176R, N168R, N170R, A172R, N173R, Y174R, V176R, R180A, S181R, T183R, D186R, E187R |
| Ab10 | K1A, F2R, S3R, S6R, L9R, N11R, E12R, A13R, V16R, R17A, R20A, K23A, S25R, V28R, D29R, Y31R, Y32R, S33R, Q34R, T35R, N36R, S38R, T41R, Q42R, R44A, N45R, V47R, G51R, Q52R, L53R, K55A, L57R, E60R, V61R, A62R, S64R, G65R, I66R, Y67R, T68R, I70R, R72A, S73R, T75R, F76R, N77R, R78A, G80R, Y81R, N83R, T85R, Y87R, K88A, K89A, Q90R, S91R, D92R, N94R, V95R, D97R, Y98R, Y101R, S102R, T103R, V104R, S107R, E108R, Y114R, T117R, D119R, L120R, Y121R, N122R, W123R, E128R, F130R, K131A, Q134R, A135R, G138R, S139R, R140A, R142A, A143R, H144R, S146R, F147R, V149R, D151R, N152R, M154R, T155R, E156R, A158R, D160R, T162R, K164A, I166R, H176R, N168R, A172R, N173R, Y174R, V176R, R180A, T183R, D186R, E187R |
| Ab29 | K1A, F2R, S3R, K4A, Q5R, S6R, W7R, L9R, E10R, E12R, A13R, L14R, I15R, V16R, R17A, R20A, Q21R, K23A, S25R, Y26R, V28R, D29R, Y31R, Y32R, S33R, Q34R, T35R, N36R, S38R, T41R, Q42R, E43R, R44A, N45R, A49R, G51R, Q52R, L53R, K55A, L57R, E60R, V61R, A62R, S64R, G65R, I66R, T68R, I70R, R72A, S73R, T75R, F76R, N77R, R78A, T79R, G80R, Y81R, T85R, Y87R, K88A, K89A, Q90R, S91R, D92R, N94R, V95R, D97R, Y98R, M100R, Y101R, S102R, T103R, S107R, E108R, K109A, N110R, Y114R, T117R, D119R, Y121R, N122R, W123R, T124R, E128R, F130R, K131A, Q134R, A135R, R140A, R142A, A143R, H144R, K145A, V149R, D151R, N152R, M154R, T155R, E156R, A158R, D160R, T162R, K164A, I166R, H176R, N168R, N170R, N173R, Y174R, S175R, V176R, T177R, R180A, S181R, T183R, V184R, K185A, D186R, E187R |

Example 12: Hydrogen/Deuterium Exchange (HDX) Analysis

In this Example, Ab2 was bound to ST2 and the effect of binding on HDX determined.

Soluble ST2 protein (domains 1-3 containing amino acids 19-322 of SEQ ID NO:1) with both FLAG-tag and His-tag on the C-terminus was transiently expressed in mammalian 293-6E cells and purified with IMAC (immobilized metal ion affinity chromatography) and further purified by preparative SEC (size exclusion chromatography). The protein was then concentrated to 3.5 mg/mL using ultra-filtration. ST2 antibody Ab2 was expressed in engineered CHO-CS9 cells and purified with protein A affinity chromatography followed by preparative SEC. Analytical SEC was used to determine that a 0.75:1.00 molar ratio of antibody:antigen was optimal to ensure that the ST2 protein is fully bound to the antibody. Both the free ST2 protein and the antigen-antibody complex were stored in PBS buffer, pH 7.2.

The HDX experiment was performed on an automated HDX system (Zhang, Zhang et al. 2012). Briefly, the H/D exchange process starts with diluting 5 uL of either the free ST2 protein solution (3.5 mg/mL) or ST2-antibody complex (with j ST2 concentration of 3.5 mg/mL, antigen:antibody ratio of 1:0.75) into 25 uL $D_2O$ buffer in 100 mM PBS, pH 7.2, which was prepared by dissolving PBS tablet in $D_2O$ water, at 25° C. The exchange reaction was allowed to insubate for various labeling duration (30 seconds, 2, 8, 30 min, and 2, 8 hours) for each HDX experiment, and the labeling reaction was quenched by mixing 20 μL labeling solution with 80 µL quenching/denaturation/reduction buffer (7.25 M urea and 625 mM tris(2-carboxyethyl)phosphine (TCEP), 0.45M glycine, pH 2.7) at 1° C.

A 40 µL aliquot of quenched solution was transferred into 120 µL 0.4 mg/mL porcine pepsin (Sigma, St. Louis, Mo.) solution. The digestion solution was immediately injected into a sample loop at 1° C. and stayed 6 min for full digestion. Furthermore, the digest was separated by C18 columns (3 columns in series, BEH C18, 2.1 mm×5 mm, Waters Corp., Milford, Mass.). The HPLC separation was performed at 1° C. with a 5-min ACN gradient of 1-40%. The LC eluant was analyzed by an Orbitrap Elite mass spectrometer (Thermo Scientific, San Jose, Calif.) in a data-dependent LC-MS/MS experiment.

Deuterium labeling, quenching, proteolytic digestion and injection were performed on a LEAP HD-X PAL system controlled by LEAP Shells (LEAP Technologies, Carrboro, N.C.).

The experiments were repeated three times and in each experiment, each time point was repeated twice. A standard peptide mixture was added to the samples to track and correct back-exchange variability. The mixture contains these three peptides: bradykinin, angiotensin I, and leucine enkephalin. A specially designed tetrapeptide PPPI (synthesized by AnaSpec, Fremont, Calif.) was used as second internal standard to minimize run to run variability. Digest of ST2 protein without H/D exchange was also analyzed as control.

The resulting data files were processed with the MassAnalyzer program (Zhang, Zhang et al. 2012). The software identifies peptides from the antigen digest, calculates the exchange rate of each peptide, corrects for back-exchange information obtained from the internal standards, and fits the data into a model that gives protection factors to each residue.

Figure 6:
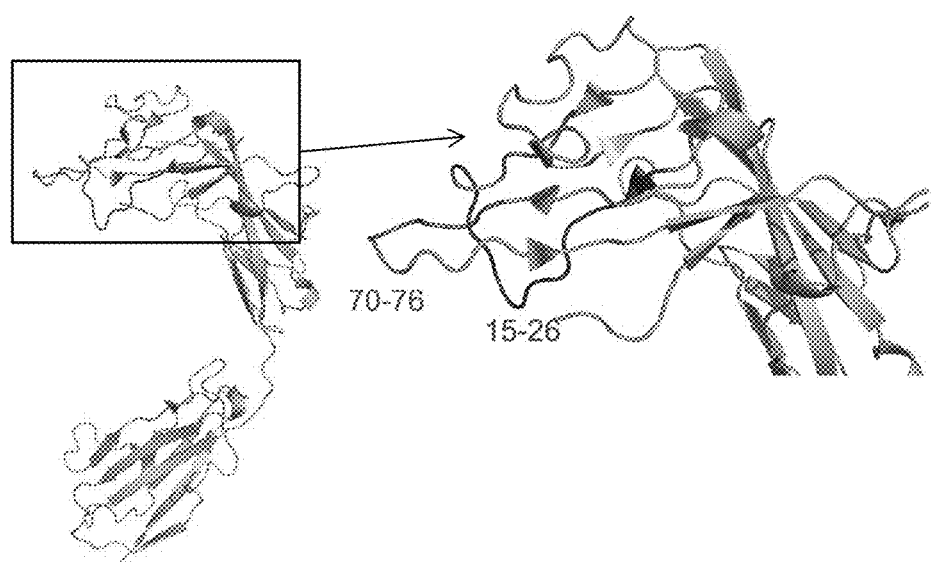
FIG. 6 The location of the regions of ST2 bound by Ab2 as determined by HDX (see Example 12). The region corresponding to amino acids 15-26 of the extracellular domain of ST2 is highlighted in red and region corresponding to amino acids 70-76 of the extracellular domain of ST2 is highlighted in magenta.

Comparison of the exchange profiles between free ST2 and antibody-bound ST2 protein revealed two regions of interest and could be the potential epitope. The two regions in the ST2 sequence were refined to IVRCPRQGKPSY (amino acids 33-44 of SEQ ID NO:1 corresponding to amino acids 15-26 of mature ST2) and IVRSPTF (amino acids 88-94 of SEQ ID NO:1 corresponding to amino acids 70-76 of mature ST2) by multiple overlapped peptides. These regions were less protected when ST2 is in the free-state, while the exchange rate decreases dramatically upon binding of ST2 and the antibody. Furthermore, based on ST2 homology structure model shown in FIG. 6, these two sequence stretches occupy similar spatial locations on the exterior surface of the protein. These results lead to the conclusion that the two peptides are involved in the binding between Ab2 and ST2 protein.

Example 13: X-Ray Crystallography

In this Example, the crystal structure of the complex of an sc-dsFv fragment of Ab2 and ST2 provides the specific amino acid residues in the interaction interface.

Ab2 sc-dsFv was expressed in BL21(DE3) Star cells. Briefly, the Ab2 sc-dsFv contains the heavy chain variable domain connected to the light chain variable domain by a linker $(G_4S)_3$. To further stabilize the molecule, a disulfide bond was engineered into the molecule by mutating to cysteine position 44 of the heavy chain variable region and position 101 of the light chain variable region. The protein was expressed as an inclusion body. The inclusion body was solubilized and refolded. Protein was further purified on size exclusion column (SEC) and ion-exchange MonoQ column, and then polished on SEC.

ST2 was expressed in 293S cells. The protein was purified by Ni-affinity column and deglycosylated with EndoH. Protein was further purified on SEC.

The complex of Ab2 sc-dsFv and ST2 was formed by mixing Ab2 sc-dsFv and excess ST2. The complex was purified on SEC and concentrated to 12 mg/ml for crystallization. The protein complex was crystallized in 32-36% PEG400 and 0.1 M Hepes, pH 7.5-8.5, at 16° C. using sitting drop vapor diffusion method.

A 1.9 Å resolution dataset was collected at the Advanced Light Source, Lawrence Berkeley National Lab (Berkeley, Calif.). The data was processed with MOSFLM (Leslie, 1992) and scaled by SCALA in CCP4 program suite (Collaborative Computational Project, No 4. (1994)). The structure was solved by molecular replacement method with program PHASER (McCoy et al., 2007) using the D1D2 domain of the published structure of IL-1RII (pdb code: 3040) and the variable domain of the Fab structure of Ab2 as search models. Iterative structure refinement and model building were carried out in with REFMAC5 (Murshudov et al., 1997) and COOT (Emsley and Cowtan, 2004).

The interface analysis was carried out with program PISA, AREAMOL and NCONTACT in CCP4 package. The figures were prepared with Pymol (The PyMOL Molecular Graphics System. Schrödinger).

Figure 7:
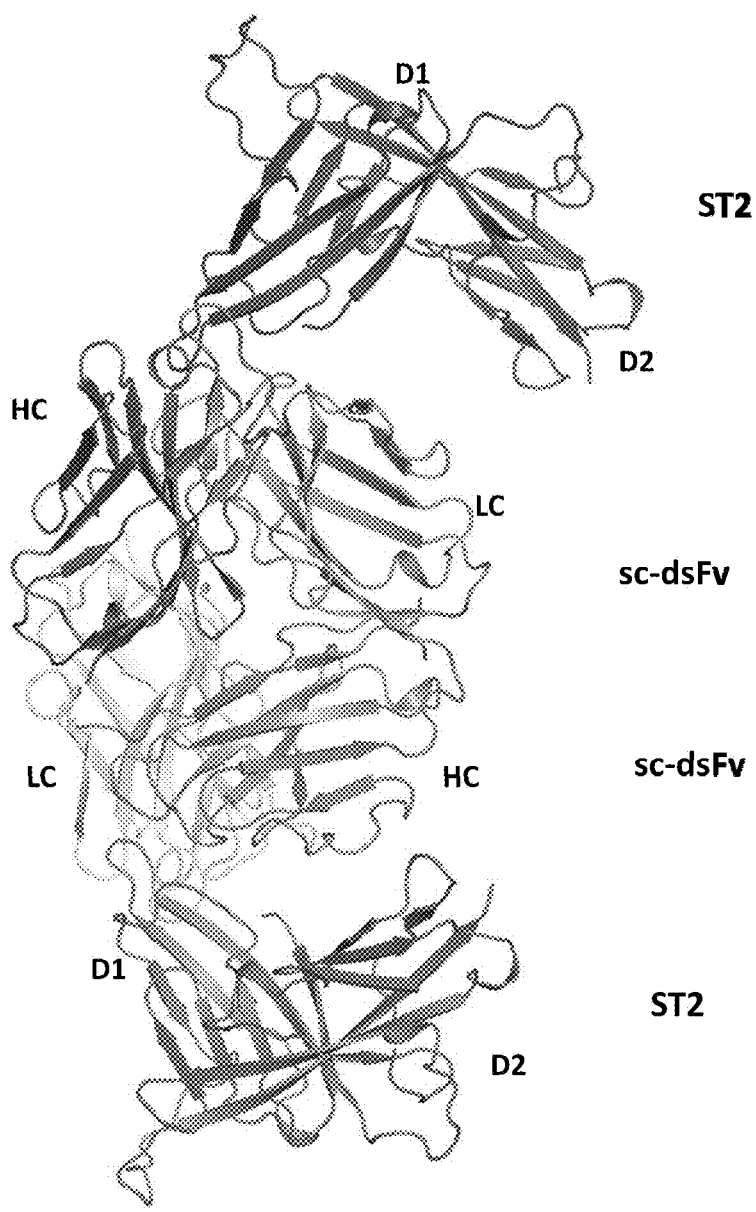
FIG. 7 Overall structure of ST2/Ab2 sc-dsFv complex. Two Ab2 sc-dsFv molecules are shown in cartoon representation and colored in cyan/blue or light yellow/gold for light chain (LC)/heavy chain (HC) pair respectively. Two ST2 molecules are shown in magenta and green cartoon.
Figure 8:
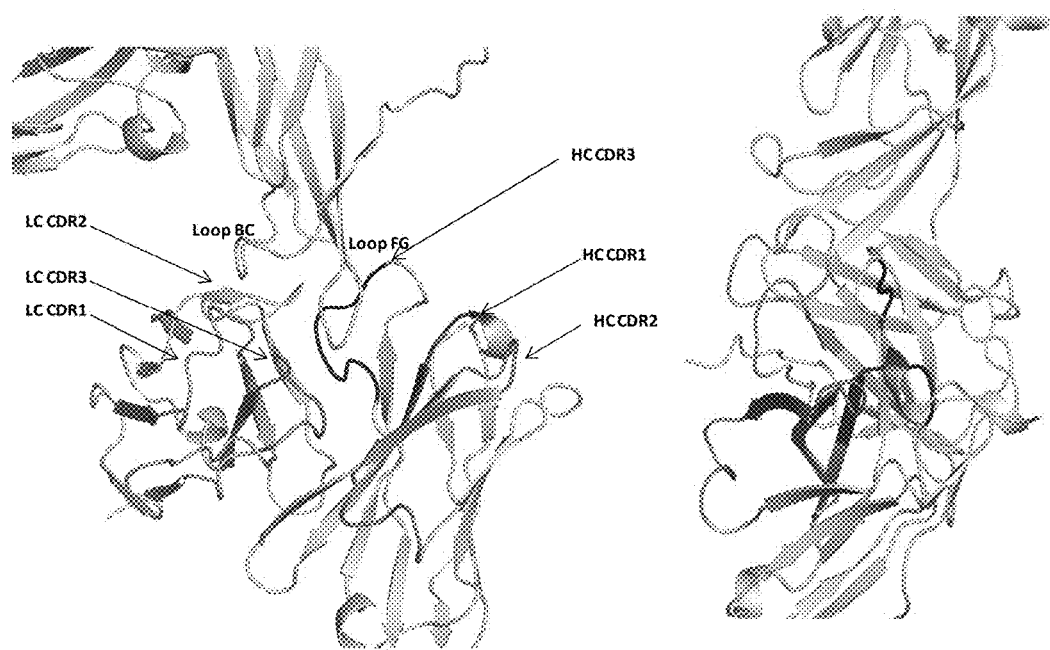
FIG. 8 Binding interface. ST2 is shown in yellow cartoon. The heavy chain and light chain of Ab2 are shown in grey and wheat cartoon. The CDR loops for heavy chain and light chain are colored in the following order: CDR1: red (HC) or light red (LC); CDR2: green (HC) or light green (LC); and CDR3: blue (HC) or light blue (LC).

The crystal structure of the ST2/Ab2 sc-dsFv complex was solved to a resolution of 1.9 Å. There are two independent pairs of ST2/Ab2 sc-dsFv complexes in the asymmetric unit (FIG. 7). Each complex consists of one ST2 molecule and one Ab2 sc-dsFv fragment. The ST2 molecule is made of two IgG-like domains (D1 and D2 domain). The Ab2 Fv domain utilizes all six CDR loops of the heavy chain and light chain to interact with the ST2 molecule (FIG. 8). For ST2, two loops (loop BC and loop FG) and the N-terminus of ST2 make direct interactions with the antibody. The total buried solvent accessible surface area between ST2 and Ab2 sc-dsFv is 1803 Å$^2$.

Figure 9A:
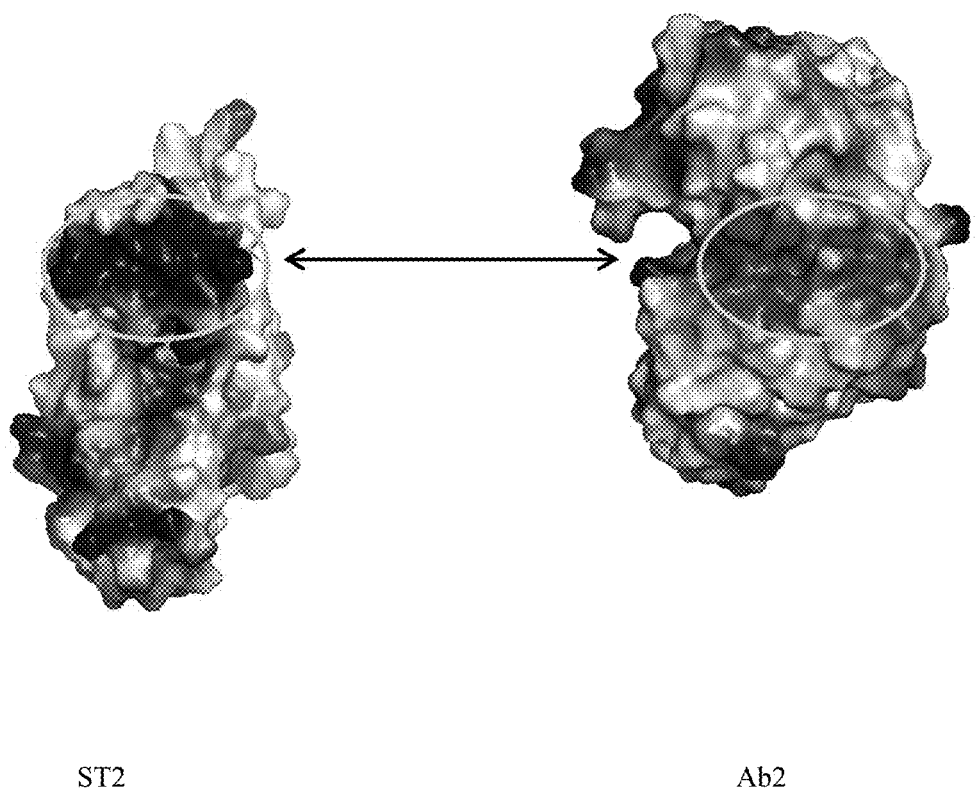
FIGS. 9A-9B Electrostatic surface potential map of ST2 and Ab2 sc-dsFv.
Figure 9B:
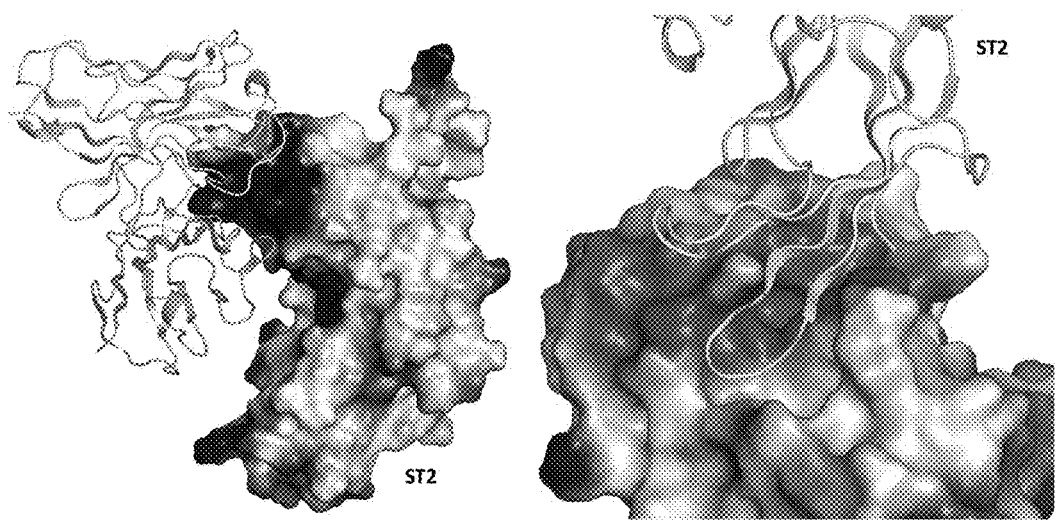

The interface between ST2 and Ab2 is highly charged. ST2 possess a cluster of basic residues (Lys and Arg) in the D1 domain. This positive-charged surface patch complements the negative-charged patch on Ab2 formed by clusters of acidic residues (Asp and Glu) in the CDR regions (FIG. 9).

Two different methods were used to define the interface residues. In the first method, the interface residues were defined using solvent exposure difference. The solvent accessible surface area of each residue in ST2 (or Ab2 sc-dsFv) in the complex was calculated and compared to the solvent accessible surface area of the corresponding residues in ST2 (or Ab2 sc-dsFv) stripped from complex. All amino acids with difference greater than 10% are listed in Table 15 and Table 16 for ST2 and Ab2, respectively. The surface exposure differences of Arg72 and Tyr81 of ST2 are less than 10%. However, inspection of the complex structure revealed that both residues form water-mediated hydrogen bonds with Ab2 heavy chain residues and hence they are included in the list.

TABLE 15

Epitope residues as defined by solvent exposure differences: ST2. Residue numbers correspond to the position of the amino acid in mature ST2, i.e., amino acid 1 corresponds to amino acid 19 of SEQ ID NO:1.

| Residue | Residue number | ASA in complex | ASA in apo | ratio | percentage change (%) |
|---|---|---|---|---|---|
| LYS | 1 | 68.5 | 196.9 | 0.348 | 65.2 |
| PHE | 2 | 48.4 | 106.2 | 0.456 | 54.4 |
| PRO | 19 | 7.9 | 10.8 | 0.731 | 26.9 |
| ARG | 20 | 0 | 79.6 | 0.000 | 100.0 |
| GLN | 21 | 81.7 | 98.1 | 0.833 | 16.7 |
| GLY | 22 | 17.8 | 59.3 | 0.300 | 70.0 |
| LYS | 23 | 51.5 | 130.6 | 0.394 | 60.6 |
| TYR | 26 | 32.4 | 56.6 | 0.572 | 42.8 |
| ILE | 70 | 16.6 | 30.9 | 0.537 | 46.3 |
| VAL | 71 | 1.7 | 5.3 | 0.321 | 67.9 |
| ARG | 72 | 52.2 | 56.9 | 0.917 | 8.3 |
| SER | 73 | 18 | 22.2 | 0.811 | 18.9 |
| PRO | 74 | 70.9 | 106.8 | 0.664 | 33.6 |
| THR | 75 | 3.8 | 84.6 | 0.045 | 95.5 |
| PHE | 76 | 0 | 134.3 | 0.000 | 100.0 |
| ASN | 77 | 2.8 | 47.6 | 0.059 | 94.1 |
| ARG | 78 | 1.1 | 83.6 | 0.013 | 98.7 |
| THR | 79 | 7 | 37 | 0.189 | 81.1 |
| TYR | 81 | 78.9 | 80.8 | 0.969 | 3.1 |
| ASN77-NAG | 502 | 148.2 | 249 | 0.595 | 40.5 |

TABLE 16

Paratope residues as defined by solvent exposure differences: Ab2

| HC residue | residue number | ASA in complex | ASA in apo | ratio | percentage change |
|---|---|---|---|---|---|
| TRP | 33 | 1.9 | 32.2 | 0.059 | 94.1 |
| ILE | 50 | 0 | 8.3 | 0.000 | 100.0 |
| ASP | 57 | 52.8 | 59.6 | 0.886 | 11.4 |
| ARG | 59 | 60.4 | 89.5 | 0.675 | 32.5 |
| HIS | 99 | 2 | 6.6 | 0.303 | 69.7 |
| GLY | 100 | 3.6 | 5.5 | 0.655 | 64.5 |
| THR | 101 | 27.5 | 35.9 | 0.766 | 23.4 |
| SER | 102 | 48.8 | 97.6 | 0.500 | 50.0 |
| SER | 103 | 45.3 | 111.8 | 0.405 | 59.5 |
| ASP | 104 | 23.1 | 93 | 0.248 | 75.2 |
| TYR | 105 | 1.9 | 75.4 | 0.025 | 97.5 |
| TYR | 106 | 36.8 | 64.6 | 0.570 | 43.0 |

| LC residue | residue number | ASA in complex | ASA in apo | ratio | percentage change |
|---|---|---|---|---|---|
| ASP | 28 | 85.1 | 105.2 | 0.809 | 19.1 |
| SER | 30 | 11.9 | 50.9 | 0.234 | 76.6 |
| ASN | 31 | 12.5 | 47.1 | 0.265 | 73.5 |
| TYR | 32 | 1.1 | 109.9 | 0.010 | 99.0 |
| TYR | 49 | 8.4 | 58.1 | 0.145 | 85.5 |
| ASP | 50 | 8.1 | 51.5 | 0.157 | 84.3 |
| ASN | 53 | 20.2 | 59.5 | 0.339 | 66.1 |
| GLU | 55 | 27.5 | 38.4 | 0.716 | 28.4 |
| THR | 56 | 116.9 | 127.4 | 0.918 | 8.2 |
| ASP | 91 | 2 | 27.4 | 0.073 | 92.7 |
| ASP | 92 | 2.5 | 54.1 | 0.046 | 95.4 |
| ASN | 93 | 50.5 | 69.5 | 0.727 | 27.3 |
| PHE | 94 | 54.9 | 110.9 | 0.495 | 50.5 |
| LEU | 96 | 2.9 | 7.8 | 0.372 | 62.8 |

In the second method, interface residues were selected that have at least one atom within a predefined distance to its partner protein. Two shells were defined based on different distance cutoff.

Core shell includes all residues with distance up to 5.0 Å.
Boundary shell includes all residues with distance longer than 5.0 Å but shorter than 8.0 Å.

The complete list of amino acid residues in each shell for ST2, the heavy and light chain of Ab2 are shown in Tables 17, 18 and 19, respectively. For residues that make hydrogen bond or salt bridges with its partner protein, the type of specific interactions are denoted in parenthesis after the residue (FIB for hydrogen bond and SB for salt bridge).

TABLE 17

Epitope residues defined by distance cutoff: ST2. Residue numbers correspond to the position of the amino acid in mature ST2, i.e., amino acid 1 corresponds to amino acid 19 of SEQ ID NO:1.

| Core (0-5 Å) | Boundary (5-8 Å) |
|---|---|
| 1(LYS) (HB/SB) | 3(SER) |
| 2(PHE) | 4(LYS) |
| 19(PRO) | 18(CYS) |
| 20(ARG) (HB/SB) | 24(PRO) |
| 21(GLN) | 27(THR) |
| 22(GLY) | 28(VAL) |
| 23(LYS) (HB/SB) | 31(TYR) |
| 26(TYR) (HB) | 68(THR) |
| 70(ILE) | 69(CYS) |
| 71(VAL) | 80(GLY) |
| 72(ARG) | 81(TYR) |
| 73(SER) | |
| 74(PRO) | |
| 75(THR) (HB) | |
| 76(PHE) | |
| 77(ASN) (HB) | |

TABLE 17-continued

Epitope residues defined by distance cutoff: ST2. Residue numbers correspond to the position of the amino acid in mature ST2, i.e., amino acid 1 corresponds to amino acid 19 of SEQ ID NO:1.

| Core (0-5 Å) | Boundary (5-8 Å) |
|---|---|
| 78(ARG) (HB/SB) | |
| 79(THR) (HB) | |
| 502(NAG)-77(ASN) | |

TABLE 18

Paratope residues defined by distance cutoff: Ab2 heavy chain.

| core (0-5 Å) | boundary (5-8 Å) |
|---|---|
| 33(TRP) | 31(ASN) |
| 50(ILE) | 32(TYR) |
| 57(ASP) | 34(ILE) |
| 59(ARG) | 47(TRP) |
| 99(HIS) | 52(TYR) |
| 100(GLY) | 55(ASN) |
| 101(THR) | 58(THR) |
| 102(SER) (HB) | 98(ARG) |
| 103(SER) (HB) | 107(GLY) |
| 104(ASP) (HB/SB) | 108(LEU) |
| 105(TYR) (HB) | 109(ASP) |
| 106(TYR) | |

TABLE 19

Paratope residues defined by distance cutoff: Ab2 light chain.

| core (0-5 Å) | boundary (5-8 Å) |
|---|---|
| 28(ASP) (HB) | 2(ILE) |
| 29(ILE) | 27(GLN) |
| 30(SER) | 33(LEU) |
| 31(ASN) (HB) | 34(ASN) |
| 32(TYR) | 46(LEU) |
| 49(TYR) | 52(SER) |
| 50(ASP) (HB/SB) | 54(LEU) |
| 53(ASN) | 67(SER) |
| 55(GLU) (HB/SB) | 68(GLY) |
| 56(THR) | 89(GLN) |
| 91(ASP) (HB/SB) | 90(GLN) |
| 92(ASP) (HB/SB) | 95(PRO) |
| 93(ASN) | 96(LEU) |
| 94(PHE) | |
| 96(LEU) | |

Epitope residues that were defined by solvent exposure differences match residues of the core interaction groups defined by distance cut-off. Table 20 lists all hydrogen bond and salt bridge pairs within the interface.

TABLE 20

Interaction pairs in the interface

| ## | Structure 1 | | | Dist. | Structure 2 | | |
|---|---|---|---|---|---|---|---|
| \multicolumn{8}{l}{Ab2 Light Chain-ST2 Hydrogen Bonds} |
| 1 | L:ASN | 31 | [ND2] | 3.4 | A:ARG | 20 | [O] |
| 2 | L:GLU | 55 | [OE1] | 2.7 | A:LYS | 1 | [NZ] |
| 3 | L:ASP | 50 | [OD2] | 2.8 | A:ARG | 20 | [NE] |
| 4 | L:ASP | 50 | [OD1] | 3.0 | A:ARG | 20 | [NH2] |
| 5 | L:ASP | 28 | [O] | 2.9 | A:LYS | 23 | [NZ] |
| 6 | L:ASP | 92 | [OD1] | 2.9 | A:LYS | 23 | [NZ] |
| 7 | L:ASP | 92 | [OD1] | 3.3 | A:TYR | 26 | [OH] |
| 8 | L:ASP | 91 | [O] | 2.7 | A:THR | 75 | [OG1] |
| 9 | L:ASP | 91 | [O] | 3.0 | A:ARG | 78 | [NH2] |
| 10 | L:ASP | 91 | [OD2] | 3.0 | A:ARG | 78 | [NH2] |
| \multicolumn{8}{l}{Salt Bridges} |
| 1 | L:GLU | 55 | [OE1] | 2.7 | A:LYS | 1 | [NZ] |
| 2 | L:GLU | 55 | [OE2] | 3.6 | A:LYS | 1 | [NZ] |
| 3 | L:ASP | 50 | [OD1] | 3.9 | A:ARG | 20 | [NE] |
| 4 | L:ASP | 50 | [OD2] | 2.8 | A:ARG | 20 | [NE] |
| 5 | L:ASP | 50 | [OD1] | 3.0 | A:ARG | 20 | [NH2] |
| 6 | L:ASP | 50 | [OD2] | 3.4 | A:ARG | 20 | [NH2] |
| 7 | L:ASP | 92 | [OD2] | 3.4 | A:LYS | 23 | [NZ] |
| 8 | L:ASP | 92 | [OD1] | 2.9 | A:LYS | 23 | [NZ] |
| 9 | L:ASP | 91 | [OD2] | 3.0 | A:ARG | 78 | [NH2] |
| \multicolumn{8}{l}{Ab2 Heavy Chain-ST2 Hydrogen Bonds} |
| 1 | H:TYR | 105 | [N] | 3.3 | A:ASN | 77 | [O] |
| 2 | H:SER | 102 | [O] | 2.6 | A:ASN | 77 | [ND2] |
| 3 | H:SER | 103 | [O] | 2.7 | A:THR | 79 | [OG1] |
| 4 | H:ASP | 104 | [OD1] | 2.7 | A:LYS | 1 | [N] |
| 5 | H:ASP | 104 | [OD2] | 2.8 | A:THR | 79 | [N] |
| 6 | H:ASP | 104 | [OD2] | 2.9 | A:ARG | 20 | [NH1] |
| 7 | H:TYR | 105 | [O] | 2.8 | A:ARG | 20 | [NH2] |
| \multicolumn{8}{l}{Salt Bridges} |
| 1 | H:ASP | 104 | [OD1] | 2.7 | A:LYS | 1 | [N] |
| 2 | H:ASP | 104 | [OD2] | 3.2 | A:LYS | 1 | [N] |
| 3 | H:ASP | 104 | [OD2] | 2.9 | A:ARG | 20 | [NH1] |

The ST2 epitope regions obtained from HDX-MS analysis of Example 12 are confirmed by the crystallography data. The two epitopes (15-26 and 70-76) from HDX were identified as epitopes in the higher resolution crystallography data. Specifically, Arg20, Gly22, Lys23 and Tyr26, as well as Thr75 were identified to be close to the antibody with a distance of less than 3.4 Å. Additional residues that were identified to have a distance to the antibody between 3.4 and 5 Å (Pro19, Gln21, Ile70, Val71, Arg72, Ser73 Pro74 and Phe76) were also covered in the HDX epitopes.

Overall, the results confirmed that ST2 epitope regions obtained from both HDX-MS and crystallography are consistent. The BC loop and FG loop in Domain 1 (see crystallography data) are the main interaction sites.

REFERENCES

Ali, M., G. Zhang, et al. (2009). "Investigations into the role of ST2 in acute asthma in children." *Tissue Antigens* 73(3): 206-212.

Beltran, C. J., L. E. Nunez, et al. (2010). "Characterization of the novel ST2/IL-33 system in patients with inflammatory bowel disease." *Inflamm Bowel Dis* 16(7): 1097-1107.

Brunner, M., C. Krenn, et al. (2004). "Increased levels of soluble ST2 protein and IgG1 production in patients with sepsis and trauma." *Intensive Care Med* 30(7): 1468-1473.

Buysschaert, I. D., V. Grulois, et al. (2010). "Genetic evidence for a role of IL33 in nasal polyposis." *Allergy* 65(5): 616-622.

Castano R, B. Y., Mfuna Endam L, Desrosiers M (2009). "Evidence of association of Interleukin 1 receptor-like 1 gene polymorphisms with surgery unresponsive Chronic Rhinosinusitis." *American Journal of Rhinology* in press (NA): NA.

Gudbjartsson, D. F., U. S. Bjornsdottir, et al. (2009). "Sequence variants affecting eosinophil numbers associate with asthma and myocardial infarction." Nat Genet 41(3): 342-347.

Hacker, S., C. Lambers, et al. (2009). "Increased soluble serum markers caspase-cleaved cytokeratin-18, histones, and ST2 indicate apoptotic turnover and chronic immune response in COPD." J Clin Lab Anal 23(6): 372-379.

Kuroiwa, K., T. Arai, et al. (2001). "Identification of human ST2 protein in the sera of patients with autoimmune diseases." Biochem Biophys Res Commun 284(5): 1104-1108.

Manetti, M., L. Ibba-Manneschi, et al. (2009). "The IL-1-like cytokine IL-33 and its receptor ST2 are abnormally expressed in the affected skin and visceral organs of patients with systemic sclerosis." Ann Rheum Dis.

Marvie, P., M. Lisbonne, et al. (2009). "Interleukin-33 overexpression is associated with liver fibrosis in mice and humans." J Cell Mol Med.

Matsuyama, Y., H. Okazaki, et al. (2010). "Increased levels of interleukin 33 in sera and synovial fluid from patients with active rheumatoid arthritis." J Rheumatol 37(1): 18-25.

Miyagaki, T., M. Sugaya, et al. (2011). "High Levels of Soluble ST2 and Low Levels of IL-33 in Sera of Patients with HIV Infection." J Invest Dermatol 131(3): 794-796.

Moffatt, M. F., I. G. Gut, et al. (2010). "A large-scale, consortium-based genomewide association study of asthma." N Engl J Med 363(13): 1211-1221.

Mok, M. Y., F. P. Huang, et al. (2010). "Serum levels of IL-33 and soluble ST2 and their association with disease activity in systemic lupus erythematosus." Rheumatology (Oxford) 49(3): 520-527.

Neill, D. R., S. H. Wong, et al. (2010). "Nuocytes represent a new innate effector leukocyte that mediates type-2 immunity." Nature 464(7293): 1367-1370.

Oshikawa, K., K. Kuroiwa, et al. (2001). "Elevated soluble ST2 protein levels in sera of patients with asthma with an acute exacerbation." Am J Respir Crit Care Med 164(2): 277-281.

Oshikawa, K., K. Kuroiwa, et al. (2001). "Acute eosinophilic pneumonia with increased soluble ST2 in serum and bronchoalveolar lavage fluid." Respir Med 95(6): 532-533.

Palmer, G., D. Talabot-Ayer, et al. (2009). "Inhibition of interleukin-33 signaling attenuates the severity of experimental arthritis." Arthritis Rheum 60(3): 738-749.

Pastorelli, L., R. R. Garg, et al. (2010). "Epithelial-derived IL-33 and its receptor ST2 are dysregulated in ulcerative colitis and in experimental Th1/Th2 driven enteritis." Proc Natl Acad Sci USA 107(17): 8017-8022.

Plager, D. A., J. C. Kahl, et al. (2010). "Gene transcription changes in asthmatic chronic rhinosinusitis with nasal polyps and comparison to those in atopic dermatitis." PLoS ONE 5(7): e11450.

Prefontaine, D., S. Lajoie-Kadoch, et al. (2009). "Increased expression of IL-33 in severe asthma: evidence of expression by airway smooth muscle cells." J Immunol 183(8): 5094-5103.

Prefontaine, D., J. Nadigel, et al. (2010). "Increased IL-33 expression by epithelial cells in bronchial asthma." J Allergy Clin Immunol 125(3): 752-754.

Pushparaj, P. N., H. K. Tay, et al. (2009). "The cytokine interleukin-33 mediates anaphylactic shock." Proc Natl Acad Sci USA 106(24): 9773-9778.

Reijmerink, N. E., D. S. Postma, et al. (2008). "Association of IL1RL1, IL18R1, and IL18RAP gene cluster polymorphisms with asthma and atopy." J Allergy Clin Immunol 122(3): 651-654 e658.

Sakashita, M., T. Yoshimoto, et al. (2008). "Association of serum interleukin-33 level and the interleukin-33 genetic variant with Japanese cedar pollinosis." Clin Exp Allergy 38(12): 1875-1881.

Shah, R. V. and J. L. Januzzi, Jr. (2010). "ST2: a novel remodeling biomarker in acute and chronic heart failure." Curr Heart Fail Rep 7(1): 9-14.

Shimizu, M., A. Matsuda, et al. (2005). "Functional SNPs in the distal promoter of the ST2 gene are associated with atopic dermatitis." Hum Mol Genet 14(19): 2919-2927.

Sponheim, J., J. Pollheimer, et al. (2010). "Inflammatory bowel disease-associated interleukin-33 is preferentially expressed in ulceration-associated myofibroblasts." Am J Pathol 177(6): 2804-2815.

Tajima, S., K. Oshikawa, et al. (2003). "The increase in serum soluble ST2 protein upon acute exacerbation of idiopathic pulmonary fibrosis." Chest 124(4): 1206-1214.

Theoharides, T. C., B. Zhang, et al. (2010). "IL-33 augments substance P-induced VEGF secretion from human mast cells and is increased in psoriatic skin." Proc Natl Acad Sci USA 107(9): 4448-4453.

Verri, W. A., Jr., A. T. Guerrero, et al. (2008). "IL-33 mediates antigen-induced cutaneous and articular hypernociception in mice." Proc Natl Acad Sci USA 105(7): 2723-2728.

Wu, H., I. Romieu, et al. (2010). "Evaluation of candidate genes in a genome-wide association study of childhood asthma in Mexicans." J Allergy Clin Immunol 125(2): 321-327 e313.

Xu, D., H. R. Jiang, et al. (2008). "IL-33 exacerbates antigen-induced arthritis by activating mast cells." Proc Natl Acad Sci USA 105(31): 10913-10918.

Yanaba, K., A. Yoshizaki, et al. (2011). "Serum IL-33 levels are raised in patients with systemic sclerosis: association with extent of skin sclerosis and severity of pulmonary fibrosis." Clin Rheumatol.

Zhang, Z.; Zhang, A. and Xiao, G.; "Improved Protein Hydrogen/Deuterium Exchange Mass Spectrometry Plateform with Fully Automated Data Processing", Analytical Chemistry, 2012, 84(11), 4942-9

Zhang Z, Smith D L. Protein Sci. 1993; 2: 522.

Engen J R, Smith D L. Anal. Chem. 2001; 73: 256A.

Codreanu S G, Ladner J E, Xiao G, Stourman N V, Hachey D L, Gilliland G L,

Armstrong R N. Biochemistry 2002; 41: 15161.

Hamuro Y, Coales S J, Morrow J A, Molnar K S, Tuske S J, Southern M R, Griffin P R. Protein Sci. 2006; 15: 1.

Baerga-Ortiz A, Hughes C A, Mandell J G, Komives E A. Protein Sci. 2002; 11: 1300.

Coales, S J. et al. Rapid Commun. Mass Spectrom. 2009; 23: 639-647.

CCP4 (Collaborative Computational Project, No 4. (1994). The CCP4 suite: programs for protein crystallography. Acta Crystallogr D Biol Crystallogr 50, 760-763.

Emsley, P., and Cowtan, K. (2004). Coot: model-building tools for molecular graphics. Acta Crystallogr D Biol Crystallogr 60, 2126-2132.

Leslie, A. G. W. (1992). Recent changes to the MOSFLM package for processing film and image plate data Joint CCP4+ESF-EAMCB Newsletter on Protein Crystallography 26.

McCoy, A. J., Grosse-Kunstleve, R. W., Adams, P. D., Winn, M. D., Storoni, L. C., and Read, R. J. (2007). Phaser crystallographic software. Journal of applied crystallography 40, 658-674.

Murshudov, G. N., Vagin, A. A., and Dodson, E. J. (1997). Refinement of macromolecular structures by the maximum-likelihood method. Acta Crystallogr D Biol Crystallogr 53, 240-255.

The PyMOL Molecular Graphics System. Schrödinger, L.

Baerga-Ortiz, A., C. A. Hughes, J. G. Mandell and E. A. Komives (2002). "Epitope mapping of a monoclonal antibody against human thrombin by H/D-exchange mass spectrometry reveals selection of a diverse sequence in a highly conserved protein." *Protein Sci.* 11(6): 1300-1308.

Coales, S. J., S. J. Tuske, J. C. Tomasso and Y. Hamuro (2009). "Epitope mapping by amide hydrogen/deuterium exchange coupled with immobilization of antibody, on-line proteolysis, liquid chromatography and mass spectrometry." *Rapid Commun. Mass Spectrom.* 23(5): 639-647.

Codreanu, S. G., J. E. Ladner, G. Xiao, N. V. Stourman, D. L. Hachey, G. L. Gilliland and R. N. Armstrong (2002). "Local Protein Dynamics and Catalysis: Detection of Segmental Motion Associated with Rate-Limiting Product Release by a Glutathione Transferase." *Biochemistry* 41(51): 15161-15172.

Engen, J. R. and D. L. Smith (2001). "Investigating protein structure and dynamics by hydrogen exchange MS." *Anal. Chem.* 73(9): 256A-265A.

Hamuro, Y., S. J. Coales, J. A. Morrow, K. S. Molnar, S. J. Tuske, M. R. Southern and P. R. Griffin (2006). "Hydrogen/deuterium-exchange (H/D-Ex) of PPARγ LBD in the presence of various modulators." *Protein Sci.* 15(8): 1883-1892.

Zhang, Z. and D. L. Smith (1993). "Determination of amide hydrogen exchange by mass spectrometry: A new tool for protein structure elucidation." *Protein Sci.* 2(4): 522-531.

Zhang, Z., A. Zhang and G. Xiao (2012). "Improved Protein Hydrogen/Deuterium Exchange Mass Spectrometry Platform with Fully Automated Data Processing." *Analytical Chemistry* 84(11): 4942-4949.

What is claimed:

1. An isolated nucleic acid encoding an antibody that binds to ST2, wherein the antibody comprises (a) HCDR1 comprising the amino acid sequence of SEQ ID NO:41; (b) HCDR2 comprising the amino acid sequence of SEQ ID NO:52; (c) HCDR3 comprising the amino acid sequence of SEQ ID NO:63; (d) LCDR1 comprising the amino acid sequence of SEQ ID NO:107; (e) LCDR2 comprising the amino acid sequence of SEQ ID NO:118; and (f) LCDR3 comprising the amino acid sequence of SEQ ID NO:129.

2. The isolated nucleic acid of claim 1, wherein the nucleic acid encodes a heavy chain variable domain comprising the sequence of SEQ ID NO: 30 and a light chain variable domain comprising the sequence of SEQ ID NO: 96.

3. The isolated nucleic acid of claim 1, wherein the nucleic acid encodes a heavy chain comprising the sequence of SEQ ID NO: 19 and a light chain comprising the sequence of SEQ ID NO: 85.

4. An expression vector comprising the isolated nucleic acid of claim 1.

5. An expression vector comprising the isolated nucleic acid of claim 2.

6. An expression vector comprising the isolated nucleic acid of claim 3.

7. An isolated host cell comprising the expression vector of claim 4.

8. An isolated host cell comprising the expression vector of claim 5.

9. An isolated host cell comprising the expression vector of claim 6.

10. An isolated host cell comprising a first nucleic acid sequence and a second nucleic acid sequence, wherein the first nucleic acid sequence encodes a heavy chain variable region of an antibody that binds to ST2, wherein the heavy chain variable region comprises (a) HCDR1 comprising the amino acid sequence of SEQ ID NO:41; (b) HCDR2 comprising the amino acid sequence of SEQ ID NO:52; and (c) HCDR3 comprising the amino acid sequence of SEQ ID NO:63; and the second nucleic acid sequence encodes a light chain variable region of an antibody that binds to ST2, wherein the light chain variable region comprises (a) LCDR1 comprising the amino acid sequence of SEQ ID NO:107; (b) LCDR2 comprising the amino acid sequence of SEQ ID NO:118; and (c) LCDR3 comprising the amino acid sequence of SEQ ID NO:129.

11. The isolated host cell of claim 10, wherein the first nucleic acid sequence encodes a heavy chain variable region comprising the sequence of SEQ ID NO: 30 and the second nucleic acid sequence encodes a light chain variable region comprising the sequence of SEQ ID NO: 96.

12. The isolated host cell of claim 10, wherein the first nucleic acid sequence encodes a heavy chain comprising the sequence of SEQ ID NO: 19 and the second nucleic acid sequence encodes a light chain comprising the sequence of SEQ ID NO: 85.

13. An isolated host cell that is capable of producing an antibody that binds to ST2, wherein the antibody comprises (a) HCDR1 comprising the amino acid sequence of SEQ ID NO:41; (b) HCDR2 comprising the amino acid sequence of SEQ ID NO:52; (c) HCDR3 comprising the amino acid sequence of SEQ ID NO:63; (d) LCDR1 comprising the amino acid sequence of SEQ ID NO:107; (e) LCDR2 comprising the amino acid sequence of SEQ ID NO:118; and (f) LCDR3 comprising the amino acid sequence of SEQ ID NO:129.

14. The isolated host cell of claim 13, wherein the antibody comprises a heavy chain variable region comprising the sequence of SEQ ID NO: 30 and a light chain variable region comprising the sequence of SEQ ID NO: 96.

15. The isolated host cell of claim 13, wherein the antibody comprises a heavy chain comprising the sequence of SEQ ID NO: 19 and a light chain comprising the sequence of SEQ ID NO: 85.

16. The isolated host cell of claim 10, which is a prokaryotic host cell.

17. The isolated host cell of claim 10, which is a eukaryotic host cell.

18. The isolated host cell of claim 17, which is a Chinese hamster ovary (CHO) cell.

19. The isolated host cell of claim 11, which is a prokaryotic host cell.

20. The isolated host cell of claim 11, which is a eukaryotic host cell.

21. The isolated host cell of claim 20, which is a Chinese hamster ovary (CHO) cell.

22. The isolated host cell of claim 12, which is a prokaryotic host cell.

23. The isolated host cell of claim 12, which is a eukaryotic host cell.

24. The isolated host cell of claim 23, which is a Chinese hamster ovary (CHO) cell.

25. The isolated host cell of claim 13, which is a prokaryotic host cell.

26. The isolated host cell of claim 13, which is a eukaryotic host cell.

27. The isolated host cell of claim 26, which is a Chinese hamster ovary (CHO) cell.

28. The isolated host cell of claim 14, which is a prokaryotic host cell.

29. The isolated host cell of claim 14, which is a eukaryotic host cell.

30. The isolated host cell of claim 29, which is a Chinese hamster ovary (CHO) cell.

31. The isolated host cell of claim 15, which is a prokaryotic host cell.

32. The isolated host cell of claim 15, which is a eukaryotic host cell.

33. The isolated host cell of claim 32, which is a Chinese hamster ovary (CHO) cell.

34. A method of making an antibody that binds to ST2 comprising culturing the host cell of claim 10 so that the antibody is produced, and isolating the antibody from the culture.

35. A method of making an antibody that binds to ST2 comprising culturing the host cell of claim 11 so that the antibody is produced, and isolating the antibody from the culture.

36. A method of making an antibody that binds to ST2 comprising culturing the host cell of claim 12 so that the antibody is produced, and isolating the antibody from the culture.

37. A method of making an antibody that binds to ST2 comprising culturing the host cell of claim 13 so that the antibody is produced, and isolating the antibody from the culture.

38. A method of making an antibody that binds to ST2 comprising culturing the host cell of claim 14 so that the antibody is produced, and isolating the antibody from the culture.

39. A method of making an antibody that binds to ST2 comprising culturing the host cell of claim 15 so that the antibody is produced, and isolating the antibody from the culture.

40. A method of making an antibody that binds to ST2 comprising culturing the host cell of claim 18 so that the antibody is produced, and isolating the antibody from the culture.

41. A method of making an antibody that binds to ST2 comprising culturing the host cell of claim 21 so that the antibody is produced, and isolating the antibody from the culture.

42. A method of making an antibody that binds to ST2 comprising culturing the host cell of claim 24 so that the antibody is produced, and isolating the antibody from the culture.

43. A method of making an antibody that binds to ST2 comprising culturing the host cell of claim 27 so that the antibody is produced, and isolating the antibody from the culture.

44. A method of making an antibody that binds to ST2 comprising culturing the host cell of claim 30 so that the antibody is produced, and isolating the antibody from the culture.

45. A method of making an antibody that binds to ST2 comprising culturing the host cell of claim 33 so that the antibody is produced, and isolating the antibody from the culture.

* * * * *